(12) United States Patent
Shen et al.

(10) Patent No.: US 10,143,681 B2
(45) Date of Patent: Dec. 4, 2018

(54) FACTOR XIA INHIBITORS

(71) Applicant: MERCK SHARP & DOHME CORP., Rahway, NJ (US)

(72) Inventors: Dong-Ming Shen, Edison, NJ (US); Rongze Kuang, Green Brook, NJ (US); Puneet Kumar, Edison, NJ (US); Joseph L. Duffy, Cranford, NJ (US); Cheng Zhu, Edison, NJ (US); Amjad Ali, Freehold, NJ (US); Meng Yang, Edison, NJ (US); John S. Debenham, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/681,478

(22) Filed: Aug. 21, 2017

(65) Prior Publication Data

US 2018/0050022 A1  Feb. 22, 2018

Related U.S. Application Data

(60) Provisional application No. 62/377,969, filed on Aug. 22, 2016.

(51) Int. Cl.
*A61K 31/4412* (2006.01)
*C07D 213/89* (2006.01)
*A61K 31/435* (2006.01)

(52) U.S. Cl.
CPC .......... *A61K 31/435* (2013.01); *C07D 213/89* (2013.01); *A61K 2121/00* (2013.01)

(58) Field of Classification Search
CPC .................................................. C07D 213/89
See application file for complete search history.

(56) References Cited

U.S. PATENT DOCUMENTS

| 7,262,210 B2 | 8/2007 | Kreutter et al. |
| 7,829,584 B2 | 11/2010 | Player et al. |
| 2010/0173899 A1 | 7/2010 | Pinto et al. |

FOREIGN PATENT DOCUMENTS

| WO | WO2015183709 A1 | 12/2015 |
| WO | 2016015593 A1 | 2/2016 |
| WO | 2016018701 A1 | 2/2016 |
| WO | WO2016018702 A1 | 2/2016 |
| WO | 2016118403 A1 | 7/2016 |
| WO | 2016168098 A1 | 10/2016 |
| WO | WO2017095760 A1 | 6/2017 |

OTHER PUBLICATIONS

International Search Report and Written Opinion for PCT/US2017/047718, dated Sep. 28, 2017; 12 pages.

*Primary Examiner* — Brian E McDowell
(74) *Attorney, Agent, or Firm* — Nicole M. Beeler; John C. Todaro

(57) ABSTRACT

The present invention provides a compound of Formula I and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

16 Claims, No Drawings

FACTOR XIA INHIBITORS

CROSS REFERENCE TO RELATED APPLICATIONS

This application claims priority from U.S. Ser. No. 62/377,969 filed Aug. 22, 2016.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on C1-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2016036893, WO2016015593, WO2016018702, WO2016018701, WO2016011940, JP2015013821, WO2015183709, WO2015120777, WO2015120062, WO2015116885, WO2015116882, WO2015107724, WO2015063093, WO2015047973, WO2015054087, WO2015044174, WO2015044173, WO2015044172, WO2015044170, WO2015044169, WO2015044167, WO2015044165, WO2015044163, WO2015002611, WO2015011087, WO2015123090, WO2015123091, WO2015123093, WO2015164308, WO2014160668, WO2014160592, WO2014059214, WO2014059203, WO2014059202, WO2014022767, WO2014022766, WO2014014050, WO2013174937, WO2013022814, WO2013022818, WO2013055984, WO2013056034, WO2013056060, WO2013118805. WO2013093484. WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

and pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

wherein X is $R^1$ is $CF_2H$, $CF_3$, $OCF_2H$, $OCF_3$, $O(C_{1-3}$ alkyl) or $OCH_2$(cyclopropyl);

$R^2$ is chloro or fluoro;

$R^3$ is hydrogen, chloro or fluoro;

$R^4$ is hydrogen, $C_{1-3}$ alkyl or $O(C_{1-3}$ alkyl), wherein said alkyl groups are optionally substituted with one to three groups independently selected from the group consisting of halo and hydroxyl;

$R^5$ is (C=O)OH or (C=O)O($C_{1-6}$ alkyl), wherein said alkyl groups are optionally substituted with one to three groups independently selected from the group consisting of halo and hydroxyl; each $R^x$ is independently selected from halo, hydroxyl, cyano, oxo, methyl, ethyl, $CH_2F$, $CHF_2$, $CF_3$ or $CH_2OH$;

$R^y$ is halo or methyl;

m is zero, one or two;

n is one, two, three or four;

p is zero or one;

or a pharmaceutically acceptable salt thereof.

Another embodiment of the invention relates to compounds of Formula I:

wherein X is

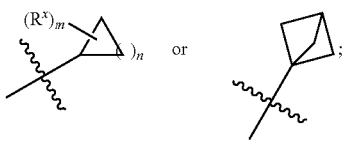

$R^1$ is $CF_2H$, $CF_3$, $OCF_2H$, $OCF_3$, $O(C_{1-3}$ alkyl) or $OCH_2$ (cyclopropyl);

$R^2$ is chloro or fluoro;

$R^3$ is hydrogen, chloro or fluoro;

$R^4$ is hydrogen, $C_{1-3}$ alkyl or $O(C_{1-3}$ alkyl), wherein said alkyl groups are optionally substituted with one to three groups independently selected from the group consisting of halo and hydroxyl;

$R^5$ is $(C=O)OH$ or $(C=O)O(C_{1-6}$ alkyl), wherein said alkyl groups are optionally substituted with one to three groups independently selected from the group consisting of halo and hydroxyl;

each $R^x$ is independently selected from halo, hydroxyl, cyano, oxo, methyl, ethyl, $CH_2F$, $CF_3$ or $CH_2OH$;

$R^y$ is halo or methyl;

m is zero, one or two;

n is one, two, three or four;

p is zero or one;

or a pharmaceutically acceptable salt thereof.

An embodiment of the present invention relates to compounds of Formula Ia:

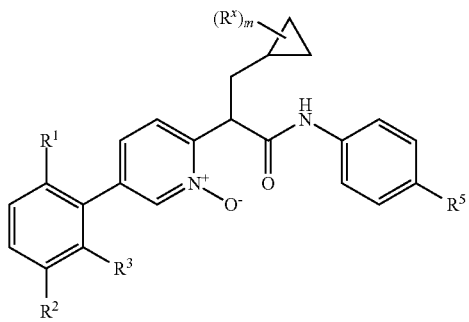

Ia wherein $R^1$ is $CF_2H$, $CF_3$, $OCF_2H$ or $OCF_3$;

$R^2$ is chloro or fluoro;

$R^3$ is hydrogen, chloro or fluoro;

$R^5$ is $(C=O)OH$ or $(C=O)O(C_{1-6}$ alkyl), wherein said alkyl groups are optionally substituted with one to three groups independently selected from the group consisting of halo and hydroxyl;

each $R^x$ is independently selected from halo, hydroxyl, cyano, oxo or methyl;

m is zero, one or two;

or a pharmaceutically acceptable salt thereof.

An embodiment of the present invention relates to compounds of Formula Ib:

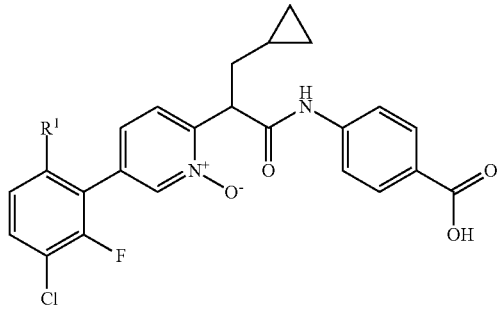

Ib wherein $R^1$ is $CF_2H$, $CF_3$ or $OCF_2H$;

or a pharmaceutically acceptable salt thereof.

In an embodiment of the invention, X is

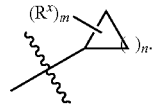

In another embodiment of the invention, X is

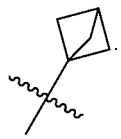 [SMILES: *C12CC(C1)C2]

In an embodiment of the invention, $R^1$ is $CF_2H$, $CF_3$, $OCF_2H$ or $OCF_3$. In a class of the embodiment, $R^1$ is $CF_2H$. In another class of the embodiment, $R^1$ is $CF_3$. In another class of the embodiment, $R^1$ is $OCF_2H$. In another class of the embodiment, $R^1$ is $OCF_3$.

In an embodiment of the invention, $R^2$ is chloro. In another embodiment of the invention, $R^2$ is fluoro.

In an embodiment of the invention, $R^3$ is fluoro. In another embodiment of the invention, $R^3$ is chloro. In another embodiment of the invention, $R^3$ is hydrogen.

In an embodiment of the invention, $R^4$ is hydrogen. In another embodiment of the invention, $R^4$ is methyl. In another embodiment of the invention, $R^4$ is ethyl. In another embodiment of the invention, $R^4$ is methoxy. In another embodiment of the invention, $R^4$ is ethoxy.

In an embodiment of the invention, $R^5$ is $(C=O)OH$. In another embodiment of the invention, $R^5$ is $(C=O)OCH_3$.

In an embodiment of the invention, $R^x$ is methyl. In another embodiment of the invention, $R^x$ is ethyl. In another embodiment of the invention, $R^x$ is fluoro. In another embodiment of the invention, $R^x$ is hydroxyl. In another embodiment of the invention, $R^x$ is cyano. In another embodiment of the invention, $R^x$ is oxo. In another embodiment of the invention, $R^x$ is $CH_2F$. In another embodiment of the invention, $R^x$ is $CF_3$. In another embodiment of the invention, $R^x$ is $CHF_2$.

In an embodiment of the invention, $R^y$ is halo. In another embodiment of the invention, $R^y$ is methyl.

In an embodiment of the invention, m is zero. In another embodiment of the invention, m is one. In another embodiment of the invention, m is two.

In an embodiment of the invention, n is one. In another embodiment of the invention, n is two. In another embodiment of the invention, n is three. In another embodiment of the invention, n is four.

In an embodiment of the invention, p is zero. In another embodiment of the invention, p is one.

Reference to the preferred classes and subclasses set forth above is meant to include all combinations of particular and preferred groups unless stated otherwise.

Specific embodiments of the present invention include, but are not limited to the compounds identified herein as Examples 1 to 124, or pharmaceutically acceptable salts thereof.

Also included within the scope of the present invention is a pharmaceutical composition which is comprised of a compound of Formula I, Formula Ia or Formula Ib as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds of the invention have improved pharmacokinetic profiles compared to compounds known in the art. Furthermore, some of the compounds of the invention have a better combination of potency, efficacy and pharmacokinetic properties compared to known compounds.

It will be understood that, as used herein, the compounds of the present invention include the pharmaceutically acceptable salts of the compounds of structural Formula I, Formula Ia and Formula Ib, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Formula Ia or Formula Ib simultaneously contain acidic and basic groups in the molecule the invention also includes, in addition to the salt forms mentioned, inner salts or betaines (zwitterions).

The present invention encompasses all stereoisomeric forms of the compounds of Formula I, Formula Ia and Formula Ib. Unless a specific stereochemistry is indicated, the present invention is meant to comprehend all such isomeric forms of these compounds. Centers of asymmetry that are present in the compounds of Formula I, Formula Ia and Formula Ib can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia or Formula Ib or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^x$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Formula Ia and Formula Ib are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

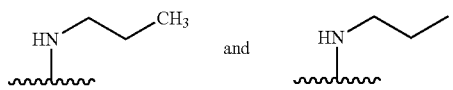

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

"Celite®" (Fluka) diatomite is diatomaceous earth, and can be referred to as "celite".

Except where noted herein, structures containing substituent variables such as variable "R" below:

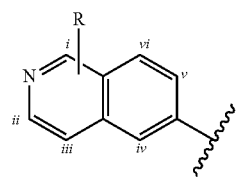

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I, Formula Ia or Formula Ib and/or of a pharmaceutically acceptable salt of the compound of the Formula I, Formula Ia or Formula Ib and/or an optionally stereoisomeric form of the compound of the Formula I, Formula Ia or Formula Ib or a pharmaceutically acceptable salt of the stereoisomeric form of the compound of Formula I, Formula Ia or Formula Ib, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

The compounds may be selective Factor XIa inhibitors or dual inhibitors of Factor XIa and plasma kallikrein. Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formulas I, Ia and Ib and other surfaces which come into contact with blood in the body is possible.

The invention also relates to a process for the production of a medicament, which comprises bringing at least one compound of the Formulas I, Ia and Ib into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia and Formula Ib can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

General Methods

Compounds of the present invention may be prepared using conventional techniques or according to the methodology outlined in the following general synthetic schemes. One skilled in the art can vary the procedures and reagents shown to arrive at similar intermediates and/or final compounds.

Abbreviations are used and defined as follows:
2nd Generation Xphos Precatalyst Chloro(2-dicyclohexylphosphino-2',4',6'-triisopropyl-1,1'-biphenyl)[2-(2'-amino-1,1'-biphenyl)]palladium(II)
AcOH Acetic acid
aq Aqueous
BAST Bis(2-methoxyethyl)aminosulfur trifluoride
$BH_3$.DMS Borane dimethylsulfide
DAST (Diethylamino)sulfur trifluoride
DBU 1,8-Diazabicyclo[5.4.0]undec-7-ene
DCM Dichloromethane
DMF Dimethylformamide
PE Petroleum ether
$Et_3N$ Triethylamine
$Et_2O$ Diethyl ether
EtOAc Ethyl acetate
HATU 1-[Bis(dimethylamino)methylene]-1H-1,2,3-triazolo[4,5-b]pyridinium-3-oxid hexafluorophosphate
IPA Isopropyl alcohol
LAH Lithium aluminum hydride
LC-MS Liquid chromatography-mass spectrometry
LDA Lithium Diiospropylamide
LiHMDS Hexamethyldisilazane lithium salt or lithium bis(trimethylsilyl)amide
mCPBA 3-chlorobenzoperoxoic acid
MeOH Methanol
MTBE Methyl tert-butyl ether
PABA Para-aminobenzoic acid or para-aminobenzoate
PCC Pyridinium chlorochromate
Pd(dppf)$Cl_2$ [1,1'-Bis(diphenylphosphino)ferrocene]dichloropalladium(II)
Pd(dppf)$Cl_2$.DCM [1,1'-Bis(diphenylphosphino)ferrocene]dichloropalladium(II) dichloromethane complex
$PPh_3$ Triphenylphosphine
rt or RT Room temperature
RP-HPLC Reverse-phase high pressure liquid chromatography
sat. Saturated
SFC Supercritical Fluid Chromatography
SM Starting material
TEA Triethylamine
TFA Trifluoroacetic acid
THF Tetrahydrofuran
MW Microwave NMR spectra were measured on VARIAN NMR Systems (400, 500 or 600 MHz). Chemical shifts are reported in ppm downfield and up field from tetramethylsilane (TMS) and referenced to either internal TMS or solvent resonances ($^1$H NMR: δ 7.27 for $CDCl_3$, δ 2.50 for $(CD_3)(CHD_2)SO$, and $^{13}C$ NMR: δ 77.02 for $CDCl_3$, δ 39.51 for $(CD_3)_2SO$. Coupling constants (J) are expressed in hertz (Hz), and spin multiplicities are given as s (singlet), d (doublet), dd (double doublet), t (triplet), m (multiplet), and br (broad). Chiral resolutions were performed on either Waters Thar 80 SFC or Berger MG II preparative SFC systems. LC-MS data were recorded on SHIMADAZU LC-MS-2020, SHIMADAZU LC-MS-2010EV, or Agilent 1100 series LC-MS, or Waters Acquity LC-MS instruments using C18 columns employing a MeCN gradient in water containing 0.02 to 0.1% TFA. UV detections were at 220 and/or 254 nm and ESI ionization was used for MS detection.

When chiral resolution was achieved by chromatography using chiral columns, the chiral columns used for SFC chiral resolutions are listed in tables. Some of the chiral columns used were CHIRALPAK AD, CHIRALCEL OJ, CHIRALPAK AS, CHIRALPAK AY, CHIRALPAK IA, CHIRALPAK AD-H, and CHIRALPAK AS-H. Henceforth, they will be referred by their two or three letter abbreviations. As a convention, the fast-eluting isomer from a chiral resolution is always listed first in this table followed immediately by the slower-eluting isomer from the same resolution. If more than two isomers were separated, they will be always listed in the tables in order they were eluted, such as Peak 1 followed by Peak 2, Peak 3 and so on. A * symbol near a chiral center in a structure denotes that this chiral center was resolved by chiral resolution without its stereochemical configuration unambiguously determined.

Also, TLC is thin layer chromatography; UV is ultraviolet; W is watts; wt. % is percentage by weight; x g is times gravity; α$_D$ is the specific rotation of polarized light at 589 nm; ° C. is degrees Celsius; % w/v is percentage in weight of the former agent relative to the volume of the latter agent; Hz is hertz; cpm is counts per minute; δ$_H$ is chemical shift; d is doublet; dd is doublet of doublets; MHz is megahertz; MS is mass spectrum, and a mass spectrum obtained by ES-MS may be denoted herein by "LC-MS"; m/z is mass to charge ratio; n is normal; N is normal; nm is nanometer; nM is nanomolar.

"Human FXIa Ki (nM)" is Human Factor XIa Ki (nM).

Schemes

Scheme 1 illustrates one synthetic sequence for the preparation of the compounds of this invention. Saponification using LiOH for example, afforded lithium salt 1-A, which is coupled directly with t-butyl para-aminobenzoate to give bromo-amide 1-B. This bromide is converted to boronic ester 1-C, which is coupled with an aryl iodide or aryl bromide to afford the t-butyl ester 1-D. The t-butyl ester is hydrolyzed with TFA to give pyridine acid 1-E, which is oxidized to give N-oxide and resolved on a chiral column using SFC to afford pure enantiomers 1-F. Scheme 2 depicts an alternative route to the compounds of this invention. In this sequence, the lithium salt 2-A is coupled with a base-labile ester such as methyl or ethyl para-aminobenzoate to give bromo-amide 2-B which is transformed to the ester amide 2-D using a Suzuki reaction. Oxidation is then carried out to give N-oxide ester 2-E, which is hydrolyzed to the racemic acid and resolved to furnish the final compounds 1-F. Alternatively, the sequence of oxidation and hydrolysis steps in Scheme 2 can be reversed, as is shown in Scheme 3. Thus, hydrolysis of 2-D provides the acid intermediate 1-E, which is subsequently oxidized and resolved to afford the final enantiomeric products 1-F.

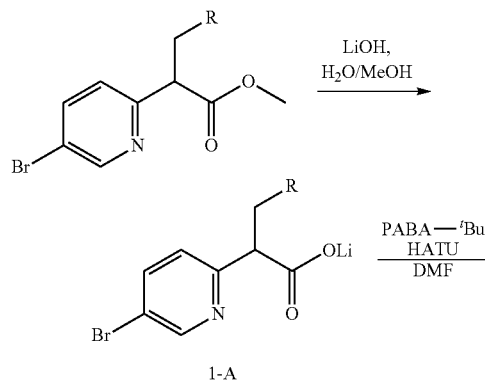

SCHEME 1

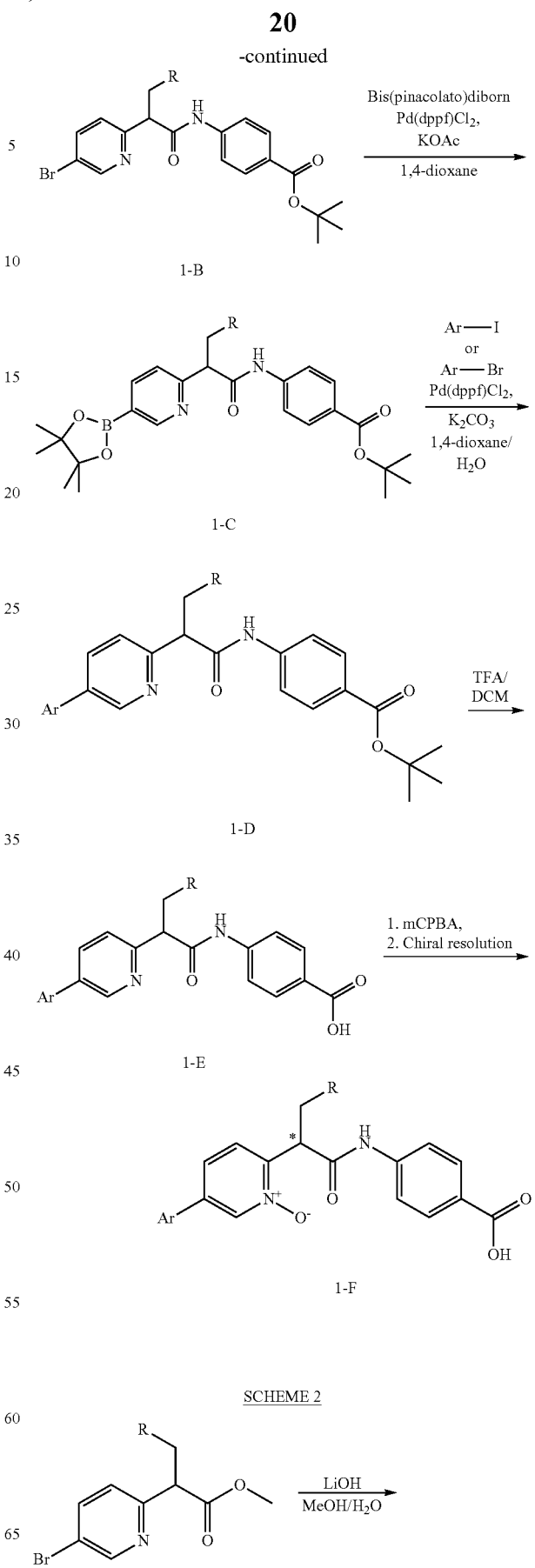

SCHEME 2

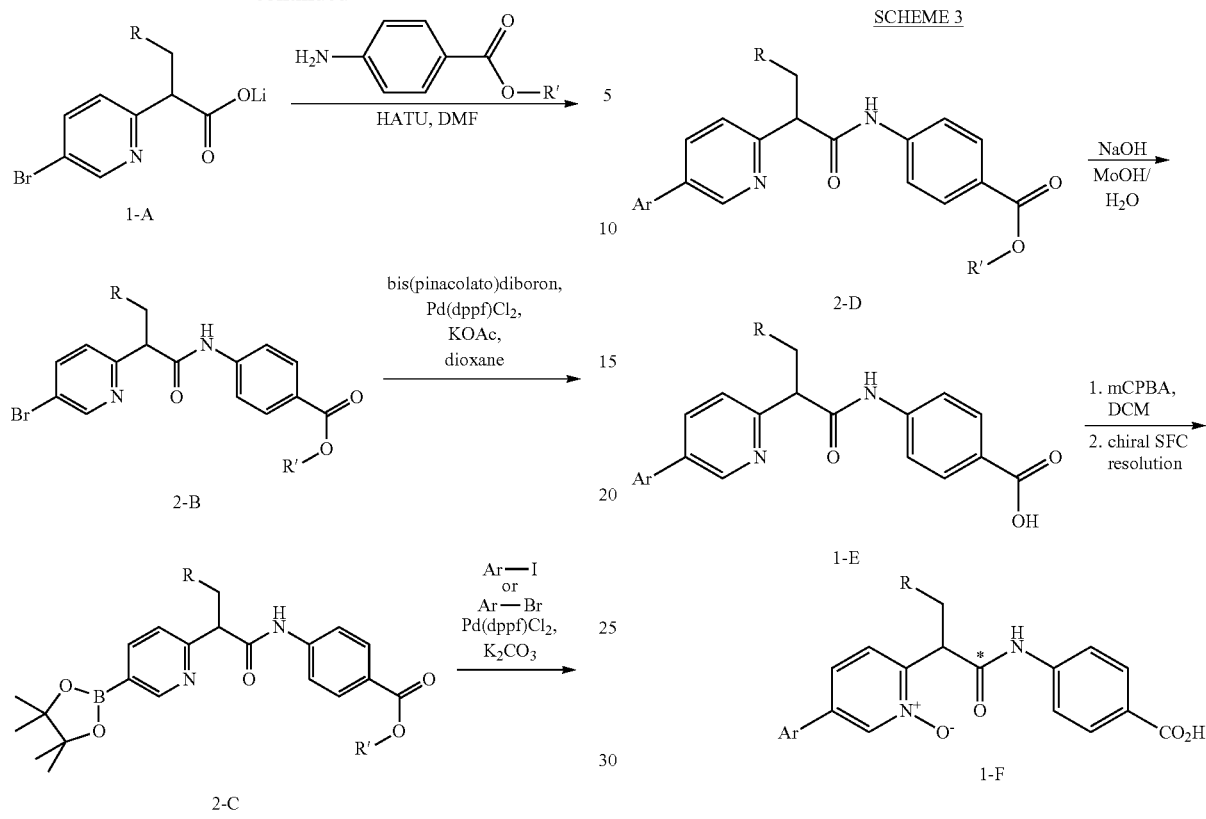

SCHEME 3

Another variation of the sequence of the reactions is shown in Scheme 4 where Suzuki and amide coupling steps were reversed compared to Scheme 1. Thus, a Suzuki coupling provided the intermediate 4-A, which was hydrolyzed to give acid 4-B. The latter was coupled with t-butyl para-aminobenzoate to give amide 1-D. Conversion of 1-D to final products 1-F used the same methods as shown in Scheme 1.

SCHEME 4

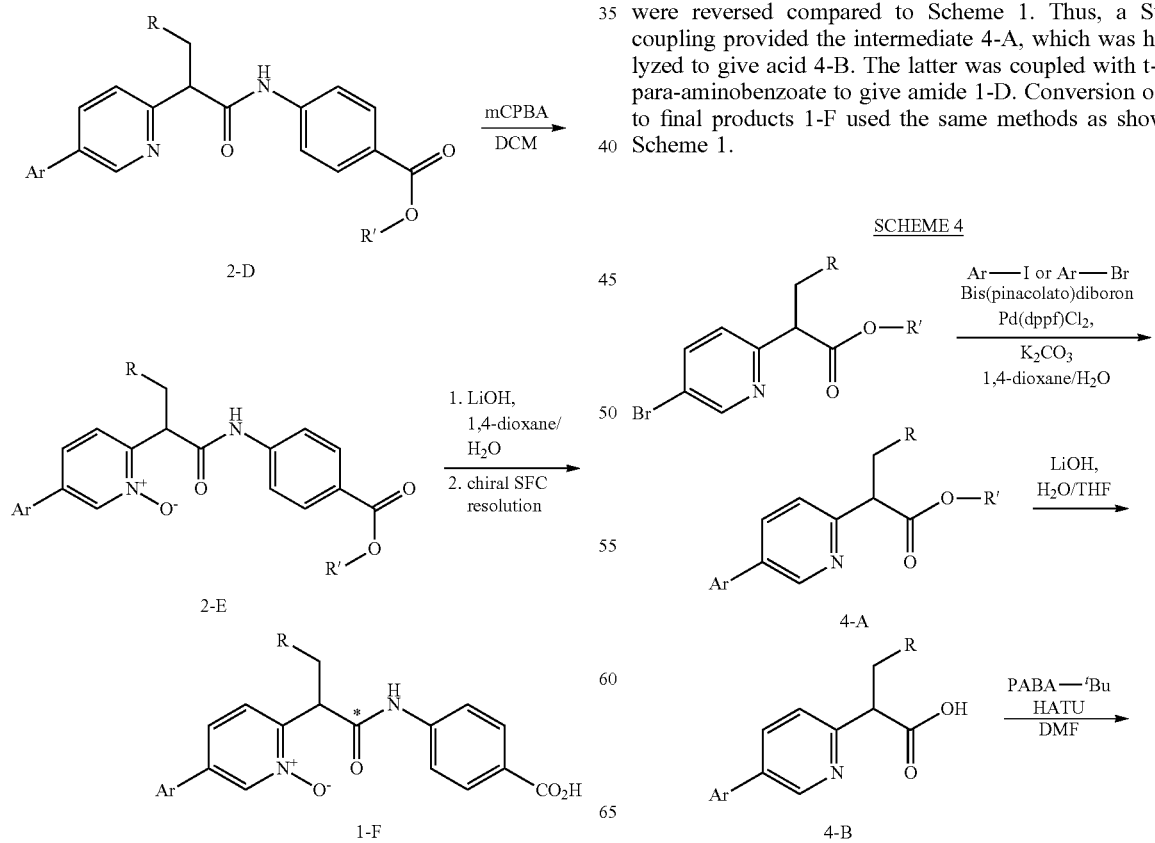

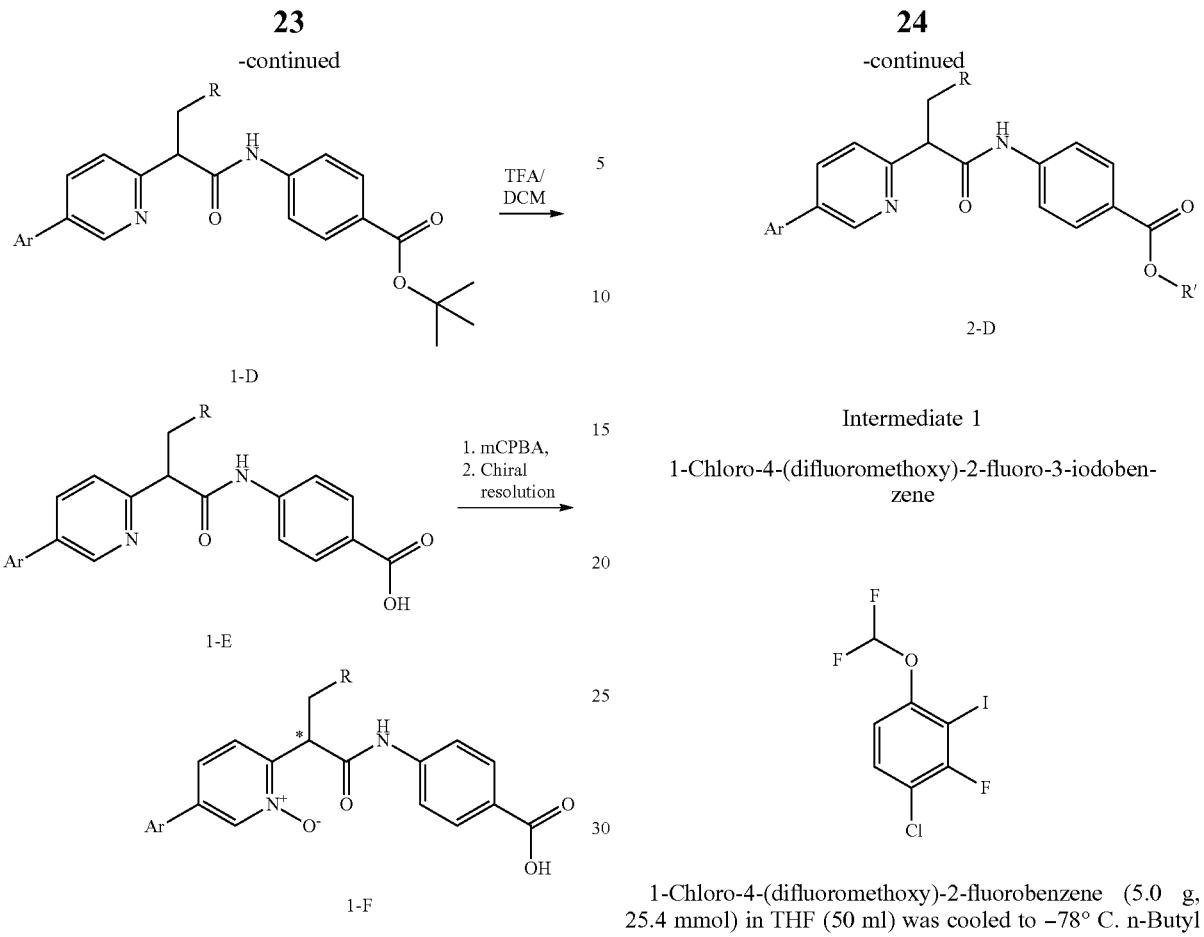

An additional method for the preparation of the compounds of this invention is shown in Scheme 5. Intermediate 4-A is hydrolyzed to give a metal salt such as 5-A, which is coupled directly with a base-labile ester such as methyl para-aminobenzoate to produce amide 2-D. The latter is converted to final products using the sequences shown in either Scheme 2 or 3.

SCHEME 5

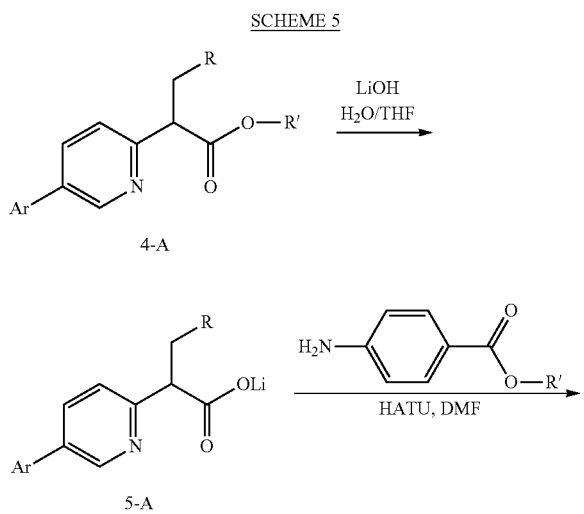

Intermediate 1

1-Chloro-4-(difluoromethoxy)-2-fluoro-3-iodobenzene

1-Chloro-4-(difluoromethoxy)-2-fluorobenzene (5.0 g, 25.4 mmol) in THF (50 ml) was cooled to −78° C. n-Butyl lithium (2.5 M in hexane, 15 ml, 38 mmol) was added dropwise over 15 minutes. The mixture was stirred at −78° C. for 1 hour, and iodine (9.7 g, 3 mmol) in THF (50 ml) was then added dropwise. The resulting mixture was stirred at −78° C. for 4 hours, then slowly warmed to −20° C. Saturated NH$_4$Cl solution (20 mL) was added to quench the reaction. A solution of sodium sulfite (4.8 g in 15 mL of water) was then added. The mixture was extracted with ethyl acetate (200 mL). The organic layer was washed with brine, and dried over anhydrous sodium sulfate. The solution was filtered then concentrated, and the crude product was purified by chromatography on silica gel, eluting with gradient 0-10% DCM in hexane to give the product. $^1$H NMR (CDCl$_3$, 500 MHz): δ 7.41 (dd, J=8.4 and 8.4 Hz, 1H), 6.96 (d, J=8.4 Hz, 1H), 6.55 (t, J=72.5 Hz, 1H).

The following Intermediates were synthesized using appropriate starting materials and following similar procedures as described for Intermediate 1:

| Intermediate | Structure | Name | $^1$H NMR (CDCl$_3$, 500 MHz) δ |
|---|---|---|---|
| 2 | 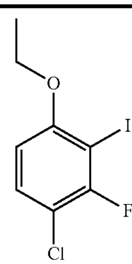 | 1-Chloro-4-ethoxy-2-fluoro-3-iodobenzene | 7.31 (dd, J = 8.4 and 8.4 Hz, 1H), 6.54 (d, J = 8.4 Hz, 1H), 4.09 (q, J = 7.0 Hz, 2H), 1.49 (t, J = 7.0 Hz, 3H). |

-continued

| Intermediate | Structure | Name | ¹H NMR (CDCl₃, 500 MHz) δ |
|---|---|---|---|
| 3 | 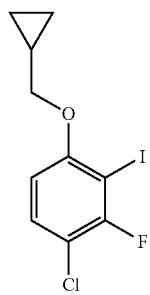 [SMILES: Fc1c(Cl)ccc(OCC2CC2)c1I] | 1-Chloro-4-(trifluoromethyl)-2-fluoro-3-iodobenzene | 7.48-7.51 (m, 1H), 7.41 (d, J = 8.5 Hz, 1H). |

Intermediate 4

1-Chloro-4-(cyclopropylmethoxy)-2-fluoro-3-iodobenzene

Step 1:
1-Chloro-4-(cyclopropylmethoxy)-2-fluorobenzene

To a solution of 4-chloro-3-fluorophenol (5 g, 34 mmol) in THF (50 ml) and DMF (5 ml), was added sodium hydride (95%, 1.1 g, 41 mmol). The mixture was stirred at rt for 15 min. Bromomethylcyclopropane (6.9 g, 51 mmol) was added. The mixture was then stirred at 55° C. for 15 hours. Brine (70 mL) was added to the reaction mixture, and the product was extracted with ethyl acetate (2×100 mL). The combined organic layer was dried over anhydrous sodium sulfate, filtered, and concentrated. The crude product was purified by chromatography on silica gel, eluting with 0-5% gradient EtOAc in isohexane to give the product. ¹H NMR (CDCl₃, 500 MHz): δ 7.22-7.26 (m, 1H), 6.68-6.71 (m, 1H), 6.64 (d, J=8.3 Hz, 1H), 3.75-3.77 (m, 2H), 1.21-1.30 (m, 1H), 0.63-0.68 (m, 2H), 0.33-0.39 (m, 2H).

Step 2: 1-Chloro-4-(cyclopropylmethoxy)-2-fluoro-3-iodobenzene

1-Chloro-4-(cyclopropylmethoxy)-2-fluorobenzene (1.5 g, 7.5 mmol) in THF (12 ml) was cooled to −78° C. n-Butyllithium (2.5 M in hexane, 4.5 ml, 11.2 mmol) was added slowly over 15 minutes. The mixture was stirred at −78° C. for 1 hour. Iodine (2.85 g, 11.2 mmol) in THF (12 ml) was then added slowly over 30 minutes. The mixture was stirred at −78° C. for 2 hours, then slowly warmed up to −20° C. Saturated NH₄Cl solution (10 mL) was added to quench the reaction. Aq. Na₂SO₃ solution (4 grams in 5 mL of water) was then added. The mixture was extracted with ethyl acetate (70 mL). The organic layer was washed with brine, and dried over anhydrous sodium sulfate. The solution was filtered and concentrated, and the crude was purified by chromatography on silica gel, eluting with 0-10% DCM gradient in hexane to give the title product. ¹H NMR (CDCl₃, 500 MHz): δ 7.29-7.32 (m, 1H), 6.54 (d, J=9.0 Hz, 1H), 3.90 (d, J=6.6 Hz, 2H), 1.27-1.34 (m, 1H), 0.65-0.68 (m, 2H), 0.41-0.44 (m, 2H).

The following Intermediate was synthesized using appropriate starting materials and following similar procedures as described for Intermediate 4:

| Intermediate | Structure | Name | ¹H NMR (CDCl₃, 500 MHz) δ |
|---|---|---|---|
| 5 | 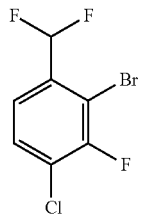 [SMILES: Fc1c(Cl)ccc(C(F)F)c1Br] | 1-Chloro-2-fluoro-3-iodo-4-isopropoxybenzene | 7.31 (m, 1H), 6.57 (d, J = 9.0 Hz, 1H), 4.57 (hep, J = 6.1 Hz, 1H), 1.40 (d, J = 6.1 Hz, 6H). |

Intermediate 6

2-Bromo-4-chloro-1-(difluoromethyl)-3-fluorobenzene

Step 1: 2-Bromo-4-chloro-3-fluorobenzoic Acid

A solution of 4-chloro-3-fluorobenzoic acid (2.0 g, 11.46 mmol) in THF (25 ml) was added by a syringe pump to a solution of LDA (13.18 ml, 26.4 mmol) in THF (50 ml) at −78° C. over 30 min. followed by stirring at −78° C. for 3 h. Then a solution of 1,2-dibromotetrachloroethane (7.5 g, 23 mmol) in THF (25 ml) was added to the reaction mixture. The reaction was run at −78° C. for 30 min, then slowly warmed up to rt and stirred overnight. The reaction mixture was quenched with water, and extracted with Et₂O. The aqueous layer was acidified with 4N HCl in dioxane (45.8 ml, 45.8 mmol) and extracted with EtOAc. The organic phase was dried over MgSO₄, filtered and concentrated to afford the crude product that was purified on RP-HPLC to give the title compound, which was used in the next step.

Step 2: (2-Bromo-4-chloro-3-fluorophenyl)methanol

BH₃.DMS (2.4 ml, 4.73 mmol) was added to a solution of 2-bromo-4-chloro-3-fluorobenzoic acid (1.0 g, 3.95 mmol) in THF (30 ml) at 0° C. After the mixture was stirred at 0°

C. for 1 h, the ice-bath was removed and the reaction was run at rt for 5 h. Additional BH₃.DMS (2.4 ml, 4.73 mmol) was added to the reaction mixture at 0° C. with continued stirring overnight while slowly warming the reaction up to rt. Then, the mixture was treated with 1 N HCl (10 ml) and extracted with EtOAc (2×50 ml). The combined organic phase was dried over MgSO₄, filtered, concentrated and purified by flash chromatography on silica-gel with 0-30% EtOAc in hexane to give the title compound. ¹H NMR (CDCl₃, 500 MHz): δ 7.40-7.43 (m, 1H), 7.26-7.28 (m, 1H), 4.78 (s, 2H).

Step 3: 2-Bromo-4-chloro-3-fluorobenzaldehyde

PCC (0.574 g, 2.66 mmol) was added to a solution of (2-bromo-4-chloro-3-fluorophenyl)methanol (0.58 g, 2.42 mmol) in CH₂Cl₂ (10 ml) at 0° C. Then the ice-bath was removed, and the reaction was run at rt for 2 h. The solvent was removed, and the residue was purified by a flash chromatography on silica-gel with 0-20% EtOAc in hexane to give the title compound. ¹H NMR (CDCl₃, 500 MHz): δ 10.33 (s, 1H), 7.71-7.73 (m, 1H), 7.51-7.54 (m, 1H).

Step 4: 2-Bromo-4-chloro-1-(difluoromethyl)-3-fluorobenzene

DAST (0.31 ml, 2.37 mmol) was added to a solution of 2-bromo-4-chloro-3-fluorobenzaldehyde (0.45 g, 1.90 mmol) in DCM (15 ml) at 0° C. After the mixture was stirred for 1 h, the ice-bath was removed and the reaction was run at rt for 5 h. The mixture was quenched with 1N HCl. The organic phase was separated. The aqueous phase was extracted with EtOAc. The combined organic phase was dried over MgSO₄, filtered, concentrated and purified by flash chromatography on silica-gel with 0-20% EtOAc in hexane to give the title compound. ¹H NMR (CDCl₃, 500 MHz): δ 7.48-7.50 (m, 1H), 7.42 (d, J=8.4 Hz, 1H), 6.86 (t, J=54.8 Hz, 1H).

Intermediate 7

Ethyl 2-(5-bromopyridin-2-yl)-3-cyclopropylpropanoate

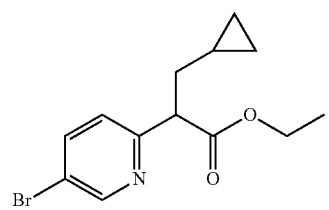 [SMILES: CCOC(=O)C(CC1CC1)c1ccc(Br)cn1]

Ethyl 2-(5-bromopyridin-2-yl)acetate (2.0 g, 8.2 mmol) in THF (25 ml) was cooled to −78° C. LiHMDS (1 M in hexane, 8.2 ml, 8.2 mmol) was added. The mixture was stirred for 1.5 hours. (Iodomethyl)cyclopropane (0.80 ml, 8.2 mmol) was added slowly. Mixture was stirred at −78° C. for one hour, then at rt overnight. The reaction was quenched with the addition of saturated aq. NH₄Cl solution (7 mL). The product was extracted with ethyl acetate and the combined organic layers was washed with brine, dried over anhydrous sodium sulfate, filtered and concentrated. The crude product was purified by chromatography on silica gel eluting with 0-30% EtOAc gradient in isohexane to give the title compound. MS (ESI) m/z 298/299.9 (M+H). The following Intermediate was synthesized using appropriate starting materials and following similar procedures as described in Intermediate 7:

| Intermediate | Structure | Name | Exact Mass [M + H]⁺ |
|---|---|---|---|
| 8 | 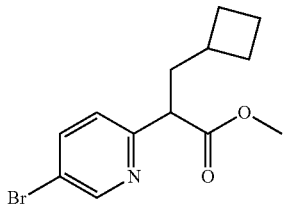 [SMILES: COC(=O)C(CC1CCC1)c1ccc(Br)cn1] | methyl 2-(5-bromopyridin-2-yl)-3-cyclopropyl propanoate | 284.1/286.1 |

Intermediate 9

Methyl 2-(5-bromopyridin-2-yl)-3-cyclobutylpropanoate

Methyl 2-(5-bromopyridin-2-yl)acetate (20 g, 87 mmol) in dry DMF (110 ml) was mixed with (bromomethyl)cyclobutane (15 g, 96 mmol). Solid sodium hydride (95%, 2.64 g, 104 mmol) was added in portions. The resulting mixture was stirred at 45° C. for 5 hours. Water (400 mL) was added to quench the reaction, and the product was extracted with EtOAc (2×200 mL). The organic layers were combined, and washed with brine. The solution was dried over anhydrous sodium sulfate, filtered, and concentrated. The resulting crude product was purified by chromatography on silica gel, eluting with 0-30% EtOAc gradient in hexane to give the title compound. MS (ESI) m/z 298/299.9 (M+H).

The following Intermediate was synthesized using appropriate starting materials and following similar procedures as described in Intermediate 9:

| Intermediate | Structure | Name | Exact Mass [M + H]+ |
|---|---|---|---|
| 10 | 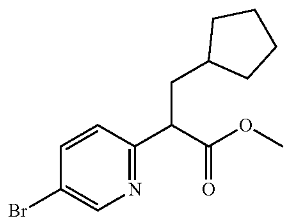 [SMILES: COC(=O)C(CC1CCCC1)c1ccc(Br)cn1] | Methyl 2-(5-bromopyridin-2-yl)-3-cyclopentylpropanoate | 312.1/314.1 |

Intermediate 11

Lithium 2-(5-bromopyridin-2-yl)-3-cyclopropylpropanoate

LiOH.H$_2$O (4.43 g, 106 mmol) was added to the mixture of methyl 2-(5-bromopyridin-2-yl)-3-cyclopropylpropanoate (25 g, 88 mmol) in methanol (250 ml) and water (50 ml), followed by stirring at 50° C. for 45 min. After the mixture was cooled down to RT, it was concentrated under reduced pressure and the residue was dried at 50° C. in a vacuum oven to give the title compound. The crude was used in the next step without further purification. MS (ESI) m/z 270/271.9 (M+H for corresponding acid).

Intermediate 12

Lithium 2-(5-bromopyridin-2-yl)-3-cyclobutylpropanoate

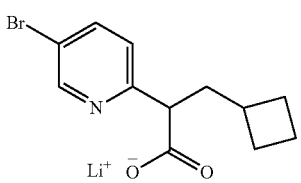 [SMILES: O=C(O)C(CC1CCC1)c1ccc(Br)cn1 ; [Li+]]

Methyl 2-(5-bromopyridin-2-yl)-3-cyclobutylpropanoate (15.5 g, 52.0 mmol) in a mixed solvent of MeOH (100 ml) and water (78 ml) was mixed with lithium hydroxide monohydrate (3.82 g, 91 mmol). The resulting mixture was stirred at 50° C. for 1 hour. The solvents were removed at reduced pressure. Toluene (5 mL) was added, and the mixture was further evaporated to dryness. The mixture was dried in vacuum oven at 50° C. overnight, and then used in the next step without further purification. MS (ESI) m/z 284/285.9 (M+H).

Intermediate 13

2-Bromo-4-chloro-1-(difluoromethyl)benzene

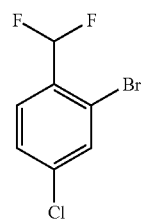

To a solution of 2-bromo-4-chlorobenzaldehyde (1.08 g, 4.92 mmol) in DCM (15 ml) was added DAST (0.975 ml, 7.38 mmol) at 0° C. The reaction was allowed to warm to rt and stirred overnight. The reaction mixture was diluted with EtOAc (50 ml), washed with saturated aq. NaHCO$_3$ (50 ml) and brine (40 ml). The organic phase was dried over MgSO$_4$, filtered and concentrated to afford the title compound. The crude was used in the next step without further purification. $^1$H NMR (CDCl$_3$, 500 MHz): δ 7.55-7.63 (m, 2H), 7.39 (br s, 1H), 6.84 (t, J=54.8 Hz, 1H).

Intermediate 14

1-Chloro-4-(difluoromethyl)-2-fluoro-3-iodobenzene

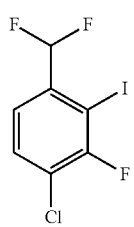

A solution of 1-chloro-4-(difluoromethyl)-2-fluorobenzene (1.546 g, 8.56 mmol) in THF (8 ml) was cooled to −78° C. n-BuLi (5.14 ml, 12.84 mmol, 2.5 M in hexanes) was added dropwise over 15 minutes. The mixture was stirred at −78° C. for 1 h; then iodine (3.26 g, 12.84 mmol) in THF (8.00 ml) was added dropwise. The resulting mixture was then stirred at −78° C. for 4 h and slowly warmed to −20° C. Saturated NH$_4$Cl solution (10 mL) was added to quench the reaction. Aq. Na$_2$SO$_3$ solution (4 grams in 5 mL) was then added until the remaining iodine was reduced. The mixture was extracted with ethyl acetate (70 mL). The organic layer was washed with brine, dried over anhydrous sodium sulfate, and concentrated. The resulting crude product was purified on silica gel, eluting with 0-10% DCM in hexanes to afford the title compound. $^1$H NMR (CDCl$_3$, 500 MHz): δ 7.49-7.52 (m, 1H), 7.37 (d, J=8.4 Hz, 1H), 6.75 (t, J=54.6 Hz, 1H).

Intermediate 15

1-Chloro-2-fluoro-3-iodo-4-(trifluoromethyl)benzene

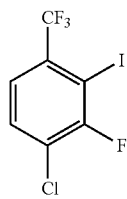

The title compound was prepared using the same procedure for Intermediate 14 using 1-chloro-2-fluoro-4-(trifluoromethyl)benzene. $^1$H NMR (CDCl$_3$, 500 MHz): δ 7.48-7.51 (m, 1H), 7.4 (d, J=8.5 Hz, 1H).

Intermediate 16

1-(Iodomethyl)cyclopropane-1-carbonitrile

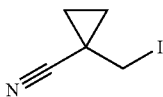

PPh$_3$ (6.48 g, 24.71 mmol) and imidazole (1.682 g, 24.71 mmol) were dissolved in DCM (35 ml) and stirred at 0° C. After 5 minutes, iodine (5.75 g, 22.65 mmol) was added. The resulting suspension was stirred at the same temperature for another 30 min. The solution of 1-(hydroxymethyl)cyclopropanecarbonitrile (2 g, 20.59 mmol) in 2 ml of DCM was added to the reaction mixture. The resulting mixture was then stirred at RT for 2 h, after which it was diluted with 20 ml water and 30 ml of satd. Na$_2$S$_2$O$_3$ solution. About 50 ml of ether was added to the flask. The organics were extracted twice using 50 ml of ether, separated and dried over anhydrous MgSO$_4$. The solids were filtered out, and the filtrate was carefully concentrated in vacuo and then directly loaded on a silica gel column and eluted with 0-30% EtOAc in hexanes to afford the title compound. $^1$H NMR (CDCl$_3$, 500 MHz): δ 3.18 (s, 2H), 1.16-1.20 (m, 2H), 0.99-1.08 (m, 2H).

Intermediate 17 tert-Butyl 4-(2-(5-(3-chloro-6-(difluoromethoxy)-2-fluorophenyl) pyridin-2-yl)-3-(4-oxocyclohexyl) propanamido)benzoate

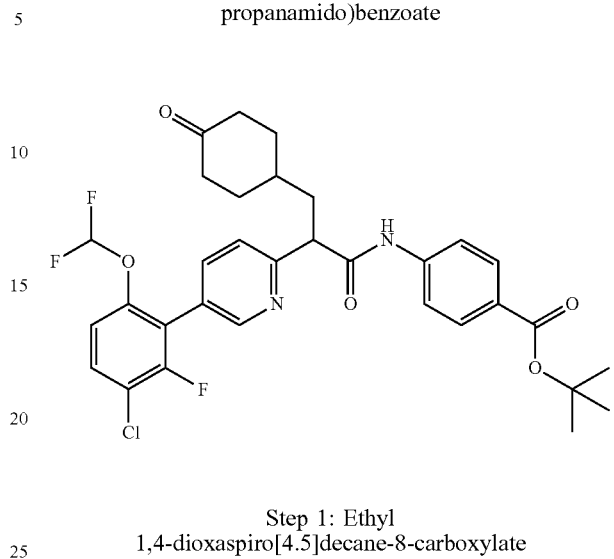

Step 1: Ethyl 1,4-dioxaspiro[4.5]decane-8-carboxylate

To a round bottom flask was added ethyl 4-oxocyclohexanecarboxylate (15.00 g, 88.00 mmol), toluene (100 mL), ethane-1,2-diol (54.70 g, 881.00 mmol) and 4-methylbenzenesulfonic acid hydrate (0.50 g, 2.64 mmol) at 10° C. The reaction mixture was stirred at 80° C. for 2 h. LC-MS showed the reaction was complete. The reaction mixture was then cooled to room temperature and quenched with a saturated solution of sodium bicarbonate (50 mL). The organic portion was washed with saturated sodium bicarbonate (200 mL), and the aqueous portion extracted with MTBE (3×150 mL). The combined organic portion was dried over anhydrous sodium sulfate, filtered and concentrated to give the title compound as an oil which was directly used for next step without further purification. $^1$H NMR (CDCl$_3$, 400 MHz): δ 4.12 (q, J=7.1 Hz, 2H), 3.94 (s, 4H), 2.32-2.33 (m, 1H), 1.81-1.93 (m, 2H), 1.73-1.85 (m, 4H), 1.51-1.61 (m, 2H), 1.24 (t, J=7.2 Hz, 3H).

Step 2: 1,4-dioxaspiro[4.5]decane-8-carbaldehyde and 1,4-dioxaspiro[4.5]decan-8-ylmethanol To a solution of ethyl 1,4-dioxaspiro[4.5]decane-8-carboxylate (10.00 g, 46.70 mmol) in DCM (120 mL) was added diisobutylaluminum hydride (117 mL, 0.117 mol, 1 M in toluene) dropwise at −78° C. The reaction mixture was stirred at −78° C. for 1.5 h. TLC showed the starting material had disappeared. The reaction was then quenched by the slow addition of a pH 8 buffer (prepared by mixing 1.66 mL ammonium hydroxide solution and 27.40 mL of saturated ammonium chloride solution) at −78° C. The mixture was then allowed to warm back up to room temperature and stirred for 45 minutes. Solid magnesium sulfate (36.00 g) was added, and the mixture was stirred at room temperature for another 16 h. The mixture was filtered and concentrated in vacuo to give a mixture of 1,4-dioxaspiro[4.5]decane-8-carbaldehyde and 1,4-dioxaspiro[4.5]decan-8-ylmethanol (1:1) which was directly used for the next step without further purification.

Step 3: 1,4-dioxaspiro[4.5]decan-8-ylmethanol

To a solution of a mixture of 1,4-dioxaspiro[4.5]decane-8-carbaldehyde compound and 1,4-dioxaspiro[4.5]decan-8- ylmethanol (1:1, 7.00 g) in MeOH (60 mL) was added NaBH$_4$ (0.56 g, 14.72 mmol) at 0° C. The reaction mixture was stirred at 0° C. for 5 min. TLC showed the reaction was complete. Water (100 mL) was added, and the mixture was concentrated in vacuo to about 100 mL, and extracted with EtOAc (50 mL×6). The combined organic layers were dried over anhydrous sodium sulfate, filtered and concentrated in vacuo. The residue was purified by chromatography (SiO$_2$, 0-45% EtOAc/PE) to give the title compound. $^1$H NMR (CDCl$_3$, 400 MHz): δ 3.94 (s, 4H), 3.49 (d, J=6.4 Hz, 2H), 1.76-1.79 (m, 4H), 1.49-1.59 (m, 3H), 1.22-1.33 (m, 2H).

Step 4: 1,4-dioxaspiro[4.5]decan-8-ylmethyl Trifluoromethanesulfonate

To a solution of 1,4-dioxaspiro[4.5]decan-8-ylmethanol (5.00 g, 29.00 mmol) in ethyl ether (120 mL) was added trifluoromethanesulfonic anhydride (9.83 g, 34.80 mmol) and triethylamine (4.86 mL, 34.80 mmol) at 0° C. The reaction mixture was stirred at 0° C. for 1.5 h. TLC showed the reaction was complete. Ethyl ether (50 mL) was added, and the mixture was quenched with diluted HCl (1 N, 100 mL). The organic layer was washed with brine (100 mL), dried over anhydrous sodium sulfate, filtered and concentrated in vacuo to give the title compound which was directly used for next step without further purification. $^1$H NMR (CDCl$_3$, 400 MHz): δ 4.34 (d, J=6.3 Hz, 2H), 3.88-3.98 (m, 4H), 1.77-1.80 (m, 5H), 1.51-1.59 (m, 2H), 1.35-1.37 (m, 2H).

Step 5: Methyl 2-(5-bromopyridin-2-yl)-3-(1,4-dioxaspiro[4.5]decan-8-yl)propanoate To a solution of methyl 2-(5-bromopyridin-2-yl)acetate (5.50 g, 23.91 mmol) and 1,4-dioxaspiro[4.5]decan-8-ylmethyl trifluoromethanesulfonate (6.85 g, 19.13 mmol) in THF (100 mL) was added LiHMDS (27.50 mL, 27.50 mmol, 1 M in THF) at −78° C. The reaction mixture was stirred at 15° C. for 16 h under a nitrogen atmosphere. LC-MS showed the reaction was complete. The mixture was quenched with saturated NH$_4$Cl solution (30 mL), diluted with water (60 mL), and extracted with EtOAc (50 mL×3). The combined organic layers were dried over anhydrous sodium sulfate, filtered and concentrated in vacuo. The residue was purified by chromatography (SiO$_2$, 0-20% EtOAc/PE) to give the title compound. $^1$H NMR (CDCl$_3$, 400 MHz): δ 8.59 (d, J=2.0 Hz, 1H), 7.76 (dd, J=8.4, 2.2 Hz, 1H), 7.20 (d, J=8.6 Hz, 1H), 3.85-3.94 (m, 5H), 3.66 (s, 3H), 2.00-2.05 (m, 1H), 1.79-1.87 (m, 1H), 1.61-1.75 (m, 4H), 1.37-1.47 (m, 2H), 1.17-1.29 (m, 3H). MS (ESI) m/z 384.1/386.1 (M+H).

Step 6: Methyl 2-(5-(3-chloro-6-(difluoromethoxy)-2-fluorophenyl)pyridin-2-yl)-3-(1,4-dioxaspiro[4.5]decan-8-yl)propanoate To a solution of methyl 2-(5-bromopyridin-2-yl)-3-(1,4-dioxaspiro[4.5]decan-8-yl)propanoate (1.00 g, 2.60 mmol), 4,4,4',4',5,5,5',5'-octamethyl-2,2'-bi(1,3,2-dioxaborolane) (0.66 g, 2.60 mmol), potassium acetate (0.77 g, 7.81 mmol) in dioxane (12 mL) was added Pd(dppf)Cl$_2$ (0.48 g, 0.65 mmol), and the mixture was stirred at 120° C. for 50 min under MW. LC-MS showed the reaction was complete. Then, 1-chloro-4-(difluoromethoxy)-2-fluoro-3-iodobenzene (0.71 g, 2.21 mmol), K$_2$CO$_3$ (0.92 g, 6.62 mmol), water (1.20 mL) and Pd(dppf)Cl$_2$ (0.16 g, 0.22 mmol) were added, and the mixture was stirred at 90° C. for 1 h under MW. LC-MS showed the reaction was complete. This reaction was done five times. The reaction was quenched with H$_2$O (100 mL) and the aqueous layer was extracted with EtOAc (50 mL×3). The combined organic phase was dried over Na$_2$SO$_4$, filtered and concentrated in vacuo. The residue was purified by chromatography (SiO$_2$, 0-25% EtOAc/PE) to give the title compound. $^1$H NMR (CDCl$_3$, 400 MHz): δ 8.56 (s, 1H), 7.69 (d, J=7.9 Hz, 1H), 7.41-7.43 (m, 2H), 7.08 (d, J=8.8 Hz, 1H), 6.36 (t, J=72.4 Hz, 1H), 4.01 (t, J=7.5 Hz, 1H), 3.92 (s, 4H), 3.72 (s, 3H), 2.13-2.15 (m, 1H), 1.87-1.89 (m, 1H), 1.69-1.82 (m, 4H), 1.44-1.50 (m, 2H), 1.26-1.32 (m, 3H). MS (ESI) m/z 500.1 (M+H).

Step 7: Methyl 2-(5-(3-chloro-6-(difluoromethoxy)-2-fluorophenyl)pyridin-2-yl)-3-(4-oxocyclohexyl)propanoate To a round bottom flask was added methyl 2-(5-(3-chloro-6-(difluoromethoxy)-2-fluorophenyl)pyridin-2-yl)-3-(1,4-dioxaspiro[4.5]decan-8-yl)propanoate (1.80 g, 3.60 mmol), acetone (25 mL) and hydrogen chloride (9.00 mL, 9.00 mmol) at 15° C. The reaction mixture was stirred at 15° C. for 3 h. LC-MS showed the reaction was complete. The mixture was adjusted to pH 7-8 with sat. NaHCO$_3$ solution. Water (50 mL) was added, and the mixture was extracted with EtOAc (3×30 mL). The organic layers were combined, washed with brine (2×30 mL), dried over anhydrous sodium sulfate, filtered and concentrated in vacuum to give the title compound which was used directly in the next step without further purification.
$^1$H NMR (CDCl$_3$, 400 MHz): δ 8.58 (s, 1H), 7.72 (d, J=7.9 Hz, 1H), 7.43-7.45 (m, 2H), 7.08 (d, J=8.8 Hz, 1H), 6.38 (t, J=72.4, 1H), 4.03 (t, J=7.7 Hz, 1H), 3.75 (s, 3H), 2.19-2.45 (m, 6H), 2.11-2.13 (m, 2H), 1.69-1.70 (m, 1H), 1.42-1.51 (m, 2H). MS (ESI) m/z 456.2 (M+H).

Step 8: 2-(5-(3-chloro-6-(difluoromethoxy)-2-fluorophenyl)pyridin-2-yl)-3-(4-oxocyclohexyl)propanoic Acid To a round bottom flask was added methyl 2-(5-(3-chloro-6-(difluoromethoxy)-2-fluorophenyl)pyridin-2-yl)-3-(4-oxocyclohexyl)propanoate (1.45 g, 3.18 mmol), THF (15 mL), lithium hydroxide hydrate (0.20 g, 4.77 mmol) and water (1.5 mL) at 15° C. The reaction mixture was stirred at 15° C. for 18 h. LC-MS showed the reaction was complete. The mixture was concentrated in vacuo. Water (25 mL) was added, and the mixture was adjusted to pH 5-6 with sat. citric acid, extracted with DCM (3×9 mL), and the combined organic layers were dried over anhydrous sodium sulfate. The mixture was filtered to give the crude title compound as a DCM solution (25 mL) which was directly used for next step. MS (ESI) m/z 442.0 (M+H).

Step 9: Tert-Butyl 4-(2-(5-(3-chloro-6-(difluoromethoxy)-2-fluorophenyl) pyridin-2-yl)-3-(4-oxocyclohexyl)propanamido)benzoate To a round bottom flask was added 2-(5-(3-chloro-6-(difluoromethoxy)-2-fluorophenyl)pyridin-2-yl)-3-(4-oxocyclohexyl)propanoic acid (25 mL in DCM from Step 8 above), HATU (1.37 g, 3.60 mmol), tert-butyl 4-aminobenzoate (0.64 g, 3.30 mmol) and triethylamine (1.25 mL, 9.00 mmol) at 15° C. The reaction mixture was stirred at 15° C. for 18 h. The temperature was raised to 35° C. and the reaction was stirred for 3.5 h at this temperature. The mixture was diluted with water (50 mL), extracted with DCM (3×35 mL), and the combined organic layers were dried over anhydrous sodium sulfate, filtered and the filtrate was concentrated in vacuo. The residue was purified by normal phase chromatography (SiO$_2$, 0-30% EtOAc/PE) to give the title compound. $^1$H NMR (CDCl$_3$, 400 MHz): δ 9.76 (s, 1H), 8.69 (s, 1H), 7.94 (d, J=8.6 Hz, 2H), 7.77 (d, J=8.2 Hz, 1H), 7.61 (d, J=8.6 Hz, 2H), 7.48 (t, J=8.5 Hz, 1H), 7.42 (d, J=8.2 Hz, 1H), 7.10 (d, J=8.8 Hz, 1H), 6.39 (t, J=72.4 Hz, 1H), 3.93 (t, J=7.8 Hz, 1H), 2.26-2.40 (m, 5H), 2.11-2.22 (m, 2H), 1.76-1.78 (m, 2H), 1.58 (s, 9H), 1.41-1.51 (m, 2H). MS (ESI) m/z 617.2 (M+H).

Intermediate 18

Ethyl 2-(5-(3-chloro-6-(difluoromethoxy)-2-fluorophenyl)pyridin-2-yl)-3-(5,8-dioxaspiro[3.4]octan-2-yl)propanoate

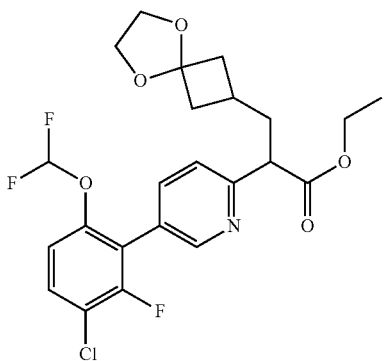 [SMILES: CCOC(=O)C(CC1CC2(C1)OCCO2)c1ccc(-c2c(OC(F)F)ccc(Cl)c2F)cn1]

Step 1: Methyl 3-oxocyclobutanecarboxylate

To a mixture of 3-oxocyclobutanecarboxylic acid (16.00 g, 140.00 mmol) in MeOH (100 mL) was added SOCl$_2$ (16.38 mL, 224.00 mmol) at 0° C. The resulting mixture was stirred at 20° C. for 2 h. TLC indicated the reaction was complete. The reaction mixture was concentrated in vacuo and the residue was purified by chromatography (SiO$_2$, PE:EtOAc=100:1 to 10:1 gradient) to give the title compound. $^1$H NMR (CDCl$_3$, 400 MHz): δ 3.73 (s, 3H), 3.22-3.40 (m, 5H).

Step 2: Methyl 5,8-dioxaspiro[3.4]octane-2-carboxylate

To a mixture of methyl 3-oxocyclobutanecarboxylate (4.00 g, 31.20 mmol) and ethane-1,2-diol (2.91 g, 46.80 mmol) in toluene (30 mL) was added 4-methylbenzenesulfonic acid (0.27 g, 1.561 mmol) at 15° C. The resulting mixture was stirred at 130° C. for 12 h. TLC indicated the reaction was complete. The reaction mixture was concentrated in vacuum, the residue purified by chromatography (SiO$_2$, PE:EtOAc=100:1 to 5:1 gradient) to give the title compound. $^1$H NMR (CDCl$_3$, 400 MHz): δ 4.22 (s, 3H), 3.83-3.90 (m, 4H), 2.75-2.91 (m, 1H), 2.53-2.65 (m, 4H).

Step 3: 5,8-dioxaspiro[3.4]octan-2-ylmethanol

To a mixture of LAH (0.88 g, 23.23 mmol) in Et$_2$O (15 mL) was added methyl 5,8-dioxaspiro[3.4]octane-2-carboxylate (2.00 g, 11.62 mmol) in Et$_2$O (15 mL) at 0° C. for 0.5 h. Then the mixture was stirred at 15° C. for 16 h. TLC indicated that the reaction was complete. The mixture was diluted with EtOAc (50 mL) and sat. NH$_4$Cl (30 mL), extracted with EtOAc (30 mL×2). The combined organic layers were dried over anhydrous sodium sulfate, filtered, and concentrated in vacuum. The residue was purified by chromatography (SiO$_2$, PE:EtOAc=50:1 to 2:1 gradient) to give the title compound. $^1$H NMR (CDCl$_3$, 400 MHz): δ 3.85-3.91 (m, 4H), 3.66 (d, J=6.6 Hz, 2H), 2.37-2.45 (m, 2H), 2.21-2.32 (m, 1H), 2.06-2.12 (m, 2H).

Step 4: 5,8-dioxaspiro[3.4]octan-2-ylmethyl 4-methylbenzenesulfonate

To a mixture of 5,8-dioxaspiro[3.4]octan-2-ylmethanol (3.00 g, 20.81 mmol) and 4-methylbenzene-1-sulfonyl chloride (3.97 g, 20.81 mmol) in DCM (100 mL) was added Et$_3$N (5.80 mL, 41.60 mmol) at 0° C. The mixture was stirred at 0° C. for 1.5 h. TLC indicated that the reaction was complete. The mixture was diluted with water (100 mL) and extracted with DCM (100 mL). The organic layer was dried over magnesium sulfate, filtered, and concentrated in vacuum. The residue was purified by chromatography (SiO$_2$, PE:EtOAc=30:1 to 3:1 gradient) to give the title compound. $^1$H NMR (CDCl$_3$, 400 MHz): δ 7.77 (d, J=8.2 Hz, 2H), 7.33 (d, J=7.8 Hz, 2H), 4.04 (d, J=6.5 Hz, 2H), 3.77-3.88 (m, 4H), 2.43 (s, 3H), 2.31-2.41 (m, 3H), 1.95-2.04 (m, 2H)

Step 5: Ethyl 2-(5-bromopyridin-2-yl)-3-(5,8-dioxaspiro[3.4]octan-2-yl)propanoate To a solution of ethyl 2-(5-bromopyridin-2-yl)acetate (1.80 g, 7.37 mmol) in DMF (50 mL) at 15° C. was added 5,8-dioxaspiro[3.4]octan-2-ylmethyl 4-methylbenzenesulfonate (2.20 g, 7.37 mmol) after stirring at 15° C. for 1 h. NaH (0.38 g, 9.59 mmol, 60%) was added slowly at 15° C. Then the mixture was stirred at 50° C. for 2 h. The mixture was diluted with EtOAc (50 mL) and quenched with sat. NH$_4$Cl (50 mL), extracted with EtOAc (50 mL×2). The combined organic layers were dried over anhydrous sodium sulfate, filtered, and concentrated in vacuum. The residue was purified by chromatography (SiO$_2$, PE:EtOAc=30:1 to 3:1) to give the title compound. $^1$H NMR (CDCl$_3$, 400 MHz): δ 8.56 (d, J=1.8 Hz, 1H), 7.73 (dd, J=8.2, 2.3 Hz, 1H), 7.18 (d, J=8.2 Hz, 1H), 4.04-4.15 (m, 2H), 3.76-3.85 (m, 4H), 3.66 (t, J=7.6 Hz, 1H), 2.29-2.40 (m, 1H), 2.16-2.28 (m, 2H), 2.02-2.09 (m, 1H), 1.80-1.99 (m, 3H), 1.12 (t, J=7.2 Hz, 3H). MS (ESI) m/z 370.0/372.0 (M+H).

Step 6: Ethyl 2-(5-(3-chloro-6-(difluoromethoxy)-2-fluorophenyl)pyridin-2-yl)-3-(5,8-dioxaspiro[3.4]octan-2-yl)propanoate A solution of ethyl 2-(5-bromopyridin-2-yl)-3-(5,8-dioxaspiro[3.4]octan-2-yl)propanoate (900 mg, 2.43 mmol), bis(pinacolato)diboron (617 mg, 2.43 mmol), Pd(dppf)Cl$_2$ (0.36 g, 0.49 mmol) and potassium acetate (239 mg, 2.43 mmol) in dioxane (10 mL) was stirred under an atmosphere of N$_2$ at 120° C. for 30 min under MW. LC-MS indicated that the reaction was complete. Then, 1-chloro-4-(difluoromethoxy)-2-fluoro-3-iodobenzene (784 mg, 2.431 mmol), aqueous K$_2$CO$_3$ solution (7.29 mL, 7.29 mmol) and Pd(dppf)Cl$_2$ (0.36 g, 0.49 mmol) was added. The mixture was stirred under an atmosphere of N$_2$ at 90° C. for 60 min under MW. LC-MS indicated that the reaction was complete. The mixture was diluted with water (20 mL) and extracted with EtOAc (30 mL×3). The combined organic layers were dried over anhydrous sodium sulfate, filtered, and concentrated in vacuum. The residue was purified by chromatography (SiO$_2$, PE:EtOAc=3:1 to 1:3 gradient) to give the title compound. $^1$H NMR (CDCl$_3$, 400 MHz): δ 8.55 (d, J=1.2 Hz, 1H), 7.64-7.71 (m, 1H), 7.39-7.48 (m, 2H), 7.04-7.10 (m, 1H), 6.36 (t, J=72.4 Hz, 1H), 4.14-4.21 (m, 2H), 3.83-3.87 (m, 4H), 3.76-3.82 (m, 1H), 2.39-2.48 (m, 1H), 2.27-2.36 (m, 2H), 2.10-2.18 (m, 1H), 1.99-2.03 (m, 2H), 1.86-1.94 (m, 1H), 1.25-1.30 (m, 3H). MS (ESI) m/z 486.1 (M+H).

Intermediate 19 tert-Butyl 4-(2-(5-bromopyridin-2-yl)-3-cyclopropylpropanamido)benzoate

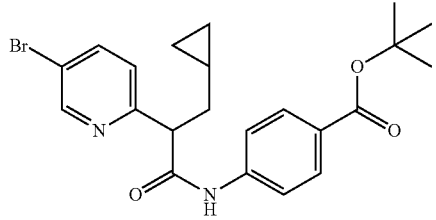 [SMILES: CC(C)(C)OC(=O)c1ccc(NC(=O)C(CC2CC2)c2ccc(Br)cn2)cc1]

Lithium 2-(5-bromopyridin-2-yl)-3-cyclopropylpropanoate (15 g, 54.3 mmol) in DMF (50 ml) was mixed with tert-butyl 4-aminobenzoate (11.55 g, 59.8 mmol). HATU (24.79 g, 65.2 mmol) was added. The resulting mixture was heated at 45° C. for 2 h. LC-MS showed reaction was complete. The reaction mixture was diluted with ethyl acetate (150 mL), and washed with satd. NaHCO$_3$ followed by brine. The organic layer was separated, dried over anhydrous magnesium sulfate, and filtered. The filtrate was concentrated to afford the crude product, which was dissolved in a small amount of DCM and purified on silica gel (0-30% EtOAc in hexanes) to afford the title compound. MS (ESI) m/z 446.8 (M+H).

Intermediate 20 tert-Butyl 4-(2-(5-(3-chloro-6-(difluoromethoxy)-2-fluorophenyl)pyridin-2-yl)-3-(4,4-difluorocyclohexyl)propanamido)benzoate

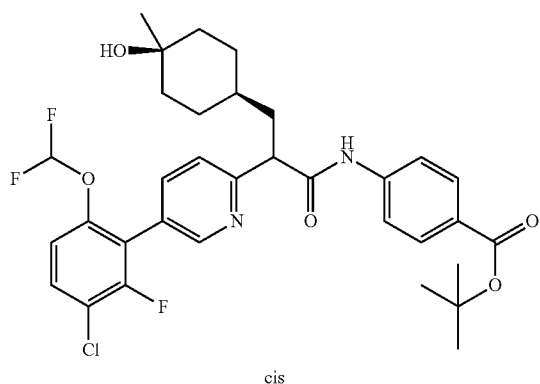

cis

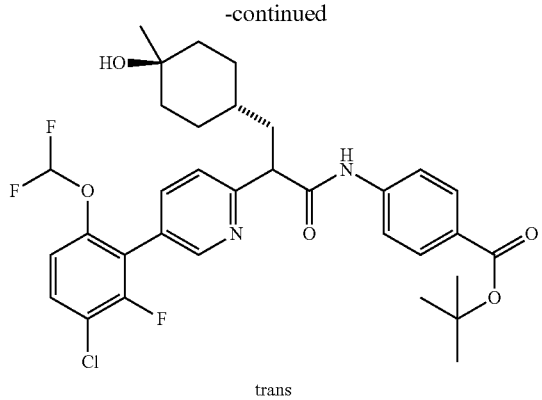

trans

To a solution of tert-butyl 4-(2-(5-(3-chloro-6-(difluoromethoxy)-2-fluorophenyl)pyridin-2-yl)-3-(4-oxocyclohexyl)propanamido)benzoate (50 mg, 0.08 mmol) in THF (1 mL) was added methylmagnesium bromide (0.057 mL, 0.17 mmol, 2 M in THF) dropwise at 0° C. The reaction mixture was stirred at 0° C. for 1 h. LC-MS showed the reaction was complete. The reaction mixture was quenched with sat. NH$_4$Cl solution (2 mL), diluted with water (10 mL), extracted with EtOAc (3×10 mL). The organic layers were combined, washed with brine (10 mL), dried over anhydrous sodium sulfate, filtered and concentrated in vacuum. The residue was purified by prep-TLC (SiO$_2$, PE:EtOAc=1:1) to give cis title compound and trans title compound. Their structures were assigned based on 2D NMR. Cis isomer $^1$H NMR (CDCl$_3$, 400 MHz): δ 8.58 (s, 1H), 7.86 (d, J=8.8 Hz, 2H), 7.67 (dd, J=8.0, 1.3 Hz, 1H), 7.53 (d, J=8.8 Hz, 2H), 7.32-7.42 (m, 2H), 7.02 (d, J=8.8 Hz, 1H), 6.31 (t, J=72.4 Hz, 1H), 3.89 (t, J=7.8 Hz, 1H), 2.08-2.15 (m, 1H), 1.84-1.93 (m, 1H), 1.55-1.59 (m, 5H), 1.50 (s, 9H), 1.26-1.29 (m, 4H), 1.12 (s, 3H). MS (ESI) m/z 633.3 (M+H). Trans isomer $^1$H NMR (CDCl$_3$, 400 MHz): δ 9.65 (s, 1H), 8.59 (s, 1H), 7.86 (d, J=8.8 Hz, 2H), 7.68 (dd, J=8.0, 1.3 Hz, 1H), 7.53 (d, J=8.5 Hz, 2H), 7.31-7.42 (m, 2H), 7.02 (d, J=9.0 Hz, 1H), 6.31 (t, J=72.4 Hz, 1H), 3.84 (t, J=7.7 Hz, 1H), 2.07-2.14 (m, 1H), 1.85-1.94 (m, 1H), 1.56-1.75 (m, 5H), 1.51 (s, 9H), 1.29-1.33 (m, 4H), 1.14 (s, 3H). MS (ESI) m/z 633.3 (M+H).

Intermediate 21

Ethyl 3-(bicyclo[1.1.1]pentan-1-yl)-2-(5-(3-chloro-6-(difluoromethoxy)-2-fluorophenyl)pyridin-2-yl)propanoate

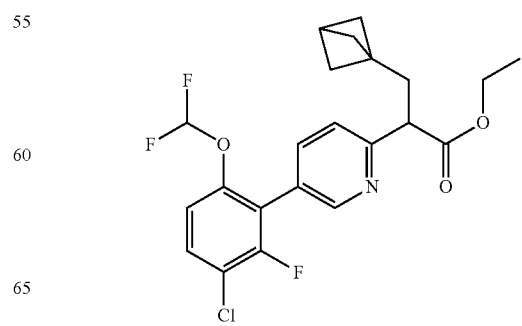

Step 1: Bicyclo[1.1.1]pentan-1-ylmethanol

To a mixture of LAH (271 mg, 7.13 mmol) in Et$_2$O (4 mL) was added a solution of bicyclo[1.1.1]pentane-1-carboxylic acid (400 mg, 3.57 mmol) in Et$_2$O (1 mL) under N$_2$ at 50° C. The mixture was stirred at 50° C. for 2 h. TLC showed the reaction was complete. The reaction mixture was diluted with DCM (10 mL) and water (0.5 mL). The organic layer was dried over magnesium sulfate, filtered, and concentrated in vacuum to give the crude title compound, which was used directly in the next step.

Step 2: Bicyclo[1.1.1]pentan-1-ylmethyl Trifluoromethanesulfonate

To a mixture of bicyclo[1.1.1]pentan-1-ylmethanol (560 mg, 5.71 mmol) and trifluoromethanesulfonic anhydride (2.42 g, 8.56 mmol) in ethyl ether (15 mL) was added TEA (1.59 mL, 11.41 mmol) at 0° C. The mixture was stirred at 0° C. for 1.5 h. TLC (SiO$_2$, PE:EtOAc=5:1) indicated that the reaction was complete. The mixture was diluted with water (50 mL) and extracted with Et$_2$O (45 mL). The organic layer was dried over magnesium sulfate, filtered, and concentrated in vacuum to give the crude title compound which was used in the next step without further purification.

Step 3: Ethyl 3-(bicyclo[1.1.1]pentan-1-yl)-2-(5-bromopyridin-2-yl)propanoate To a solution of ethyl 2-(5-bromopyridin-2-yl)acetate (1.53 g, 6.28 mmol) and bicyclo[1.1.1]pentan-1-ylmethyl trifluoromethanesulfonate (1.53 g, 3.99 mmol) in THF (8 mL) was added LiHMDS (9.41 mL, 9.41 mmol, 1 M in THF) slowly at −78° C. Then the mixture was stirred at 15° C. for 16 h. LC-MS indicated that the reaction was complete. The mixture was diluted with EtOAc (30 mL) and sat. NH$_4$Cl (30 mL), and extracted with EtOAc (30 mL×2). The combined organic layers were dried over anhydrous sodium sulfate, filtered, and concentrated in vacuum. The residue was purified by prep-TLC (SiO$_2$, PE:EtOAc=5:1) to give the title compound. MS (ESI) m/z 324.0/326.0 (M+H).

Step 4: Ethyl 3-(bicyclo[1.1.1]pentan-1-yl)-2-(5-(3-chloro-6-(difluoromethoxy)-2-fluorophenyl)pyridin-2-yl)propanoate Ethyl 3-(bicyclo[1.1.1]pentan-1-yl)-2-(5-bromopyridin-2-yl)propanoate (120 mg, 0.37 mmol) was mixed with 4,4,4',4',5,5,5',5'-octamethyl-2,2'-bi(1,3,2-dioxaborolane) (94 mg, 0.37 mmol), chloro(2-dicyclohexylphosphino-2',4',6'-tri-i-propyl-1,1'-biphenyl)(2'-amino-1,1'-biphenyl-2-yl)palladium(II) (29.1 mg, 0.037 mmol), and potassium acetate (72.7 mg, 0.74 mmol) in a microwave reaction vial. The vial was capped and nitrogen gas was used to purge the residual air three times. Then, dioxane (3 mL) was introduced with syringe. The mixture was stirred at 100° C. for 30 minutes under MW. LC-MS showed the reaction was complete. Then, 1-chloro-4-(difluoromethoxy)-2-fluoro-3-iodobenzene (131 mg, 0.41 mmol), aqueous potassium phosphate tribasic (1.11 mL, 1.11 mmol, 1 M) solution and chloro(2-dicyclohexylphosphino-2',4',6'-triisopropyl-1,1'-biphenyl)[2-(2'-amino-1,1'-biphenyl)]palladium(II) (146 mg, 0.19 mmol) were added, the mixture was purged with nitrogen three times, then heated to 80° C. for 1 h under MW. LC-MS indicated the reaction was complete. The mixture was diluted with EtOAc (20 mL) and water (10 mL), and filtered through Celite. The filtrate was separated and the aqueous phase was extracted with EtOAc (20 mL×3). The combined organic layers were washed with water (10 mL) and brine (10 mL), dried over anhydrous sodium sulfate, filtered and concentrated, and the crude product was purified with prep-TLC (SiO$_2$, PE/EtOAc=1/1) to give the title compound. MS (ESI) m/z 440.1 (M+H).

Intermediate 22

Ethyl Trans-2-(5-(3-chloro-6-(difluoromethoxy)-2-fluorophenyl)pyridin-2-yl)-3-(2-methylcyclopropyl)propanoate

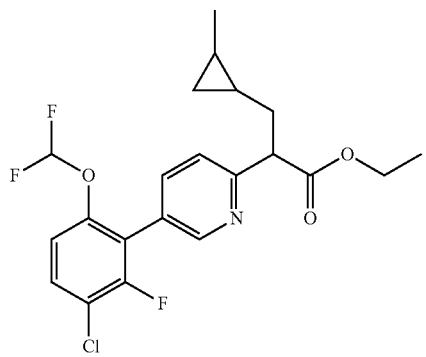 [SMILES: CCOC(=O)C(CC1CC1C)c1ccc(-c2c(OC(F)F)ccc(Cl)c2F)cn1]

Step 1: 1-(Bromomethyl)-2-methylcyclopropane

To a solution of (2-methylcyclopropyl)methanol (4.02 g, 46.70 mmol, predominantly trans) in DCM (20 mL) was added tribromophosphine (13.9 g, 51.4 mmol) at 0° C. under N$_2$ in a round bottom flask. The mixture was stirred at 0° C. for 1 h, TLC (PE/EtOAc=3/1) showed the SM had disappeared. Then, the reaction mixture was quenched with sat. NaHCO$_3$ (aqueous solution, 20 mL), extracted with DCM (10 mL×2), and the combined organic layers were dried over Na$_2$SO$_4$ and filtered. The filtrate was used directly as a DCM solution without further purification.

Step 2: Ethyl trans-2-(5-bromopyridin-2-yl)-3-(2-methylcyclopropyl)propanoate To the above DCM solution of 1-(bromomethyl)-2-methylcyclopropane (20 mL) was added a solution of ethyl 2-(5-bromopyridin-2-yl)acetate (3.80 g, 15.6 mmol) in THF (20 mL). The mixture was cooled to −78° C. and LiHMDS (20.2 mL, 20.2 mmol, 1 M in THF) was added slowly under N$_2$. The reaction was stirred at −78° C. to 15° C. for 16 h. LC-MS showed the reaction was complete. The reaction mixture was quenched with sat. NH$_4$Cl (20 mL), extracted with EtOAc (30 mL×4), and the combined organic layers were dried over Na$_2$SO$_4$ and filtered. The filtrate was concentrated in vacuo and purified by column chromatography (silica, PE/EtOAc=1/0-10/1) to give the title compound. $^1$H NMR (CDCl$_3$, 400 MHz): δ 8.61-8.62 (m, 1H), 7.76-7.80 (m, 1H), 7.24-7.26 (m, 1H), 4.13-4.19 (m, 2H), 3.85-3.88 (m, 1H), 1.95-2.04 (m, 1H), 1.79-1.89 (m, 1H), 1.22-1.26 (m, 3H), 0.87-1.00 (m, 3H), 0.14-0.34 (m, 4H). MS (ESI) m/z 311.9/313.9 (M+H).

Step 3: Ethyl trans-2-(5-(3-chloro-6-(difluoromethoxy)-2-fluorophenyl)pyridin-2-yl)-3-(2-methylcyclopropyl)propanoate To a solution of 4,4,4',4',5,5,5',5'-octamethyl-2,2'-bi(1,3,2-dioxaborolane) (1.21 g, 4.75 mmol), ethyl trans-2-(5- bromopyridin-2-yl)-3-(2-methylcyclopropyl)propanoate (1.20 g, 3.65 mmol) and potassium acetate (0.72 g, 7.30 mmol) in dioxane (12 mL) was added Pd(dppf)Cl$_2$ (0.27 g, 0.37 mmol) under N$_2$ in a 30 mL sealed tube. The mixture was stirred at 120° C. for 40 min under MW. LC-MS showed the reaction was complete. Then, 1-chloro-4-(difluoromethoxy)-2-fluoro-3-iodobenzene (1.18 g, 3.65 mmol), Pd(dppf)Cl$_2$ (0.27 g, 0.37 mmol) and a solution of potassium carbonate (1.01 g, 7.30 mmol) in 6 mL of water was added at 15° C. under N$_2$. The mixture was stirred at 85° C. for 16 h under MW. LC-MS showed the reaction was complete. The reaction mixture was diluted with water (30 mL), extracted with EtOAc (20 mL×3), and the combined organic layers were dried over Na$_2$SO$_4$ and filtered. The filtrate was concentrated in vacuo and purified by column chromatography (SiO$_2$, 0-10% EtOAc in PE) to give the title compound. MS (ESI) m/z 428.2 (M+H).

Intermediate 23

Ethyl 2-(5-bromo-4-methylpyridin-2-yl)-3-cyclopropylpropanoate

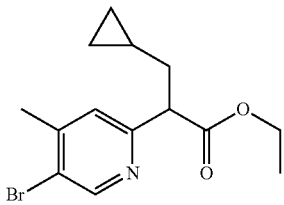 [SMILES: CCOC(=O)C(CC1CC1)c1cc(C)c(Br)cn1]

Step 1: 5-Bromo-2-iodo-4-methylpyridine

To a solution of 2,5-dibromo-4-methylpyridine (20.00 g, 80.00 mmol) in acetonitrile (350 mL) was added sodium iodide (24.00 g, 160.0 mmol) and acetyl chloride (4.70 g, 59.9 mmol) at 0° C. under N$_2$ in a 500 mL round bottom flask. The mixture was heated to 90° C. and stirred for 16 h. LC-MS showed the reaction was complete. The mixture was filtered, the precipitate was dissolved with DCM (50 mL) and water (50 mL), the organic layer was washed with water (30 mL×2), dried over Na$_2$SO$_4$ and filtered. The filtrate was concentrated in vacuo to give the title compound, which was used directly for next step without further purification. NMR (CDCl$_3$, 400 MHz): δ 8.39 (s, 1H), 7.60 (s, 1H), 2.33 (s, 3H). MS (ESI) m/z 297.8/299.8 (M+H).

Step 2: 1-tert-Butyl 3-ethyl 2-(5-bromo-4-methylpyridin-2-yl)malonate

To a solution of 5-bromo-2-iodo-4-methylpyridine (23.00 g, 73.30 mmol) in 1,4-dioxane (250 mL) was added tert-butyl ethyl malonate (27.60 g, 147.00 mmol), cuprous iodide (1.40 g, 7.33 mmol), picolinic acid (1.81 g, 14.67 mmol) and cesium carbonate (71.70 g, 220.00 mmol) at 15° C. under a N$_2$ atmosphere. The reaction mixture was stirred at 60° C. for 2 h. LC-MS showed the reaction was complete. The mixture was filtered and concentrated in vacuo. The residue was purified by column chromatography (SiO$_2$, PE:EtOAc from 100:1 to 40:1) to give the title compound. MS (ESI) m/z 357.8/359.8 (M+H).

Step 3: Ethyl 2-(5-bromo-4-methylpyridin-2-yl)acetate

To a solution of 1-tert-butyl 3-ethyl 2-(5-bromo-4-methylpyridin-2-yl)malonate (39.25 g, 65.70 mmol) in DCM (100 mL) was added TFA (22.49 g, 197 mmol), the mixture was stirred at 15° C. for 12 h under a N$_2$ atmosphere. LC-MS showed the reaction was complete. The mixture was concentrated in vacuo and diluted with water (100 mL). NaHCO$_3$ solution was added to the mixture until it reached pH=8 and it was extracted with DCM (20 mL×3). The combined organic layers were dried over Na$_2$SO$_4$, filtered and the filtrate was concentrated in vacuo. The crude product was purified by column chromatography (SiO$_2$, PE:EtOAc from 100:1 to 30:1) to give the title compound. NMR (CDCl$_3$, 400 MHz): δ 8.60 (s, 1H), 7.19 (s, 1H), 4.18 (q, J=7.2 Hz, 2H), 3.76 (s, 2H), 2.39 (s, 3H), 1.26 (t, J=7.2 Hz, 3H). MS (ESI) m/z 258.0/260.0 (M+H).

Step 4: Ethyl 2-(5-bromo-4-methylpyridin-2-yl)-3-cyclopropylpropanoate

To a solution of ethyl 2-(5-bromo-4-methylpyridin-2-yl)acetate (4.00 g, 15.50 mmol) and (bromomethyl)cyclopropane (10.46 g, 77.00 mmol) in THF (50 mL) was added LiHMDS (20.15 mL, 20.15 mmol, 1 M in THF) at −78° C. The reaction mixture was stirred at 18° C. for 18 h. LC-MS showed the reaction was complete. Then, the mixture was quenched with sat. NH$_4$Cl solution (15 mL), diluted with water (50 mL), and extracted with EtOAc (30 mL×3). The combined organic layers were dried over anhydrous sodium sulfate, filtered and concentrated in vacuo. The residue was purified by chromatography (SiO$_2$, PE:EtOAc=100:1 to 50:1) to give the title compound. $^1$H NMR (CDCl$_3$, 400 MHz): δ 8.57 (s, 1H), 7.22 (s, 1H), 4.14-4.19 (m, 2H), 3.85 (t, J=7.6 Hz, 1H), 2.39 (s, 3H), 1.81-1.97 (m, 2H), 1.23 (t, J=7.1 Hz, 3H), 0.56-0.74 (m, 1H), 0.32-0.46 (m, 2H), 0.06-0.14 (m, 1H), −0.04-0.04 (m, 1H). MS (ESI) m/z 312.0/314.0 (M+H).

Intermediate 24

Ethyl 2-(5-bromo-4-methoxypyridin-2-yl)-3-cyclopropylpropanoate

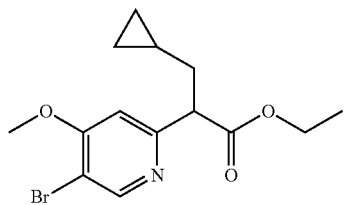 [SMILES: CCOC(=O)C(CC1CC1)c1cc(OC)c(Br)cn1]

Step 1: Ethyl 2-(5-bromo-4-methoxypyridin-2-yl)acetate

Lithium diisopropylamide (4.84 mL, 9.68 mmol, 2 M in THF and heptane) was added to a solution of 5-bromo-4-methoxy-2-methylpyridine (850 mg, 4.21 mmol) in THF (20 mL) at −78° C., followed by stirring at −78° C. for 30 min. Then, diethyl carbonate (1.10 g, 9.26 mmol) was added, and the reaction mixture was stirred at −78° C. for 2 h. LC-MS showed the reaction was complete. The reaction was quenched with sat. NH₄Cl (10 mL), diluted with water (25 mL), and extracted with EtOAc (3×15 mL). The combined organic phases were dried over Na₂SO₄, filtered and concentrated in vacuo. The residue was purified by column chromatography (SiO₂, PE:EtOAc=10:1 to 5:1) to give the title compound. ¹H NMR (CDCl₃, 400 MHz): δ 8.48 (s, 1H), 6.85 (s, 1H), 4.18 (q, J=7.3 Hz, 2H), 3.95 (s, 3H), 3.77 (s, 2H), 1.26 (t, J=7.2 Hz, 3H). MS (ESI) m/z 274.0/276.0 (M+H).

Step 2: Ethyl 2-(5-bromo-4-methoxypyridin-2-yl)-3-cyclopropylpropanoate

To a solution of ethyl 2-(5-bromo-4-methoxypyridin-2-yl)acetate (1.00 g, 3.65 mmol) and (bromomethyl)cyclopropane (2.46 g, 18.24 mmol) in THF (25 mL) was added LiHMDS (4.74 mL, 4.74 mmol, 1 M in THF) at −78° C. Then, the reaction mixture was stirred at 18° C. for 18 h. LC-MS showed the reaction was complete. Then, the mixture was quenched with sat. NH₄Cl solution (5 mL), diluted with water (15 mL), and extracted with EtOAc (10 mL×3). The combined organic layers were dried over anhydrous sodium sulfate, filtered and concentrated in vacuo. The residue was purified by column chromatography (SiO₂, PE:EtOAc=30:1 to 10:1) to give the title compound. ¹H NMR (CDCl₃, 400 MHz): δ 8.46 (s, 1H), 6.86 (s, 1H), 4.11-4.15 (m, 2H), 3.93 (s, 3H), 3.83 (t, J=7.6 Hz, 1H), 1.78-1.94 (m, 2H), 1.20 (t, J=7.1 Hz, 3H), 0.57-0.68 (m, 1H), 0.31-0.44 (m, 2H), 0.05-0.12 (m, 1H), −0.05-0.04 (m, 1H). MS (ESI) m/z 327.6/329.6 (M+H).

Intermediate 25

Ethyl 2-(5-bromopyridin-2-yl)-3-(3-methylcyclobutyl)propanoate

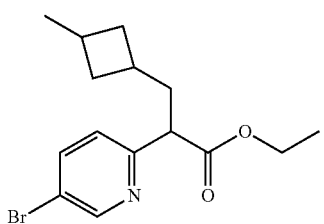 [SMILES: CCOC(=O)C(CC1CC(C)C1)c1ccc(Br)cn1]

Step 1: (3-methylcyclobutyl)methanol

To a mixture of LAH (1.0 g, 26.3 mmol) in Et₂O (20 mL) was added 3-methylcyclobutanecarboxylic acid (1.5 g, 13.1 mmol) in Et₂O (10 mL) under N₂. The mixture was stirred at 50° C. for 2 h. TLC showed the reaction was complete. To the reaction mixture was added DCM (20 mL) and water (5 mL). The organic layers were dried over magnesium sulfate, filtered, and concentrated in vacuum to give the crude title compound, which was used directly in the next step. ¹H NMR (CDCl₃, 400 MHz): δ=3.52-3.62 (m, 2H), 2.23-2.48 (m, 1H), 2.12-2.21 (m, 1H), 1.81-1.87 (m, 2H), 1.62-1.72 (m, 2H), 0.99-1.12 (m, 3H).

Step 2: (3-methylcyclobutyl)methyl 4-methylbenzenesulfonate

In a round bottom flask, to a mixture of (3-methylcyclobutyl)methanol (1.32 g, 13.1 mmol) in pyridine (30 mL) was added 4-methylbenzene-1-sulfonyl chloride (5.0 g, 26.3 mmol) at 0° C. The mixture was stirred at 0° C. for 3 h. TLC indicated that the reaction was complete. The mixture was diluted with water (20 mL) and 1M HCl (100 mL), extracted with DCM (3×30 mL). The combined organic layers were dried over magnesium sulfate, filtered, and concentrated in vacuum. The residue was purified by silica gel gradient chromatography (SiO₂, petroleum ether:ethyl acetate=100:1-80:1) to give the title compound. ¹H NMR (CDCl₃, 400 MHz): δ=7.77-7.82 (m, 2H), 7.35 (d, J=8.2 Hz, 2H), 4.03 (d, J=7.0 Hz, 1H), 3.92 (d, J=6.3 Hz, 1H), 2.22-2.59 (m, 5H), 2.10-2.16 (m, 1H), 1.81-1.88 (m, 1H), 1.61-1.69 (m, 1H), 1.24-1.30 (m, 1H), 0.96-1.08 (m, 3H).

Step 3: ethyl 2-(5-bromopyridin-2-yl)-3-(3-methylcyclobutyl)propanoate

In a round bottom flask, to a solution of ethyl 2-(5-bromopyridin-2-yl)acetate (1.73 g, 7.08 mmol) and (3-methylcyclobutyl)methyl 4-methylbenzenesulfonate (1.8 g, 7.08 mmol) in DMF (30 mL) was added NaH (0.28 g, 7.08 mmol, 60% in oil) at 15° C. The mixture was stirred at 50° C. for 3 h. The mixture was diluted with EtOAc (10 mL) and saturated NH₄Cl (20 mL), extracted with EtOAc (10 mL×2). The combined organic layers were dried over anhydrous sodium sulfate, filtered, and concentrated in vacuum. The residue was purified by column chromatography (SiO₂, PE:ethyl acetate=50:1-10:1) to give the title compound. MS (ESI) m/z 325.9/327.9 (M+H).

Intermediate 26

Ethyl 2-(5-bromopyridin-2-yl)-3-(2,2-difluorocyclopropyl)propanoate

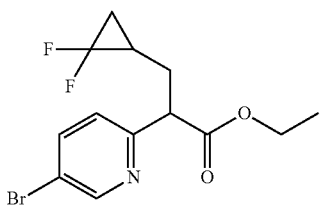 [SMILES: CCOC(=O)C(CC1CC1(F)F)c1ccc(Br)cn1]

Step 1: Ethyl 2-(5-bromopyridin-2-yl)-3-(2,2-difluorocyclopropyl)propanoate

In a round bottom flask, to a solution of ethyl 2-(5-bromopyridin-2-yl)acetate (908 mg, 3.72 mmol) and 2-(bromomethyl)-1,1-difluorocyclopropane (530 mg, 3.10 mmol) in DMF (8 mL) was added NaH (149 mg, 3.72 mmol, 60% in oil) at 15° C. The mixture was stirred at 50° C. for 3 h. The mixture was diluted with DCM (20 mL) and saturated NH₄Cl (20 mL), extracted with DCM (20 mL×3). The combined organic layers were washed with brine, dried over anhydrous sodium sulfate, filtered, and concentrated in vacuum to give the crude title compound which was used for the next step without further purification. MS (ESI) m/z 334.0/336.0 (M+H).

Intermediate 27

Ethyl 2-(5-bromopyridin-2-yl)-3-(2-(trifluoromethyl)cyclopropyl)propanoate

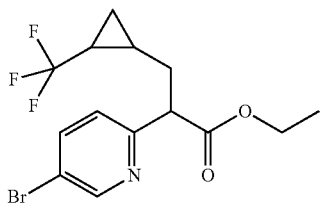 [SMILES: CCOC(=O)C(CC1CC1C(F)(F)F)c1ccc(Br)cn1]

Step 1: (E)-4,4,4-trifluoro-N-methoxy-N-methylbut-2-enamide

To a solution of (E)-4,4,4-trifluorobut-2-enoic acid (2.0 g, 14 mmol) in DCM (50 mL) was added EDC (3.28 g, 17.1 mmol), N,O-dimethylhydroxylamine hydrochloride (1.77 g, 18.1 mmol) and DIEA (4.0 mL, 23 mmol) at 0° C., which was then warmed to 25° C. and stirred for 6 h. The reaction mixture was concentrated, diluted with EtOAc (90 mL), and washed with 1N HCl (50 mL) and brine (80 mL). The organic layers were dried over $Na_2SO_4$ and filtered. The filtrate was concentrated to give the title compound which was used in next step without further purification. MS (ESI) m/z 184.0 (M+H). $^1$H NMR ($CDCl_3$, 400 MHz): δ=7.09 (d, J=15.6 Hz, 1H), 6.82 (dq, J=15.5, 6.7 Hz, 1H), 3.72-3.79 (m, 3H), 3.30 (s, 3H).

Step 2: N-methoxy-N-methyl-2-(trifluoromethyl)cyclopropanecarboxamide

To a solution of trimethylsulfoxonium iodide (3.24 g, 14.7 mmol) in DMSO (20 mL) was added sodium hydride (1.18 g, 29.5 mmol, 60% in oil). The reaction mixture was stirred at 25° C. for 1 h. Next, a solution of (E)-4,4,4-trifluoro-N-methoxy-N-methylbut-2-enamide (2.7 g, 14.7 mmol) in DMSO (15 mL) was added to the reaction mixture and stirred for 12 h. The reaction was quenched with saturated $NH_4Cl$ solution, and the product was extracted with ethyl acetate (30 mL×3). The combined organic fractions were washed with brine (50 mL), dried over $Na_2SO_4$, filtered and the solvent was evaporated under reduced pressure to give the title compound. MS (ESI) m/z 198.0 (M+H).

Step 3: 2-(trifluoromethyl)cyclopropanecarboxylic Acid

To a solution of N-methoxy-N-methyl-2-(trifluoromethyl) cyclopropanecarboxamide (1 g, 5.07 mmol) in THF (5 mL) and water (0.18 g, 10 mmol) was added potassium 2-methylpropan-2-olate (25.4 mL, 25.4 mmol, 1M in THF) at 25° C. The reaction mixture was stirred at 25° C. for 16 h. TLC showed the reaction was complete. Ice was added to the reaction mixture until it became homogeneous. The aqueous layer was acidified with 1N HCl to adjust the pH=4. The mixture was extracted with EtOAc (3×30 mL). The combined organic layers were washed with brine, dried over anhydrous sodium sulfate, filtered and the filtrate was concentrated in vacuo to give the title compound. $^1$H NMR ($CDCl_3$, 400 MHz): δ=2.17-2.26 (m, 1H), 2.01-2.06 (m, 1H), 1.35-1.45 (m, 2H).

Step 4: (2-(trifluoromethyl) cyclopropyl) Methanol

To a suspension of LAH (0.68 g, 17.9 mmol) in ether (10 mL) was added 2-(trifluoromethyl) cyclopropanecarboxylic acid (2.5 g, 16.2 mmol) in ether (10 mL) at 25° C. The reaction mixture was stirred at 50° C. for 2 h. TLC showed the reaction was complete. The mixture was quenched with water (2 mL) and diluted with DCM (40 mL). $MgSO_4$ was added and stirred for 4 h. The mixture was filtered, and concentrated in vacuum to give the title compound which was directly used for next step without further purification. $^1$H NMR ($CDCl_3$, 400 MHz): δ=3.59-3.65 (m, 1H), 3.52-3.58 (m, 1H), 1.47-1.57 (m, 2H), 0.97-1.05 (m, 1H), 0.78 (dt, J=8.4, 5.6 Hz, 2H).

Step 5: (2-(trifluoromethyl)cyclopropyl)methyl 4-(trifluoromethyl)benzenesulfonate In a round bottom flask, to a solution of (2-(trifluoromethyl) cyclopropyl) methanol (4.19 g, 30 mmol) in THF (30 mL) was added NaH (1.2 g, 30 mmol, 60% in oil) at 0° C. The mixture was stirred for 30 min. Then 4-(trifluoromethyl) benzene-1-sulfonyl chloride (8.78 g, 35.9 mmol) was added and stirred at 30° C. for 12 h. The reaction mixture was poured into sat. $NH_4Cl$ (10 mL) solution and extracted with DCM (3×20 mL). The combined organic layers were washed with brine (30 mL), dried ($Na_2SO_4$), filtered, concentrated and purified by chromatography column ($SiO_2$, PE:EA from 100:1 to 10:1) to give the title compound. $^1$H NMR ($CDCl_3$, 400 MHz): δ=8.06 (d, J=8.2 Hz, 2H), 7.86 (d, J=8.2 Hz, 2H), 4.11 (dd, J=11.0, 6.7 Hz, 1H), 4.00 (dd, J=10.8, 7.2 Hz, 1H), 1.48-1.67 (m, 2H), 1.11 (dt, J=9.1, 5.8 Hz, 1H), 0.79-0.88 (m, 1H).

Step 6: Ethyl 2-(5-bromopyridin-2-yl)-3-(2-(trifluoromethyl)cyclopropyl)propanoate To a solution of ethyl 2-(5-bromopyridin-2-yl)acetate (1 g, 4.10 mmol) and (2-(trifluoromethyl)cyclopropyl)methyl 4-(trifluoromethyl)benzenesulfonate (1.43 g, 4.10 mmol) in DMF (15 mL) was added NaH (0.16 g, 4.1 mmol, 60% in oil) at 0° C. under $N_2$ protection. The mixture was stirred at 50° C. for 1 h, LCMS showed the reaction was complete. The mixture was quenched with sat. $NH_4Cl$ and water (15 mL), and extracted with DCM (20 mL×3). The combined organic layers were dried over $Na_2SO_4$, filtered and concentrated in vacuum to give the crude product, which was purified by column chromatography ($SiO_2$, PE:EA=5:1) to give the title compound. MS (ESI) m/z 366.0/368.0 (M+H).

Intermediate 28 tert-Butyl 4-(2-(5-(3-chloro-6-(difluoromethyl)-2-fluorophenyl)pyridin-2-yl)-3-(3-fluorocyclobutyl) propanamido)benzoate

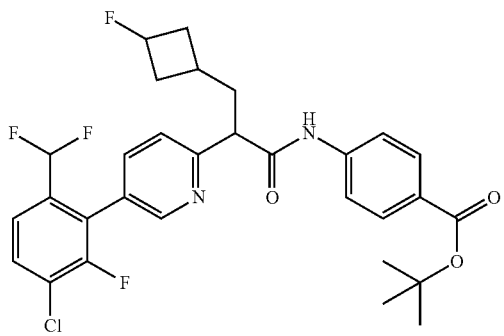 [SMILES: CC(C)(C)OC(=O)c1ccc(NC(=O)C(CC2CC(F)C2)c2ccc(-c3c(C(F)F)ccc(Cl)c3F)cn2)cc1]

Step 1: 2-(5-bromopyridin-2-yl)-3-(5,8-dioxaspiro[3.4]octan-2-yl)propanoic Acid In a round bottom flask, to a solution of ethyl 2-(5-bromopyridin-2-yl)-3-(5,8-dioxaspiro[3.4]octan-2-yl)propanoate (see INTERMEDIATE 18, 2.4 g, 5.83 mmol) in THF (20 mL) and water (5 mL) was added NaOH (0.47 g, 11.7 mmol) at 25° C. The mixture was stirred at 25° C. for 12 h. LCMS indicated the reaction was completed. The mixture was concentrated, diluted with water (20 mL) and 1N HCl was added to adjust to pH=5. The mixture was extracted with DCM (20 mL×3), and the combined organic layers were dried over anhydrous sodium sulfate and filtered to give a solution of the title compound which was used without further purification. MS (ESI) m/z 342.0/344.0 (M+H).

Step 2: Tert-Butyl 4-(2-(5-bromopyridin-2-yl)-3-(5,8-dioxaspiro[3.4]octan-2-yl)propanamido)benzoate In a round bottom flask, tert-butyl 4-aminobenzoate (1.13 g, 5.8 mmol) and EDC (1.67 g, 8.7 mmol) were mixed with the solution of 2-(5-bromopyridin-2-yl)-3-(5,8-dioxaspiro[3.4]octan-2-yl)propanoic acid (60 mL, 5.82 mmol) from step 1. Pyridine (1.4 mL, 17 mmol) was added at 0° C. The reaction mixture was stirred at 0° C. for 2 h. LCMS showed reaction was complete. The reaction mixture was diluted with water (50 mL) and extracted with ethyl acetate (50 mL×3). The combined organic layers were washed with brine (50 mL), dried over anhydrous sodium sulfate, filtered and concentrated to give the crude product which was was purified by silica gel gradient chromatography (SiO$_2$, petroleum ether:ethyl acetate=50:1-2:1) to give the title compound. MS (ESI) m/z 517.2/519.2 (M+H). $^1$H NMR (CDCl$_3$, 400 MHz): δ 9.53 (s, 1H), 8.72 (d, J=2.2 Hz, 1H), 7.92-7.99 (m, 2H), 7.84 (dd, J=8.4, 2.2 Hz, 1H), 7.59 (d, J=8.8 Hz, 2H), 7.20 (d, J=7.9 Hz, 1H), 3.81-3.89 (m, 4H), 3.66 (dd, J=8.4, 6.6 Hz, 1H), 2.39-2.47 (m, 1H), 2.26-2.37 (m, 2H), 2.16-2.24 (m, 1H), 2.01-2.06 (m, 1H), 1.94-2.00 (m, 1H), 1.83-1.90 (m, 1H), 1.61 (s, 9H).

Step 3: Tert-Butyl 4-(2-(5-(3-chloro-6-(difluoromethyl)-2-fluorophenyl)pyridin-2-yl)-3-(5,8-dioxaspiro[3.4]octan-2-yl)propanamido)benzoate A solution of tert-butyl 4-(2-(5-bromopyridin-2-yl)-3-(5,8-dioxaspiro[3.4]octan-2-yl)propanamido)benzoate (1.0 g, 1.93 mmol), bis(pinacolato)diboron (0.54 g, 2.1 mmol), Pd(dppf)Cl$_2$ (0.14 g, 0.19 mmol) and potassium acetate (0.57 g, 5.8 mmol) in 1,4-dioxane (8 mL) was stirred under an atmosphere of N$_2$ at 120° C. for 40 mins in MW. LCMS indicated that the reaction was complete. After it was cooled to room temperature, 1-chloro-4-(difluoromethyl)-2-fluoro-3-iodobenzene (0.59 g, 1.9 mmol), K$_2$CO$_3$ aqueous solution (5.8 mL, 5.8 mmol) and Pd(dppf)Cl$_2$ (0.14 g, 0.19 mmol) were added. The mixture was stirred under an atmosphere of N$_2$ at 90° C. for 60 mins in MW. LCMS indicated that the reaction was complete. The mixture was diluted with water (20 mL) and extracted with EtOAc (30 mL×3). The combined organic layers were dried over anhydrous sodium sulfate, filtered, and concentrated in vacuum. The residue was purified by silica gel gradient chromatography (SiO$_2$, petroleum ether:ethyl acetate=20:1-1:1) to give the title compound. MS (ESI) m/z 617.2 (M+H).

Step 4: Tert-Butyl 4-(2-(5-(3-chloro-6-(difluoromethyl)-2-fluorophenyl)pyridin-2-yl)-3-(3-oxocyclobutyl)propanamido)benzoate In a round bottom flask, to a solution of tert-butyl 4-(2-(5-(3-chloro-6-(difluoromethyl)-2-fluorophenyl)pyridin-2-yl)-3-(5,8-dioxaspiro[3.4]octan-2-yl)propanamido)benzoate (1 g, 1.6 mmol) in acetonitrile (50 mL) was added TsOH (0.31 g, 1.62 mmol) at 25° C. The mixture was stirred at 25° C. for 14 h. LCMS indicated that the reaction was complete. The mixture was concentrated in vacuum to give the title compound which was used into next step without further purification. MS (ESI) m/z 573.0 (M+H).

Step 5: Tert-Butyl 4-(2-(5-(3-chloro-6-(difluoromethyl)-2-fluorophenyl)pyridin-2-yl)-3-(3-hydroxycyclobutyl)propanamido)benzoate In a round bottom flask, to a solution of tert-butyl 4-(2-(5-(3-chloro-6-(difluoromethyl)-2-fluorophenyl)pyridin-2-yl)-3-(3-oxocyclobutyl)propanamido)benzoate (950 mg, 1.66 mmol) in MeOH (20 mL) was added NaBH$_4$ (125 mg, 3.32 mmol) at 0° C. The mixture was stirred at 25° C. for 1 h. LCMS indicated the reaction was complete. The mixture was diluted with EtOAc (50 mL) and sat. NH$_4$Cl (30 mL), the mixture was extracted with EtOAc (50 mL×2). The combined organic layers were dried over Na$_2$SO$_4$, then filtered. The filtrate was concentrated to give crude product which was purified by silica gel gradient chromatography (SiO$_2$, petroleum ether:ethyl acetate=50:1-3:1) to give the title compound. MS (ESI) m/z 575.2 (M+H).

Step 6: Tert-Butyl 4-(2-(5-(3-chloro-6-(difluoromethyl)-2-fluorophenyl)pyridin-2-yl)-3-(3-fluorocyclobutyl)propanamido)benzoate In a round bottom flask, to a solution of tert-butyl 4-(2-(5-(3-chloro-6-(difluoromethyl)-2-fluorophenyl)pyridin-2-yl)-3-(3-hydroxycyclobutyl)propanamido)benzoate (100 mg, 0.17 mmol) in toluene (2 mL) was added pyridine-2-sulfonyl fluoride (56 mg, 0.35 mmol) and DBU (0.11 mL, 0.70 mmol). The reaction mixture was stirred at 80° C. for 12 h. LCMS showed reaction was complete. The reaction mixture was diluted with water (20 mL) and extracted with EtOAc (20 mL×3). The combined organic layers were washed with brine (20 mL), dried over anhydrous sodium sulfate, filtered and concentrated to give the crude product. The crude product was purified by prep-TLC (SiO$_2$, petroleum ether:ethyl acetate=3:1) to give the title compound. MS (ESI) m/z 577.2 (M+H).

Intermediate 29 tert-Butyl 4-(2-(5-(3-chloro-6-(difluoromethyl)-2-fluorophenyl)pyridin-2-yl)-3-(3-hydroxy-3-methylcyclobutyl)propanamido)benzoate

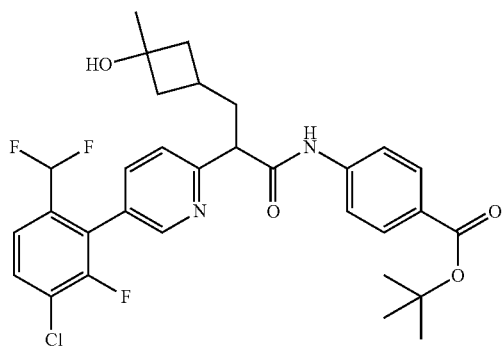 [SMILES: CC1(O)CC(CC(C(=O)Nc2ccc(C(=O)OC(C)(C)C)cc2)c2ccc(-c3c(C(F)F)ccc(Cl)c3F)cn2)C1]

Step 1: tert-butyl 4-(2-(5-(3-chloro-6-(difluoromethyl)-2-fluorophenyl)pyridin-2-yl)-3-(3-hydroxy-3-methylcyclobutyl)propanamido)benzoate In a round bottom flask, to a solution of tert-butyl 4-(2-(5-(3-chloro-6-(difluoromethyl)-2-fluorophenyl)pyridin-2-yl)-3-(3-oxocyclobutyl)propanamido)benzoate (see INTERMEDIATE 28, 300 mg, 0.52 mmol) in THF (3 mL) was added methyllithium (1.96 mL, 3.14 mmol, 1.6 M) at −78° C. The mixture was stirred at −78° C. for 0.5 h. LCMS indicated that the reaction was complete. The mixture was diluted with EtOAc (10 mL) and sat. NH$_4$Cl (10 mL). The mixture was extracted with EtOAc (10 mL×2). The combined organic layers were dried over anhydrous sodium sulfate, filtered, and concentrated in vacuum. The residue was purified by prep-TLC (SiO$_2$, petroleum ether:ethyl acetate=50:1-2:1) to give the title compound. MS (ESI) m/z 589.3 (M+H).

Intermediate 30

Ethyl 2-(5-bromopyridin-2-yl)-3-(2-(difluoromethyl)cyclopropyl)propanoate

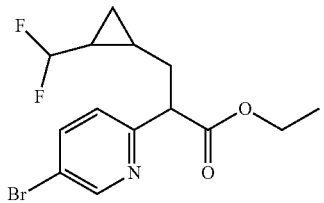 [SMILES: CCOC(=O)C(CC1CC1C(F)F)c1ccc(Br)cn1]

Step 1: Methyl 2-(difluoromethyl)cyclopropanecarboxylate

To a solution of methyl 2-formylcyclopropanecarboxylate (1 g, 7.8 mmol) in DCM (10 mL) was added DAST (1.55 mL, 11.7 mmol) at 0° C. The reaction mixture was stirred at 15° C. for 12 h. TLC showed reaction was complete. The mixture was quenched by sat. NaHCO$_3$ and extracted with DCM (20 mL×3), the combined organic layers were washed with brine and concentrated to give the crude title compound which was used directly for the next step without further purification.

Step 2: (2-(difluoromethyl) cyclopropyl) Methanol

To a solution of LAH (0.26 g, 7.0 mmol) in ether (20 mL) was added methyl 2-(difluoromethyl) cyclopropanecarboxylate (1 g, crude) in ether (10 mL) at −78° C. The reaction mixture was stirred for 2 h. TLC showed the reaction was complete. The mixture was quenched with water (2.5 mL), dried over MgSO$_4$ for 12 h. The mixture was filtered, and the filtrate was concentrated in vacuum to give the title compound which was used directly for the next step without further purification.

Step 3: (2-(difluoromethyl)cyclopropyl)methyl 4-(trifluoromethyl)benzenesulfonate In a round bottom flask, to a solution of (2-(difluoromethyl) cyclopropyl)methanol (760 mg, 6.22 mmol) in THF (10 mL) was added NaH (249 mg, 6.22 mmol, 60%) at 0° C., then stirred for 30 min. 4-(Trifluoromethyl) benzene-1-sulfonyl chloride (1.8 g, 7.5 mmol) was added and the mixture was stirred at 20° C. for 12 h. The mixture was poured into sat. NH$_4$Cl (10 mL) and extracted with DCM (3×20 mL). The combined organic layers were washed with brine (30 mL), dried (Na$_2$SO$_4$), filtered, concentrated, and purified by chromatography column (SiO$_2$, PE:EA from 100:1 to 20:1) to give the title compound. $^1$H NMR (CDCl$_3$, 400 MHz): δ=8.05 (d, J=8.4 Hz, 2H), 7.84 (d, J=8.6 Hz, 2H), 5.52-5.81 (td, J=56 Hz, 1H), 3.96-4.11 (m, 2H), 1.39-1.50 (m, 1H), 1.23-1.36 (m, 1H), 0.96 (dt, J=8.7, 5.7 Hz, 1H), 0.67-0.76 (m, 1H).

Step 4: Ethyl 2-(5-bromopyridin-2-yl)-3-(2-(difluoromethyl)cyclopropyl)propanoate To a solution of ethyl 2-(5-bromopyridin-2-yl)acetate (370 mg, 1.5 mmol) and (2-(difluoromethyl)cyclopropyl) methyl 4-(trifluoromethyl)benzenesulfonate (500 mg, 1.5 mmol) in DMF (3 mL) was added NaH (67 mg, 1.7 mmol, 60%) at 0° C. The mixture was stirred at 50° C. for 1 h, LCMS showed the reaction was complete. The reaction was quenched with water (3 mL), and product was extracted with DCM (5 mL×3), the combined organic layers were washed with brine and concentrated. The crude was purify by chromatography column (SiO$_2$, PE:EA from 100:1 to 5:1) to give the title compound. MS (ESI) m/z 348.0/350.0 (M+H).

Intermediate 31

Methyl 2-(5-bromopyridin-2-yl)-3-(trans-2-fluorocyclopropyl)propanoate

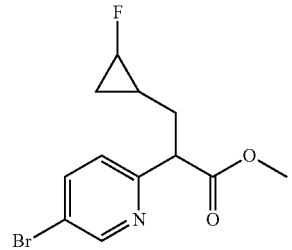 [SMILES: COC(=O)C(CC1CC1F)c1ccc(Br)cn1]

Step 1: (trans-2-fluorocyclopropyl)methyl 4-methylbenzenesulfonate

To a stirring solution of (trans-2-fluorocyclopropyl) methanol (350 mg, 3.88 mmol) in DCM (19 mL), was added Ts-Cl (1.1 g, 5.8 mmol) and DMAP (23.7 mg, 0.19 mmol) at 0° C., followed by slow addition of TEA (0.81 mL, 5.83 mmol). The reaction was stirred at r.t. under N$_2$ overnight. The reaction mixture was diluted with water (15 mL) and neutralized with 1N HCl solution to pH=5-6. The aqueous layer was extracted with ethyl acetate (3×70 mL). The combined organic layer was dried over Na$_2$SO$_4$, then filtered and the solvent was evaporated under reduced pressure. The residue was purified by column chromatography on 40-g silica gel column, eluting with 0 to 20% ethyl acetate in hexane to give the title compound.

Step 2: Methyl 2-(5-bromopyridin-2-yl)-3-(trans-2-fluorocyclopropyl)propanoate

To a stirred solution of methyl 2-(5-bromopyridin-2-yl) acetate (560 mg, 2.46 mmol) in DMF (25 mL), was added NaH (120 mg, 3.0 mmol) at 0° C. The reaction mixture was stirred at r.t. under N₂ for 20 min, then (trans-2-fluorocyclopropyl)methyl 4-methylbenzenesulfonate (660 mg, 2.70 mmol) in DMF (2 mL) was added. The reaction mixture was stirred at r.t. under N₂ overnight. The reaction was quenched with water (30 mL), then the aqueous layer was extracted with ethyl acetate (3×50 mL). The combined organic layer was dried over Na₂SO₄, filtered, and concentrated. The residue was purified by column chromatography on a 80-g silica gel column, eluting with 0 to 15% ethyl acetate in hexane to give the title compound. MS (ESI) m/z 302.1/305.1 (M+H).

Intermediate 32

Ethyl 2-(5-bromopyridin-2-yl)-3-(2-(fluoromethyl)cyclopropyl)propanoate

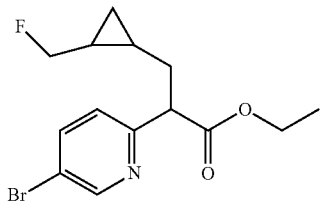 [SMILES: CCOC(=O)C(CC1CC1CF)c1ccc(Br)cn1]

Step 1: 1-(bromomethyl)-2-(fluoromethyl)cyclopropane

To a solution of (2-(fluoromethyl)cyclopropyl)methanol (2 g, 9.6 mmol) in DCM (20 mL) was added tribromophosphine (1.8 mL, 19.2 mmol) at 0° C. in a round bottom flask under N₂. The reaction was stirred at 0° C. for 2 h. Then the mixture was quenched with sat. NaHCO₃ (a.q., 40 mL) at 0° C., extracted with DCM (10 mL×2). The combined organic layers were dried over Na₂SO₄ and filtered. The filtrate was concentrated (<30° C.) to give the title compound which was used in the next step without further purification.

Step 2: ethyl 2-(5-bromopyridin-2-yl)-3-(2-(fluoromethyl)cyclopropyl)propanoate

To a solution of ethyl 2-(5-bromopyridin-2-yl)acetate (1.5 g, 6.2 mmol) and 1-(bromomethyl)-2-(fluoromethyl)cyclopropane (2 g, 12 mmol) in DMF (3 mL) was added NaH (0.32 g, 8.0 mmol, 60%) at 0° C. under N₂. The mixture was stirred at 50° C. for 2 h. LCMS showed the reaction was complete. The reaction was quenched with water, and the product was extracted with ethyl acetate (10 mL×3), the combined organic layers were washed with brine (20 mL×2), dried over Na₂SO₄ and filtered. The filtrate was concentrated and purified by column chromatography (SiO₂, PE/EA=1/0-9/1) to give the title compound. MS (ESI) m/z 330.0/332.0 (M+H).

Intermediate 33

Ethyl 2-(5-bromopyridin-2-yl)-3-(2,3-dimethylcyclopropyl)propanoate

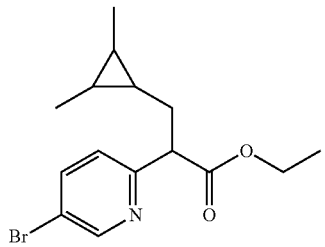 [SMILES: CCOC(=O)C(CC1C(C)C1C)c1ccc(Br)cn1]

Step 1: Ethyl 2,3-dimethylcyclopropanecarboxylate

To ethyl 2-diazoacetate (10 g, 88 mmol) and (Z)-but-2-ene (25 g, 438 mmol) in a seal tube was added Rh(OAc)₂ dimer (0.19 g, 0.44 mmol) at −78° C. The mixture was stirred at 25° C. for 16 h. The mixture was cooled to −78° C. and the seal tube was opened. The tube was then placed at 25° C. for 2 h. The residue was obtained as the title compound which was used in the next step without further purification.

Step 2: (2,3-dimethylcyclopropyl)methanol

To a solution of ethyl 2,3-dimethylcyclopropanecarboxylate (4.7 g, 33 mmol) in diethyl ether (50 mL) in a round bottom flask was added LiAlH₄ (1.63 g, 43.0 mmol) at 0° C. The mixture was stirred at 0° C. for 30 min. TLC showed the reaction was complete. Water (5 mL) was added, and the mixture was dried over MgSO₄ and filtered. The filtrate was concentrate at 28° C. to give the title compound which was used in the next step without further purification.

Step 3: 1-(bromomethyl)-2,3-dimethylcyclopropane

To a solution of (2,3-dimethylcyclopropyl)methanol (2.7 g, 27 mmol) in DCM (50 mL) was added tribromophosphine (3.3 mL, 35 mmol) at 0° C. in a round bottom flask under N₂. The mixture was stirred at 0° C. for 2 h. The reaction was quenched with NaHCO₃ (a.q., 100 mL) and the mixture was extracted with DCM (20 mL×3), the combined organic layers were dried over Na₂SO₄ and filtered. The filtrate was concentrated at 28° C. to give the title compound which was used in the next step without further purification.

Step 4: Ethyl 2-(5-bromopyridin-2-yl)-3-(2,3-dimethylcyclopropyl)propanoate

To a solution of 1-(bromomethyl)-2,3-dimethylcyclopropane (2.0 g, 12.3 mmol) and ethyl 2-(5-bromopyridin-2-yl)acetate (1.5 g, 6.2 mmol) in DMF (15 mL) was added NaH (370 mg, 9.2 mmol, 60%) at 0° C. in a round bottom flask under N₂. The mixture was stirred at 50° C. for 3 h. LCMS showed the reaction was complete. Water (50 mL) was added, the mixture was extracted with ethyl acetate (50 mL×3), the organic layers were combined and washed with brine (50 mL×3), dried over Na₂SO₄ and filtered. The filtrate was concentrated and purified by chromatography (silica, PE/EA=1/0-10/1) to give the title compound. MS (ESI) m/z 326.0/328.0 (M+H).

Intermediate 34

Ethyl 2-(5-bromopyridin-2-yl)-3-(2-methylcyclobutyl)propanoate

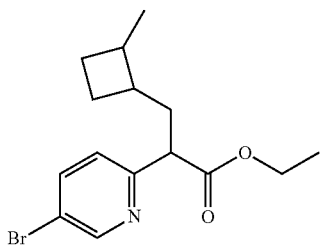 [SMILES: CCOC(=O)C(CC1CCC1C)c1ccc(Br)cn1]

Step 1: Diethyl 2-methylcyclobutane-1,1-dicarboxylate

To a solution of diethyl malonate (90 g, 560 mmol) in DMF (600 mL) was added NaH (22.5 g, 562 mmol, 60%) at 0° C. under $N_2$, and the mixture was stirred at 0° C. for 30 mins. 1,3-Dibromobutane (121 g, 562 mmol) was added, and stirred at 20° C. for 2 h, then another batch of NaH (22.5 g, 562 mmol, 60%) was added to the above mixture at 0° C., then the mixture was warmed up to 20° C. and stirred further for 12 h. LCMS showed the reaction was complete. The reaction was quenched with water (300 mL), extracted with EtOAc (800 mL×3), the combined organic layers was washed with brine (1000 mL×3), dried over $Na_2SO_4$, filtered and the filtrate was concentrated in vacuum, the residue was purified by column chromatography ($SiO_2$, PE:EA=10:1) to give the title compound. MS (ESI) m/z 251.1 (M+H).

Step 2: 2-methylcyclobutane-1,1-dicarboxylic Acid

To a solution of diethyl 2-methylcyclobutane-1,1-dicarboxylate (34 g, 159 mmol) in MeOH:$H_2O$=1:1 (150 mL) was added KOH (20.5 g, 365 mmol) at 0° C. under $N_2$, and the mixture was stirred at 20° C. for 2 h. The reaction mixture was concentrated, and the residue was diluted with water (100 mL), adjusted with HCl (conc.) to pH 3-4, extracted with EtOAc:MeOH (10:1, 150 mL×3), the combined organic layers were dried over $Na_2SO_4$, filtered and the filtrate was concentrated in vacuum to give the title compound which was directly used in the next step without further purification. $^1$H NMR (DMSO-$d_6$, 400 MHz): δ=2.80-2.95 (m, 1H), 2.32-2.43 (m, 1H), 1.83-2.02 (m, 2H), 1.40-1.53 (m, 1H), 0.95 (d, J=7.0 Hz, 3H).

Step 3: 2-methylcyclobutanecarboxylic Acid

A solution of 2-methylcyclobutane-1,1-dicarboxylic acid (8 g, 50.6 mmol) in $H_2O$ (20 mL) was sealed and the mixture was stirred at 170° C. for 24 h. TLC showed the reaction was nearly complete. The mixture extracted with ethyl acetate (100 mL×3), the combined organic layers were dried over $Na_2SO_4$, filtered and the filtrate was concentrated to give the title compound which was directly used in the next step without further purification.

Step 4: (2-methylcyclobutyl)methanol

To a mixture of LAH (2.3 g, 61 mmol) in $Et_2O$ (40 mL) was added 2-methylcyclobutanecarboxylic acid (3.5 g, 30.7 mmol) under $N_2$. The mixture was stirred at 50° C. for 12 h. TLC showed the reaction was complete. To the reaction mixture was added DCM (40 mL), water (2.5 mL), and aqueous NaOH solution (15%, 2.5 mL). The organic layer was dried over magnesium sulfate, filtered, and concentrated in vacuum to give the title compound which was used in the next step without further purification.

Step 5: 2-methylcyclobutane-1-carbaldehyde

To a stirred mixture of DMSO (3.8 mL, 54 mmol) in DCM (60 mL) was added oxalyl dichloride (2.3 mL, 27 mmol) at −78° C. and the mixture was stirred at −78° C. for 1 h under $N_2$ atmosphere. (2-Methylcyclobutyl)methanol (2 g, 20 mmol) was added. The mixture was stirred at −78° C. for 2 h, then TEA (11 mL, 80 mmol) was added and the mixture was stirred at −78° C. for 1 h. TLC (PE:EA=10:1) showed the reaction was complete. Aqueous sodium bicarbonate (saturated, 30 mL) was added and the mixture was extracted with dichloromethane (50 mL). The organic layer was dried over $Na_2SO_4$, filtered and the solvent was evaporated at 30° C. to give the title compound which was used in next step without further purification.

Step 6: Ethyl 2-(5-bromopyridin-2-yl)-3-(2-methylcyclobutyl)acrylate

In a round bottom flask, to a solution of ethyl 2-(5-bromopyridin-2-yl)acetate (4.0 g, 16 mmol) in DMF (40 mL) was added NaH (0.65 g, 16.3 mmol, 60%) at 0° C. The mixture was stirred for 30 mins, then 2-methylcyclobutanecarbaldehyde (1.6 g, 16 mmol) was added. The mixture was stirred at 50° C. for 12 h. LCMS indicated that the reaction was almost complete. The mixture was diluted with EtOAc (10 mL) and sat. $NH_4Cl$ (30 mL). The mixture was extracted with EtOAc (40 mL×2). The combined organic layers were dried over anhydrous sodium sulfate, filtered, and concentrated in vacuum. The residue was purified by column chromatography ($SiO_2$, PE:ethyl acetate=50:1-10:1) to give the title compound. MS (ESI) m/z 324.0/326.0 (M+H).

Step 7: Ethyl 2-(5-bromopyridin-2-yl)-3-(2-methylcyclobutyl)propanoate

In a round bottom flask, to a solution of ethyl 2-(5-bromopyridin-2-yl)-3-(2-methylcyclobutyl)acrylate (160 mg, 0.49 mmol) in HOAc (5 mL) was added zinc (320 mg, 4.9 mmol) at 0° C. Then the mixture was stirred at 20° C. for 12 h. LCMS indicated the reaction was almost complete. The mixture was filtered, and concentrated in vacuum to give the crude title compound which was directly used for next step without further purification. MS (ESI) m/z 326.0/328.0 (M+H).

Intermediate 35

Ethyl 2-(5-bromopyridin-2-yl)-3-(2,2-dimethylcyclopropyl)propanoate

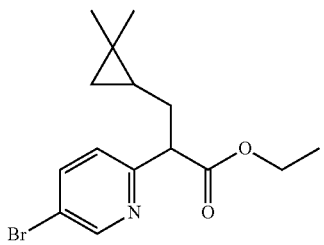 [SMILES: CCOC(=O)C(CC1CC1(C)C)c1ccc(Br)cn1]

Step 1: (2,2-dimethylcyclopropyl)methanol

In a round bottom flask, to a mixture of LAH (12 g, 315 mmol) in Et$_2$O (240 mL) was added 2,2-dimethylcyclopropanecarboxylic acid (24 g, 210 mmol) at 0° C. The mixture was stirred at 50° C. for 2 h. TLC indicated that the reaction was complete. Then the reaction mixture was quenched by the addition of 15% NaOH (50 mL) and water (20 mL). The product was extracted with DCM (100 mL×3), the combined organic layers were dried over anhydrous Na$_2$SO$_4$, filtered and concentrated to give the title compound which was used in the next step without further purification.

Step 2: 2,2-dimethylcyclopropane-1-carbaldehyde

In a round bottom flask, to a solution of (2,2-dimethylcyclopropyl)methanol (5 g, 50 mmol) in DCM (50 mL) was added pyridinium chlorochromate (13.5 g, 63 mmol) at 15° C. The mixture was stirred at 15° C. for 2 h. TLC indicated that the reaction was complete. Then the reaction mixture was filtered, and the filtrate was washed with water (50 mL×3) and brine (50 mL×2), dried over anhydrous Na$_2$SO$_4$, filtered and concentrated to give title compound which was used in the next step without further purification.

Step 3: Ethyl 2-(5-bromopyridin-2-yl)-3-(2,2-dimethylcyclopropyl)acrylate

In a round bottom flask, to a solution of 2,2-dimethylcyclopropanecarbaldehyde (4.9 g, 49 mmol) in 2-methyltetrahydrofuran (15 mL) was added ethyl 2-(5-bromopyridin-2-yl)acetate (1.5 g, 6.15 mmol) and piperidine (0.52 g, 6.15 mmol) at 15° C. The mixture was stirred at 82° C. for 3 h. LCMS showed the reaction was complete. Water (20 mL) was added and the reaction mixture was extracted with DCM (20 mL×3), the combined organic layers were washed with brine, dried over Na$_2$SO$_4$, filtered and concentrated to give a crude product which was purified by column chromatography (SiO$_2$, PE:EtOAc=150:1 to 120:1) to give the title compound. MS (ESI) m/z 324.0/326.0 (M+H). $^1$H NMR (CDCl$_3$, 400 MHz): δ=8.72 (d, J=2.4 Hz, 1H), 7.83 (d, J=8.5 Hz, 1H), 7.23 (d, J=8.4 Hz, 1H), 6.88 (d, J=11.2 Hz, 1H), 4.16-4.24 (m, 2H), 1.36 (ddd, J=11.2, 8.2, 5.1 Hz, 1H), 1.21-1.26 (m, 6H), 1.04 (s, 3H), 0.96 (dd, J=8.3, 4.5 Hz, 1H), 0.77 (t, J=4.6 Hz, 1H).

Step 4: Ethyl 2-(5-bromopyridin-2-yl)-3-(2,2-dimethylcyclopropyl)propanoate

In a round bottom flask, to a solution of ethyl 2-(5-bromopyridin-2-yl)-3-(2,2-dimethylcyclopropyl)acrylate (920 mg, 2.8 mmol) in HOAc (1.8 mL) was added zinc (3.7 g, 57 mmol) at 18° C. The mixture was stirred at 55° C. for 18 h. LCMS showed the reaction was complete. The reaction mixture was filtered and DCM (10 mL) was added. Then the reaction mixture was quenched with NaHCO$_3$ (20 mL, saturated aqueous solution), extracted with DCM (10 mL×3). The combined organic layers were dried over anhydrous Na$_2$SO$_4$, filtered and concentrated to give a crude product which was purified by chromatography (SiO$_2$, PE:EtOAc=5:1) to give the title compound. MS (ESI) m/z 326.1/328.1 (M+H).

Examples 1 and 2

(R)- and (S)-2-(1-((4-carboxyphenyl)amino)-3-cyclopropyl-1-oxopropan-2-yl)-5-(3-chloro-6-(difluoromethoxy)-2-fluorophenyl)pyridine 1-oxide

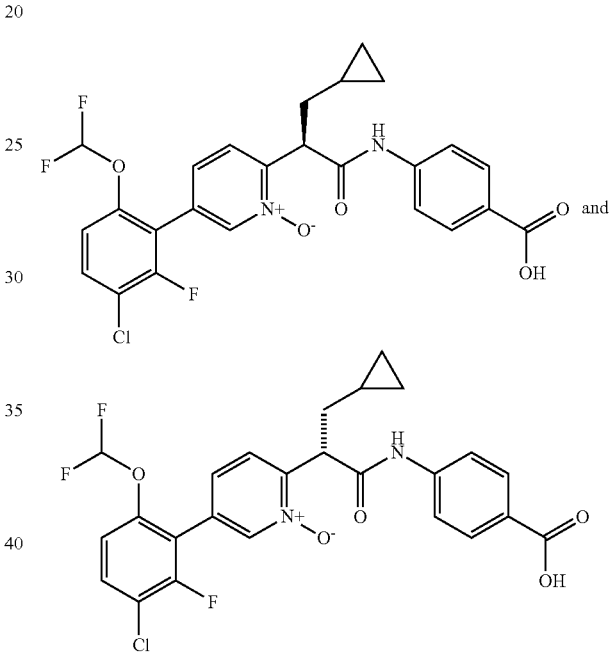

Step 1. tert-Butyl 4-(2-(5-bromopyridin-2-yl)-3-cyclopropylpropanamido)benzoate Lithium 2-(5-bromopyridin-2-yl)-3-cyclopropylpropanoate (1.57 g, 5.7 mmol) in DMF (10 ml) was mixed with tert-butyl 4-aminobenzoate (1.35 g, 6.84 mmol) and HATU (2.60 g, 6.84 mmol), then heated to 50° C. for 2 hours. After it was cooled to rt, the mixture was slowly poured into 200 mL of water while stirring. The precipitate was collected by filtration, washed with water, then dried in vacuum oven at 50° C. overnight to give the title compound. The product was used in the next step without further purification.

Step 2. Tert-Butyl 4-(3-cyclopropyl-2-(5-(4,4,5,5-tetramethyl-1,3,2-dioxaborolan-2-yl)pyridin-2-yl)propanamido)benzoate tert-Butyl 4-(2-(5-bromopyridin-2-yl)-3-cyclopropylpropanamido)benzoate (200 mg, 0.449 mmol) was mixed with 4,4,4',4',5,5,5',5'-octamethyl-2,2'-bi(1,3,2-dioxaborolane) (125 mg, 0.494 mmol), Pd(dppf)Cl$_2$ (65.7 mg, 0.090 mmol), and potassium acetate (132 mg, 1.35 mmol) in a microwave reaction vial. The vial was capped. Air was removed by vacuum, and back-filled with nitrogen (×3). 1,4-Dioxane (2 ml) was introduced with a syringe. The reaction mixture was stirred at 120° C. for 30 minutes. This mixture was used directly in the next reaction.

Step 3. tert-Butyl 4-(2-(5-(3-chloro-6-(difluoromethoxy)-2-fluorophenyl)pyridin-2-yl)-3-cyclopropylpropanamido)benzoate 1-Chloro-4-(difluoromethoxy)-2-fluoro-3-iodobenzene (0.158 g, 0.49 mmol) and Pd(dppf)Cl₂ (33 mg, 0.045 mmol) were added to the reaction mixture from Step 2 above. The vial was capped. Air was removed by vacuum, and back-filled with nitrogen (×3). Aqueous potassium carbonate (1.3 ml, 1.3 mmol) was introduced with a syringe. The mixture was stirred at 90° C. for one hour. The reaction mixture was diluted with ethyl acetate (20 mL), and filtered. The organic layer was separated, and dried over anhydrous sodium sulfate. The mixture was filtered, and the solution was concentrated. The crude product was purified by chromatography on silica gel column eluting with 0-40% EtOAc gradient in isohexane to give the title compound. MS (ESI) m/z 561.1/563.1 (M+H).

Step 4. 4-(2-(5-(3-Chloro-6-(difluoromethoxy)-2-fluorophenyl)pyridin-2-yl)-3-cyclopropyl propanamido)benzoic Acid tert-Butyl 4-(2-(5-(3-chloro-6-(difluoromethoxy)-2-fluorophenyl)pyridin-2-yl)-3-cyclopropyl propanamido)benzoate (250 mg, 0.446 mmol) in DCM (1 ml) was mixed with TFA (1 ml). The resulting mixture was stirred at rt for 30 minutes. The mixture was concentrated. The residue was purified by chromatography on silica gel, eluting with 0-7% MeOH gradient in CH₂Cl₂ to give the title compound. MS (ESI) m/z 505.0/507.0 (M+H).

Step 5. (R)- and (S)-2-(1-((4-Carboxyphenyl)amino)-3-cyclopropyl-1-oxopropan-2-yl)-5-(3-chloro-6-(difluoromethoxy)-2-fluorophenyl)pyridine 1-oxide 4-(2-(5-(3-Chloro-6-(difluoromethoxy)-2-fluorophenyl)pyridin-2-yl)-3-cyclopropyl propanamido) benzoic acid (200 mg, 0.4 mmol) in DCM (2 ml) was mixed with mCPBA (127 mg, 0.52 mmol). The resulting mixture was stirred at rt for 3 days. The crude was directly purified by chromatography on silica gel, eluting with 0-50% gradient of DCM with 10% MeOH and 0.4% AcOH in DCM to give the title compound. This racemic mixture was further separated by chiral SFC on IA column, eluting with 65% 2:1 MeOH-MeCN in CO₂, 100 bar, 35° C., to give two enantiomers of the title compound: fast eluting isomer (Example 1) and slow eluting isomer (Example 2). Example 1: MS (ESI) m/z 521.0/523.0 (M+H).

Example 2: MS (ESI) m/z 521.0/523.0 (M+H). ¹H NMR [(CD₃)₂SO, 500 MHz]: δ 12.73 (v br s, 1H), 10.77 (s, 1H), 8.50 (s, 1H), 7.87 (d, J=8.2 Hz, 2H), 7.78-7.81 (m, 1H), 7.72 (d, J=8.2 Hz, 2H), 7.68 (d, J=8.2 Hz, 1H), 7.48 (d, J=8.1 Hz, 1H), 7.26 (t, J=72.8 Hz, 1H), 7.25 (d, J=7.4 Hz, 1H), 4.54-4.57 (m, 1H), 1.94-1.99 (m, 1H), 177-1.83 (m, 1H), 0.77-0.84 (m, 1H), 0.34-0.45 (m, 2H), 0.11-0.16 (m, 2H).

Examples 3 and 4

(S)- and (R)-2-(1-((4-Carboxyphenyl)amino)-3-cyclobutyl-1-oxopropan-2-yl)-5-(3-chloro-6-(difluoromethyl)-2-fluorophenyl)pyridine 1-oxide

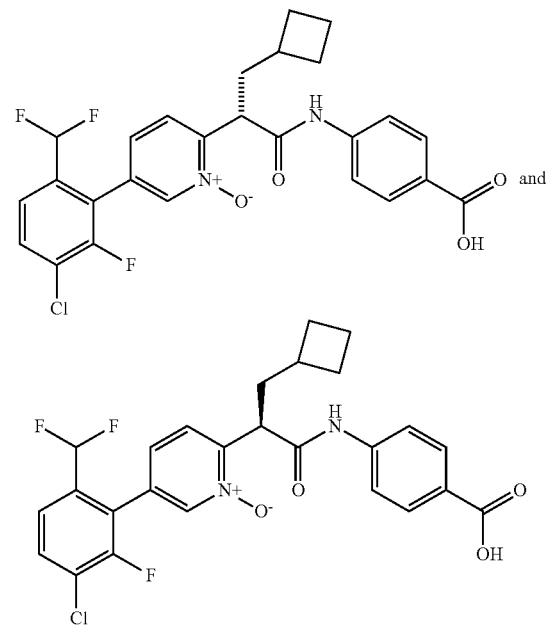

Step 1. tert-Butyl 4-(2-(5-bromopyridin-2-yl)-3-cyclobutylpropanamido)benzoate

Lithium 2-(5-bromopyridin-2-yl)-3-cyclobutylpropanoate (0.97 g, 3.35 mmol) and tert-butyl 4-aminobenzoate (0.71 g, 3.7 mmol) were mixed in DMF (7 ml). HATU (1.53 g, 4.0 mmol) was added. The mixture was stirred at 40° C. overnight. The mixture was diluted with ethyl acetate (100 mL), and washed with water and brine. The organic layer was separated and dried over anhydrous sodium sulfate. The solution was filtered and concentrated. The resulting crude product was purified by chromatography on silica gel column, eluting with 0-50% EtOAc gradient in hexane to give the title compound. MS (ESI) m/z 459/460.9 (M+H).

Step 2. tert-Butyl 4-(3-cyclobutyl-2-(5-(4,4,5,5-tetramethyl-1,3,2-dioxaborolan-2-yl)pyridin-2-yl) propanamido)benzoate tert-Butyl 4-(2-(5-bromopyridin-2-yl)-3-cyclobutylpropanamido)benzoate (250 mg, 0.54 mmol) was mixed with 4,4,4',4',5,5,5',5'-octamethyl-2,2'-bi(1,3,2-dioxaborolane) (152 mg, 0.6 mmol), Pd(dppf)Cl₂ (80 mg, 0.11 mmol) and potassium acetate (160 mg, 1.63 mmol) in a microwave reaction vial. The vial was capped and air was removed by vacuum and back-filled with nitrogen (×3). 1,4-Dioxane (2.5 ml) was introduced with a syringe. The resulting mixture was heated at 120° C. for 40 minutes. After it was cooled to rt, the whole mixture was used in the next step directly.

Step 3. Tert-Butyl 4-(2-(5-(3-chloro-6-(difluoromethyl)-2-fluorophenyl)pyridin-2-yl)-3-cyclobutylpropanamido)benzoate 1-Chloro-4-(difluoromethyl)-2-fluoro-3-iodobenzene (165 mg, 0.54 mmol) and Pd(dppf)Cl$_2$ (39.5 mg, 0.054 mmol) were added to the reaction mixture from Step 2. The vial was capped, and air was removed by vacuum and back-filled with nitrogen (×3). Potassium carbonate solution (1 M, 1.62 ml, 1.62 mmol) and 1,4-dioxane (1 mL) were introduced with syringes. The resulting mixture was heated at 90° C. for one hour. The mixture was diluted with ethyl acetate (70 mL) and washed with water and brine. The organic layer was separated, dried over anhydrous sodium sulfate, filtered, and the solution was concentrated. The crude was purified by chromatography on silica gel column, eluting with 0-100% EtOAc gradient in isohexane to give the title compound. MS (ESI) m/z 559.1/561 (M+H).

Step 4. 4-(2-(5-(3-Chloro-6-(difluoromethyl)-2-fluorophenyl)pyridin-2-yl)-3-cyclobutylpropanamido) benzoic Acid tert-Butyl 4-(2-(5-(3-chloro-6-(difluoromethyl)-2-fluorophenyl)pyridin-2-yl)-3-cyclobutylpropanamido)benzoate (0.27 g, 0.48 mmol) in DCM (1.5 ml) was mixed with TFA (1.4 ml). The resulting mixture was stirred at rt for one hour. The mixture was concentrated, and the crude was purified by chromatography on silica gel, eluting with 0-8% MeOH in DCM to give the title compound. MS (ESI) m/z 503.0/505.1 (M+H). $^1$H NMR [(CD$_3$)$_2$SO, 500 MHz]: δ 12.73 (v br s, 1H), 10.59 (s, 1H), 8.52 (s, 1H), 7.83-7.89 (m, 4H), 7.75 (d, J=Hz, 2H), 7.61-7.63 (m, 2H), 6.78 (t, J=54.0 Hz, 1H), 3.95-3.98 (m, 1H), 2.20-2.28 (m, 2H), 1.94-2.04 (m, 3H), 1.58-1.84 (m, 4H).

Step 5. (S)- and (R)-2-(1-((4-Carboxyphenyl)amino)-3-cyclobutyl-1-oxopropan-2-yl)-5-(3-chloro-6-(difluoromethyl)-2-fluorophenyl)pyridine 1-oxide 4-(2-(5-(3-Chloro-6-(difluoromethyl)-2-fluorophenyl)pyridin-2-yl)-3-cyclobutylpropanamido) benzoic acid (230 mg, 0.457 mmol) in DCM (2 ml) was mixed with mCPBA (147 mg, 0.595 mmol, 70%). The resulting mixture was stirred at rt for 2 hours. The mixture was purified by chromatography on silica gel, eluting with 0-8% MeOH gradient in DCM to give a product contaminated with some mCPBA. This was further purified by flash chromatography on a reverse phase C18 column, eluting with 0-70% acetonitrile gradient in water with 0.1% TFA to give the racemic product. MS (ESI) m/z 519.0/520.8 (M+H). The racemic mixture was separated by SFC on chiral AS column (21×250 mm), eluting with 15% MeOH with 0.2% NH$_4$OH in CO$_2$, 60 mL/min, 100 bar, to give two enantiomers of the title compound as ammonium salts: Fast eluting isomer (Example 3), MS (ESI) m/z 518.9/520.8 (M+H). Slow eluting isomer (Example 4), MS (ESI) m/z 518.9/520.9 (M+H). $^1$H NMR [(CD$_3$)$_2$SO, 500 MHz]: δ 10.73 (s, 1H), 8.46 (s, 1H), 7.86-7.88 (m, 3H), 7.72 (d, J=8.1 Hz, 2H), 7.67 (d, J=7.9 Hz, 1H), 7.60 (d, J=8.2 Hz, 1H), 7.39 (d, J=8.0 Hz, 1H), 6.88 (t, J=53.9 Hz, 1H), 4.40-4.43 (m, 1H), 2.31-2.39 (m, 1H), 1.92-2.16 (m, 4H), 1.64-1.80 (m, 4H). A single crystal structure of Example 4 bound within the catalytic domain of human FXIa enzyme showed that Example 4 had (R)-configuration at the chiral center. By inference, Example 3 is the (S)-enantiomer.

Alternative Syntheses of Examples 3 and 4

Step 1. Methyl 4-(2-(5-bromopyridin-2-yl)-3-cyclobutylpropanamido)benzoate

Lithium 2-(5-bromopyridin-2-yl)-3-cyclobutylpropanoate (15.08 g, 52.0 mmol) in DMF (90 ml) was mixed with methyl 4-aminobenzoate (8.25 g, 54.6 mmol). HATU (23.7 g, 62.4 mmol) was added. The resulting mixture was heated at 45° C. for 2 hours. The whole reaction mixture was poured into 600 mL of water. The product was extracted with ethyl acetate (2×300 mL). The combined organic layers were washed with brine, dried over anhydrous sodium sulfate, and concentrated. The resulting crude product was dissolved in DCM (50 mL) and filtered. The solution was purified by chromatography on silica gel, eluting with 0-30% EtOAc gradient in isohexane to give the title compound. MS (ESI) m/z 417/418.9 (M+H).

Step 2. Methyl 4-(3-cyclobutyl-2-(5-(4,4,5,5-tetramethyl-1,3,2-dioxaborolan-2-yl)pyridin-2-yl)propanamido)benzoate Methyl 4-(2-(5-bromopyridin-2-yl)-3-cyclobutylpropanamido) benzoate (19.1 g, 45.8 mmol) was mixed with 4,4,4',4',5,5,5',5'-octamethyl-2,2'-bi(1,3,2-dioxaborolane) (12.79 g, 50.3 mmol), Pd(dppf)Cl$_2$ (6.70 g, 9.15 mmol) and potassium acetate (13.48 g, 137 mmol) in a round bottle flask. The flask was capped and air was removed by vacuum and back-filled with nitrogen (×3). 1,4-Dioxane (180 ml) was introduced with a cannula. The resulting mixture was heated at 105° C. for 2 hours. LC-MS detected mostly boronic acid, MS (ESI) m/z 383 (M+H). After being cooled to rt, the whole mixture was used in the next step directly.

Step 3. Methyl 4-(2-(5-(3-chloro-6-(difluoromethyl)-2-fluorophenyl)pyridin-2-yl)-3-cyclobutylpropanamido)benzoate 1-Chloro-4-(difluoromethyl)-2-fluoro-3-iodobenzene (15.44 g, 50.4 mmol), Pd(dppf)Cl$_2$ (3.35 g, 4.58 mmol), K$_2$CO$_3$ (18.99 g, 137 mmol), and water (130 ml) were added to the reaction mixture from Step 2. The flask was capped and air was removed by vacuum and back-filled with nitrogen (×3). The resulting mixture was heated at 80° C. for 6 hour. After being cooled to rt, the mixture was extracted with ethyl acetate (500 mL). The organic layer was washed with water and brine, dried over anhydrous sodium sulfate, filtered, and the solution was concentrated. The resulting crude product was purified by chromatography on silica gel, eluting with 0-60% EtOAc gradient isohexane to give the title compound. MS (ESI) m/z 517.1/519.1 (M+H).

Step 4. 5-(3-Chloro-6-(difluoromethyl)-2-fluorophenyl)-2-(3-cyclobutyl-1-((4-(methoxycarbonyl)phenyl)amino)-1-oxopropan-2-yl)pyridine 1-oxide Methyl 4-(2-(5-(3-chloro-6-(difluoromethyl)-2-fluorophenyl)pyridin-2-yl)-3-cyclobutylpropanamido)benzoate (19.2 g, 37.1 mmol) in DCM (100 ml) was mixed with mCPBA (13.7 g, 55.7 mmol, 70%). The resulting mixture was stirred at rt for 5 h. The reaction mixture was diluted with 500 mL of ethyl acetate, and washed with diluted sodium bicarbonate (200 mL) and brine (50 mL). The organic layer was separated, dried over anhydrous sodium sulfate, filtered and the solution was concentrated. The resulting crude product was purified by chromatography on silica gel, eluting with 0-100% EtOAc in isohexane to give the title compound. MS (ESI) m/z 533.1/535.2 (M+H).

Step 5. (S)- and (R)-2-(1-((4-Carboxyphenyl)amino)-3-cyclobutyl-1-oxopropan-2-yl)-5-(3-chloro-6-(difluoromethyl)-2-fluorophenyl)pyridine 1-oxide 5-(3-Chloro-6-(difluoromethyl)-2-fluorophenyl)-2-(3-cyclobutyl-1-((4-(methoxycarbonyl)phenyl)amino)-1-oxopropan-2-yl)pyridine 1-oxide (17.20 g, 32.3 mmol) in 1,4-dioxane (135 ml) was mixed with a 1 M aqueous solution of lithium hydroxide (64.5 ml, 64.5 mmol). The resulting mixture was stirred at 45° C. for 30 minutes and then cooled in an ice-water bath. Solid citric acid (13.6 g, 71 mmol) was added to adjust the pH to 4-5. The product was extracted with EtOAc (200 mL×3). The combined solution was concentrated to almost dryness. The product was then partitioned between ethyl acetate (100 mL) and brine (100 mL, pH was adjusted to ~5 with diluted citric acid solution). The solid was collected by filtration, and washed with water (50 mL) and diethyl ether (50 mL), then dried in a vacuum oven at 50° C. overnight to afford the major portion of the title compound. The organic layer was separated from the filtrate and concentrated. The crude was purified by chromatography on a silica gel, eluting with 0-8% MeOH in DCM to give more product, which was washed with diethyl ether/hexane (1:1, 50 mL) to afford a second crop of the title compound. MS (ESI) m/z 519.0/521.0 (M+H).

The racemic product was dissolved in 1:1 MeOH:DCM at 20 mg/mL and separated by chiral SFC on IA column eluting with 50% EtOH in $CO_2$ to give two enantiomers of the title compound: fast eluting isomer (Example 3): MS (ESI) m/z 519 (M+H). Slow eluting isomer (Example 4): MS (ESI) m/z 519 (M+H). $^1$H NMR [$(CD_3)_2SO$, 500 MHz]: δ 12.71 (br s, 1H), 10.74 (s, 1H), 8.47 (s, 1H), 7.88-7.91 (m, 3H), 7.74 (d, J=8.7 Hz, 2H), 7.69 (d, J=8.3 Hz, 1H), 7.62 (d, J=8.5 Hz, 1H), 7.41 (d, J=8.1 Hz, 1H), 6.91 (t, J=53.9 Hz, 1H), 4.42-4.45 (m, 1H), 2.33-2.42 (m, 1H), 1.93-2.18 (m, 4H), 1.66-1.84 (m, 4H).

Example 5

(R)-5-(3-chloro-6-(difluoromethyl)-2-fluorophenyl)-2-(3-cyclobutyl-1-((4-(ethoxycarbonyl)phenyl)amino)-1-oxopropan-2-yl)pyridine 1-oxide

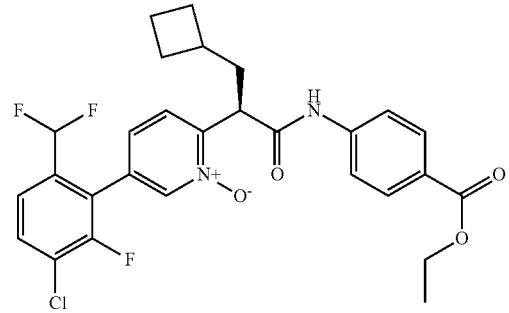 [SMILES: CCOC(=O)c1ccc(NC(=O)[C@H](CC2CCC2)c2ccc(-c3c(C(F)F)ccc(Cl)c3F)c[n+]2[O-])cc1]

(R)-4-(2-(5-(3-chloro-6-(difluoromethyl)-2-fluorophenyl)pyridin-2-yl)-3-cyclobutylpropanamido)benzoic (Example 4, 100 mg, 0.2 mmol) in DCM (0.5 ml) was mixed with iodoethane (0.019 ml, 0.24 mmol) and DBU (0.036 ml, 0.24 mmol). The resulting mixture was stirred at rt for 3 days. The reaction mixture was purified by chromatography on silica gel column, eluting with 0-50% EtOAc in isohexane to give the title compound. MS (ESI) m/z 547.1/549.1 (M+H). $^1$H NMR [$(CD_3)_2SO$, 500 MHz]: δ 10.78 (s, 1H), 8.47 (s, 1H), 7.87-7.93 (m, 3H), 7.77 (d, J=7.2 Hz, 2H), 7.69 (d, J=7.1 Hz, 1H), 7.62 (d, J=7.5 Hz, 1H), 7.41 (d, J=6.0 Hz, 1H), 6.90 (t, J=53.9 Hz, 1H), 4.41-4.46 (m, 1H), 4.26-4.31 (m, 2H), 2.35-2.40 (m, 1H), 1.94-2.18 (m, 4H), 1.66-1.82 (m, 4H), 1.29-1.33 (m, 3H).

By using procedures similar to those described above in Scheme 1 and Examples 1-4, Examples 6 to 19 were synthesized using appropriate starting materials and characterized. The Suzuki steps in these syntheses were carried out either using microwave or conventional thermal heating. Therefore, there are slight variations in reaction time and/or temperature from what were used in Examples 1-4. The stereochemistry of Example 13 was determined by X-ray co-crystal with catalytic domain of FXIa to be the (R)-enantiomer.

| Ex. | Structure | Name | Exact Mass [M + H]$^+$ | Chiral Separation |
|---|---|---|---|---|
| 6 | (structure shown) | (S)- or (R)-4-[(2-{5-[5-chloro-2-(difluoromethoxy)phenyl]-1-oxidopyridin-2-yl}-3-cyclopropylpropanoyl)amino]benzoic acid | 503.0/ 505.0 | AD-H |

| Ex. | Structure | Name | Exact Mass [M + H]+ | Chiral Separation |
|---|---|---|---|---|
| 7 | 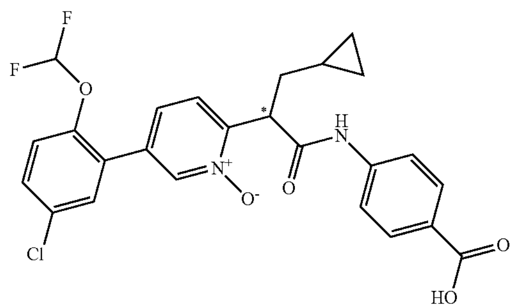 [SMILES: O=C(O)c1ccc(NC(=O)C(CC2CC2)c2ccc(-c3cc(Cl)ccc3OC(F)F)c[n+]2[O-])cc1] | (R)- or (S)-4-[(2-{5-[5-chloro-2-(difluoromethoxy)phenyl]-1-oxidopyridin-2-yl}-3-cyclopropylpropanoyl)amino]benzoic acid | 503.0/ 504.9 | AD-H |
| 8 | 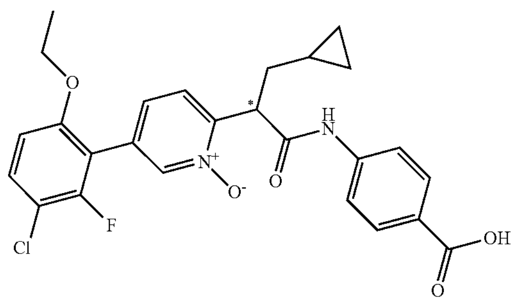 [SMILES: CCOc1ccc(Cl)c(F)c1-c1ccc(C(CC2CC2)C(=O)Nc2ccc(C(=O)O)cc2)[n+]([O-])c1] | (S)- or (R)-4-({2-[5-(3-chloro-6-ethoxy-2-fluorophenyl)-1-oxidopyridin-2-yl]-3-cyclopropylpropanoyl}amino)benzoic acid | 499.1/ 501.1 | AS-H |
| 9 | 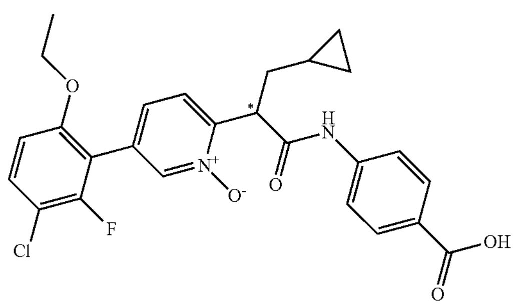 [SMILES: CCOc1ccc(Cl)c(F)c1-c1ccc(C(CC2CC2)C(=O)Nc2ccc(C(=O)O)cc2)[n+]([O-])c1] | (R)- or (S)-4-({2-[5-(3-chloro-6-ethoxy-2-fluorophenyl)-1-oxidopyridin-2-yl]-3-cyclopropylpropanoyl}amino)benzoic acid | 499.1/ 501.1 | AS-H |
| 10 | 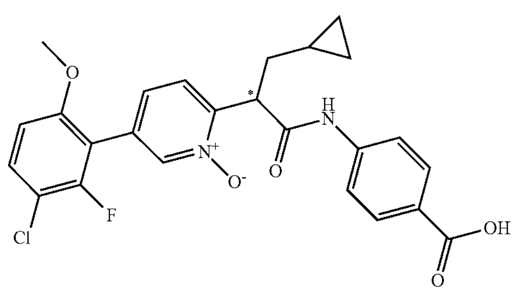 [SMILES: COc1ccc(Cl)c(F)c1-c1ccc(C(CC2CC2)C(=O)Nc2ccc(C(=O)O)cc2)[n+]([O-])c1] | (S)- or (R)-4-({2-[5-(3-chloro-2-fluoro-6-methoxyphenyl)-1-oxidopyridin-2-yl]-3-cyclopropylpropanoyl}amino)benzoic acid | 485.0/ 487.0 | AS-H |
| 11 | 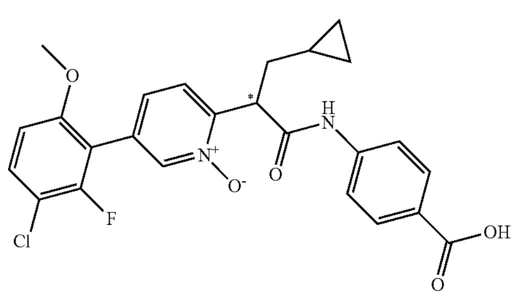 [SMILES: COc1ccc(Cl)c(F)c1-c1ccc(C(CC2CC2)C(=O)Nc2ccc(C(=O)O)cc2)[n+]([O-])c1] | (R)- or (S)-4-({2-[5-(3-chloro-2-fluoro-6-methoxyphenyl)-1-oxidopyridin-2-yl]-3-cyclopropylpropanoyl}amino)benzoic acid | 485.0/ 487.0 | AS-H |

| Ex. | Structure | Name | Exact Mass [M + H]+ | Chiral Separation |
|---|---|---|---|---|
| 12 | 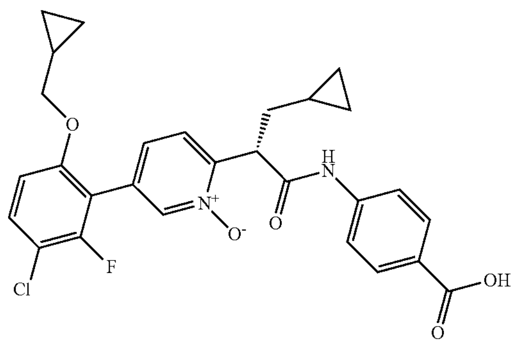 [SMILES: O=C(O)c1ccc(NC(=O)[C@@H](CC2CC2)c2ccc(-c3c(OCC4CC4)ccc(Cl)c3F)c[n+]2[O-])cc1] | (S)-4-[(2-{5-[3-chloro-6-(cyclopropylmethoxy)-2-fluorophenyl]-1-oxidopyridin-2-yl}-3-cyclopropylpropanoyl)amino]benzoic acid | 525.1/ 527.1 | AD-H |
| 13 | 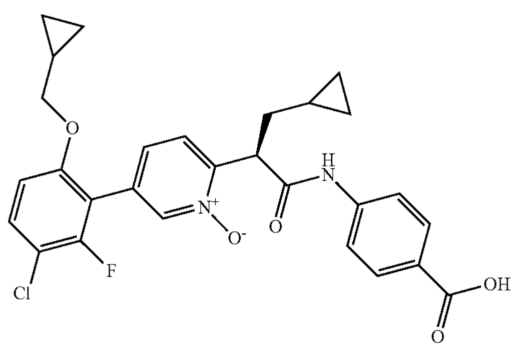 [SMILES: O=C(O)c1ccc(NC(=O)[C@H](CC2CC2)c2ccc(-c3c(OCC4CC4)ccc(Cl)c3F)c[n+]2[O-])cc1] | (R)-4-[(2-{5-[3-chloro-6-(cyclopropylmethoxy)-2-fluorophenyl]-1-oxidopyridin-2-yl}-3-cyclopropylpropanoyl)amino]benzoic acid | 525.1/ 527.1 | AD-H |
| 14 | 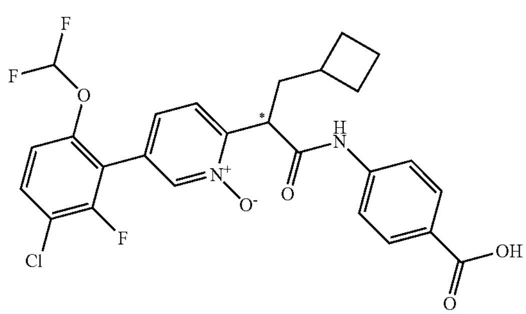 [SMILES: O=C(O)c1ccc(NC(=O)C(CC2CCC2)c2ccc(-c3c(OC(F)F)ccc(Cl)c3F)c[n+]2[O-])cc1] | (S)- or (R)-4-[(2-{5-[3-chloro-6-(difluoromethoxy)-2-fluorophenyl]-1-oxidopyridin-2-yl}-3-cyclobutylpropanoyl)amino]benzoic acid | 534.9/ 537.0 | AS-H |
| 15 | 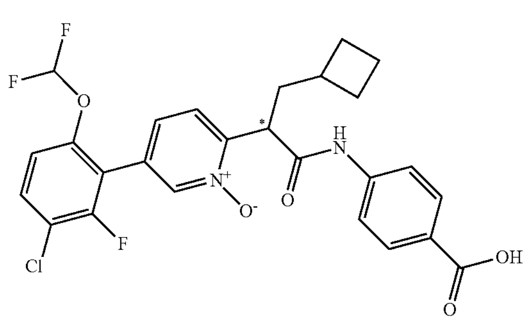 [SMILES: O=C(O)c1ccc(NC(=O)C(CC2CCC2)c2ccc(-c3c(OC(F)F)ccc(Cl)c3F)c[n+]2[O-])cc1] | (R)- or (S)-4-[(2-{5-[3-chloro-6-(difluoromethoxy)-2-fluorophenyl]-1-oxidopyridin-2-yl}-3-cyclobutylpropanoyl)amino]benzoic acid | 535.0/ 537.0 | AS-H |

-continued

| Ex. | Structure | Name | Exact Mass [M + H]⁺ | Chiral Separation |
|---|---|---|---|---|
| 16 | 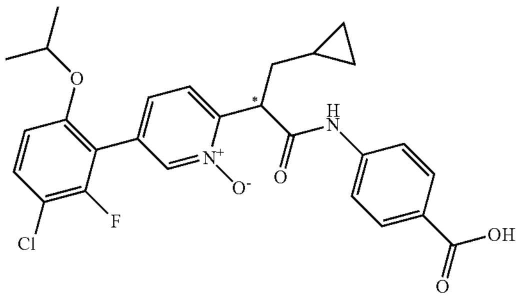 [SMILES: CC(C)Oc1ccc(Cl)c(F)c1-c1ccc(C(CC2CC2)C(=O)Nc2ccc(C(=O)O)cc2)[n+]([O-])c1] | (S)- or (R)-4-[(2-{5-[3-chloro-2-fluoro-6-(1-methylethoxy)phenyl]-1-oxidopyridin-2-yl}-3-cyclopropylpropanoyl)amino]benzoic acid | 513.0/ 515.1 | AS-H |
| 17 | 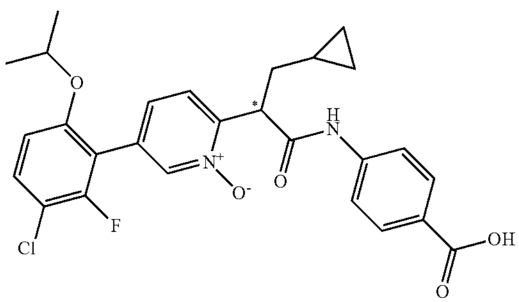 [SMILES: CC(C)Oc1ccc(Cl)c(F)c1-c1ccc(C(CC2CC2)C(=O)Nc2ccc(C(=O)O)cc2)[n+]([O-])c1] | (R)- or (S)-4-[(2-{5-[3-chloro-2-fluoro-6-(1-methylethoxy)phenyl]-1-oxidopyridin-2-yl}-3-cyclopropylpropanoyl)amino]benzoic acid | 513.0/ 515 | AS-H |
| 18 | 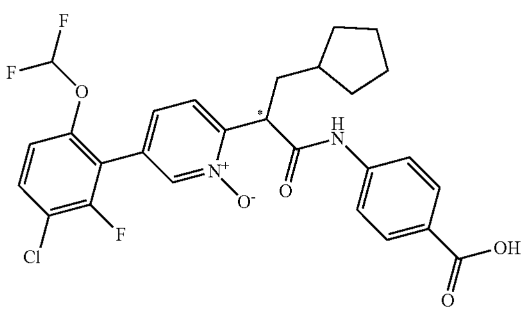 [SMILES: O=C(O)c1ccc(NC(=O)C(CC2CCCC2)c2ccc(-c3c(OC(F)F)ccc(Cl)c3F)c[n+]2[O-])cc1] | (S)- or (R)-4-[(2-{5-[3-chloro-6-(difluoromethoxy)-2-fluorophenyl]-1-oxidopyridin-2-yl}-3-cyclopentylpropanoyl)amino]benzoic acid | 549.0/ 551.1 | AS-H |
| 19 | 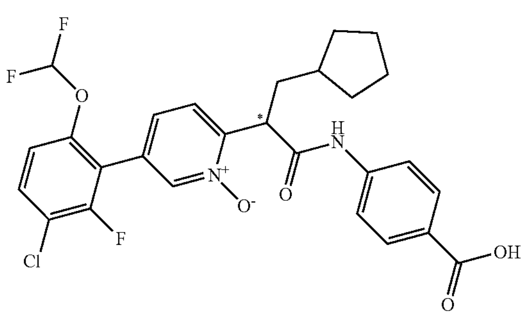 [SMILES: O=C(O)c1ccc(NC(=O)C(CC2CCCC2)c2ccc(-c3c(OC(F)F)ccc(Cl)c3F)c[n+]2[O-])cc1] | (R)- or (S)-4-[(2-{5-[3-chloro-6-(difluoromethoxy)-2-fluorophenyl]-1-oxidopyridin-2-yl}-3-cyclopentylpropanoyl)amino]benzoic acid | 549.0/ 551.0 | AS-H |

By using procedures similar to those described in Scheme 2, Examples 20 and 21 were synthesized using appropriate starting materials and characterized.

| Ex. # | Structure | Name | Exact Mass [M + H]+ | Chiral Separation |
|---|---|---|---|---|
| 20 | 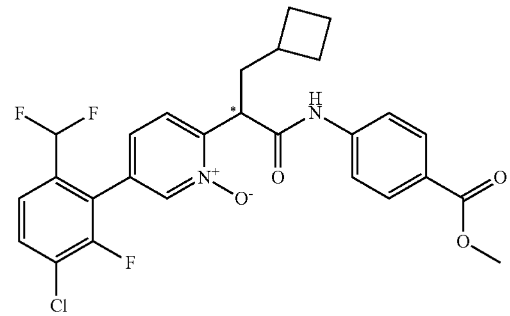 [SMILES: COC(=O)c1ccc(NC(=O)C(CC2CCC2)c2ccc(-c3c(C(F)F)ccc(Cl)c3F)c[n+]2[O-])cc1] | (S)- or (R)-methyl 4-[(2-{5-[3-chloro-6-(difluoromethyl)-2-fluorophenyl]-1-oxidopyridin-2-yl}-3-cyclobutylpropanoyl)amino]benzoate | 533.0/ 535.1 | AS-H |
| 21 | 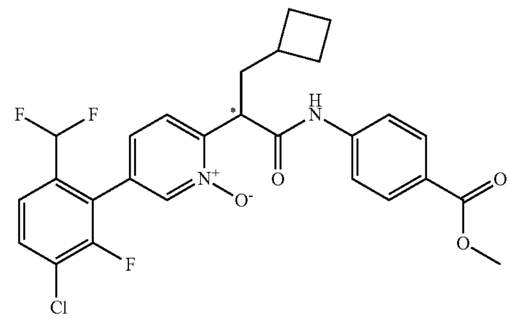 [SMILES: COC(=O)c1ccc(NC(=O)C(CC2CCC2)c2ccc(-c3c(C(F)F)ccc(Cl)c3F)c[n+]2[O-])cc1] | (R)- or (S)-methyl 4-[(2-{5-[3-chloro-6-(difluoromethyl)-2-fluorophenyl]-1-oxidopyridin-2-yl}-3-cyclobutylpropanoyl)amino]benzoate | 533.0/ 535 | AS-H |

Examples 22 and 23
(S)- and (R)-2-(1-((4-carboxyphenyl)amino)-3-cyclopropyl-1-oxopropan-2-yl)-5-(3-chloro-6-(difluoromethyl)-2-fluorophenyl)pyridine 1-oxide

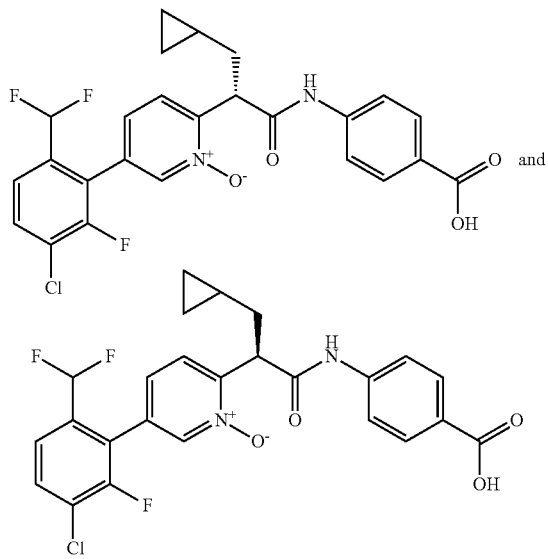

and

Step 1. tert-Butyl 4-(2-(5-(3-chloro-6-(difluoromethyl)-2-fluorophenyl)pyridin-2-yl)-3-cyclopropylpropanamido)benzoate tert-Butyl 4-(2-(5-bromopyridin-2-yl)-3-cyclopropylpropanamido)benzoate (300 mg, 0.674 mmol) was mixed with 4,4,4',4',5,5,5',5'-octamethyl-2,2'-bi(1,3,2-dioxaborolane) (205 mg, 0.808 mmol), Pd(dppf)Cl$_2$·DCM (110 mg, 0.135 mmol), and KOAc (198 mg, 2.021 mmol) in a microwave reaction vial. The vial was capped. Dioxane (3.37 ml) was introduced using a syringe. Air was removed by vacuum, and back-filled with nitrogen (×2). The resulting suspension was stirred at 120° C. for 70 minutes in a microwave reactor. The reaction vial was cooled to RT and 1-chloro-4-(difluoromethyl)-2-fluoro-3-iodobenzene (248 mg, 0.809 mmol) in 1,4-dioxane (0.5 ml) and aq. K$_2$CO$_3$ (2.0 ml, 2.0 mmol, 1 M) and Pd(dppf)Cl$_2$·DCM (55 mg, 0.067 mmol) were added to the reaction mixture. The vial was capped. Air was removed by vacuum, and back-filled with nitrogen (×2). The reaction mixture was stirred at 100° C. for 2 h in a microwave reactor. After cooling to RT, the reaction mixture was diluted with ethyl acetate (70 mL), and filtered through Celite. The organic layer was separated, washed with brine, dried over anhydrous magnesium sulfate, and filtered. The solution was concentrated in vacuo and purified using on silica gel (0-50% EtOAc in hexanes) to afford the title compound. MS (ESI) m/z 545.1/547.2 (M+H). These two stages of the reaction were also run at 105° C. for 2 h and 85° C. for 2 h, respectively, using thermal heating to give comparable results.

Step 2. 4-(2-(5-(3-Chloro-6-(difluoromethyl)-2-fluorophenyl)pyridin-2-yl)-3-cyclopropylpropanamido)benzoic Acid To a solution of tert-butyl 4-(2-(5-(3-chloro-6-(difluoromethyl)-2-fluorophenyl)pyridin-2-yl)-3-cyclopropylpropanamido)benzoate (367 mg, 0.673 mmol) in DCM (2 ml) was added TFA (1 ml, 13 mmol), and the solution was stirred at RT until completion. Volatiles were removed in vacuo and the crude residue was then loaded on silica gel using a small amount of DCM and eluted with 0-50% 3:1 v/v EtOAc-EtOH in hexanes to afford the title compound. MS (ESI) m/z 489.0/490.9 (M+H).

Step 3. (S)- and (R)-2-(1-((4-carboxyphenyl)amino)-3-cyclopropyl-1-oxopropan-2-yl)-5-(3-chloro-6-(difluoromethyl)-2-fluorophenyl)pyridine 1-oxide To a solution of 4-(2-(5-(3-chloro-6-(difluoromethyl)-2-fluorophenyl)pyridin-2-yl)-3 cyclopropylpropanamido)benzoic acid (260 mg, 0.533 mmol) in DCM (5 ml) was added mCPBA (132 mg, 0.533 mmol, 70% purity) and the solution was stirred until completion. The product crashed out from solution. The resulting reaction mixture was then treated with 10 ml of EtOAc and 10 ml of MeOH and stirred at 40° C. for about 15 minutes. The solid started to go into solution. Then, volatiles were removed and 10 ml of DCM was added and it was stirred at 40° C. Then, the crude was directly loaded on silica and eluted with 0-100% 3:1 v/v EtOAc-EtOH in hexanes to afford the racemate. The racemate was resolved on AD-H column (250×20 mm) using 35% IPA in $CO_2$ to give (S)-enantiomer of the title compound (Example 22, first peak) and (R)-enantiomer of the title compound (Example 23, second peak). The stereochemistry of Example 23 was determined from X-ray crystal structure of its co-crystal with catalytic domain of FXIa. Example 22: MS (ESI) m/z 505.0/506.8 (M+H). Example 23: MS (ESI) m/z 505.0/507.1 (M+H), $^1$H NMR [$(CD_3)_2SO$, 500 MHz]: δ 12.7 (br, 1H), 10.77 (s, 1H), 8.48 (s, 1H), 7.87-7.91 (m, 3H), 7.74 (d, J=8.6 Hz, 2H), 7.69 (d, J=8.4 Hz, 1H), 7.62 (d, J=8.6 Hz, 1H), 7.39-7.42 (m, 1H), 6.90 (t, J=54 Hz, 1H), 4.58-4.61 (m, 1H), 1.93-1.99 (m, 1H), 1.80-1.86 (m, 1H), 0.79-0.86 (m, 1H), 0.43-0.47 (m, 1H), 0.36-0.39 (m, 1H), 0.12-0.17 (m, 2H).

By using procedures similar to those shown in Scheme 1 and Examples 22 and 23, Examples 24 to 31 were synthesized using appropriate starting materials and characterized.

| Ex. # | Structure | Name | Exact Mass [M + H]⁺ | Chiral separation |
|---|---|---|---|---|
| 24 | 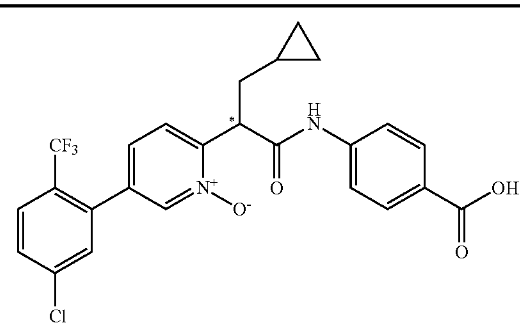 | (S)- or (R)-2-(1-((4-carboxyphenyl)amino)-3-cyclopropyl-1-oxopropan-2-yl)-5-(5-chloro-2-(trifluoromethyl)phenyl)pyridine 1-oxide | 504.8/ 506.8 | AD-H, 50% IPA (0.1% DEA) in $CO_2$ |
| 25 | 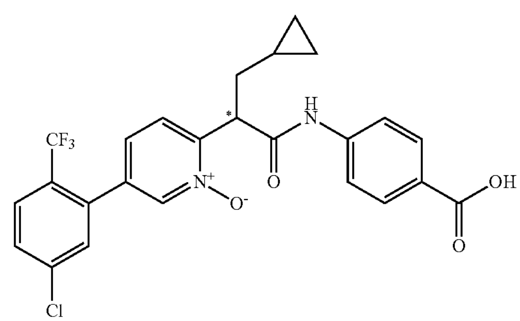 [SMILES: O=C(O)c1ccc(NC(=O)C(CC2CC2)c2ccc(-c3cc(Cl)ccc3C(F)(F)F)c[n+]2[O-])cc1] | (R)- or (S)-2-(1-((4-carboxyphenyl)amino)-3-cyclopropyl-1-oxopropan-2-yl)-5-(5-chloro-2-(trifluoromethyl)phenyl)pyridine 1-oxide | 504.8/ 506.8 | AD-H, 50% IPA (0.1% DEA) in $CO_2$ |
| 26 | 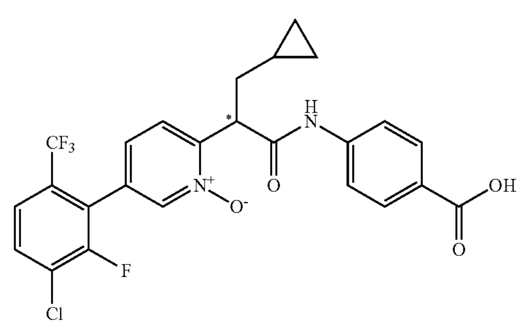 [SMILES: O=C(O)c1ccc(NC(=O)C(CC2CC2)c2ccc(-c3c(C(F)(F)F)ccc(Cl)c3F)c[n+]2[O-])cc1] | (S)- or (R)-2-(1-((4-carboxyphenyl)amino)-3-cyclopropyl-1-oxopropan-2-yl)-5-(3-chloro-2-fluoro-6-(trifluoromethyl)phenyl)pyridine 1-oxide | 522.8/ 524.8 | IA, 40% EtOH (0.1% DEA) in $CO_2$ |

-continued

| Ex. # | Structure | Name | Exact Mass [M + H]+ | Chiral separation |
|---|---|---|---|---|
| 27 | 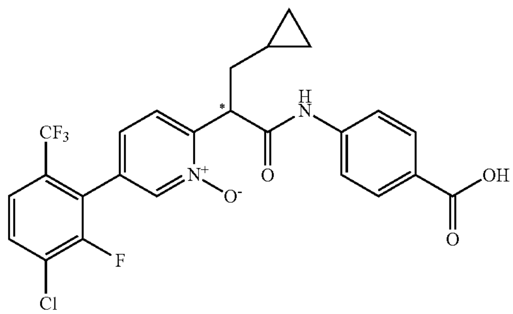 [SMILES: O=C(O)c1ccc(NC(=O)C(CC2CC2)c2ccc(-c3c(C(F)(F)F)ccc(Cl)c3F)c[n+]2[O-])cc1] | (R)- or (S)-2-(1-((4-carboxyphenyl)amino)-3-cyclopropyl-1-oxopropan-2-yl)-5-(3-chloro-2-fluoro-6-(trifluoromethyl)phenyl)pyridine 1-oxide | 522.8/ 524.7 | IA, 40% EtOH (0.1% DEA) in $CO_2$ |
| 28 | 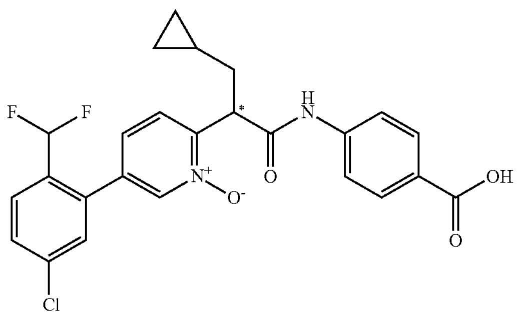 [SMILES: O=C(O)c1ccc(NC(=O)C(CC2CC2)c2ccc(-c3cc(Cl)ccc3C(F)F)c[n+]2[O-])cc1] | (S)- or (R)-2-(1-((4-carboxyphenyl)amino)-3-cyclopropyl-1-oxopropan-2-yl)-5-(5-chloro-2-(difluoromethyl)phenyl)pyridine 1-oxide | 486.8/ 488.7 | AD-H, 45% IPA (0.1% DEA) in $CO_2$ |
| 29 | 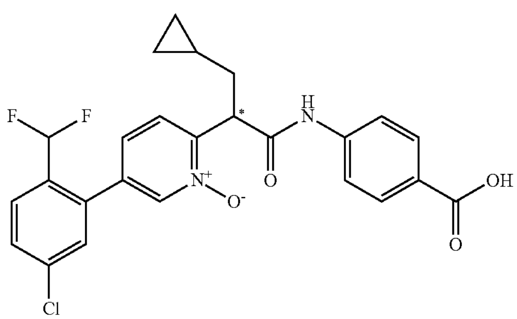 [SMILES: O=C(O)c1ccc(NC(=O)C(CC2CC2)c2ccc(-c3cc(Cl)ccc3C(F)F)c[n+]2[O-])cc1] | (R)- or (S)-2-(1-((4-carboxyphenyl)amino)-3-cyclopropyl-1-oxopropan-2-yl)-5-(5-chloro-2-(difluoromethyl)phenyl)pyridine 1-oxide | 486.8/ 488.7 | AD-H, 45% IPA (0.1% DEA) in $CO_2$ |
| 30 | 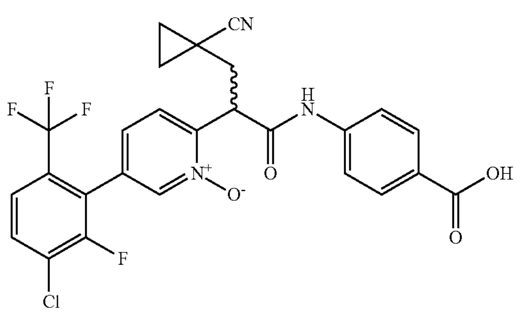 [SMILES: N#CC1(CC(C(=O)Nc2ccc(C(=O)O)cc2)c2ccc(-c3c(C(F)(F)F)ccc(Cl)c3F)c[n+]2[O-])CC1] | 2-(1-((4-carboxyphenyl)amino)-3-(1-cyanocyclopropyl)-1-oxopropan-2-yl)-5-(3-chloro-2-fluoro-6-(trifluoromethyl)phenyl)pyridine 1-oxide | 548.1/ 550.1 | N/A (Racemic) |
| 31 | 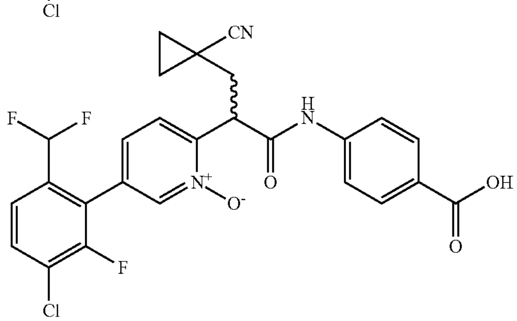 | 2-(1-((4-carboxyphenyl)amino)-3-(1-cyanocyclopropyl)-1-oxopropan-2-yl)-5-(3-chloro-6-(difluoromethyl)-2-fluorophenyl)pyridine 1-oxide | 530.1/ 532 | N/A (Racemic) |

Examples 32 and 33

(S)- and (R)-4-{[2-{5-[3-chloro-6-(difluoromethoxy)-2-fluorophenyl]-1-oxidopyridin-2-yl}-3-(4-oxocyclohexyl)propanoyl]amino}benzoic Acid

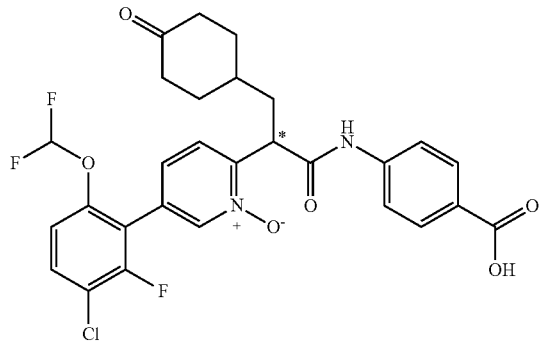

Step 1: 4-(2-(5-(3-chloro-6-(difluoromethoxy)-2-fluorophenyl)pyridin-2-yl)-3-(4-oxocyclohexyl)propanamido)benzoic Acid To a round bottom flask was added tert-butyl 4-(2-(5-(3-chloro-6-(difluoromethoxy)-2-fluorophenyl)pyridin-2-yl)-3-(4-oxocyclohexyl)propanamido)benzoate (20 mg, 0.03 mmol) and HCl/dioxane (4 N) (2 mL) at 12° C. The reaction mixture was stirred at 12° C. for 2 h. LC-MS showed the reaction was complete. The reaction mixture was adjusted to pH 7-8 with sat. NaHCO$_3$ solution, then adjust to pH 5-6 with sat. citric acid solution. Water (15 mL) was added and the mixture was extracted with EtOAc (3×15 mL). The organic layers were combined, washed with brine (20 mL), dried over anhydrous sodium sulfate, filtered and concentrated in vacuo. The residue was purified by prep-RP-HPLC to give the title compound. $^1$H NMR (CD$_3$OD, 400 MHz): δ 8.71 (s, 1H), 8.16 (d, J=8.2 Hz, 1H), 7.98 (d, J=8.6 Hz, 2H), 7.87 (d, J=8.2 Hz, 1H), 7.72 (d, J=8.4 Hz, 2H), 7.64 (t, J=8.6 Hz, 1H), 7.21 (d, J=9.0 Hz, 1H), 6.86 (t, J=72.8, 1H), 4.23 (t, J=7.6 Hz, 1H), 2.19-2.21 (m, 1H), 1.97-2.02 (m, 3H), 1.70-1.75 (m, 2H), 1.25-1.29 (m, 5H). MS (ESI) m/z 560.9 (M+H).

Step 2: 2-(1-((4-carboxyphenyl)amino)-1-oxo-3-(4-oxocyclohexyl)propan-2-yl)-5-(3-chloro-6-(difluoromethoxy)-2-fluorophenyl)pyridine 1-oxide To a round bottom flask was added 4-(2-(5-(3-chloro-6-(difluoromethoxy)-2-fluorophenyl)pyridin-2-yl)-3-(4-oxocyclohexyl)propanamido)benzoic acid (180 mg, 0.27 mmol), DCM (3 mL) and 3-chlorobenzoperoxoic acid (91 mg, 0.41 mmol, 77% purity) at 12° C. The reaction mixture was stirred at 12° C. for 18 h. LC-MS showed the reaction was complete. The reaction mixture was adjusted to pH 7-8 with sat.NaHCO$_3$ solution, then adjusted to pH 5-6 with sat. citric acid. Water (15 mL) was added and the mixture was extracted with DCM (3×15 mL). The organic layers were combined, washed with brine (20 mL), dried over anhydrous sodium sulfate, filtered and concentrated in vacuo. The residue was purified by prep-RP-HPLC to give the title compound. MS (ESI) m/z 577.1 (M+H).

Step 3: (R)- and (S)-2-(1-((4-carboxyphenyl)amino)-1-oxo-3-(4-oxocyclohexyl)propan-2-yl)-5-(3-chloro-6-(difluoromethoxy)-2-fluorophenyl)pyridine 1-oxide (Examples 32 & 33)

2-(1-((4-carboxyphenyl)amino)-1-oxo-3-(4-oxocyclohexyl)propan-2-yl)-5-(3-chloro-6-(difluoromethoxy)-2-fluorophenyl)pyridine 1-oxide (87 mg, 0.15 mmol) was resolved by SFC on AD column (250×30 mm, 5 um) eluting with 45% EtOH containing 0.1% v/v concentrated aq. NH$_3$ in CO$_2$ at 50 ml/min to give enantiomer A (Example 32, first peak) and enantiomer B (Example 33, second peak). Example 32: MS (ESI) m/z 576.9 (M+H). Example 33: $^1$H NMR (CD$_3$OD, 400 MHz): δ 8.43 (s, 1H), 7.87 (d, J=8.7 Hz, 2H), 7.73 (d, J=8.4 Hz, 1H), 7.52-7.65 (m, 4H), 7.11 (d, J=9.0 Hz, 1H), 6.79 (t, J=72.4 Hz, 1H), 4.74.76 (m, 1H), 2.01-2.36 (m, 5H), 1.73-1.95 (m, 3H), 1.23-1.53 (m, 3H). MS (ESI) m/z 577.0 (M+H).

Examples 34 and 35

(S)- and (R)-trans-4-{[2-{5-[3-chloro-6-(difluoromethoxy)-2-fluorophenyl]-1-oxidopyridin-2-yl}-3-(4-hydroxycyclohexyl)propanoyl]amino}benzoic Acid

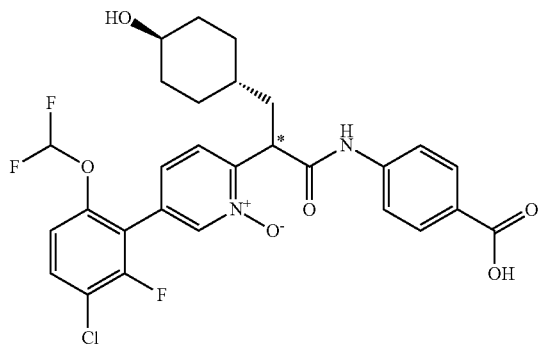 [SMILES: O=C(O)c1ccc(NC(=O)C(C[C@H]2CC[C@H](O)CC2)c2ccc(-c3c(OC(F)F)ccc(Cl)c3F)c[n+]2[O-])cc1]

Step 1: tert-butyl 4-(2-(5-(3-chloro-6-(difluoromethoxy)-2-fluorophenyl)pyridin-2-yl)-3-(4-hydroxycyclohexyl)propanamido)benzoate To a solution of tert-butyl 4-(2-(5-(3-chloro-6-(difluoromethoxy)-2-fluorophenyl)pyridin-2-yl)-3-(4-oxocyclohexyl)propanamido)benzoate (0.3 g, 0.49 mmol) in THF (5 mL) was added NaBH$_4$ (22.07 mg, 0.58 mmol) at 0° C. The reaction mixture was stirred at 15° C. for 2 h. LC-MS showed the reaction was complete. The reaction was quenched with water (20 mL), extracted with EtOAc (3×20 mL), the combined organic layers were dried over anhydrous sodium sulfate, filtered and concentrated. The residue was purified by chromatography (SiO$_2$, 0-30% EtOAc/PE) to give the title compound. MS (ESI) m/z 619.3 (M+H).

Step 2: 4-(2-(5-(3-chloro-6-(difluoromethoxy)-2-fluorophenyl)pyridin-2-yl)-3-(4-hydroxycyclohexyl)propanamido)benzoic Acid To a round bottom flask was added tert-butyl 4-(2-(5-(3-chloro-6-(difluoromethoxy)-2-fluorophenyl)pyridin-2-yl)-

3-(4-hydroxycyclohexyl)propanamido)benzoate (15 mg, 0.024 mmol) and HCl/dioxane (4 N, 2 mL) at 12° C. The reaction mixture was stirred at 12° C. for 2 h. LC-MS showed the reaction was complete. The mixture was concentrated in vacuo and the residue was purified by prep-RP-HPLC to give the title compound. $^1$H NMR (CD$_3$OD, 400 MHz): δ 8.67 (s, 1H), 8.09 (d, J=7.9 Hz, 1H), 7.98 (d, J=8.6 Hz, 2H), 7.81 (d, J=8.2 Hz, 1H), 7.72 (d, J=8.6 Hz, 2H), 7.63 (t, J=8.6 Hz, 1H), 7.21 (d, J=9.0 Hz, 1H), 7.02 (t, J=72.8 Hz, 1H), 4.19 (t, J=7.7 Hz, 1H), 3.44-3.51 (m, 1H), 2.14-2.21 (m, 1H), 1.87-1.96 (m, 4H), 0.98-1.37 (m, 6H). MS (ESI) m/z 562.9 (M+H).

Step 3: 2-(1-((4-carboxyphenyl)amino)-3-(4-hydroxycyclohexyl)-1-oxopropan-2-yl)-5-(3-chloro-6-(difluoromethoxy)-2-fluorophenyl)pyridine 1-oxide To a round bottom flask was added 4-(2-(5-(3-chloro-6-(difluoromethoxy)-2-fluorophenyl)pyridin-2-yl)-3-(4-hydroxycyclohexyl)propanamido)benzoic acid (110 mg, 0.20 mmol), DCM (2 mL) and mCPBA (64.80 mg, 0.29 mmol, 77% purity) at 12° C. The reaction mixture was stirred at 12° C. for 36 h. The reaction was stirred at 30° C. for 20 h. LC-MS showed the reaction was complete. The reaction was quenched with sat. Na$_2$SO$_3$ (3 mL), diluted with water (15 mL), extracted with DCM (3×15 mL), and the combined organic layers were dried over anhydrous sodium sulfate, filtered and concentrated in vacuo. The residue was purified by prep-RP-HPLC to give the title compound. MS (ESI) m/z 579.2 (M+H).

Step 4: 4-{[2-{5-[3-chloro-6-(difluoromethoxy)-2-fluorophenyl]-1-oxidopyridin-2-yl}-3-(4-hydroxycyclohexyl)propanoyl]amino}benzoic Acid (Examples 34 & 35)

2-(1-((4-carboxyphenyl)amino)-3-(4-hydroxycyclohexyl)-1-oxopropan-2-yl)-5-(3-chloro-6-(difluoromethoxy)-2-fluorophenyl)pyridine 1-oxide (87 mg, 0.15 mmol) was resolved by SFC on AD column (250×30 mm, 5 um) eluting with 45% IPA containing 0.1% v/v concentrated aq. NH$_3$ in CO$_2$ at 50 ml/min to give enantiomer A (Example 34, first peak) and enantiomer B (Example 35, second peak). Example 34: MS (ESI) m/z 578.9 (M+H). Example 35: $^1$H NMR (CD$_3$OD, 400 MHz): δ 8.51 (s, 1H), 7.97 (d, J=8.8 Hz, 2H), 7.79 (d, J=8.4 Hz, 1H), 7.62-7.73 (m, 4H), 7.20 (d, J=9.0 Hz, 1H), 6.88 (t, J=72.4 Hz, 1H), 4.78 (t, J=7.5 Hz, 1H), 3.47-3.49 (m, 1H), 2.08-2.17 (m, 1H), 1.81-2.04 (m, 5H), 1.21-1.38 (m, 1H), 1.12-1.18 (m, 4H). MS (ESI) m/z 578.9 (M+H).

By using procedures similar to those described above for Examples 34 and 35, the following compounds were synthesized using appropriate starting materials and characterized.

| Ex. # | Structure | Name | Exact Mass [M + H]⁺ | Chiral Separation |
|---|---|---|---|---|
| 36 | 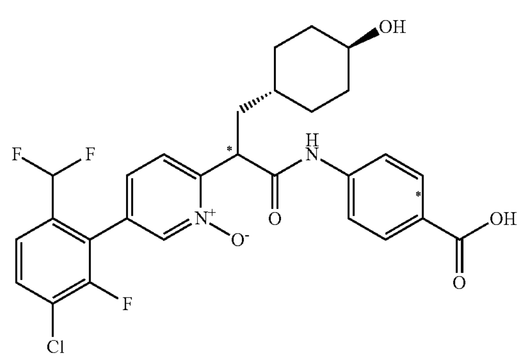 [SMILES: O=C(O)c1ccc(NC(=O)C(C[C@H]2CC[C@H](O)CC2)c2ccc(-c3c(C(F)F)ccc(Cl)c3F)c[n+]2[O-])cc1] | (S)- or (R)-2-(1-((4-carboxyphenyl)amino)-3-((1r,4r)-4-hydroxycyclohexyl)-1-oxopropan-2-yl)-5-(3-chloro-6-(difluoromethyl)-2-fluorophenyl)pyridine 1-oxide | 563.2 | OJ |
| 37 | 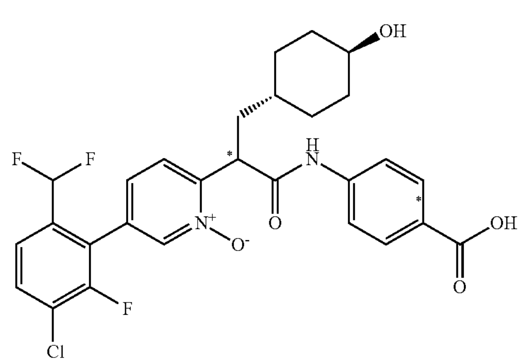 [SMILES: O=C(O)c1ccc(NC(=O)C(C[C@H]2CC[C@H](O)CC2)c2ccc(-c3c(C(F)F)ccc(Cl)c3F)c[n+]2[O-])cc1] | (R)- or (S)-2-(1-((4-carboxyphenyl)amino)-3-((1r,4r)-4-hydroxycyclohexyl)-1-oxopropan-2-yl)-5-(3-chloro-6-(difluoromethyl)-2-fluorophenyl)pyridine 1-oxide | 563.2 | OJ |

Examples 38 and 39

(S)- and (R)-4-{[2-{5-[3-chloro-6-(difluoromethoxy)-2-fluorophenyl]-1-oxidopyridin-2-yl}-3-(4,4-difluorocyclohexyl)propanoyl]amino}benzoic Acid

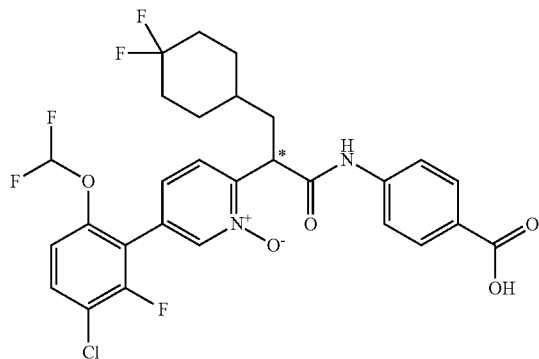 [SMILES: O=C(O)c1ccc(NC(=O)C(CC2CCC(F)(F)CC2)c2ccc(-c3c(OC(F)F)ccc(Cl)c3F)c[n+]2[O-])cc1]

Step 1: Tert-Butyl 4-(2-(5-(3-chloro-6-(difluoromethoxy)-2-fluorophenyl)pyridin-2-yl)-3-(4,4-difluorocyclohexyl)propanamido)benzoate To a solution of tert-butyl 4-(2-(5-(3-chloro-6-(difluoromethoxy)-2-fluorophenyl)pyridin-2-yl)-3-(4-oxocyclohexyl)propanamido)benzoate (50 mg, 0.08 mmol) in DCM (1.5 mL) was added BAST (35.9 mg, 0.16 mmol) at 15° C. The reaction mixture was stirred at 15° C. for 18 h. LC-MS showed the reaction was complete. The reaction mixture was quenched with sat. NaHCO$_3$ (1 mL), diluted with water (10 mL), and extracted with DCM (3×10 mL). The organic layers were combined, dried over anhydrous sodium sulfate, filtered and concentrated in vacuum. The residue was purified by prep-TLC (SiO$_2$, PE:EtOAc=2:1) to give the title compound. $^1$H NMR(CDCl$_3$, 400 MHz): δ 9.66 (s, 1H), 8.60 (s, 1H), 7.87 (d, J=8.8 Hz, 2H), 7.69 (d, J=7.9 Hz, 1H), 7.53 (d, J=8.4 Hz, 2H), 7.41 (t, J=8.6 Hz, 1H), 7.34 (d, J=8.4 Hz, 1H), 7.03 (d, J=8.8 Hz, 1H), 6.32 (t, J=72.4 Hz, 1H), 3.84 (t, J=7.9 Hz, 1H), 2.12-2.15 (m, 2H), 1.95-2.05 (m, 2H), 1.73-1.91 (m, 3H), 1.58-1.67 (m, 2H), 1.47-1.54 (m, 9H), 1.26-1.32 (m, 2H). MS (ESI) m/z 639.2 (M+H).

Step 2: 4-(2-(5-(3-chloro-6-(difluoromethoxy)-2-fluorophenyl)pyridin-2-yl)-3-(4,4-difluorocyclohexyl)propanamido)benzoic Acid To a round bottom flask was added tert-butyl 4-(2-(5-(3-chloro-6-(difluoromethoxy)-2-fluorophenyl)pyridin-2-yl)-3-(4,4-difluorocyclohexyl)propanamido)benzoate (26 mg, 0.04 mmol) and HCl/dioxane (4 N, 2 mL) at 15° C. The reaction mixture was stirred at 15° C. for 2 h. LC-MS showed the reaction was complete. The reaction mixture was adjusted to pH 7-8 with sat. NaHCO$_3$ solution. Then, the mixture was adjusted to pH 5-6 with sat. citric acid solution, diluted with water (15 mL), and extracted with EtOAc (3×15 mL). The organic layers were combined, washed with brine (20 mL), dried over anhydrous sodium sulfate, filtered and concentrated in vacuo. The residue was purified by prep-RP-HPLC to give the title compound. $^1$H NMR (CD$_3$OD, 400 MHz): δ 8.55 (s, 1H), 7.95 (d, J=8.8 Hz, 2H), 7.87 (dd, J=8.0, 1.2 Hz, 1H), 7.67-7.69 (m, 3H), 7.59 (t, J=8.6 Hz, 1H), 7.18 (d, J=9.0 Hz, 1H), 6.81 (t, J=72.8 Hz, 1H), 4.11 (dd, J=8.6, 6.6 Hz, 1H), 2.19-2.22 (m, 2H), 1.86-2.07 (m, 5H), 1.72-1.76 (m, 1H), 1.22-1.51 (m, 3H). MS (ESI) m/z 582.9 (M+H).

Step 3: 2-(1-((4-carboxyphenyl)amino)-3-(4,4-difluorocyclohexyl)-1-oxopropan-2-yl)-5-(3-chloro-6-(difluoromethoxy)-2-fluorophenyl)pyridine 1-oxide To a round bottom flask was added 4-(2-(5-(3-chloro-6-(difluoromethoxy)-2-fluorophenyl)pyridin-2-yl)-3-(4,4-difluorocyclohexyl)propanamido)benzoic acid (140 mg, 0.24 mmol), DCM (3 mL) and mCPBA (63.80 mg, 0.29 mmol, 77% purity) at 15° C. The reaction mixture was stirred at 15° C. for 18 h. LC-MS showed the reaction was complete. The reaction mixture was adjusted to pH 7-8 with sat. NaHCO$_3$ solution, then adjusted to pH 5-6 with sat. citric acid, diluted with water (15 mL), and extracted with DCM (3×15 mL). The organic layers were combined, washed with brine (20 mL), dried over anhydrous sodium sulfate, filtered and concentrated in vacuo. The residue was purified by prep-RP-HPLC to give the title compound. MS (ESI) m/z 599.0 (M+H).

Step 4: 2-(1-((4-carboxyphenyl)amino)-3-(4,4-difluorocyclohexyl)-1-oxopropan-2-yl)-5-(3-chloro-6-(difluoromethoxy)-2-fluorophenyl)pyridine 1-oxide (Examples 38 & 39)

2-(1-((4-carboxyphenyl)amino)-3-(4,4-difluorocyclohexyl)-1-oxopropan-2-yl)-5-(3-chloro-6-(difluoromethoxy)-2-fluorophenyl)pyridine 1-oxide (65 mg, 0.11 mmol) was resolved by SFC on AD column (250×30 mm, 5 um) eluting with 40% EtOH containing 0.1% v/v concentrated aq. NH$_3$ in CO$_2$ at 60 ml/min to give enantiomer A (Example 38, first peak) and enantiomer B (Example 39, second peak). Example 38: MS (ESI) m/z 598.9 (M+H). Example 39: $^1$H NMR (CD$_3$OD, 400 MHz): δ 8.41 (br s, 1H), 7.87 (d, J=8.2 Hz, 2H), 7.70 (d, J=8.4 Hz, 1H), 7.52-7.64 (m, 4H), 7.11 (d, J=9.0 Hz, 1H), 6.78 (t, J=72.8 Hz, 1H), 4.70-4.72 (m, 1H), 2.05-2.13 (m, 1H), 1.77-1.99 (m, 5H), 1.54-1.71 (m, 2H), 1.25-1.45 (m, 3H). MS (ESI) m/z 598.9 (M+H).

Examples 40 and 41

(S)- and (R)-Cis-4-{[2-{5-[3-chloro-6-(difluoromethoxy)-2-fluorophenyl]-1-oxidopyridin-2-yl}-3-(4-hydroxy-4-methylcyclohexyl)propanoyl]amino}benzoic Acid

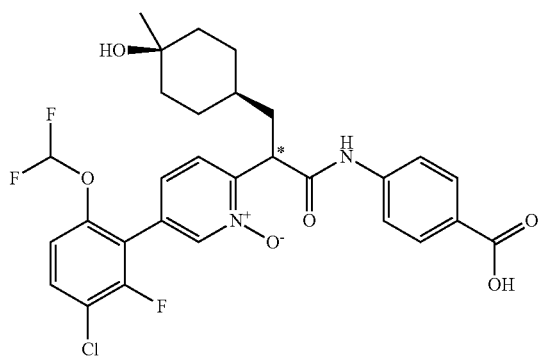 [SMILES: C[C@]1(O)CC[C@@H](CC(C(=O)Nc2ccc(C(=O)O)cc2)c2ccc(-c3c(OC(F)F)ccc(Cl)c3F)c[n+]2[O-])CC1]

Step 1: Cis-4-(2-(5-(3-chloro-6-(difluoromethoxy)-2-fluorophenyl)pyridin-2-yl)-3-(4-hydroxy-4-methylcyclohexyl)propanamido)benzoic Acid and 4-(2-(5-(3-chloro-6-(difluoromethoxy)-2-fluorophenyl)pyridin-2-yl)-3-(4-methyl-4-(2,2,2-trifluoroacetoxy)cyclohexyl)propanamido)benzoic Acid To a solution of tert-butyl cis-4-(2-(5-(3-chloro-6-(difluoromethoxy)-2-fluorophenyl)pyridin-2-yl)-3-(4-hydroxy-4-methylcyclohexyl)propanamido)benzoate (130 mg, 0.21 mmol) in DCM (3 mL) was added TFA (1 mL) at 15° C. The reaction mixture was stirred at 40° C. for 2 h. LC-MS showed the reaction was complete. The mixture was adjusted to pH 7-8 with sat. NaHCO$_3$ solution, then adjusted to pH 5-6 with sat. citric acid, diluted with water (10 mL), and extracted with DCM (3×10 mL). The combined organic layers were dried over anhydrous sodium sulfate, filtered and the filtrate was concentrated in vacuo to give a mixture of 4-(2-(5-(3-chloro-6-(difluoromethoxy)-2-fluorophenyl)pyridin-2-yl)-3-(4-hydroxy-4-methylcyclohexyl)propanamido)benzoic acid and 4-(2-(5-(3-chloro-6-(difluoromethoxy)-2-fluorophenyl)pyridin-2-yl)-3-(4-methyl-4-(2,2,2-trifluoroacetoxy)cyclohexyl)propanamido)benzoic acid (1:2) which was directly used for next step without further purification.

Step 2: Cis-4-(2-(5-(3-chloro-6-(difluoromethoxy)-2-fluorophenyl)pyridin-2-yl)-3-(4-methyl-4-(2,2,2-trifluoroacetoxy)cyclohexyl)propanamido)benzoic Acid To a round bottom flask was added a mixture of 4-(2-(5-(3-chloro-6-(difluoromethoxy)-2-fluorophenyl)pyridin-2-yl)-3-(4-hydroxy-4-methylcyclohexyl)propanamido)benzoic acid and 4-(2-(5-(3-chloro-6-(difluoromethoxy)-2-fluorophenyl)pyridin-2-yl)-3-(4-methyl-4-(2,2,2-trifluoroacetoxy)cyclohexyl)propanamido)benzoic acid (1:2) (125 mg, 0.083 mmol), THF (3 mL), lithium hydroxide hydrate (6.97 mg, 0.166 mmol) and water (0.3 mL) at 12° C. The reaction mixture was stirred at 12° C. for 1 h. LC-MS showed the reaction was complete. The mixture was adjusted to pH 5-6 with sat. citric acid, diluted with water (10 mL), and extracted with EtOAc (3×10 mL). The combined organic layers were dried over anhydrous sodium sulfate, filtered and the filtrate was concentrated in vacuo to give the title compound which was directly used for next step without further purification. MS (ESI) m/z 577.2 (M+H).

Step 3: 2-(1-((4-carboxyphenyl)amino)-3-(4-hydroxy-4-methylcyclohexyl)-1-oxopropan-2-yl)-5-(3-chloro-6-(difluoromethoxy)-2-fluorophenyl)pyridine 1-oxide To a round bottom flask was added 4-(2-(5-(3-chloro-6-(difluoromethoxy)-2-fluorophenyl)pyridin-2-yl)-3-(4-hydroxy-4-methylcyclohexyl)propanamido)benzoic acid (100 mg, 0.14 mmol), DCM (3 mL), THF (0.5 mL) and mCPBA (34.2 mg, 0.168 mmol, 77% purity) at 15° C. The reaction mixture was stirred at 15° C. for 18 h. LC-MS showed the reaction was complete. The reaction mixture was quenched with sat. Na$_2$S$_2$O$_3$ (3 mL), diluted with water (15 mL), extracted with DCM (3×15 mL). The organic layers were combined, washed with brine (20 mL), dried over anhydrous sodium sulfate, filtered and concentrated in vacuo. The residue was purified by prep-RP-HPLC to give the title compound. MS (ESI) m/z 593.2 (M+H).

Step 4: 2-(1-((4-carboxyphenyl)amino)-3-(4-hydroxy-4-methylcyclohexyl)-1-oxopropan-2-yl)-5-(3-chloro-6-(difluoromethoxy)-2-fluorophenyl)pyridine 1-oxide (Examples 40 & 41)

2-(1-((4-carboxyphenyl)amino)-3-(4-hydroxy-4-methylcyclohexyl)-1-oxopropan-2-yl)-5-(3-chloro-6-(difluoromethoxy)-2-fluorophenyl)pyridine 1-oxide (51 mg, 0.086 mmol) was resolved by SFC AS column (250×30 mm, 10 um) eluting with 35% MeOH containing 0.1% v/v concentrated aq. NH$_3$ in CO$_2$ at 80 ml/min to give enantiomer A (Example 40, first peak) and enantiomer B (Example 41, second peak). Example 40: $^1$H NMR (CD$_3$OD, 400 MHz): δ 8.50 (s, 1H), 7.97 (d, J=8.6 Hz, 2H), 7.80 (d, J=8.4 Hz, 1H), 7.61-7.73 (m, 4H), 7.21 (d, J=9.0 Hz, 1H), 6.88 (t, J=72.4 Hz, 1H), 4.82 (t, J=7.5 Hz, 1H), 2.11-2.21 (m, 1H), 1.87-1.97 (m, 1H), 1.58-1.80 (m, 4H), 1.28-1.51 (m, 5H), 1.15 (s, 3H). MS (ESI) m/z 592.9 (M+H). Example 41: $^1$H NMR (CD$_3$OD, 400 MHz): δ 8.51 (s, 1H), 7.97 (d, J=8.4 Hz, 2H), 7.81 (d, J=8.4 Hz, 1H), 7.61-7.73 (m, 4H), 7.22 (d, J=9.0 Hz, 1H), 6.88 (t, J=72.4 Hz, 1H), 4.83 (t, J=7.6 Hz, 1H), 2.11-2.23 (m, 1H), 1.89-1.98 (m, 1H), 1.58-1.80 (m, 4H), 1.41-1.55 (m, 2H), 1.29-1.38 (m, 3H), 1.16 (s, 3H). MS (ESI) m/z 592.9 (M+H).

By using procedures similar to those described above, the following compounds were synthesized using appropriate starting materials and characterized.

| Ex. # | Structure | Name | Exact Mass [M + H]$^+$ | Chiral Separation |
|---|---|---|---|---|
| 40 | 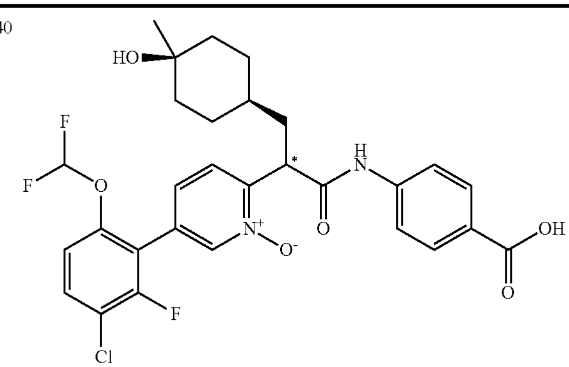 | 2-(1-((4-carboxyphenyl)amino)-3-((1s,4s)-4-hydroxy-4-methylcyclohexyl)-1-oxopropan-2-yl)-5-(3-chloro-6-(difluoromethoxy)-2-fluorophenyl)pyridine 1-oxide | 592.9 | Cis, fast-eluting peak from AS column |

| Ex. # | Structure | Name | Exact Mass [M + H]+ | Chiral Separation |
|---|---|---|---|---|
| 41 | 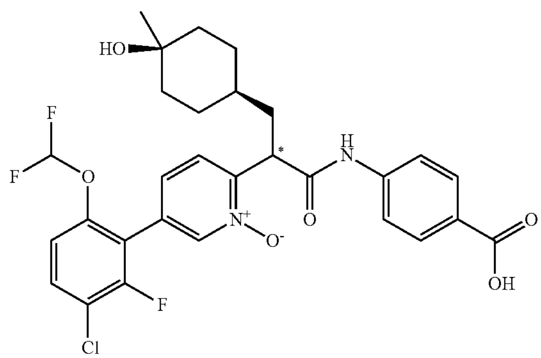 [SMILES: C[C@]1(O)CC[C@@H](CC(C(=O)Nc2ccc(C(=O)O)cc2)c2ccc(-c3c(OC(F)F)ccc(Cl)c3F)c[n+]2[O-])CC1] | 2-(1-((4-carboxyphenyl)amino)-3-((1s,4s)-4-hydroxy-4-methylcyclohexyl)-1-oxopropan-2-yl)-5-(3-chloro-6-(difluoromethoxy)-2-fluorophenyl)pyridine 1-oxide | 592.9 | Cis, slow-eluting peak from AS column |
| 42 | 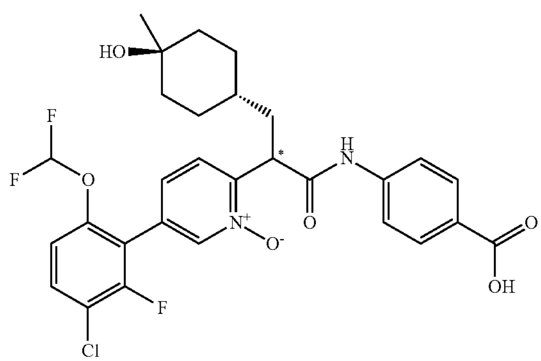 [SMILES: C[C@]1(O)CC[C@H](CC(C(=O)Nc2ccc(C(=O)O)cc2)c2ccc(-c3c(OC(F)F)ccc(Cl)c3F)c[n+]2[O-])CC1] | 2-(1-((4-carboxyphenyl)amino)-3-((1r,4r)-4-hydroxy-4-methylcyclohexyl)-1-oxopropan-2-yl)-5-(3-chloro-6-(difluoromethoxy)-2-fluorophenyl)pyridine 1-oxide | 593.0 | Trans, fast-eluting peak from OJ column |
| 43 | 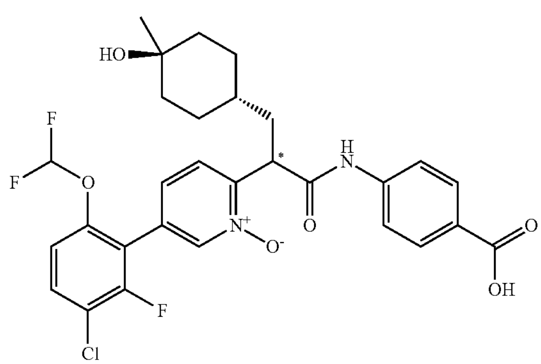 [SMILES: C[C@]1(O)CC[C@H](CC(C(=O)Nc2ccc(C(=O)O)cc2)c2ccc(-c3c(OC(F)F)ccc(Cl)c3F)c[n+]2[O-])CC1] | 2-(1-((4-carboxyphenyl)amino)-3-((1r,4r)-4-hydroxy-4-methylcyclohexyl)-1-oxopropan-2-yl)-5-(3-chloro-6-(difluoromethoxy)-2-fluorophenyl)pyridine 1-oxide | 592.9 | Trans, slow-eluting peak from OJ column |
| 44 | 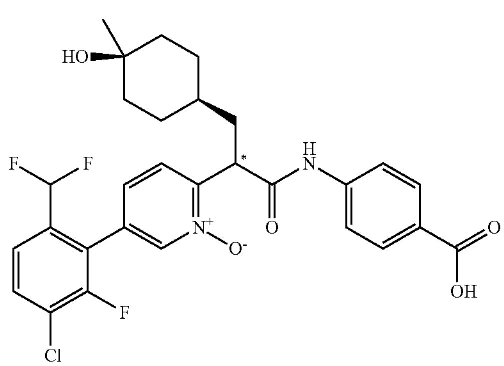 [SMILES: C[C@]1(O)CC[C@@H](CC(C(=O)Nc2ccc(C(=O)O)cc2)c2ccc(-c3c(C(F)F)ccc(Cl)c3F)c[n+]2[O-])CC1] | 2-(1-((4-carboxyphenyl)amino)-3-((1s,4s)-4-hydroxy-4-methylcyclohexyl)-1-oxopropan-2-yl)-5-(3-chloro-6-(difluoromethyl)-2-fluorophenyl)pyridine 1-oxide | 576.9 | Cis, fast-eluting peak from AD column |

-continued

| Ex. # | Structure | Name | Exact Mass [M + H]+ | Chiral Separation |
|---|---|---|---|---|
| 45 | 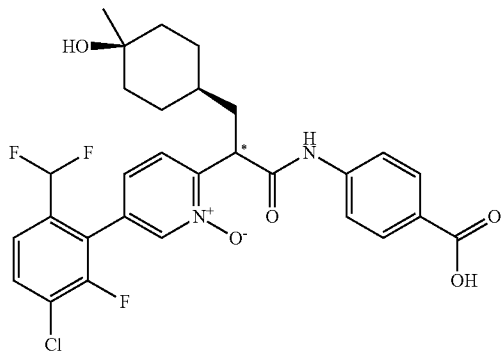 [SMILES: C[C@]1(O)CC[C@@H](CC(C(=O)Nc2ccc(C(=O)O)cc2)c2ccc(-c3c(C(F)F)ccc(Cl)c3F)c[n+]2[O-])CC1] | 2-(1-((4-carboxyphenyl)amino)-3-((1s,4s)-4-hydroxy-4-methylcyclohexyl)-1-oxopropan-2-yl)-5-(3-chloro-6-(difluoromethyl)-2-fluorophenyl)pyridine 1-oxide | 577.0 | Cis, slow-eluting peak from AD column |
| 46 | 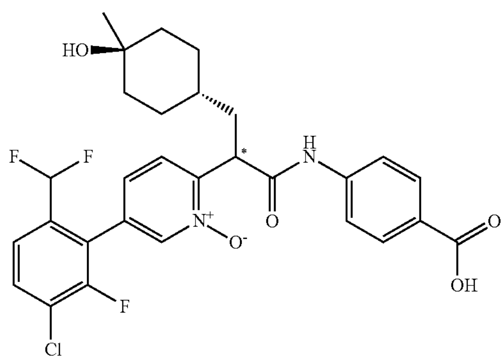 [SMILES: C[C@]1(O)CC[C@H](CC(C(=O)Nc2ccc(C(=O)O)cc2)c2ccc(-c3c(C(F)F)ccc(Cl)c3F)c[n+]2[O-])CC1] | 2-(1-((4-carboxyphenyl)amino)-3-((1r,4r)-4-hydroxy-4-methylcyclohexyl)-1-oxopropan-2-yl)-5-(3-chloro-6-(difluoromethyl)-2-fluorophenyl)pyridine 1-oxide | 576.9 | Trans, fast-eluting peak from OJ column |
| 47 | 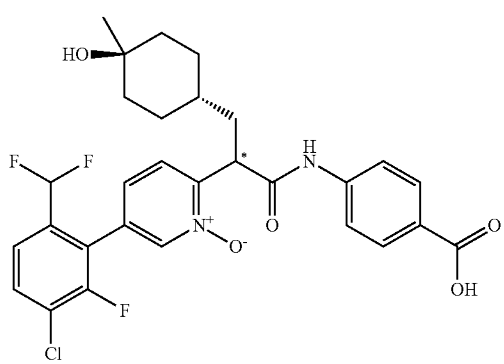 [SMILES: C[C@]1(O)CC[C@H](CC(C(=O)Nc2ccc(C(=O)O)cc2)c2ccc(-c3c(C(F)F)ccc(Cl)c3F)c[n+]2[O-])CC1] | 2-(1-((4-carboxyphenyl)amino)-3-((1r,4r)-4-hydroxy-4-methylcyclohexyl)-1-oxopropan-2-yl)-5-(3-chloro-6-(difluoromethyl)-2-fluorophenyl)pyridine 1-oxide | 576.9 | Trans, slow-eluting peak from OJ column |

Examples 48-50

(±)-, (S)-, and (R)-2-(1-((4-carboxyphenyl)amino)-3-(3,3-difluorocyclobutyl)-1-oxopropan-2-yl)-5-(3-chloro-6-(difluoromethoxy)-2-fluorophenyl)pyridine 1-oxide

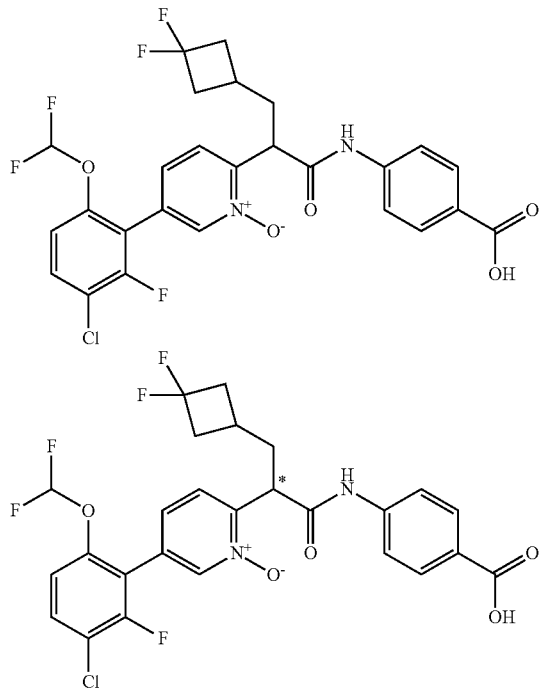

Step 1: Lithium 2-(5-(3-chloro-6-(difluoromethoxy)-2-fluorophenyl)pyridin-2-yl)-3-(5,8-dioxaspiro[3.4]octan-2-yl)propanoate To a solution of ethyl 2-(5-(3-chloro-6-(difluoromethoxy)-2-fluorophenyl)pyridin-2-yl)-3-(5,8-dioxaspiro[3.4]octan-2-yl)propanoate (800 mg, 1.65 mmol) in THF (10 mL) and water (5 mL) was added lithium hydroxide hydrate (76.0 mg, 1.81 mmol) at 15° C. The resulting mixture was stirred at 50° C. for 5 h. LC-MS indicated the reaction was complete. The reaction mixture was concentrated in vacuum to give the crude title compound, which was used without further purification. MS (ESI) m/z 458.1 (M+H) (as the acid form).

Step 2: Methyl 4-(2-(5-(3-chloro-6-(difluoromethoxy)-2-fluorophenyl)pyridin-2-yl)-3-(5,8-dioxaspiro[3.4]octan-2-yl)propanamido)benzoate To a 100 mL round bottom flask was added lithium 2-(5-(3-chloro-6-(difluoromethoxy)-2-fluorophenyl)pyridin-2-yl)-3-(5,8-dioxaspiro[3.4]octan-2-yl)propanoate (500 mg, 1.08 mmol), methyl 4-aminobenzoate (163 mg, 1.08 mmol) and HATU (492 mg, 1.29 mmol) at 20° C. The reaction mixture was stirred at 20° C. for 12 h. LC-MS showed reaction was complete. The reaction mixture was diluted with water (50 mL) and extracted with EtOAc (50 mL×3), the combined organic layers were washed with brine (50 mL), dried over anhydrous sodium sulfate, filtered and concentrated. The crude product was purified by chromatography (SiO$_2$, PE:EtOAc=50:1 to 2:1 gradient) to give the title compound. $^1$H NMR (CDCl$_3$, 400 MHz): δ 9.99 (s, 1H), 8.62 (s, 1H), 7.97 (d, J=8.6 Hz, 2H), 7.73 (dd, J=8.0, 1.2 Hz, 1H), 7.62 (d, J=8.8 Hz, 2H), 7.40-7.49 (m, 1H), 7.37 (d, J=7.6 Hz, 1H), 7.03-7.11 (m, 1H), 6.37 (t, J=72.4 Hz, 1H), 3.87 (s, 3H), 3.81-3.82 (m, 4H), 3.70-3.76 (m, 1H), 2.33-2.46 (m, 2H), 2.16-2.30 (m, 2H), 1.98-2.02 (m, 1H), 1.79-1.87 (m, 1H), 1.41-1.43 (m, 1H). MS (ESI) m/z 591.1 (M+H).

Step 3: Methyl 4-(2-(5-(3-chloro-6-(difluoromethoxy)-2-fluorophenyl)pyridin-2-yl)-3-(3-oxocyclobutyl)propanamido)benzoate To a solution of methyl 4-(2-(5-(3-chloro-6-(difluoromethoxy)-2-fluorophenyl)pyridin-2-yl)-3-(5,8-dioxaspiro[3.4]octan-2-yl)propanamido)benzoate (350 mg, 0.59 mmol) in acetone (10 mL) was added HCl (2.96 mL, 2.96 mmol) at 20° C. The mixture was stirred at 20° C. for 12 h. LC-MS showed the reaction was complete. The mixture was diluted with sat. NaHCO$_3$ (30 mL), extracted with EtOAc (30 mL×3), the combined organic layers were washed with brine (30 mL), dried over anhydrous sodium sulfate, filtered and concentrated to give the title compound which was used in the next step without further purification. $^1$H NMR (CDCl$_3$, 400 MHz): δ 10.01 (s, 1H), 8.67 (s, 1H), 7.99 (d, J=8.8 Hz, 2H), 7.74-7.79 (m, 1H), 7.63 (d, J=8.8 Hz, 2H), 7.47 (t, J=8.5 Hz, 1H), 7.35-7.41 (m, 1H), 7.08 (d, J=9.0 Hz, 1H), 6.38 (t, J=72.4 Hz, 1H), 3.88 (s, 3H), 3.80 (t, J=7.5 Hz, 1H), 3.12-3.22 (m, 1H), 2.98-3.10 (m, 1H), 2.73-2.84 (m, 1H), 2.48-2.66 (m, 2H), 2.31-2.45 (m, 2H). MS (ESI) m/z 547.1 (M+H).

Step 4: Methyl 4-(2-(5-(3-chloro-6-(difluoromethoxy)-2-fluorophenyl)pyridin-2-yl)-3-(3,3-difluorocyclobutyl)propanamido)benzoate To a solution of methyl 4-(2-(5-(3-chloro-6-(difluoromethoxy)-2-fluorophenyl)pyridin-2-yl)-3-(3-oxocyclobutyl)propanamido)benzoate (250 mg, 0.46 mmol) in DCM (5 mL) was added a solution of BAST (4.21 mL, 22.86 mmol) in DCM (5 mL) at 15° C. The reaction mixture was stirred at 15° C. for 18 h. LC-MS showed the reaction was complete. The reaction mixture was quenched with sat. NaHCO$_3$ (3 mL), diluted with water (10 mL), and extracted with DCM (3×10 mL). The organic layers were combined, dried over anhydrous sodium sulfate, filtered and concentrated in vacuum. The residue was purified by prep-TLC (SiO$_2$, PE:EtOAc=1:1) to give the title compound. MS (ESI) m/z 569.1 (M+H).

Step 5: 4-(2-(5-(3-Chloro-6-(difluoromethoxy)-2-fluorophenyl)pyridin-2-yl)-3-(3,3-difluorocyclobutyl)propanamido)benzoic Acid To a round bottom flask was added methyl 4-(2-(5-(3-chloro-6-(difluoromethoxy)-2-fluorophenyl)pyridin-2-yl)-3-(3,3-difluorocyclobutyl)propanamido)benzoate (10 mg, 0.018 mmol), NaOH (3.5 mg, 0.088 mmol), MeOH (1 mL) and water (0.2 mL) at 25° C. The reaction mixture was stirred at 25° C. for 12 h. LC-MS showed reaction was complete. The reaction mixture was concentrated in vacuo and purified by prep-RP-HPLC to give the title compound. $^1$H NMR (CD$_3$OD, 400 MHz): δ 8.64 (s, 1H), 7.96-8.04 (m, 3H), 7.71-7.78 (m, 3H), 7.64 (t, J=8.7 Hz, 1H), 7.22 (d, J=9.0 Hz, 1H), 6.85 (t, J=72.8 Hz, 1H), 4.02 (t, J=7.5 Hz, 1H), 2.65-2.68 (m, 2H), 2.40-2.50 (m, 1H), 2.14-2.29 (m, 4H). MS (ESI) m/z 554.9 (M+H).

Step 6: (±)-2-(1-((4-carboxyphenyl)amino)-3-(3,3-difluorocyclobutyl)-1-oxopropan-2-yl)-5-(3-chloro-6-(difluoromethoxy)-2-fluorophenyl)pyridine 1-oxide (Example 48)

To a solution of 4-(2-(5-(3-chloro-6-(difluoromethoxy)-2-fluorophenyl)pyridin-2-yl)-3-(3,3-difluorocyclobutyl)propanamido)benzoic acid (20 mg, 0.036 mmol) in DCM (2 mL) was added mCPBA (9.3 mg, 0.054 mmol, 70% purity). The mixture was stirred at 25° C. for 2 h. LC-MS indicated that the reaction was complete. The reaction mixture was concentrated and purified by prep-RP-HPLC to give the title compound. MS (ESI) m/z 570.9 (M+H).

Step 7: (S)- and (R)-2-(1-((4-carboxyphenyl)amino)-3-(3,3-difluorocyclobutyl)-1-oxopropan-2-yl)-5-(3-chloro-6-(difluoromethoxy)-2-fluorophenyl)pyridine 1-oxide (Examples 49 & 50)

2-(1-((4-carboxyphenyl)amino)-3-(3,3-difluorocyclobutyl)-1-oxopropan-2-yl)-5-(3-chloro-6-(difluoromethoxy)-2-fluorophenyl)pyridine 1-oxide (Example 48) (80 mg, 0.14 mmol) was resolved by SFC on AD column (250×30 mm, 5 um) eluting with 55% EtOH containing 0.1% v/v concentrated aq. NH$_3$ in CO$_2$ at 80 ml/min to give enantiomer A (Example 49, first peak) and enantiomer B (Example 50, second peak). Example 49: MS (ESI) m/z 570.9 (M+H). Example 50: $^1$H NMR (CD$_3$OD, 400 MHz): δ 8.48 (s, 1H), 7.96 (d, J=8.8 Hz, 2H), 7.80 (d, J=8.4 Hz, 1H), 7.60-7.71 (m, 4H), 7.20 (d, J=9.0 Hz, 1H), 6.87 (t, J=72.4 Hz, 1H), 4.55-4.59 (m, 1H), 2.62-2.75 (m, 2H), 2.24-2.44 (m, 4H), 2.18-2.20 (m, 1H). MS (ESI) m/z 570.9 (M+H).

Examples 51 and 52

(S)- and (R)-4-[(3-bicyclo[1.1.1]pent-1-yl-2-{5-[3-chloro-6-(difluoromethoxy)-2-fluorophenyl]-1-oxidopyridin-2-yl}propanoyl)amino]benzoic Acid

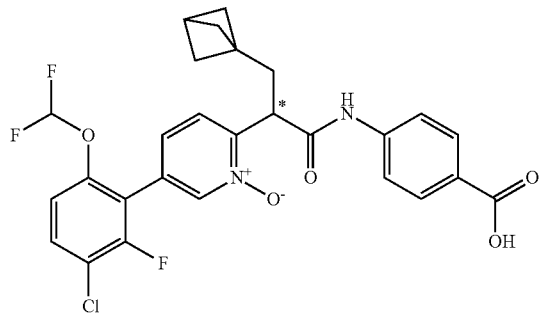

Step 1: 3-(Bicyclo[1.1.1]pentan-1-yl)-2-(5-(3-chloro-6-(difluoromethoxy)-2-fluorophenyl)pyridin-2-yl)propanoic Acid To a round bottom flask was added ethyl 3-(bicyclo[1.1.1]pentan-1-yl)-2-(5-(3-chloro-6-(difluoromethoxy)-2-fluorophenyl)pyridin-2-yl)propanoate (56 mg, 0.13 mmol), MeOH (1 mL), water (0.2 mL), THF (1 mL) and sodium hydroxide (30.60 mg, 0.76 mmol) at 16° C. The reaction mixture was stirred at 16° C. for 50 min. LC-MS showed reaction was complete. The reaction mixture was concentrated in vacuo, re-dissolved in 10 mL of water and adjusted to pH=3 with 1M HCl, extracted with DCM (2 mL×2), the combined organic layers were washed with brine (10 mL), dried over anhydrous sodium sulfate, and filtered to give the title compound as a DCM solution (4 mL) which was directly used for next step without further purification. MS (ESI) m/z 412.1 (M+H).

Step 2: Methyl 4-(3-(bicyclo[1.1.1]pentan-1-yl)-2-(5-(3-chloro-6-(difluoromethoxy)-2-fluorophenyl)pyridin-2-yl)propanamido)benzoate To a round bottom flask was added 3-(bicyclo[1.1.1]pentan-1-yl)-2-(5-(3-chloro-6-(difluoromethoxy)-2-fluorophenyl)pyridin-2-yl)propanoic acid (4 mL, DCM solution), methyl 4-aminobenzoate (23.08 mg, 0.15 mmol), HATU (58.10 mg, 0.15 mmol) and TEA (0.05 mL, 0.38 mmol) at 16° C. The reaction mixture was stirred at 16° C. for 8 h. LC-MS showed reaction was complete. The reaction mixture was quenched with water (8 mL), and extracted with EtOAc (10 mL×3). The combined organic fractions were washed with brine, dried (Na$_2$SO$_4$), filtered and the solvent was evaporated under reduced pressure to give the crude title compound, which was used in the next step without further purification. MS (ESI) m/z 545.2 (M+H).

Step 3: 2-(3-(bicyclo[1.1.1]pentan-1-yl)-1-((4-(methoxycarbonyl)phenyl)amino)-1-oxopropan-2-yl)-5-(3-chloro-6-(difluoromethoxy)-2-fluorophenyl)pyridine 1-oxide To a solution of methyl 4-(3-(bicyclo[1.1.1]pentan-1-yl)-2-(5-(3-chloro-6-(difluoromethoxy)-2-fluorophenyl)pyridin-2-yl)propanamido)benzoate (60 mg, 0.11 mmol) in DCM (3 mL) was added mCPBA (54.30 mg, 0.22 mmol, 70% purity) at 16° C. in a round bottom flask. The mixture was stirred at 16° C. for 12 h. LC-MS showed the reaction was complete. It was concentrated in vacuo to give the crude title compound, which was directly used for next step without further purification. MS (ESI) m/z 561.2 (M+H).

Step 4: 4-[(3-bicyclo[1.1.1]pent-1-yl-2-{5-[3-chloro-6-(difluoromethoxy)-2-fluorophenyl]-1-oxidopyridin-2-yl}propanoyl)amino]benzoic Acid To a round bottom flask was added 2-(3-(bicyclo[1.1.1]pentan-1-yl)-1-((4-(methoxycarbonyl)phenyl)amino)-1-oxopropan-2-yl)-5-(3-chloro-6-(difluoromethoxy)-2-fluorophenyl)pyridine 1-oxide (60 mg, 0.11 mmol), MeOH (0.4 mL), water (0.4 mL), THF (2 mL) and NaOH (17.11 mg, 0.43 mmol). The reaction mixture was stirred at 20° C. for 18 h. LC-MS showed the reaction was complete. The mixture was concentrated in vacuo and purified by HPLC (acidic condition) to give the title compound. MS (ESI) m/z 547.1 (M+H).

Step 5: (S)- and (R)-4-[(3-bicyclo[1.1.1]pent-1-yl-2-{5-[3-chloro-6-(difluoromethoxy)-2-fluorophenyl]-1-oxidopyridin-2-yl}propanoyl)amino]benzoic Acid (Examples 51 & 52)

4-[(3-bicyclo[1.1.1]pent-1-yl-2-{5-[3-chloro-6-(difluoromethoxy)-2-fluorophenyl]-1-oxidopyridin-2-yl}propanoyl)amino]benzoic acid (20 mg) was resolved by SFC on OJ column (250×30 mm, 5 um) eluting with 25% MeOH containing 0.1% v/v concentrated aq. NH$_3$ in CO$_2$ at 60 ml/min to give enantiomer A (Example 51, first peak) and enantiomer B (Example 52, second peak). Example 51: MS (ESI) m/z 547.1 (M+H). Example 52: $^1$H NMR (CD$_3$OD, 400 MHz): δ 8.50 (s, 1H), 7.96 (d, J=8.6 Hz, 2H), 7.78 (d, J=8.6 Hz, 1H), 7.60-7.71 (m, 4H), 7.21 (d, J=8.8 Hz, 1H), 6.87 (t, J=72.4 Hz, 1H), 4.74 (t, J=7.4 Hz, 1H), 1.64-1.80 (m, 7H), 1.28-1.34 (m, 2H). MS (ESI) m/z 547.1 (M+H).

Examples 53-56

Trans-4-{[2-{5-[3-chloro-6-(difluoromethoxy)-2-fluorophenyl]-1-oxidopyridin-2-yl}-3-(2-methylcyclopropyl)propanoyl]amino}benzoic Acid

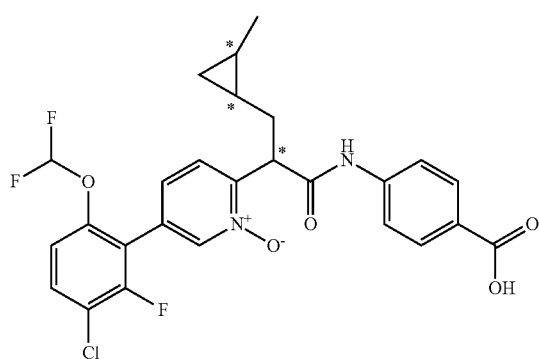

Examples 53~56 (trans cyclopropane)

Step 1: Trans-2-(5-(3-chloro-6-(difluoromethoxy)-2-fluorophenyl)pyridin-2-yl)-3-(2-methylcyclopropyl)propanoic Acid To a solution of ethyl 2-(5-(3-chloro-6-(difluoromethoxy)-2-fluorophenyl)pyridin-2-yl)-3-(2-methylcyclopropyl)propanoate (900 mg, 2.10 mmol) in MeOH (10 mL) and water (2 mL) was added NaOH (168 mg, 4.21 mmol) at 15° C. in a round bottom flask. The mixture was stirred at 15° C. for 16 h. LC-MS showed the reaction was complete. The solvent was removed, diluted with water (2 mL), and HCl (1M) was added until it reached pH 5. The mixture was extracted with DCM (5 mL×3), the combined organic layers were dried over Na$_2$SO$_4$ and filtered. The filtrate was used to the next step without further purification. MS (ESI) m/z 400.1 (M+H).

Step 2: Methyl trans-4-(2-(5-(3-chloro-6-(difluoromethoxy)-2-fluorophenyl)pyridin-2-yl)-3-(2-methylcyclopropyl)propanamido)benzoate To a solution of 2-(5-(3-chloro-6-(difluoromethoxy)-2-fluorophenyl)pyridin-2-yl)-3-(2-methylcyclopropyl)propanoic acid (0.84 g, 2.10 mmol) in 15 mL of DCM was added methyl 4-aminobenzoate (0.38 g, 2.52 mmol), HATU (1.20 g, 3.16 mmol) and TEA (0.88 mL, 6.31 mmol) in a round bottom flask at 15° C. The mixture was stirred at 15° C. for 16 h. LC-MS showed the reaction was complete. The mixture was concentrated in vacuo and purified by column chromatography (SiO$_2$, 0-25% EtOAc in PE) to give the title compound. $^1$H NMR (CDCl$_3$, 400 MHz): δ 8.67-8.58 (m, 1H), 7.99-8.01 (m, 2H), 7.74-7.78 (m, 1H), 7.65-7.68 (m, 2H), 7.46-7.48 (m, 1H), 7.40-7.44 (m, 1H), 7.11 (d, J=9.0 Hz, 1H), 6.39 (t, J=72.0 Hz, 1H), 3.88-4.09 (m, 4H), 1.85-2.35 (m, 2H), 0.74-1.01 (m, 3H), 0.06-0.58 (m, 4H). MS (ESI) m/z 533.2 (M+H).

Step 3: Trans-4-(2-(5-(3-Chloro-6-(difluoromethoxy)-2-fluorophenyl)pyridin-2-yl)-3-(2-methylcyclopropyl)propanamido)benzoic Acid To a solution of methyl 4-(2-(5-(3-chloro-6-(difluoromethoxy)-2-fluorophenyl)pyridin-2-yl)-3-(2-methylcyclopropyl)propanamido)benzoate (1.00 g, 1.88 mmol) in MeOH (10 mL) and water (2 mL) was added NaOH (0.15 g, 3.75 mmol) at 15° C. in a round bottom flask. The mixture was stirred at 15° C. for 16 h. LC-MS showed the reaction was complete. The solvent was removed and the residue was diluted with water (2 mL), and HCl (1 M) was added until it reached pH 5. The mixture was extracted with DCM (5 mL×3), the combined organic layers were dried over Na$_2$SO$_4$, and filtered. The filtrate was concentrated in vacuo to give the title compound which was used to the next step without further purification. MS (ESI) m/z 519.1 (M+H).

Step 4: 2-(1-((4-carboxyphenyl)amino)-3-(2-methylcyclopropyl)-1-oxopropan-2-yl)-5-(3-chloro-6-(difluoromethoxy)-2-fluorophenyl)pyridine 1-oxide To a solution of 4-(2-(5-(3-chloro-6-(difluoromethoxy)-2-fluorophenyl)pyridin-2-yl)-3-(2-methylcyclopropyl)propanamido)benzoic acid (53-G) (800 mg, 1.54 mmol) in DCM (20 mL) was added mCPBA (760 mg, 3.08 mmol, 70% purity) at 15° C. in a round bottom flask. The mixture was stirred at 15° C. for 16 h. LC-MS showed the reaction was complete. The mixture was washed with NaHCO$_3$ (sat., 20 mL×3), dried over Na$_2$SO$_4$ and filtered. The filtrate was concentrated in vacuo and purified by prep-RP-HPLC (TFA condition) to give the title compound. MS (ESI) m/z 535.2 (M+H).

Step 5: Trans-2-(1-((4-carboxyphenyl)amino)-3-(2-methylcyclopropyl)-1-oxopropan-2-yl)-5-(3-chloro-6-(difluoromethoxy)-2-fluorophenyl)pyridine 1-oxide (Example 53-56)

2-(1-((4-carboxyphenyl)amino)-3-(2-methylcyclopropyl)-1-oxopropan-2-yl)-5-(3-chloro-6-(difluoromethoxy)-2-fluorophenyl)pyridine 1-oxide (540 mg, 0.84 mmol) was resolved by SFC on AD column (250×30 mm, 5 um) eluting with 35% IPA containing 0.1% v/v concentrated aq. NH$_3$ in CO$_2$ at 60 ml/min to give isomer A (Example 53, first peak), isomer B (Example 54, second peak), 2-((R)-1-((4-carboxyphenyl)amino)-3-((1R,2S)-2-methylcyclopropyl)-1-oxopropan-2-yl)-5-(3-chloro-6-(difluoromethoxy)-2-fluorophenyl)pyridine 1-oxide (Example 55, third peak) and 2-((R)-1-((4-carboxyphenyl)amino)-3-((1S,2R)-2-methylcyclopropyl)-1-oxopropan-2-yl)-5-(3-chloro-6-(difluoromethoxy)-2-fluorophenyl)pyridine 1-oxide (Example 56, forth peak). The stereochemistries of Examples 55 and 56 were determined using X-ray structures of these compounds bound to catalytic domain of FXIa.

Example 53: MS (ESI) m/z 534.9 (M+H).
Example 54: MS (ESI) m/z 534.9 (M+H).
Example 55: $^1$H NMR (CD$_3$OD, 400 MHz): δ 8.46 (s, 1H), 7.97 (d, J=8.8 Hz, 2H), 7.71-7.84 (m, 3H), 7.58-7.68 (m, 2H), 7.20 (d, J=9.0 Hz, 1H), 6.86 (t, J=72.8 Hz, 1H), 4.66 (dd, J=10.0, 5.1 Hz, 1H), 2.02-2.16 (m, 1H), 1.88-2.00 (m, 1H), 0.89 (d, J=5.5 Hz, 3H), 0.54-0.63 (m, 2H), 0.30-0.42 (m, 1H), 0.17-0.29 (m, 1H). MS (ESI) m/z 534.9 (M+H).
Example 56: $^1$H NMR (CD$_3$OD, 400 MHz): δ 8.48 (s, 1H), 7.96 (d, J=8.8 Hz, 2H), 7.81 (d, J=8.4 Hz, 1H), 7.71 (d, J=8.8 Hz, 2H), 7.61-7.68 (m, 2H), 7.20 (d, J=9.0 Hz, 1H), 6.87 (t, J=72.8 Hz, 1H), 4.69 (t, J=7.5 Hz, 1H), 2.04-2.15 (m, 1H), 1.93-2.03 (m, 1H), 0.97 (d, J=5.3 Hz, 3H), 0.52-0.59 (m, 2H), 0.32-0.41 (m, 1H), 0.15-0.23 (m, 1H). MS (ESI) m/z 534.9 (M+H).

By using procedures similar to those described for Example 53-56 above, the following compounds were synthesized using appropriate starting materials and characterized. The product containing all four isomers of Examples 57-60 was first separated by prep-RP-HPLC to afford two fractions. The fast-eluting fraction was further resolved by SFC on AD column (250×30 mm, 10 um) eluting with 45% IPA containing 0.1% v/v concentrated aq. $NH_3$ in $CO_2$ to afford Example 57, followed by Example 58. The slower-eluting fraction from prep-RP-HPLC was resolved by SFC on AD column (250×30 mm, 10 um) eluting with 35% IPA containing 0.1% v/v concentrated aq. $NH_3$ in $CO_2$ to afford Example 59, followed by Example 60.

| Ex. # | Structure | Name | Exact Mass $[M + H]^+$ | Chiral Separation |
|---|---|---|---|---|
| 53 | 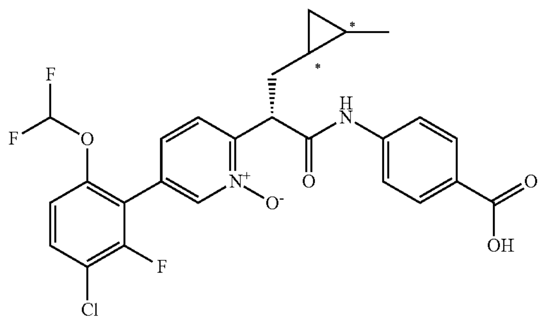 [SMILES: CC1CC1C[C@H](C(=O)Nc1ccc(C(=O)O)cc1)c1ccc(-c2c(OC(F)F)ccc(Cl)c2F)c[n+]1[O-]] | 2-((2S)-1-((4-carboxyphenyl)amino)-3-(2-methylcyclopropyl)-1-oxopropan-2-yl)-5-(3-chloro-6-(difluoromethoxy)-2-fluorophenyl)pyridine 1-oxide | 534.9 | Trans, Peak 1 from AD |
| 54 | 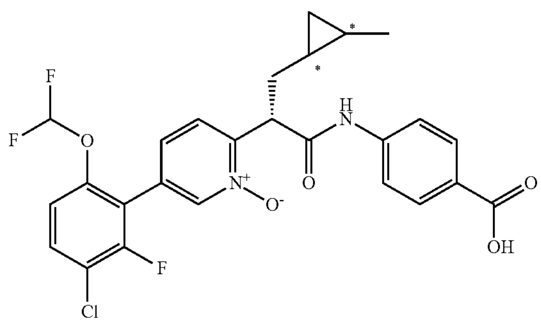 [SMILES: CC1CC1C[C@H](C(=O)Nc1ccc(C(=O)O)cc1)c1ccc(-c2c(OC(F)F)ccc(Cl)c2F)c[n+]1[O-]] | 2-((2S)-1-((4-carboxyphenyl)amino)-3-(2-methylcyclopropyl)-1-oxopropan-2-yl)-5-(3-chloro-6-(difluoromethoxy)-2-fluorophenyl)pyridine 1-oxide | 534.9 | Trans, Peak 2 from AD |
| 55 | 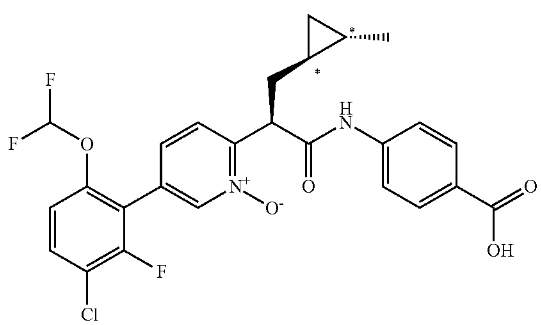 [SMILES: C[C@H]1C[C@@H]1C[C@@H](C(=O)Nc1ccc(C(=O)O)cc1)c1ccc(-c2c(OC(F)F)ccc(Cl)c2F)c[n+]1[O-]] | 2-((R)-1-((4-carboxyphenyl)amino)-3-((1R,2S)-2-methylcyclopropyl)-1-oxopropan-2-yl)-5-(3-chloro-6-(difluoromethoxy)-2-fluorophenyl)pyridine 1-oxide | 534.9 | Trans, Peak 3 from AD |
| 56 | 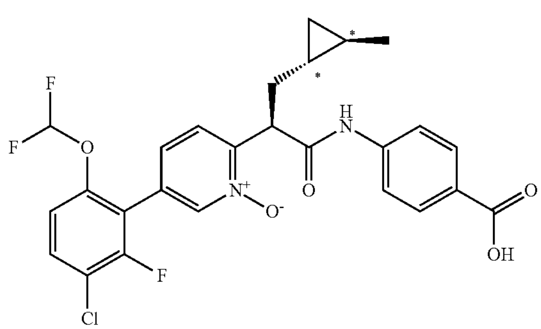 [SMILES: C[C@@H]1C[C@H]1C[C@@H](C(=O)Nc1ccc(C(=O)O)cc1)c1ccc(-c2c(OC(F)F)ccc(Cl)c2F)c[n+]1[O-]] | 2-((R)-1-((4-carboxyphenyl)amino)-3-((1S,2R)-2-methylcyclopropyl)-1-oxopropan-2-yl)-5-(3-chloro-6-(difluoromethoxy)-2-fluorophenyl)pyridine 1-oxide | 534.9 | Trans, Peak 4 from AD |

| Ex. # | Structure | Name | Exact Mass [M + H]+ | Chiral Separation |
|---|---|---|---|---|
| 57 | 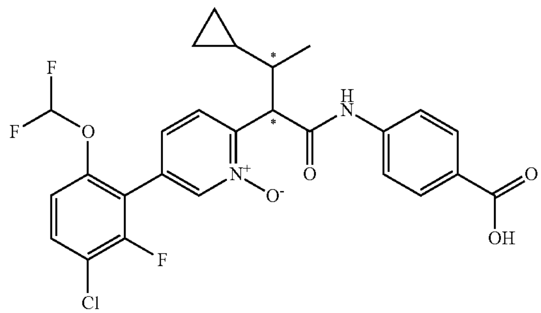 [SMILES: CC(C1CC1)C(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-cyclopropyl-1-oxobutan-2-yl)-5-(3-chloro-6-(difluoromethoxy)-2-fluorophenyl)pyridine 1-oxide | 534.9 | Peak 1 on AD, after Peak 1 on prep-RP-HPLC |
| 58 | 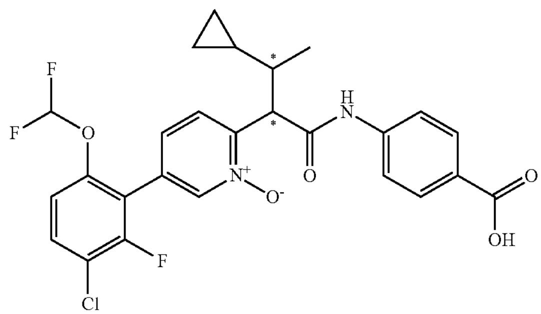 [SMILES: CC(C1CC1)C(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-cyclopropyl-1-oxobutan-2-yl)-5-(3-chloro-6-(difluoromethoxy)-2-fluorophenyl)pyridine 1-oxide | 534.9 | Peak 2 on AD, after Peak 1 on prep-RP-HPLC |
| 59 | 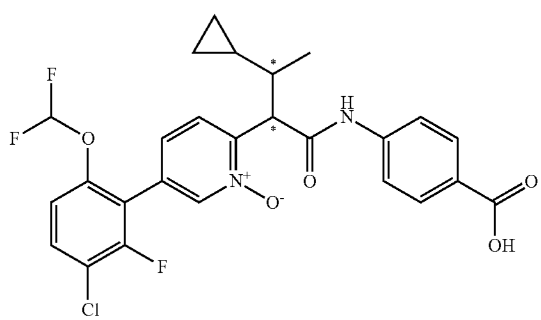 [SMILES: CC(C1CC1)C(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-cyclopropyl-1-oxobutan-2-yl)-5-(3-chloro-6-(difluoromethoxy)-2-fluorophenyl)pyridine 1-oxide | 534.9 | Peak 1 on AD, after Peak 2 on prep-RP-HPLC |
| 60 | 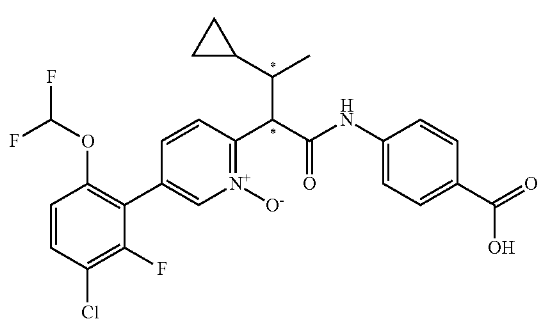 [SMILES: CC(C1CC1)C(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-cyclopropyl-1-oxobutan-2-yl)-5-(3-chloro-6-(difluoromethoxy)-2-fluorophenyl)pyridine 1-oxide | 534.9 | Peak 2 on AD, after Peak 2 on prep-RP-HPLC |

Examples 61-63

Trans-2-(1-((4-Carboxyphenyl)amino)-3-(2-methylcyclopropyl)-1-oxopropan-2-yl)-5-(3-chloro-6-(difluoromethyl)-2-fluorophenyl)pyridine 1-oxide

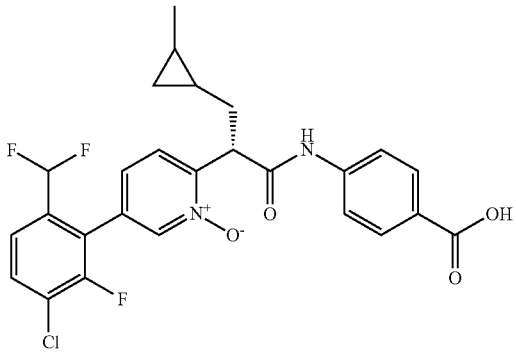 [SMILES: CC1CC1C[C@H](C(=O)Nc1ccc(C(=O)O)cc1)c1ccc(-c2c(C(F)F)ccc(Cl)c2F)c[n+]1[O-]]

Example 61 (trans, 2 isomers)

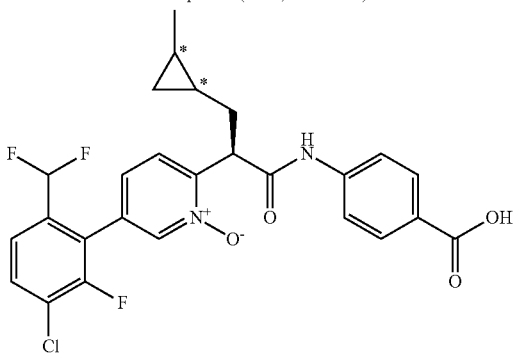

Examples 62 and 63 (trans)

Step 1: Trans-2-(5-Bromopyridin-2-yl)-3-(2-methylcyclopropyl)propanoic Acid

To a solution of ethyl trans-2-(5-bromopyridin-2-yl)-3-(2-methylcyclopropyl)propanoate (1.60 g, 5.12 mmol) in MeOH (10 mL) and water (3 mL) was added NaOH (0.41 g, 10.25 mmol) at 15° C. in a round bottom flask. The mixture was stirred at 15° C. for 16 h. LC-MS showed the reaction was complete. The solvent was removed, diluted with water (2 mL), and HCl (1 M) was added until it reached pH 5. The mixture was extracted with DCM (5 mL×3), and the combined organic layers were dried over $Na_2SO_4$ and filtered. The filtrate was used in the next step without further purification. MS (ESI) m/z 284.0/286.0 (M+H).

Step 2: tert-Butyl trans-4-(2-(5-bromopyridin-2-yl)-3-(2-methylcyclopropyl)propanamido)benzoate To a solution of trans-2-(5-bromopyridin-2-yl)-3-(2-methylcyclopropyl)propanoic acid (1.46 g, 5.12 mmol) in 15 mL of DCM from step 1 was added tert-butyl 4-aminobenzoate (0.99 g, 5.12 mmol), HATU (1.95 g, 5.12 mmol) and TEA (0.71 mL, 5.12 mmol) at 15° C. The mixture was stirred at 15° C. for 16 h. LC-MS showed the reaction was complete. It was concentrated in vacuo and purified by column chromatography ($SiO_2$, PE/EtOAc=1/0-5/1) to give the title compound. MS (ESI) m/z 459.1/461.1 (M+H).

Step 3: tert-Butyl trans-4-(2-(5-(3-chloro-6-(difluoromethyl)-2-fluorophenyl)pyridin-2-yl)-3-(2-methylcyclopropyl)propanamido)benzoate To a solution of 4,4,4',4',5,5,5',5'-octamethyl-2,2'-bi(1,3,2-dioxaborolane) (204 mg, 0.80 mmol), tert-butyl trans-4-(2-(5-bromopyridin-2-yl)-3-(2-methylcyclopropyl)propanamido)benzoate (400 mg, 0.62 mmol) and potassium acetate (121 mg, 1.24 mmol) in dioxane (6 mL) was added Pd(dppf)$Cl_2$ (45.20 mg, 0.06 mmol) under $N_2$ in a 30 mL sealed tube. The mixture was stirred at 120° C. for 40 min under MW. LC-MS showed the reaction was complete. Then, 1-chloro-4-(difluoromethyl)-2-fluoro-3-iodobenzene (294 mg, 0.96 mmol), aqueous potassium carbonate (1.74 mL, 1.74 mmol, 1 M) solution and Pd(dppf)$Cl_2$ (63.70 mg, 0.087 mmol) were added at 15° C. under $N_2$. The mixture was stirred at 85° C. for 1 h under MW. LC-MS showed the reaction was complete. Water (20 mL) was added. The mixture was extracted with EtOAc (20 mL×3), and the combined organic layers were dried over $Na_2SO_4$ and filtered. The filtrate was concentrated in vacuo and purified by column chromatography ($SiO_2$, PE/EtOAc=1/0-2/1) to give the title compound. MS (ESI) m/z 559.2 (M+H).

Step 4: Trans-4-(2-(5-(3-Chloro-6-(difluoromethyl)-2-fluorophenyl)pyridin-2-yl)-3-(2-methylcyclopropyl)propanamido)benzoic Acid To a solution of tert-butyl trans-4-(2-(5-(3-chloro-6-(difluoromethyl)-2-fluorophenyl)pyridin-2-yl)-3-(2-methylcyclopropyl)propanamido)benzoate (500 mg, 0.89 mmol) in DCM (10 mL) was added TFA (1 mL, 12.98 mmol) at 15° C. in a round bottom flask. The mixture was stirred at 15° C. for 16 h. LC-MS showed the reaction was complete. The mixture was concentrated in vacuo and DCM (20 mL) was added, washed with $NaHCO_3$ (sat., 30 mL) and brine (20 mL×2), the combined organic layers were dried over $Na_2SO_4$ and filtered. The filtrate was concentrated in vacuo to give the title compound. MS (ESI) m/z 503.1 (M+H).

Step 5: Trans-2-(1-((4-Carboxyphenyl)amino)-3-(2-methylcyclopropyl)-1-oxopropan-2-yl)-5-(3-chloro-6-(difluoromethyl)-2-fluorophenyl)pyridine 1-oxide To a solution of trans-4-(2-(5-(3-chloro-6-(difluoromethyl)-2-fluorophenyl)pyridin-2-yl)-3-(2-methylcyclopropyl)propanamido)benzoic acid (818 mg, 1.07 mmol, 66% purity) in DCM (10 mL) was added mCPBA (370 mg, 1.61 mmol, 75% purity) at 15° C. in a round bottom flask. The mixture was stirred at 15° C. for 16 h. LC-MS showed the reaction was complete. The mixture was concentrated in vacuo and purified by prep-RP-HPLC (TFA condition) to give the title compound. MS (ESI) m/z 519.2 (M+H).

Step 6: Trans-2-(1-((4-Carboxyphenyl)amino)-3-(2-methylcyclopropyl)-1-oxopropan-2-yl)-5-(3-chloro-6-(difluoromethyl)-2-fluorophenyl)pyridine 1-oxide (Example 61 and Another Pair of Isomers Trans-2-(1-((4-carboxyphenyl)amino)-3-(2-methylcyclopropyl)-1-oxopropan-2-yl)-5-(3-chloro-6-(difluoromethyl)-2-fluorophenyl)pyridine 1-oxide (130 mg, 0.25 mmol) was resolved by SFC on OJ column (250×30 mm, 5 um) using 20% MeOH containing 0.1% v/v concentrated aq. $NH_3$ in $CO_2$ (60 ml/min) to give Trans-2-((2S)-1-((4-carboxyphenyl)amino)-3-(2-methylcyclopropyl)-1-oxopropan-2-yl)-5-(3-chloro-6-(difluoromethyl)-2-fluorophenyl)pyridine 1-oxide (Example 61, first peak) and Trans-2-((2R)-1-((4-carboxyphenyl)amino)-3-(2-methylcyclopropyl)-1-oxopropan-2-yl)-5-(3-chloro-6-(difluoromethyl)-2-fluorophenyl)pyridine 1-oxide (second peak). Example 61: MS (ESI) m/z 518.9 (M+H).

Step 7: Trans-2-((2R)-1-((4-Carboxyphenyl)amino)-3-(2-methylcyclopropyl)-1-oxopropan-2-yl)-5-(3-chloro-6-(difluoromethyl)-2-fluorophenyl)pyridine 1-oxide (Examples 62 & 63)

Trans-2-(1-((4-carboxyphenyl)amino)-3-(2-methylcyclopropyl)-1-oxopropan-2-yl)-5-(3-chloro-6-(difluoromethyl)-2-fluorophenyl)pyridine 1-oxide (second peak from OJ column) (30 mg, 0.058 mmol) was resolved by SFC on AD column (250×30 mm, 10 um) eluting with 45% IPA containing 0.1% v/v concentrated aq. $NH_3$ in $CO_2$ (80 ml/min) to give one isomer of the title compound (Example 62, first peak) as a solid and another isomer of the title compound (Example 63, second peak) as a solid.

Example 62: $^1$H NMR (CD$_3$OD, 400 MHz): δ 8.43 (s, 1H), 7.99 (d, J=8.6 Hz, 2H), 7.72-7.83 (m, 4H), 7.54-7.63 (m, 2H), 6.63 (t, J=54.0, 1H), 4.68 (dd, J=9.9, 5.2 Hz, 1H), 2.07-2.17 (m, 1H), 1.90-2.01 (m, 1H), 0.92 (d, J=5.5 Hz, 3H), 0.55-0.63 (m, 2H), 0.34-0.43 (m, 1H), 0.22-0.31 (m, 1H). MS (ESI) m/z 518.9 (M+H).

Example 63: $^1$H NMR (CD$_3$OD, 400 MHz): δ 8.45 (s, 1H), 7.98 (d, J=8.8 Hz, 2H), 7.84 (d, J=8.2 Hz, 1H), 7.69-7.81 (m, 3H), 7.59 (t, J=7.7 Hz, 2H), 6.65 (t, J=54.4, 1H), 4.69 (t, J=7.5 Hz, 1H), 1.96-2.16 (m, 2H), 1.00 (d, J=5.5 Hz, 3H), 0.54-0.64 (m, 2H), 0.35-0.43 (m, 1H), 0.18-0.27 (m, 1H). MS (ESI) m/z 518.9 (M+H).

By using procedures similar to those described above, the following compounds were synthesized using appropriate starting materials and characterized. The stereochemistry assigned to Examples 61-65 is based on their inhibitory activity towards FXIa in comparison to those of Examples 53-56 and the established structures of Examples 53-56.

| Ex. # | Structure | Name | Exact Mass [M + H]$^+$ | Chiral Separation |
|---|---|---|---|---|
| 61 | 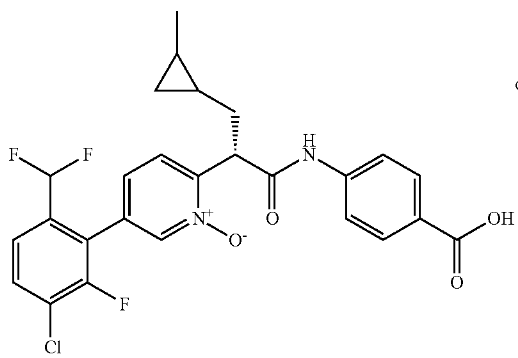 | 2-((2S)-1-((4-carboxyphenyl)amino)-3-(2-methylcyclopropyl)-1-oxopropan-2-yl)-5-(3-chloro-6-(difluoromethyl)-2-fluorophenyl)pyridine 1-oxide | 518.9 | Two trans isomers, Peak 1 from OJ column |
| 62 | 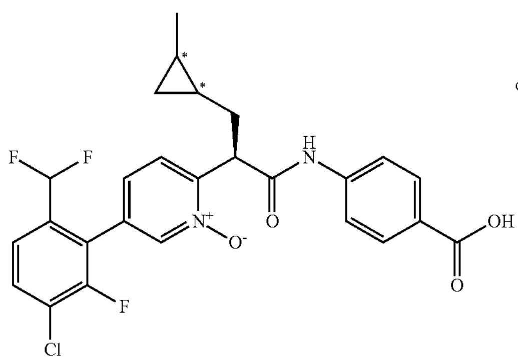 | 2-((2R)-1-((4-carboxyphenyl)amino)-3-(2-methylcyclopropyl)-1-oxopropan-2-yl)-5-(3-chloro-6-(difluoromethyl)-2-fluorophenyl)pyridine 1-oxide | 518.9 | Trans, Peak 1/AD column from Peak 2/OJ column |
| 63 | 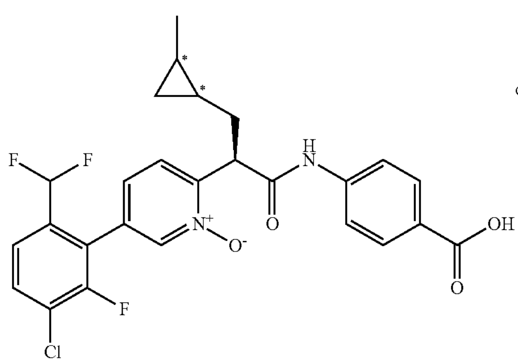 | 2-((2R)-1-((4-carboxyphenyl)amino)-3-(2-methylcyclopropyl)-1-oxopropan-2-yl)-5-(3-chloro-6-(difluoromethyl)-2-fluorophenyl)pyridine 1-oxide | 518.9 | Trans, Peak 2/AD column from Peak 2/OJ column |

| Ex. # | Structure | Name | Exact Mass [M + H]+ | Chiral Separation |
|---|---|---|---|---|
| 64 | 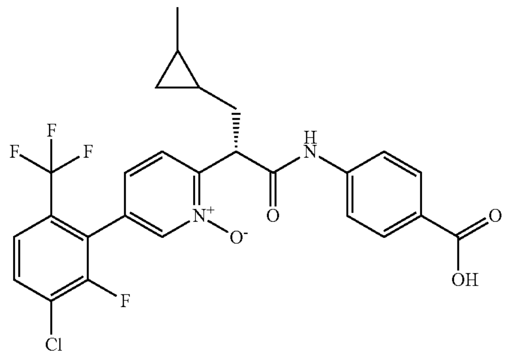 [SMILES: CC1CC1C[C@H](C(=O)Nc1ccc(C(=O)O)cc1)c1ccc(-c2c(C(F)(F)F)ccc(Cl)c2F)c[n+]1[O-]] | 2-((2S)-1-((4-carboxyphenyl)amino)-3-(2-methylcyclopropyl)-1-oxopropan-2-yl)-5-(3-chloro-2-fluoro-6-(trifluoromethyl)phenyl) pyridine 1-oxide | 536.9 | Two trans isomers, Peak 1 from AY column |
| 65 | 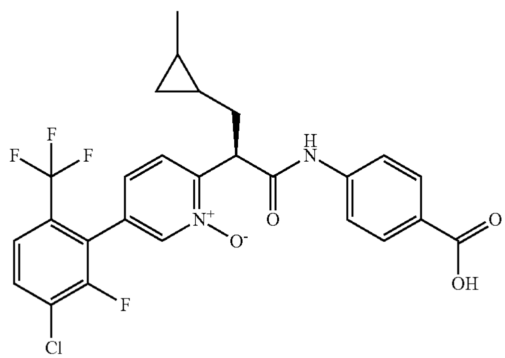 [SMILES: CC1CC1C[C@@H](C(=O)Nc1ccc(C(=O)O)cc1)c1ccc(-c2c(C(F)(F)F)ccc(Cl)c2F)c[n+]1[O-]] | 2-((2R)-1-((4-carboxyphenyl)amino)-3-(2-methylcyclopropyl)-1-oxopropan-2-yl)-5-(3-chloro-2-fluoro-6-(trifluoromethyl)phenyl) pyridine 1-oxide | 536.9 | Two trans isomers, Peak 2 from AY column |

Examples 66 and 67

(S)- and (R)-2-(1-(((4-carboxyphenyl)amino)-3-cyclopropyl-1-oxopropan-2-yl)-5-(3-chloro-6-(difluoromethoxy)-2-fluorophenyl)-4-methylpyridine 1-oxide

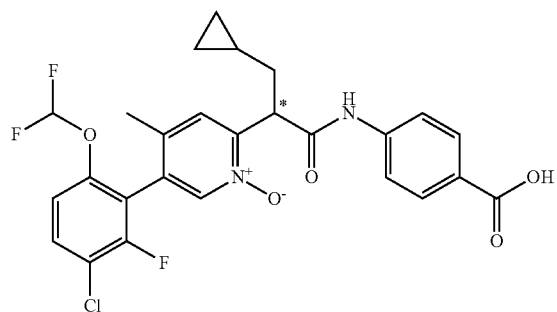 [SMILES: Cc1cc(C(CC2CC2)C(=O)Nc2ccc(C(=O)O)cc2)[n+]([O-])cc1-c1c(OC(F)F)ccc(Cl)c1F]

Step 1: Ethyl 3-cyclopropyl-2-(4-methyl-5-(4,4,5,5-tetramethyl-1,3,2-dioxaborolan-2-yl)pyridin-2-yl) propanoate Ethyl 2-(5-bromo-4-methylpyridin-2-yl)-3-cyclopropylpropanoate (3.90 g, 12.5 mmol) was mixed with 4,4,4',4',5,5,5',5'-octamethyl-2,2'-bi(1,3,2-dioxaborolane) (3.17 g, 12.5 mmol), Pd(dppf)Cl$_2$ (2.29 g, 3.12 mmol) and potassium acetate (3.68 g, 37.5 mmol) in a microwave reaction vial. The vial was capped and nitrogen gas was used to purge the residual air three times. Then 1,4-dioxane (8 mL) was introduced with a syringe. The resulting mixture was treated with microwave at 110° C. for 0.5 h. LC-MS showed the reaction was complete. The reaction mixture was diluted with water (20 mL) and extracted with DCM (15 mL×3), the combined organic layers were washed with brine (20 mL), dried over anhydrous sodium sulfate, filtered and concentrated. The crude product was purified by chromatography (SiO$_2$, PE:EtOAc from 100:1 to 5:1) to give the title compound. $^1$H NMR (CDCl$_3$, 400 MHz): δ 8.77 (s, 1H), 7.10 (s, 1H), 4.05-4.24 (m, 2H), 3.88 (t, J=7.6 Hz, 1H), 2.50 (s, 3H), 1.78-1.90 (m, 2H), 1.33 (s, 12H), 1.18-1.22 (m, 3H), 0.58-0.68 (m, 1H), 0.32-0.44 (m, 2H), 0.05-0.13 (m, 1H), −0.05-0.04 (m, 1H). MS (ESI) m/z 278.1 (M+H) (boronic acid).

Step 2: Ethyl 2-(5-(3-chloro-6-(difluoromethoxy)-2-fluorophenyl)-4-methylpyridin-2-yl)-3-cyclopropyl-propanoate To a round bottom flask was added ethyl 3-cyclopropyl-2-(4-methyl-5-(4,4,5,5-tetramethyl-1,3,2-dioxaborolan-2-yl)pyridin-2-yl)propanoate (502 mg, 1.40 mmol), 1-chloro-4-(difluoromethoxy)-2-fluoro-3-iodobenzene (451 mg, 1.40 mmol), potassium phosphate (741 mg, 3.49 mmol), 1,1'-bis(di-tert-butylphosphino)ferrocene palladium dichloride (182 mg, 0.28 mmol), THF (5 mL) and water (1 mL) under a nitrogen atmosphere. The reaction mixture was stirred at 20° C. for 12 h. LC-MS showed the reaction was complete. Water (10 mL) was added to the mixture, and it was extracted with EtOAc (3×6 mL). The combined organic layers were dried over anhydrous sodium sulfate, filtered and concentrated in vacuo. The residue was purified by column chromatography (SiO$_2$, PE:EtOAc from 100:1 to 5:1) to give the title compound. MS (ESI) m/z 428.1 (M+H).

Step 3: 2-(5-(3-Chloro-6-(difluoromethoxy)-2-fluorophenyl)-4-methylpyridin-2-yl)-3-cyclopropylpropanoic Acid To a round bottom flask was added ethyl 2-(5-(3-chloro-6-(difluoromethoxy)-2-fluorophenyl)-4-methylpyridin-2-yl)-3-cyclopropylpropanoate (220 mg, 0.51 mmol), MeOH (2 mL), water (1 mL), DCM (1 mL) and sodium hydroxide (41.10 mg, 1.03 mmol) at 18° C. The reaction mixture was stirred at 18° C. for 6 h. LC-MS showed the reaction was mostly completed. The reaction mixture was concentrated in vacuo, re-dissolved in 10 mL water and 1M HCl was added until the mixture reached pH=3. It was extracted with DCM (4 mL×2), and the combined organic layers were washed with brine (10 mL), dried over anhydrous sodium sulfate and filtered. The solution was directly used for next step without further purification. MS (ESI) m/z 400.2 (M+H).

Step 4: tert-Butyl 4-(2-(5-(3-chloro-6-(difluoromethoxy)-2-fluorophenyl)-4-methylpyridin-2-yl)-3-cyclopropylpropanamido)benzoate To a solution of 2-(5-(3-chloro-6-(difluoromethoxy)-2-fluorophenyl)-4-methylpyridin-2-yl)-3-cyclopropylpropanoic acid (0.52 mmol) in DCM from step 7 was added tert-butyl 4-aminobenzoate (99 mg, 0.51 mmol), HATU (235 mg, 0.62 mmol) and TEA (215.00 µL, 1.54 mmol) at 12° C. The reaction mixture was stirred at 12° C. for 8 h. LC-MS showed reaction was complete. The reaction mixture was diluted with water (10 mL) and extracted with DCM (8 mL×3), the combined organic layers were washed with brine (20 mL), dried over anhydrous sodium sulfate, filtered and concentrated to give the crude product. The crude product was purified by column chromatography (SiO$_2$, PE:EtOAc from 100:1 to 5:1) to give the title compound. $^1$H NMR (CDCl$_3$, 400 MHz): δ 8.34-8.36 (m, 1H), 7.90-7.93 (m, 2H), 7.73-7.81 (m, 2H), 7.59-7.62 (m, 2H), 7.43-7.52 (m, 1H), 6.33 (t, J=72.0 Hz, 1H), 3.83-3.85 (m, 1H), 2.14-2.20 (m, 3H), 1.89-2.03 (m, 2H), 1.56 (s, 9H), 0.66-0.68 (m, 1H), 0.27-0.48 (m, 2H), 0.07-0.15 (m, 1H), −0.20-−0.02 (m, 1H). MS (ESI) m/z 575.2 (M+H).

Step 5: 4-(2-(5-(3-Chloro-6-(difluoromethoxy)-2-fluorophenyl)-4-methylpyridin-2-yl)-3-cyclopropylpropanamido)benzoic Acid To a solution of tert-butyl 4-(2-(5-(3-chloro-6-(difluoromethoxy)-2-fluorophenyl)-4-methylpyridin-2-yl)-3-cyclopropylpropanamido)benzoate (250 mg, 0.32 mmol) in DCM (1 mL) was added TFA (109 mg, 0.95 mmol), the mixture was stirred at 15° C. for 4 h under a N$_2$ atmosphere. LC-MS showed the reaction was complete. The mixture was concentrated in vacuo and diluted with water (10 mL), and NaHCO$_3$ solution was added to the mixture until it reached pH=8. After that, HCl (1N) was added until it reached pH=3. The solution was extracted with DCM (8 mL×3), the combined organic layers were dried over Na$_2$SO$_4$, filtered and the filtrate was concentrated in vacuo to afford the title compound, which was directly used for next step without further purification. $^1$H NMR (CDCl$_3$, 400 MHz): δ 8.54-8.55 (m, 1H), 7.99 (d, J=8.6 Hz, 2H), 7.86-7.87 (m, 1H), 7.66-7.77 (m, 3H), 7.25 (d, J=9.0 Hz, 1H), 6.87 (t, J=72.8 Hz, 1H), 4.19-4.24 (m, 1H), 2.33-2.34 (m, 3H), 2.11-2.24 (m, 1H), 1.87-2.03 (m, 1H), 0.77-0.79 (m, 1H), 0.37-0.55 (m, 2H), 0.12-0.24 (m, 1H), −0.06-0.10 (m, 1H). MS (ESI) m/z 519.2 (M+H).

Step 6: 2-(1-((4-carboxyphenyl)amino)-3-cyclopropyl-1-oxopropan-2-yl)-5-(3-chloro-6-(difluoromethoxy)-2-fluorophenyl)-4-methylpyridine 1-oxide To a round bottom flask was added 4-(2-(5-(3-chloro-6-(difluoromethoxy)-2-fluorophenyl)-4-methylpyridin-2-yl)-3-cyclopropylpropanamido)benzoic acid (160 mg, 0.31 mmol), mCPBA (83 mg, 0.37 mmol, 77% purity) and DCM (2 mL) at 15° C. The reaction mixture was stirred at 15° C. for 18 h. LC-MS showed the reaction was complete. The mixture was quenched with sat. Na$_2$SO$_3$ solution (10 mL), and extracted with DCM (8 mL×3). The combined organic layers were washed with sat. NaHCO$_3$ (10 mL×3) solution, dried over anhydrous sodium sulfate, filtered and the filtrate was concentrated in vacuo. The crude product was purified by prep-RP-HPLC to give the title compound. MS (ESI) m/z 535.2 (M+H).

Step 7: (S)- and (R)-2-(1-((4-carboxyphenyl)amino)-3-cyclopropyl-1-oxopropan-2-yl)-5-(3-chloro-6-(difluoromethoxy)-2-fluorophenyl)-4-methylpyridine 1-oxide (Example 66 and 67)

(1-((4-carboxyphenyl)amino)-3-cyclopropyl-1-oxopropan-2-yl)-5-(3-chloro-6-(difluoromethoxy)-2-fluorophenyl)-4-methylpyridine 1-oxide (90 mg, 0.17 mmol) was resolved with SFC on AD column (250×30 mm, 5 um) eluted with 35% EtOH containing 0.1% v/v concentrated aq. NH$_3$ in CO$_2$ at 60 ml/min to give one isomer of the title compound (Example 66, mixture of Peak 1 and Peak 3, which interconverted on standing at rt) and another isomer of the title compound (Example 67, mixture of Peak 2 and Peak 4, which interconverted on standing at rt).

Example 66: MS (ESI) m/z 534.9 (M+H).

Example 67: $^1$H NMR (CD$_3$OD, 400 MHz): δ 8.31 (s, 1H), 7.98 (d, J=8.8 Hz, 2H), 7.65-7.77 (m, 4H), 7.24 (d, J=9.0 Hz, 1H), 6.88 (t, J=72.0 Hz, 1H), 4.64-4.75 (m, 1H), 2.21 (s, 3H), 1.93-2.10 (m, 2H), 0.83-0.94 (m, 1H), 0.41-0.59 (m, 2H), 0.15-0.27 (m, 2H). MS (ESI) m/z 534.9 (M+H).

Examples 68 and 69

(S)- and (R)-2-(1-((4-carboxyphenyl)amino)-3-cyclopropyl-1-oxopropan-2-yl)-5-(3-chloro-6-(difluoromethyl)-2-fluorophenyl)-4-methoxypyridine 1-oxide

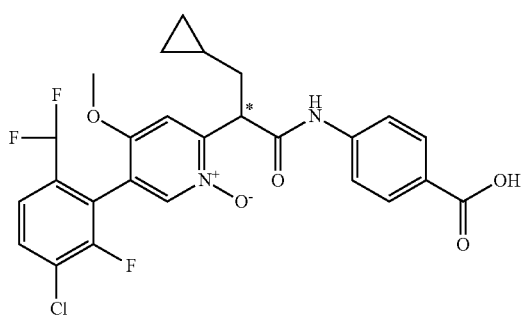 [SMILES: COc1cc(C(CC2CC2)C(=O)Nc2ccc(C(=O)O)cc2)[n+]([O-])cc1-c1c(C(F)F)ccc(Cl)c1F]

Step 1: Ethyl 2-(5-(3-chloro-6-(difluoromethyl)-2-fluorophenyl)-4-methoxypyridin-2-yl)-3-cyclopropylpropanoate To a degassed solution of ethyl 2-(5-bromo-4-methoxypyridin-2-yl)-3-cyclopropylpropanoate (650 mg, 1.98 mmol), 4,4,4',4',5,5,5',5'-octamethyl-2,2'-bi(1,3,2-dioxaborolane) (604 mg, 2.38 mmol) and potassium acetate (389 mg, 3.96 mmol) in 1,4-dioxane (5 mL) was added 2nd Generation Xphos Precatalyst (156 mg, 0.20 mmol) at 25° C. in a round bottom flask under $N_2$. The resulting mixture was irradiated with a microwave at 100° C. for 1.5 h. LC-MS showed the reaction was complete. Then, 1-chloro-4-(difluoromethyl)-2-fluoro-3-iodobenzene (667 mg, 2.18 mmol) and 2nd Generation Xphos Precatalyst (156 mg, 0.20 mmol) were added. The vial was capped and nitrogen gas was used to purge the residual air three times. 1 M aqueous potassium phosphate (5.94 mL, 5.94 mmol) solution was introduced with a syringe. The resulting mixture was irradiated with a microwave at 80° C. for 1 h. LC-MS showed the reaction was complete. After being cooled to room temperature, the reaction mixture was diluted with EtOAc (15 mL), and washed with water and brine. The organic layer was dried over anhydrous sodium sulfate, and the solution was filtered and the filtrate was concentrated in vacuo and the residue was purified by column chromatography ($SiO_2$, PE:EtOAc from 100:1 to 30:1) to give the title compound. MS (ESI) m/z 428.3 (M+H).

Step 2: ethyl 2-(5-(3-chloro-6-(difluoromethyl)-2-fluorophenyl)-4-methoxypyridin-2-yl)-3-cyclopropylpropanoate To a round bottom flask was added ethyl 2-(5-(3-chloro-6-(difluoromethyl)-2-fluorophenyl)-4-methoxypyridin-2-yl)-3-cyclopropylpropanoate (290 mg, 0.54 mmol), MeOH (2 mL), water (1 mL), DCM (1 mL) and sodium hydroxide (43.40 mg, 1.09 mmol) at 18° C. The reaction mixture was stirred at 18° C. for 10 h. The reaction mixture was concentrated in vacuo, re-dissolved in 10 mL water and 1 M HCl was added until it reached pH=3. The mixture was extracted with DCM (4 mL×2), and the combined organic layers were washed with brine (10 mL), dried over anhydrous sodium sulfate and filtered. The solution was directly used for next step without further purification. MS (ESI) m/z 400.2 (M+H).

Step 3: tert-Butyl 4-(2-(5-(3-chloro-6-(difluoromethyl)-2-fluorophenyl)-4-methoxypyridin-2-yl)-3-cyclopropylpropanamido)benzoate To a solution of 2-(5-(3-chloro-6-(difluoromethyl)-2-fluorophenyl)-4-methoxypyridin-2-yl)-3-cyclopropylpropanoic acid (0.54 mmol) in DCM from step 4 was added tert-butyl 4-aminobenzoate (105 mg, 0.54 mmol), HATU (247 mg, 0.65 mmol) and TEA (227.00 μL, 1.63 mmol) at 12° C. The reaction mixture was stirred at 12° C. for 8 hrs. LC-MS showed the reaction was complete. The reaction mixture was diluted with water (10 mL) and extracted with DCM (8 mL×3), and the combined organic layers were washed with brine (20 mL), dried over anhydrous sodium sulfate, filtered and concentrated. The crude product was purified by prep-TLC ($SiO_2$, PE:EtOAc=5:1) to give the title compound. MS (ESI) m/z 575.2 (M+H).

Step 4: 4-(2-(5-(3-Chloro-6-(difluoromethyl)-2-fluorophenyl)-4-methoxypyridin-2-yl)-3-cyclopropylpropanamido)benzoic Acid To a solution of tert-butyl 4-(2-(5-(3-chloro-6-(difluoromethyl)-2-fluorophenyl)-4-methoxypyridin-2-yl)-3-cyclopropylpropanamido)benzoate (160 mg, 0.28 mmol) in DCM (2 mL) was added TFA (95 mg, 0.84 mmol), and the mixture was stirred at 15° C. for 12 h under $N_2$ atmosphere. LC-MS showed the reaction was complete. The mixture was concentrated in vacuo and diluted with water (10 mL), and $NaHCO_3$ solution was added to the mixture until it reached pH=8. HCl (1N) was added until it reached pH=3, and it was extracted with DCM (8 mL×3). The combined organic layers were dried over $Na_2SO_4$, filtered and the filtrate was concentrated in vacuo to afford the title compound. $^1$H NMR ($CD_3OD$, 400 MHz): δ 8.55 (s, 1H), 8.00 (d, J=8.6 Hz, 2H), 7.69-7.84 (m, 4H), 7.58 (d, J=8.4 Hz, 1H), 6.61 (t, J=54.0 Hz, 1H), 4.31 (t, J=7.1 Hz, 1H), 4.11 (s, 3H), 2.20 (br s, 1H), 1.99-2.12 (m, 1H), 0.80-0.84 (m, 1H), 0.48-0.52 (m, 2H), 0.21-0.23 (m, 1H), 0.06-0.08 (m, 1H). MS (ESI) m/z 519.2 (M+H).

Step 5: 2-(1-((4-carboxyphenyl)amino)-3-cyclopropyl-1-oxopropan-2-yl)-5-(3-chloro-6-(difluoromethyl)-2-fluorophenyl)-4-methoxypyridine 1-oxide To a round bottom flask was added 4-(2-(5-(3-chloro-6-(difluoromethyl)-2-fluorophenyl)-4-methoxypyridin-2-yl)-3-cyclopropylpropanamido)benzoic acid (125 mg, 0.24 mmol), mCPBA (64.80 mg, 0.29 mmol, 77% purity) and DCM (5 mL) at 15° C. The reaction mixture was stirred at 15° C. for 18 h. Water (10 mL) was added and the mixture was extracted with DCM (8 mL×3). The combined organic layers were dried over anhydrous sodium sulfate, filtered and the filtrate was concentrated. The crude product was purified by prep-RP-HPLC to give the title compound. MS (ESI) m/z 535.2 (M+H).

Step 6: (S)- and (R)-2-(1-((4-carboxyphenyl)amino)-3-cyclopropyl-1-oxopropan-2-yl)-5-(3-chloro-6-(difluoromethyl)-2-fluorophenyl)-4-methoxypyridine 1-oxide (Examples 68 & 69)

2-(1-((4-carboxyphenyl)amino)-3-cyclopropyl-1-oxopropan-2-yl)-5-(3-chloro-6-(difluoromethyl)-2-fluorophenyl)-4-methoxypyridine 1-oxide (68-H) (90 mg, 0.15 mmol) was resolved by SFC on AD column (250×30 mm, 5 um) eluted with 30% EtOH containing 0.1% v/v concentrated aq. $NH_3$ in $CO_2$ at 60 mL/min to give one isomer of the title compound (Example 68, mixture of Peak 1 and Peak 2 which interconverted at rt after separation) and another isomer of the title compound (Example 69, mixture of Peak 3 and Peak 4 which interconverted at rt after separation).

Example 68: MS (ESI) m/z 534.9 (M+H).

Example 69: $^1$H NMR ($CD_3OD$, 400 MHz): δ 8.31 (s, 1H), 7.97 (d, J=8.6 Hz, 2H), 7.72 (d, J=8.8 Hz, 3H), 7.55 (d, J=8.4 Hz, 1H), 7.40 (d, J=6.1 Hz, 1H), 6.61 (t, J=56.4 Hz, 1H), 4.67-4.81 (m, 1H), 3.95 (s, 3H), 2.01-2.21 (m, 2H), 0.88-0.92 (m, 1H), 0.48-0.52 (m, 2H), 0.21-0.23 (m, 2H). MS (ESI) m/z 534.9 (M+H).

By using procedures similar to those described above, the following compounds were synthesized using appropriate starting materials and characterized.

| Ex. # | Structure | Name | Exact Mass [M + H]+ | Chiral Separation |
|---|---|---|---|---|
| 70 | 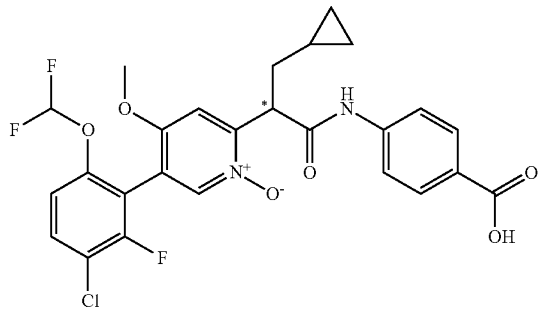 [SMILES: COc1cc(C(CC2CC2)C(=O)Nc2ccc(C(=O)O)cc2)[n+]([O-])cc1-c1c(OC(F)F)ccc(Cl)c1F] | 2-(1-((4-carboxyphenyl)amino)-3-cyclopropyl-1-oxopropan-2-yl)-5-(3-chloro-6-(difluoromethoxy)-2-fluorophenyl)-4-methoxypyridine 1-oxide | 550.9 | a pair of axial isomers, Peaks 1 and 4, AD |
| 71 | 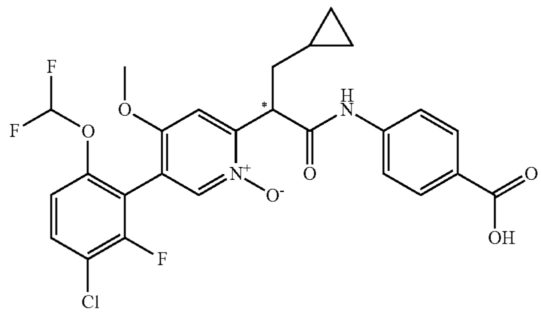 [SMILES: COc1cc(C(CC2CC2)C(=O)Nc2ccc(C(=O)O)cc2)[n+]([O-])cc1-c1c(OC(F)F)ccc(Cl)c1F] | 2-(1-((4-carboxyphenyl)amino)-3-cyclopropyl-1-oxopropan-2-yl)-5-(3-chloro-6-(difluoromethoxy)-2-fluorophenyl)-4-methoxypyridine 1-oxide | 550.9 | a pair of axial isomers, Peaks 2 and 3, AD |

Examples 72 & 73

(S)- and (R)-4-[(2-{5-[3-chloro-6-(difluoromethoxy)-2-fluorophenyl]-1-oxidopyridin-2-yl}-3-cyclopropylpropanoyl)amino]-2-fluorobenzoic Acid

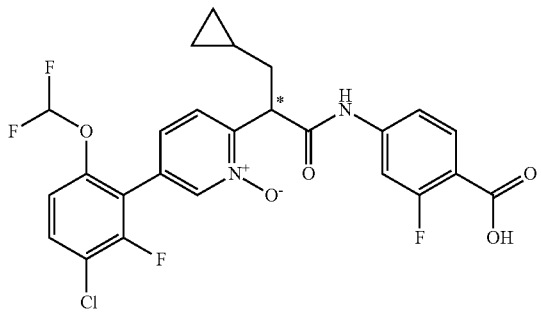

Step 1: Methyl 2-(5-(3-chloro-6-(difluoromethoxy)-2-fluorophenyl)pyridin-2-yl)-3-cyclopropylpropanoate Methyl 2-(5-bromopyridin-2-yl)-3-cyclopropylpropanoate (1.00 g, 3.52 mmol) was mixed with 4,4,4',4',5,5,5',5'-octamethyl-2,2'-bi(1,3,2-dioxaborolane) (0.89 g, 3.52 mmol), Pd(dppf)Cl$_2$ (0.64 g, 0.88 mmol) and potassium acetate (1.04 g, 10.56 mmol) in a microwave reaction vial. The vial was capped and nitrogen gas was used to purge the residual air three times. Then 1,4-dioxane (5 mL) was introduced with syringe. The resulting mixture was irradiated with a microwave at 100° C. for 0.5 h. LC-MS showed the reaction was complete. Then 1-chloro-4-(difluoromethoxy)-2-fluoro-3-iodobenzene (1.14 g, 3.52 mmol) and Pd(dppf)Cl$_2$ (0.52 g, 0.70 mmol) were added. The vial was capped and nitrogen gas was used to purge the residual air three times. 1 M aqueous K$_2$CO$_3$ solution (10.56 mL, 10.56 mmol) was introduced with a syringe. The mixture was stirred at 85° C. for 1 hour under MW. LC-MS showed the reaction was complete. After being cooled to rt, the reaction mixture was diluted with EtOAc (20 mL), washed with water (20 mL) and brine (20 mL). The organic layer was dried over anhydrous sodium sulfate, and the solution was filtered. The solution was concentrated in vacuo, and the crude product was purified by column chromatography (SiO$_2$, PE:EtOAc from 100:1 to 10:1) to give the title compound. $^1$H NMR (CDCl$_3$, 400 MHz): δ 8.59 (s, 1H), 7.71 (dd, J=8.0, 1.0 Hz, 1H), 7.51-7.58 (m, 1H), 7.10 (d, J=9.0 Hz, 2H), 6.86 (t, J=72.4 Hz, 1H), 4.03 (t, J=7.6 Hz, 1H), 3.76 (s, 3H), 2.02-2.15 (m, 1H), 1.82-2.00 (m, 1H), 0.64-0.79 (m, 1H), 0.35-0.54 (m, 2H), 0.09-0.19 (m, 1H), −0.04-0.06 (m, 1H). MS (ESI) m/z 400.1 (M+H).

Step 2: 2-(5-(3-Chloro-6-(difluoromethoxy)-2-fluorophenyl)pyridin-2-yl)-3-cyclopropylpropanoic Acid To a round bottom flask was added methyl 2-(5-(3-chloro-6-(difluoromethoxy)-2-fluorophenyl)pyridin-2-yl)-3-cyclopropylpropanoate (100 mg, 0.20 mmol), NaOH (16.01 mg, 0.40 mmol), water (1.5 mL) and THF (3 mL) at 15° C. The reaction mixture was stirred at 50° C. for 5 h. LC-MS showed the reaction was complete. The reaction mixture was concentrated in vacuo, re-dissolved in 20 mL water and 1M HCl was added until it reached pH=3. The mixture was extracted with DCM (3 mL×2), and the combined organic layers were washed with brine (10 mL), dried over anhydrous sodium sulfate and filtered. The solution was directly used for next step without further purification. MS (ESI) m/z 386.1 (M+H).

Step 3: Methyl 4-(2-(5-(3-chloro-6-(difluoromethoxy)-2-fluorophenyl)pyridin-2-yl)-3-cyclopropylpropanamido)-2-fluorobenzoate To a 25 mL round bottom flask was added a solution of 2-(5-(3-chloro-6-(difluoromethoxy)-2-fluorophenyl)pyridin-2-yl)-3-cyclopropylpropanoic acid in DCM (6 mL) from Step 2 above, methyl 4-amino-2-fluorobenzoate (33.80 mg, 0.20 mmol), HATU (91 mg, 0.24 mmol) and TEA (0.08 mL, 0.60 mmol) at 12° C. The reaction mixture was stirred at 12° C. for 18 h. The reaction mixture was diluted with water (15 mL) and extracted with DCM (8 mL×3), the combined organic layers were washed with brine (30 mL), dried over anhydrous sodium sulfate, filtered and concentrated. The crude product was purified by prep-TLC (SiO$_2$, PE:EtOAc=3:1) to give the title compound. MS (ESI) m/z 537.2 (M+H).

Step 4: 4-(2-(5-(3-Chloro-6-(difluoromethoxy)-2-fluorophenyl)pyridin-2-yl)-3-cyclopropylpropanamido)-2-fluorobenzoic Acid To a round bottom flask was added methyl 4-(2-(5-(3-chloro-6-(difluoromethoxy)-2-fluorophenyl)pyridin-2-yl)-3-cyclopropylpropanamido)-2-fluorobenzoate (520 mg, 0.63 mmol), THF (4 mL), water (2 mL) and NaOH (50.4 mg, 1.26 mmol) at 50° C. The reaction mixture was stirred at 50° C. for 10 h. LC-MS showed the reaction was mostly completed. The reaction mixture was concentrated in vacuo, re-dissolved in 25 mL water and 1M HCl was added until it reached pH=3. The mixture was extracted with DCM (15 mL×3), and the combined organic layers were washed with brine (50 mL), dried over anhydrous sodium sulfate and filtered. The filtrate was concentrated in vacuo to give the title compound, which was directly used for next step without further purification. $^1$H NMR (CD$_3$OD, 400 MHz): δ 8.63 (s, 1H), 8.06 (dd, J=8.2, 1.0 Hz, 1H), 7.75-7.90 (m, 2H), 7.67 (dd, J=13.3, 2.0 Hz, 1H), 7.58 (t, J=8.7 Hz, 1H), 7.32 (dd, J=8.6, 1.8 Hz, 1H), 7.15 (d, J=9.0 Hz, 1H), 6.86 (t, J=72.8 Hz, 1H), 4.14 (dd, J=8.3, 6.7 Hz, 1H), 2.05-2.18 (m, 1H), 1.88 (dt, J=13.8, 6.8 Hz, 1H), 0.66-0.79 (m, 1H), 0.32-0.52 (m, 2H), 0.06-0.19 (m, 1H), −0.07-0.06 (m, 1H). MS (ESI) m/z 523.1 (M+H).

Step 5: 2-(1-((4-Carboxy-3-fluorophenyl)amino)-3-cyclopropyl-1-oxopropan-2-yl)-5-(3-chloro-6-(difluoromethoxy)-2-fluorophenyl)pyridine 1-oxide To a round bottom flask was added 4-(2-(5-(3-chloro-6-(difluoromethoxy)-2-fluorophenyl)pyridin-2-yl)-3-cyclopropylpropanamido)-2-fluorobenzoic acid (370 mg, 0.43 mmol), mCPBA (124 mg, 0.55 mmol, 77% purity) and DCM (5 mL) at 15° C. The reaction mixture was stirred at 15° C. for 6 h. LC-MS showed the reaction was complete. The mixture was quenched with sat. Na$_2$SO$_3$ solution (10 mL). The mixture was extracted with DCM (8 mL×3). The combined organic layers were washed with sat. NaHCO$_3$ (10 mL×3) solution, dried over anhydrous sodium sulfate, filtered and the filtrate was concentrated in vacuo, the residue was purified by prep-RP-HPLC to give the title compound. MS (ESI) m/z 539.2 (M+H).

Step 6: 2-(1-((4-Carboxy-3-fluorophenyl)amino)-3-cyclopropyl-1-oxopropan-2-yl)-5-(3-chloro-6-(difluoromethoxy)-2-fluorophenyl)pyridine 1-oxide (Examples 72 & 73)

2-(1-((4-carboxy-3-fluorophenyl)amino)-3-cyclopropyl-1-oxopropan-2-yl)-5-(3-chloro-6-(difluoromethoxy)-2-fluorophenyl)pyridine 1-oxide (120 mg, 0.22 mmol) was resolved by SFC on AD column (250×30 mm, 10 um) eluted with 35% IPA containing 0.1% v/v concentrated aq. NH$_3$ in CO$_2$ at 80 mL/min to give one isomer of the title compound (Example 72, first peak) and another isomer of the title compound (Example 73, second peak).

Example 72: MS (ESI) m/z 538.9 (M+H).

Example 73: $^1$H NMR (CD$_3$OD, 400 MHz): δ 8.29 (s, 1H), 7.70 (t, J=8.4 Hz, 1H), 7.60 (d, J=8.4 Hz, 1H), 7.41-7.54 (m, 3H), 7.17 (dd, J=8.7, 1.9 Hz, 1H), 7.02 (d, J=9.2 Hz, 1H), 6.89 (t, J=72.4 Hz, 1H), 4.47 (t, J=7.5 Hz, 1H), 1.83 (t, J=7.1 Hz, 2H), 1.11 (d, J=6.7 Hz, 1H), 0.69 (d, J=6.5 Hz, 1H), 0.21-0.34 (m, 2H), 0.01 (br s, 1H). MS (ESI) m/z 538.9 (M+H).

By using procedures similar to those described above, the following compounds were synthesized using appropriate starting materials and characterized.

| Ex. # | Structure | Name | Exact Mass [M + H]$^+$ | Chiral Separation |
|---|---|---|---|---|
| 74 | 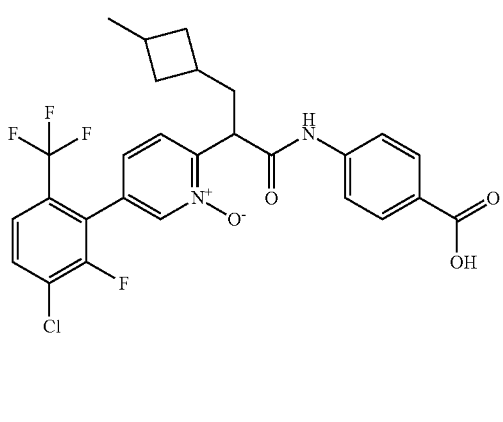 [SMILES: CC1CC(CC(C(=O)Nc2ccc(C(=O)O)cc2)c2ccc(-c3c(C(F)(F)F)ccc(Cl)c3F)c[n+]2[O-])C1] | 2-(1-((4-carboxyphenyl)amino)-3-(3-methylcyclobutyl)-1-oxopropan-2-yl)-5-(3-chloro-2-fluoro-6-(trifluoromethyl)phenyl)pyridine 1-oxide | 551.3 | Trans second eluted isomer SFC AD column |

| Ex. # | Structure | Name | Exact Mass [M + H]⁺ | Chiral Separation |
|---|---|---|---|---|
| 75 | 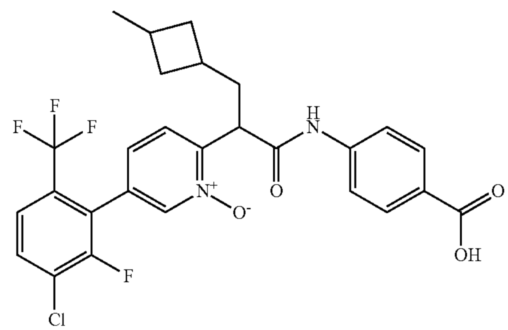 [SMILES: CC1CC(CC(C(=O)Nc2ccc(C(=O)O)cc2)c2ccc(-c3c(C(F)(F)F)ccc(Cl)c3F)c[n+]2[O-])C1] | 2-(1-((4-carboxyphenyl)amino)-3-(3-methylcyclobutyl)-1-oxopropan-2-yl)-5-(3-chloro-2-fluoro-6-(trifluoromethyl)phenyl)pyridine 1-oxide | 551.3 | Cis third eluted isomer SFC AD column |
| 76 | 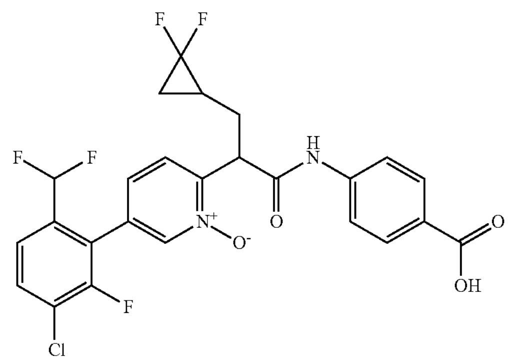 [SMILES: O=C(O)c1ccc(NC(=O)C(CC2CC2(F)F)c2ccc(-c3c(C(F)F)ccc(Cl)c3F)c[n+]2[O-])cc1] | 2-(1-((4-carboxyphenyl)amino)-3-(2,2-difluorocyclopropyl)-1-oxopropan-2-yl)-5-(3-chloro-6-(difluoromethyl)-2-fluorophenyl)pyridine 1-oxide | 541.3 | Second eluted isomer SFC AD column |
| 77 | 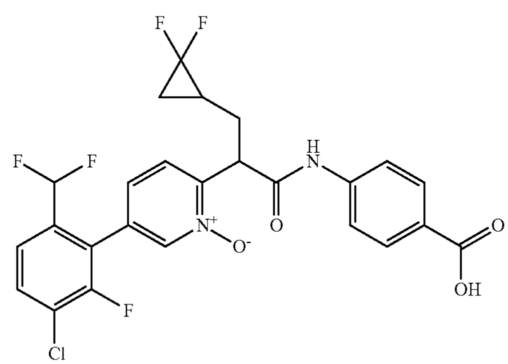 [SMILES: O=C(O)c1ccc(NC(=O)C(CC2CC2(F)F)c2ccc(-c3c(C(F)F)ccc(Cl)c3F)c[n+]2[O-])cc1] | 2-(1-((4-carboxyphenyl)amino)-3-(2,2-difluorocyclopropyl)-1-oxopropan-2-yl)-5-(3-chloro-6-(difluoromethyl)-2-fluorophenyl)pyridine 1-oxide | 541.3 | Third eluted isomer SFC AD column |
| 78 | 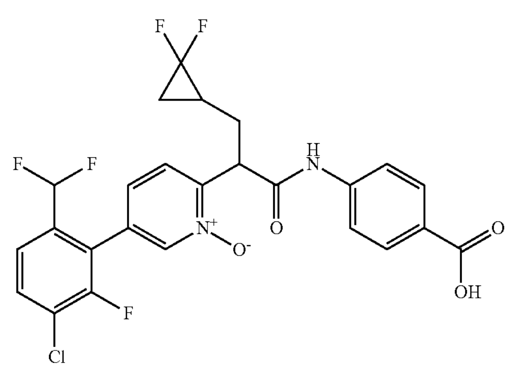 [SMILES: O=C(O)c1ccc(NC(=O)C(CC2CC2(F)F)c2ccc(-c3c(C(F)F)ccc(Cl)c3F)c[n+]2[O-])cc1] | 2-(1-((4-carboxyphenyl)amino)-3-(2,2-difluorocyclopropyl)-1-oxopropan-2-yl)-5-(3-chloro-6-(difluoromethyl)-2-fluorophenyl)pyridine 1-oxide | 541.2 | From final reaction mixture the first eluted peak on AD column is further separated by AD column to give example as first eluted isomer. |

-continued

| Ex. # | Structure | Name | Exact Mass [M + H]+ | Chiral Separation |
|---|---|---|---|---|
| 79 | 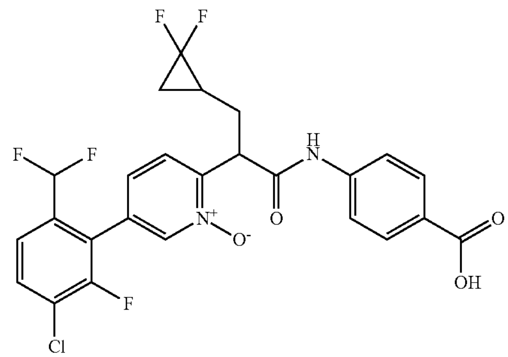 [SMILES: O=C(O)c1ccc(NC(=O)C(CC2CC2(F)F)c2ccc(-c3c(C(F)F)ccc(Cl)c3F)c[n+]2[O-])cc1] | 2-(1-((4-carboxyphenyl)amino)-3-(2,2-difluorocyclopropyl)-1-oxopropan-2-yl)-5-(3-chloro-6-(difluoromethyl)-2-fluorophenyl)pyridine 1-oxide | 541.3 | From final reaction mixture the first eluted peak on AD column is further separated by AD column to give example as second eluted isomer. |
| 80 | 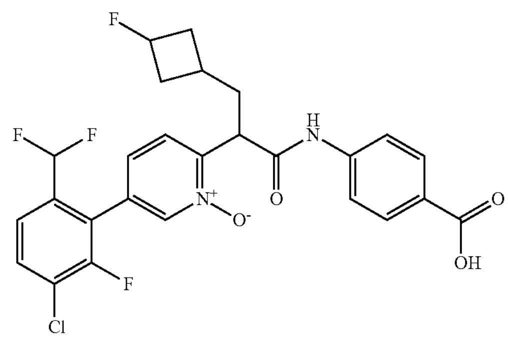 [SMILES: O=C(O)c1ccc(NC(=O)C(CC2CC(F)C2)c2ccc(-c3c(C(F)F)ccc(Cl)c3F)c[n+]2[O-])cc1] | 2-(1-((4-carboxyphenyl)amino)-3-(3-fluorocyclobutyl)-1-oxopropan-2-yl)-5-(3-chloro-6-(difluoromethyl)-2-fluorophenyl)pyridine 1-oxide | 537.3 | First eluted isomer SFC AD column |
| 81 | 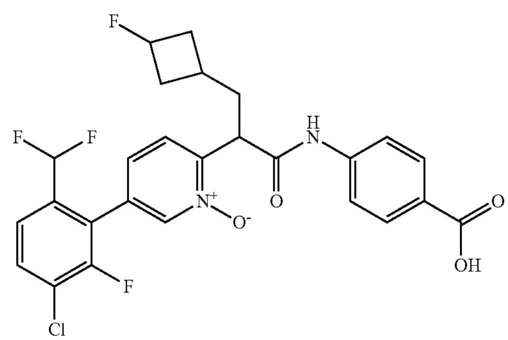 [SMILES: O=C(O)c1ccc(NC(=O)C(CC2CC(F)C2)c2ccc(-c3c(C(F)F)ccc(Cl)c3F)c[n+]2[O-])cc1] | 2-(1-((4-carboxyphenyl)amino)-3-(3-fluorocyclobutyl)-1-oxopropan-2-yl)-5-(3-chloro-6-(difluoromethyl)-2-fluorophenyl)pyridine-1-oxide | 537.3 | Second eluted isomer SFC AD column |
| 82 | 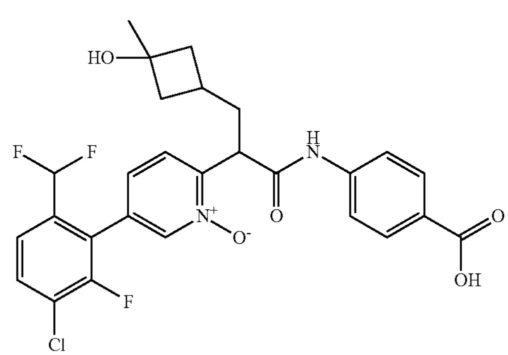 [SMILES: CC1(O)CC(CC(C(=O)Nc2ccc(C(=O)O)cc2)c2ccc(-c3c(C(F)F)ccc(Cl)c3F)c[n+]2[O-])C1] | 2-(1-((4-carboxyphenyl)amino)-3-(3-hydroxy-3-methylcyclobutyl)-1-oxopropan-2-yl)-5-(3-chloro-6-(difluoromethyl)-2-fluorophenyl)pyridine 1-oxide | 549.3 | First eluted cis isomer SFC OJ column |

-continued

| Ex. # | Structure | Name | Exact Mass [M + H]⁺ | Chiral Separation |
|---|---|---|---|---|
| 83 | 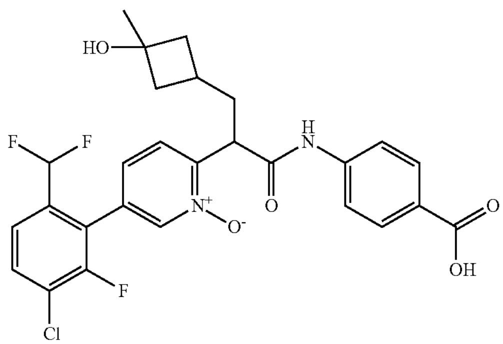 [SMILES: CC1(O)CC(CC(C(=O)Nc2ccc(C(=O)O)cc2)c2ccc(-c3c(C(F)F)ccc(Cl)c3F)c[n+]2[O-])C1] | 2-(1-((4-carboxyphenyl)amino)-3-(3-hydroxy-3-methylcyclobutyl)-1-oxopropan-2-yl)-5-(3-chloro-6-(difluoromethyl)-2-fluorophenyl)pyridine 1-oxide | 549.3 | Second eluted cis isomer SFC OJ column |
| 84 | 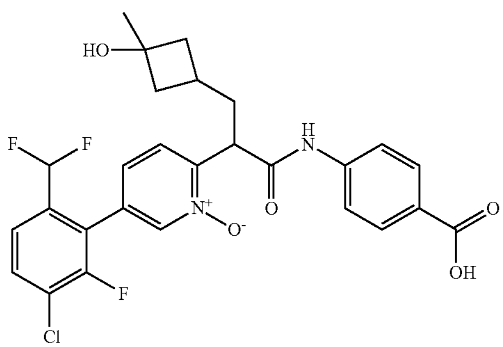 [SMILES: CC1(O)CC(CC(C(=O)Nc2ccc(C(=O)O)cc2)c2ccc(-c3c(C(F)F)ccc(Cl)c3F)c[n+]2[O-])C1] | 2-(1-((4-carboxyphenyl)amino)-3-(3-hydroxy-3-methylcyclobutyl)-1-oxopropan-2-yl)-5-(3-chloro-6-(difluoromethyl)-2-fluorophenyl)pyridine 1-oxide | 549.3 | First eluted trans isomer SFC OJ column |
| 85 | 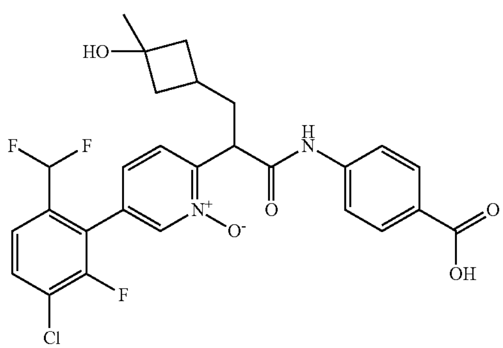 [SMILES: CC1(O)CC(CC(C(=O)Nc2ccc(C(=O)O)cc2)c2ccc(-c3c(C(F)F)ccc(Cl)c3F)c[n+]2[O-])C1] | 2-(1-((4-carboxyphenyl)amino)-3-(3-hydroxy-3-methylcyclobutyl)-1-oxopropan-2-yl)-5-(3-chloro-6-(difluoromethyl)-2-fluorophenyl)pyridine 1-oxide | 549.3 | Second eluted trans isomer SFC OJ column |
| 86 | 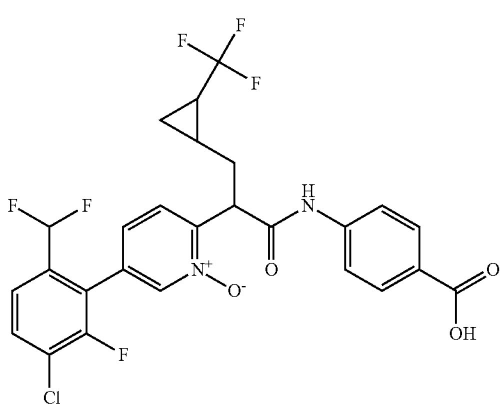 [SMILES: O=C(O)c1ccc(NC(=O)C(CC2CC2C(F)(F)F)c2ccc(-c3c(C(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethyl)-2-fluorophenyl)pyridine 1-oxide | 572.9 | Mixture of first and second eluted isomers SFC AD column |

-continued

| Ex. # | Structure | Name | Exact Mass [M + H]+ | Chiral Separation |
|---|---|---|---|---|
| 87 | 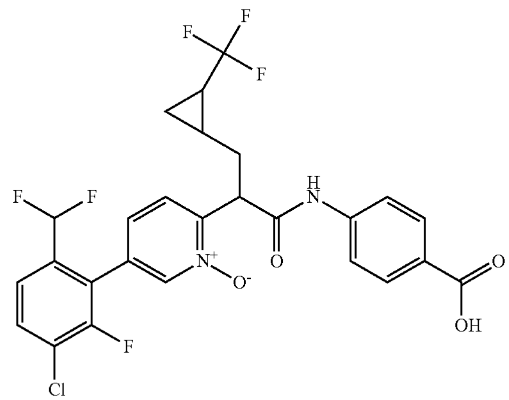 [SMILES: O=C(O)c1ccc(NC(=O)C(CC2CC2C(F)(F)F)c2ccc(-c3c(C(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethyl)-2-fluorophenyl)pyridine 1-oxide | 572.9 | Third eluted isomer SFC AD column |
| 88 | 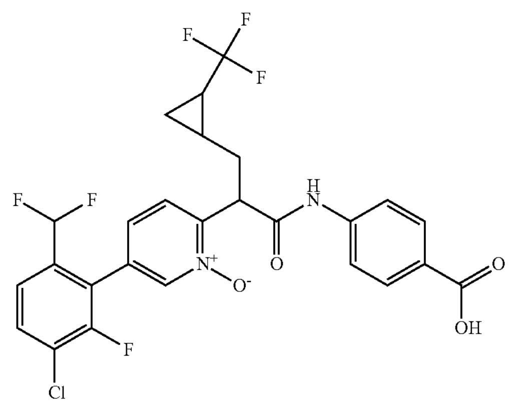 [SMILES: O=C(O)c1ccc(NC(=O)C(CC2CC2C(F)(F)F)c2ccc(-c3c(C(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethyl)-2-fluorophenyl)pyridine 1-oxide | 572.9 | Fourth eluted isomer SFC AD column |
| 89 | 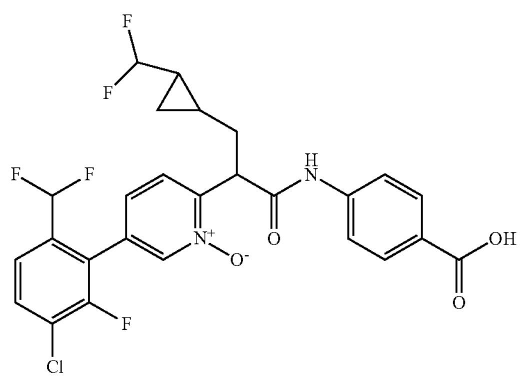 [SMILES: O=C(O)c1ccc(NC(=O)C(CC2CC2C(F)F)c2ccc(-c3c(C(F)F)ccc(Cl)c3F)c[n+]2[O-])cc1] | 2-(1-((4-carboxyphenyl)amino)-3-(2-(difluoromethyl)cyclopropyl)-1-oxopropan-2-yl)-5-(3-chloro-6-(difluoromethyl)-2-fluorophenyl)pyridine-1-oxide | 544.9 | Third eluted isomer SFC AD column |
| 90 | 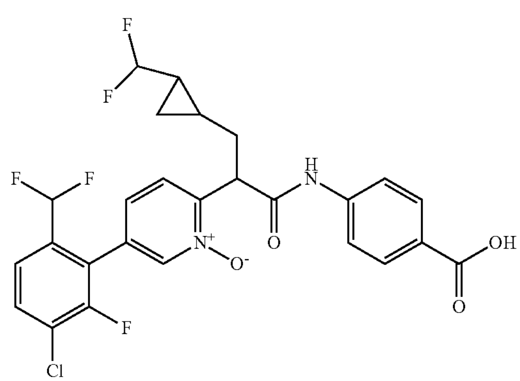 [SMILES: O=C(O)c1ccc(NC(=O)C(CC2CC2C(F)F)c2ccc(-c3c(C(F)F)ccc(Cl)c3F)c[n+]2[O-])cc1] | 2-(1-((4-carboxyphenyl)amino)-3-(2-(difluoromethyl)cyclopropyl)-1-oxopropan-2-yl)-5-(3-chloro-6-(difluoromethyl)-2-fluorophenyl)pyridine 1-oxide | 544.9 | Second eluted isomer SFC AD column |

| Ex. # | Structure | Name | Exact Mass [M + H]⁺ | Chiral Separation |
|---|---|---|---|---|
| 91 | 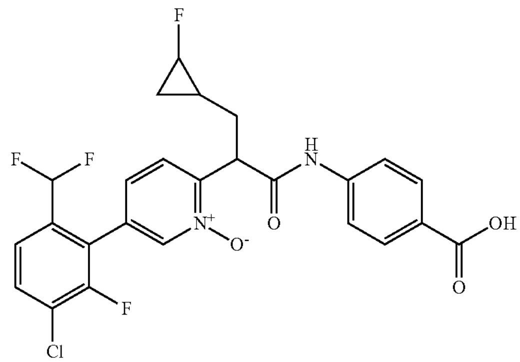 [SMILES: O=C(O)c1ccc(NC(=O)C(CC2CC2F)c2ccc(-c3c(C(F)F)ccc(Cl)c3F)c[n+]2[O-])cc1] | 2-(1-((4-carboxyphenyl)amino)-3-(2-fluorocyclopropyl)-1-oxopropan-2-yl)-5-(3-chloro-6-(difluoromethyl)-2-fluorophenyl)pyridine 1-oxide | 523.1 | First eluted isomer SFC OJ-H column |
| 92 | 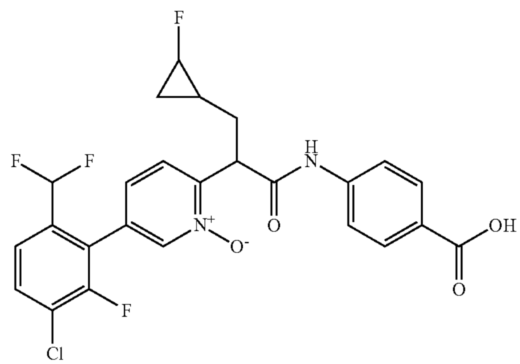 [SMILES: O=C(O)c1ccc(NC(=O)C(CC2CC2F)c2ccc(-c3c(C(F)F)ccc(Cl)c3F)c[n+]2[O-])cc1] | 2-(1-((4-carboxyphenyl)amino)-3-(2-fluorocyclopropyl)-1-oxopropan-2-yl)-5-(3-chloro-6-(difluoromethyl)-2-fluorophenyl)pyridine 1-oxide | 523.1 | Second eluted isomer SFC OJ-H column |
| 93 | 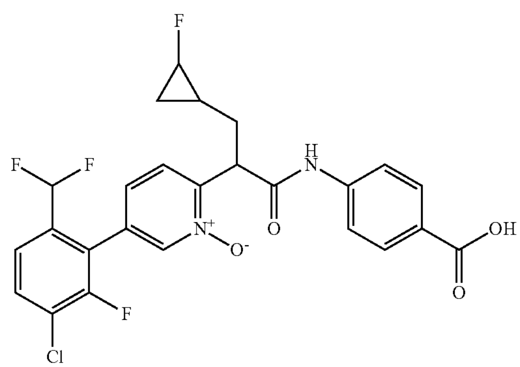 [SMILES: O=C(O)c1ccc(NC(=O)C(CC2CC2F)c2ccc(-c3c(C(F)F)ccc(Cl)c3F)c[n+]2[O-])cc1] | 2-(1-((4-carboxyphenyl)amino)-3-(2-fluorocyclopropyl)-1-oxopropan-2-yl)-5-(3-chloro-6-(difluoromethyl)-2-fluorophenyl)pyridine-1-oxide | 523.3 | Third eluted isomer SFC OJ-H column |
| 94 | 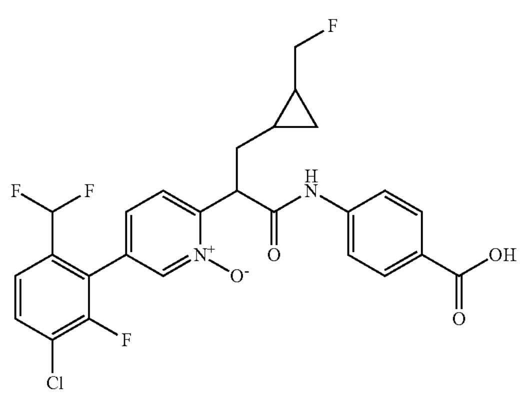 [SMILES: O=C(O)c1ccc(NC(=O)C(CC2CC2CF)c2ccc(-c3c(C(F)F)ccc(Cl)c3F)c[n+]2[O-])cc1] | 2-(1-((4-carboxyphenyl)amino)-3-(2-(fluoromethyl)cyclopropyl)-1-oxopropan-2-yl)-5-(3-chloro-6-(difluoromethyl)-2-fluorophenyl)pyridine 1-oxide | 536.9 | From final reaction mixture the second eluted peak on OJ column is further separated by AD column to give example as first eluted isomer. |

| Ex. # | Structure | Name | Exact Mass [M + H]+ | Chiral Separation |
|---|---|---|---|---|
| 95 | 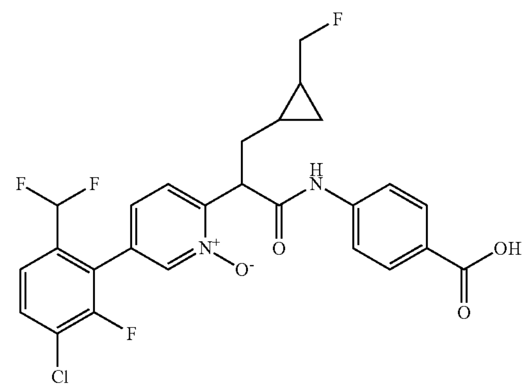 [SMILES: O=C(O)c1ccc(NC(=O)C(CC2CC2CF)c2ccc(-c3c(C(F)F)ccc(Cl)c3F)c[n+]2[O-])cc1] | 2-(1-((4-carboxyphenyl)amino)-3-(2-(fluoromethyl)cyclopropyl)-1-oxopropan-2-yl)-5-(3-chloro-6-(difluoromethyl)-2-fluorophenyl)pyridine-1-oxide | 536.9 | From final reaction mixture the second eluted peak on OJ column is further spearated by AD column to give example as second eluted isomer. |
| 96 | 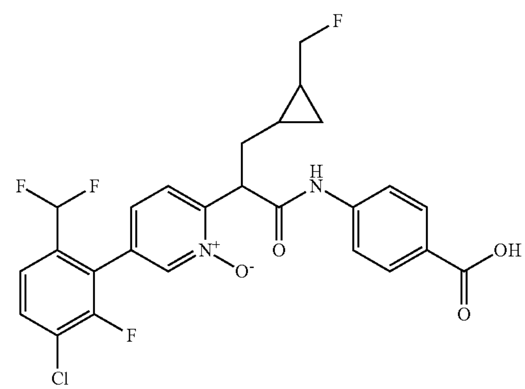 [SMILES: O=C(O)c1ccc(NC(=O)C(CC2CC2CF)c2ccc(-c3c(C(F)F)ccc(Cl)c3F)c[n+]2[O-])cc1] | 2-(1-((4-carboxyphenyl)amino)-3-(2-(fluoromethyl)cyclopropyl)-1-oxopropan-2-yl)-5-(3-chloro-6-(difluoromethyl)-2-fluorophenyl)pyridine 1-oxide | 536.9 | From final reaction mixture the first eluted peak on OJ column is further spearated by AD column to give example as first eluted isomer. |
| 97 | 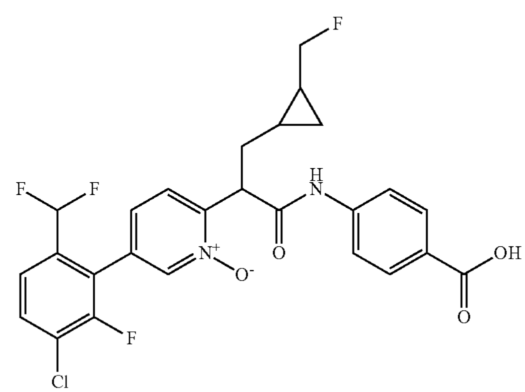 [SMILES: O=C(O)c1ccc(NC(=O)C(CC2CC2CF)c2ccc(-c3c(C(F)F)ccc(Cl)c3F)c[n+]2[O-])cc1] | 2-(1-((4-carboxyphenyl)amino)-3-(2-(fluoromethyl)cyclopropyl)-1-oxopropan-2-yl)-5-(3-chloro-6-(difluoromethyl)-2-fluorophenyl)pyridine 1-oxide | 536.9 | From final reaction mixture the first eluted peak on OJ column is further separated by AD column to give example as second eluted isomer. |
| 98 | 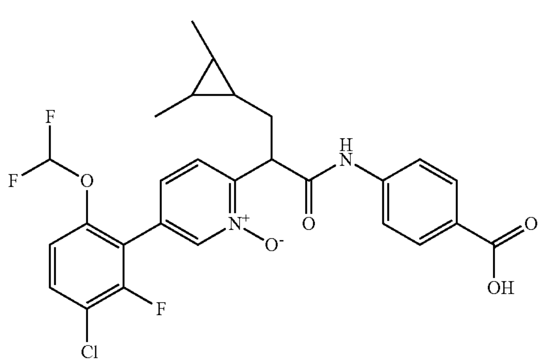 [SMILES: CC1C(C)C1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2,3-dimethylcyclopropyl)-1-oxopropan-2-yl)-5-(3-chloro-6-(difluoromethoxy)-2-fluorophenyl)pyridine 1-oxide | 549.3 | From final reaction mixture the second eluted peak on AD column is further separated by IC column to give example as first eluted isomer |

| Ex. # | Structure | Name | Exact Mass [M + H]+ | Chiral Separation |
|---|---|---|---|---|
| 99 | 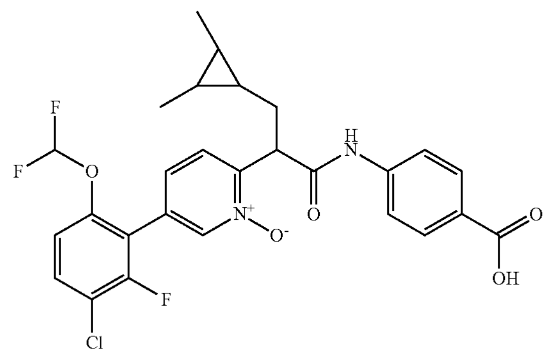 [SMILES: CC1C(C)C1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2,3-dimethylcyclopropyl)-1-oxopropan-2-yl)-5-(3-chloro-6-(difluoromethoxy)-2-fluorophenyl)pyridine 1-oxide | 549.3 | From final reaction mixture the second eluted peak on AD column is further separated by IC column to give example as second eluted isomer |
| 100 | 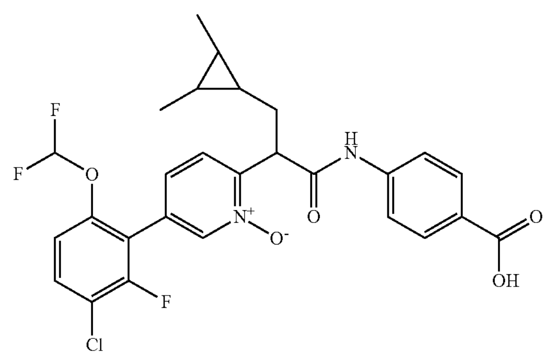 [SMILES: CC1C(C)C1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2,3-dimethylcyclopropyl)-1-oxopropan-2-yl)-5-(3-chloro-6-(difluoromethoxy)-2-fluorophenyl)pyridine 1-oxide | 549.3 | First eluted peak AD column. Example is mixture of two isomers |
| 101 | 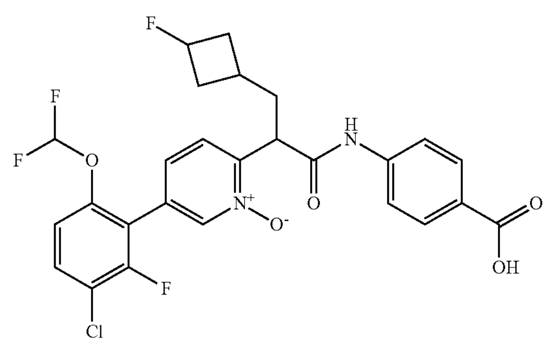 [SMILES: O=C(O)c1ccc(NC(=O)C(CC2CC(F)C2)c2ccc(-c3c(OC(F)F)ccc(Cl)c3F)c[n+]2[O-])cc1] | 2-(1-((4-carboxyphenyl)amino)-3-(3-fluorocyclobutyl)-1-oxopropan-2-yl)-5-(3-chloro-6-(difluoromethoxy)-2-fluorophenyl)pyridine 1-oxide | 553.2 | First eluted isomer SFC AD column |
| 102 | 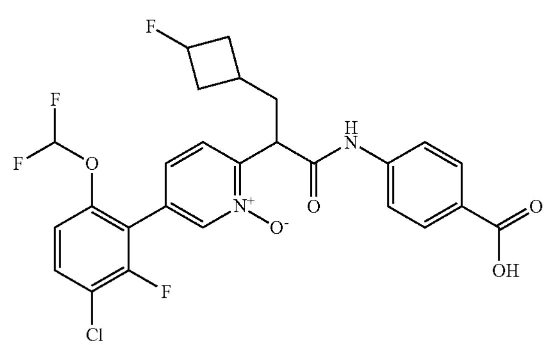 [SMILES: O=C(O)c1ccc(NC(=O)C(CC2CC(F)C2)c2ccc(-c3c(OC(F)F)ccc(Cl)c3F)c[n+]2[O-])cc1] | 2-(1-((4-carboxyphenyl)amino)-3-(3-fluorocyclobutyl)-1-oxopropan-2-yl)-5-(3-chloro-6-(difluoromethoxy)-2-fluorophenyl)pyridine 1-oxide | 553.3 | Second eluted isomer SFC AD column |

-continued

| Ex. # | Structure | Name | Exact Mass [M + H]+ | Chiral Separation |
|---|---|---|---|---|
| 103 | 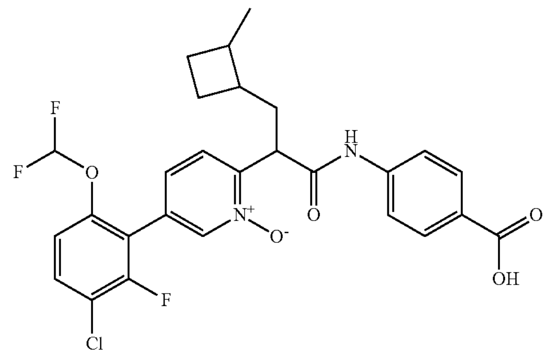 [SMILES: CC1CCC1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2-methylcyclobutyl)-1-oxopropan-2-yl)-5-(3-chloro-6-(difluoromethoxy)-2-fluorophenyl)pyridine 1-oxide | 549.1 | First eluted isomer SFC AD column |
| 104 | 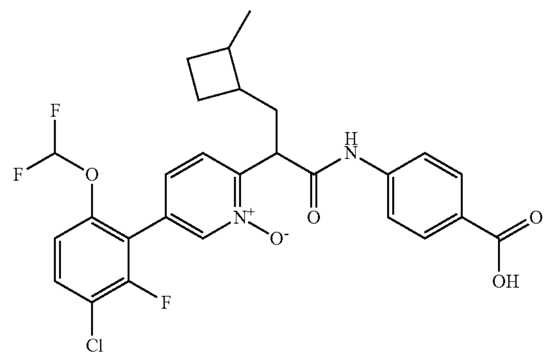 [SMILES: CC1CCC1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2-methylcyclobutyl)-1-oxopropan-2-yl)-5-(3-chloro-6-(difluoromethoxy)-2-fluorophenyl)pyridine 1-oxide | 549.3 | Second eluted isomer SFC AD column |
| 105 | 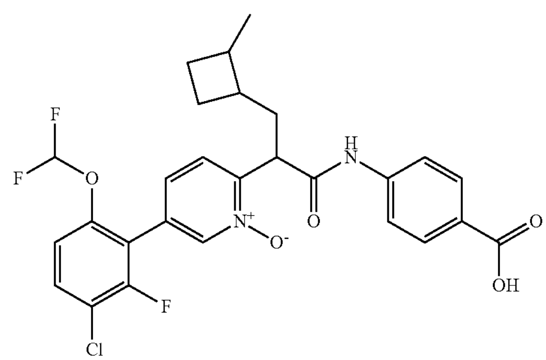 [SMILES: CC1CCC1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2-methylcyclobutyl)-1-oxopropan-2-yl)-5-(3-chloro-6-(difluoromethoxy)-2-fluorophenyl)pyridine 1-oxide | 549.3 | Third eluted isomer SFC AD column |
| 106 | 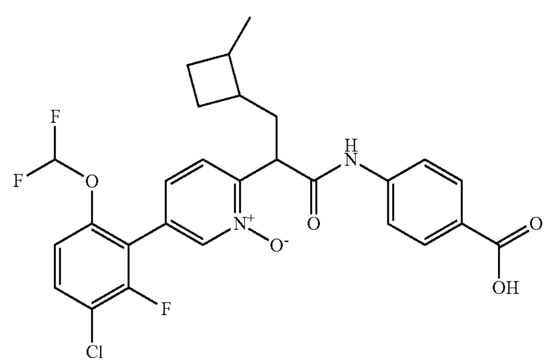 [SMILES: CC1CCC1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2-methylcyclobutyl)-1-oxopropan-2-yl)-5-(3-chloro-6-(difluoromethoxy)-2-fluorophenyl)pyridine 1-oxide | 549.3 | Fourth eluted isomer SFC AD column |

-continued

| Ex. # | Structure | Name | Exact Mass [M + H]⁺ | Chiral Separation |
|---|---|---|---|---|
| 107 | 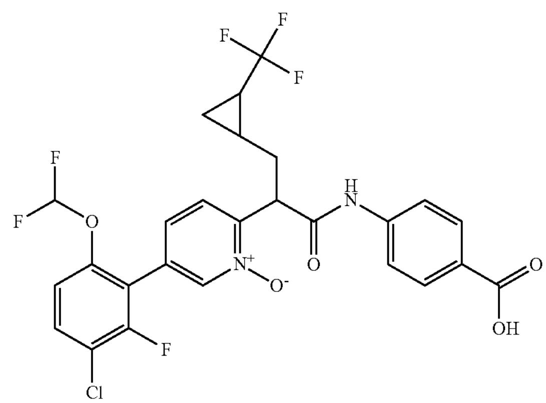 [SMILES: O=C(O)c1ccc(NC(=O)C(CC2CC2C(F)(F)F)c2ccc(-c3c(OC(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethoxy)-2-fluorophenyl)pyridine 1-oxide | 589.2 | From final reaction mixture the second eluted peak on AD column is further separated by AD column to give example as first eluted isomer |
| 108 | 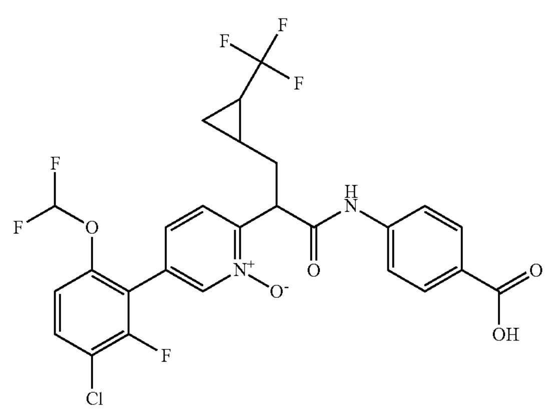 [SMILES: O=C(O)c1ccc(NC(=O)C(CC2CC2C(F)(F)F)c2ccc(-c3c(OC(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethoxy)-2-fluorophenyl)pyridine 1-oxide | 588.8 | From final reaction mixture the first eluted peak on AD column is further separated by AD column to give example as second eluted isomer |
| 109 | 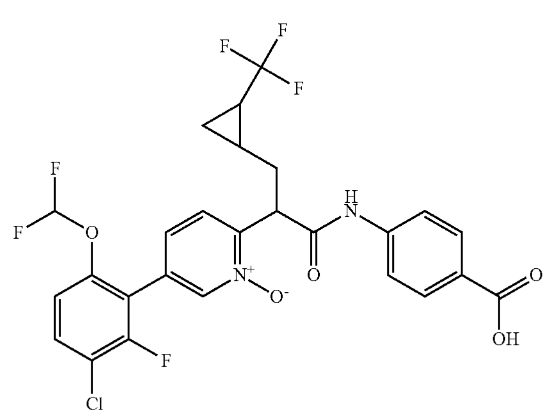 [SMILES: O=C(O)c1ccc(NC(=O)C(CC2CC2C(F)(F)F)c2ccc(-c3c(OC(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethoxy)-2-fluorophenyl)pyridine 1-oxide | 588.9 | From final reaction mixture the second eluted peak on AD column is further separated by AD column to give example as second eluted isomer |

| Ex. # | Structure | Name | Exact Mass [M + H]+ | Chiral Separation |
|---|---|---|---|---|
| 110 | 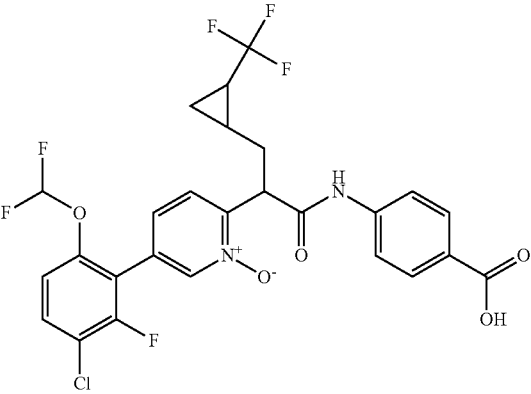 [SMILES: O=C(O)c1ccc(NC(=O)C(CC2CC2C(F)(F)F)c2ccc(-c3c(OC(F)F)ccc(Cl)c3F)c[n+]2[O-])cc1] | 2-(1-((4-carboxyphenyl)amino)-1-oxo-3-(2-(trifluoromethyl)cyclopropyl)propan-2-yl)-5-(3-chloro-6-(difluoromethoxy)-2-fluorophenyl)pyridine 1-oxide | 588.8 | From final reaction mixture the first eluted peak on AD column is further separated by AD column to give example as first eluted isomer. |
| 111 | 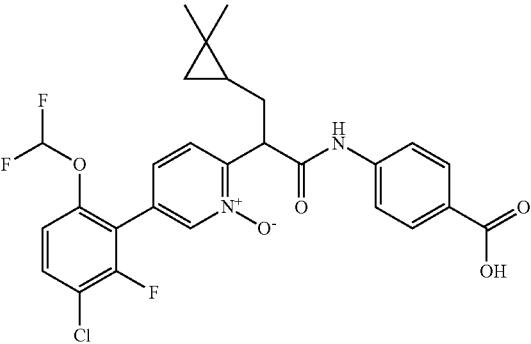 [SMILES: CC1(C)CC1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2,2-dimethylcyclopropyl)-1-oxopropan-2-yl)-5-(3-chloro-6-(difluoromethoxy)-2-fluorophenyl)pyridine 1-oxide | 549.2 | First eluted isomer SFC AS column |
| 112 | 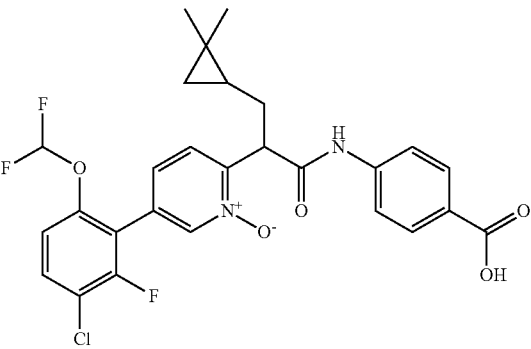 [SMILES: CC1(C)CC1CC(C(=O)Nc1ccc(C(=O)O)cc1)c1ccc(-c2c(OC(F)F)ccc(Cl)c2F)c[n+]1[O-]] | 2-(1-((4-carboxyphenyl)amino)-3-(2,2-dimethylcyclopropyl)-1-oxopropan-2-yl)-5-(3-chloro-6-(difluoromethoxy)-2-fluorophenyl)pyridine 1-oxide | 549.1 | Second eluted isomer SFC AS column |
| 113 | 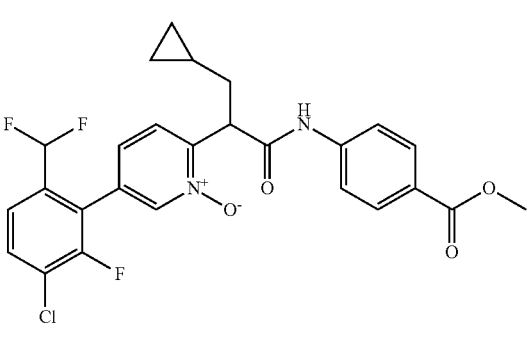 [SMILES: COC(=O)c1ccc(NC(=O)C(CC2CC2)c2ccc(-c3c(C(F)F)ccc(Cl)c3F)c[n+]2[O-])cc1] | 5-(3-chloro-6-(difluoromethyl)-2-fluorophenyl)-2-(3-cyclopropyl-1-((4-(methoxycarbonyl)phenyl)amino)-1-oxopropan-2-yl)pyridine 1-oxide | 519.3 | First eluted isomer SFC OJ-H column |

| Ex. # | Structure | Name | Exact Mass [M + H]⁺ | Chiral Separation |
|---|---|---|---|---|
| 114 | 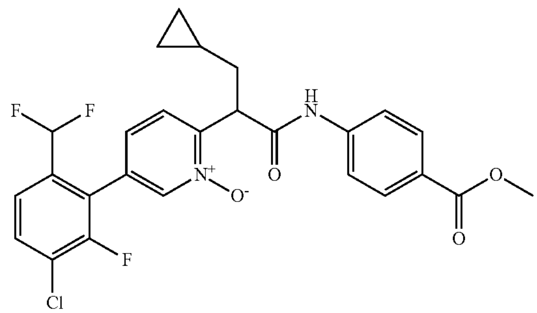 [SMILES: COC(=O)c1ccc(NC(=O)C(CC2CC2)c2ccc(-c3c(C(F)F)ccc(Cl)c3F)c[n+]2[O-])cc1] | 5-(3-chloro-6-(difluoromethyl)-2-fluorophenyl)-2-(3-cyclopropyl-1-((4-(methoxycarbonyl)phenyl)amino)-1-oxopropan-2-yl)pyridine 1-oxide | 519.3 | Second eluted isomer SFC OJ-H column |
| 115 | 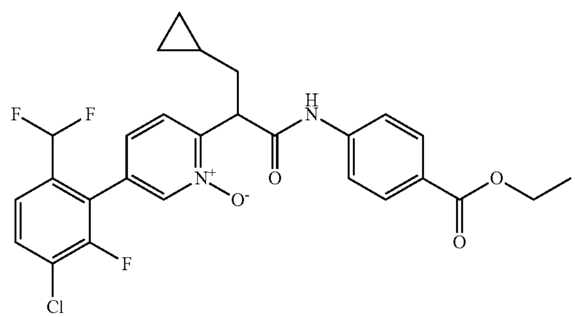 [SMILES: CCOC(=O)c1ccc(NC(=O)C(CC2CC2)c2ccc(-c3c(C(F)F)ccc(Cl)c3F)c[n+]2[O-])cc1] | 5-(3-chloro-6-(difluoromethyl)-2-fluorophenyl)-2-(3-cyclopropyl-1-((4-(ethoxycarbonyl)phenyl)amino)-1-oxopropan-2-yl)pyridine 1-oxide | 533.3 | First eluted isomer SFC OJ-H column |
| 116 | 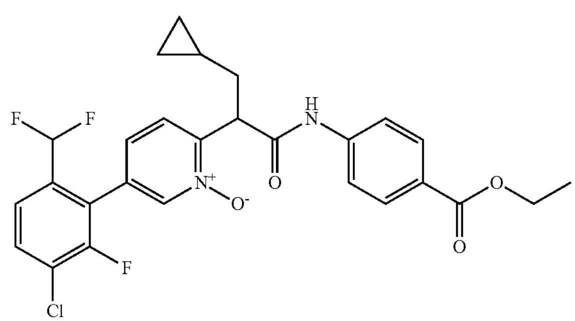 [SMILES: CCOC(=O)c1ccc(NC(=O)C(CC2CC2)c2ccc(-c3c(C(F)F)ccc(Cl)c3F)c[n+]2[O-])cc1] | 5-(3-chloro-6-(difluoromethyl)-2-fluorophenyl)-2-(3-cyclopropyl-1-((4-(ethoxycarbonyl)phenyl)amino)-1-oxopropan-2-yl)pyridine 1-oxide | 533.3 | Second eluted isomer SFC OJ-H column |
| 117 | 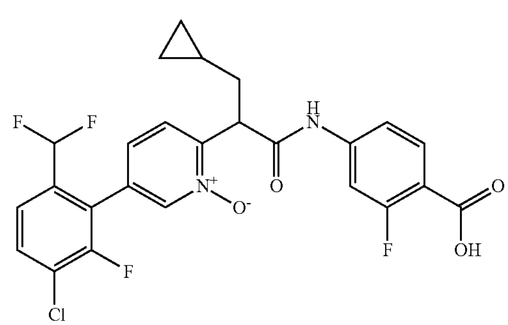 [SMILES: O=C(O)c1ccc(NC(=O)C(CC2CC2)c2ccc(-c3c(C(F)F)ccc(Cl)c3F)c[n+]2[O-])cc1F] | 2-(1-((4-carboxy-3-fluorophenyl)amino)-3-cyclopropyl-1-oxopropan-2-yl)-5-(3-chloro-6-(difluoromethyl)-2-fluorophenyl)pyridine 1-oxide | 523.3 | First eluted isomer SFC AD column |

-continued

| Ex. # | Structure | Name | Exact Mass [M + H]+ | Chiral Separation |
|---|---|---|---|---|
| 118 | 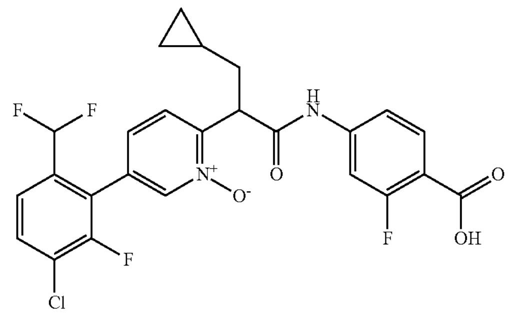 [SMILES: O=C(O)c1ccc(NC(=O)C(CC2CC2)c2ccc(-c3c(C(F)F)ccc(Cl)c3F)c[n+]2[O-])cc1F] | 2-(1-((4-carboxy-3-fluorophenyl)amino)-3-cyclopropyl-1-oxopropan-2-yl)-5-(3-chloro-6-(difluoromethyl)-2-fluorophenyl)pyridine 1-oxide | 523.3 | Second eluted isomer SFC AD column |
| 119 | 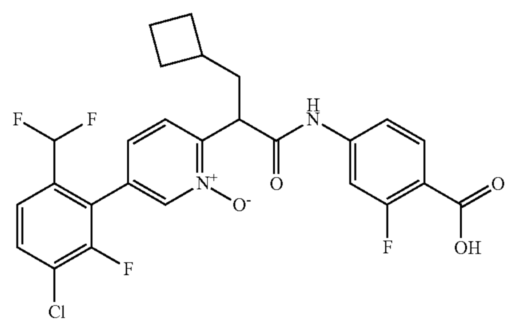 [SMILES: O=C(O)c1ccc(NC(=O)C(CC2CCC2)c2ccc(-c3c(C(F)F)ccc(Cl)c3F)c[n+]2[O-])cc1F] | 2-(1-((4-carboxy-3-fluorophenyl)amino)-3-cyclobutyl-1-oxopropan-2-yl)-5-(3-chloro-6-(difluoromethyl)-2-fluorophenyl)pyridine 1-oxide | 537.3 | First eluted isomer SFC AD column |
| 120 | 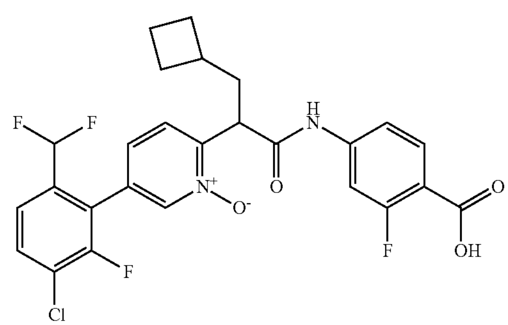 [SMILES: O=C(O)c1ccc(NC(=O)C(CC2CCC2)c2ccc(-c3c(C(F)F)ccc(Cl)c3F)c[n+]2[O-])cc1F] | 2-(1-((4-carboxy-3-fluorophenyl)amino)-3-cyclobutyl-1-oxopropan-2-yl)-5-(3-chloro-6-(difluoromethyl)-2-fluorophenyl)pyridine 1-oxide | 537.3 | Second eluted isomer SFC AD column |
| 121 | 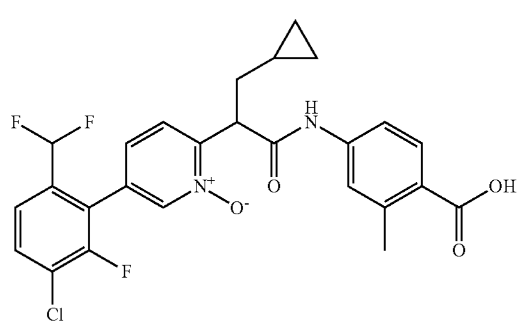 [SMILES: Cc1cc(NC(=O)C(CC2CC2)c2ccc(-c3c(C(F)F)ccc(Cl)c3F)c[n+]2[O-])ccc1C(=O)O] | 2-(1-((4-carboxy-3-methylphenyl)amino)-3-cyclopropyl-1-oxopropan-2-yl)-5-(3-chloro-6-(difluoromethyl)-2-fluorophenyl)pyridine 1-oxide | 519.3 | First eluted isomer SFC AD column |

-continued

| Ex. # | Structure | Name | Exact Mass [M + H]+ | Chiral Separation |
|---|---|---|---|---|
| 122 | 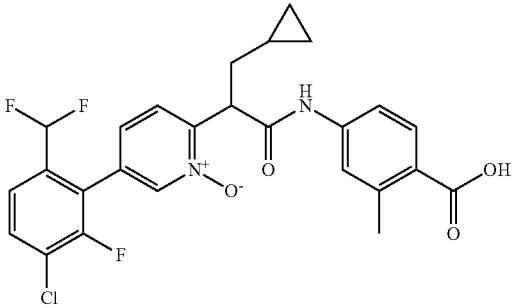 | 2-(1-((4-carboxy-3-methylphenyl)amino)-3-cyclopropyl-1-oxopropan-2-yl)-5-(3-chloro-6-(difluoromethyl)-2-fluorophenyl)pyridine 1-oxide | 519.3 | Second eluted isomer SFC AD column |
| 123 | 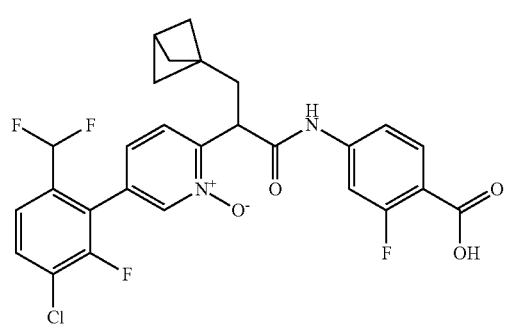 | 2-(3-(bicyclo[1.1.1]pentan-1-yl)-1-((4-carboxy-3-fluorophenyl)amino)-1-oxopropan-2-yl)-5-(3-chloro-6-(difluoromethyl)-2-fluorophenyl)pyridine 1-oxide | 549.3 | First eluted isomer SFC AD column |
| 124 | 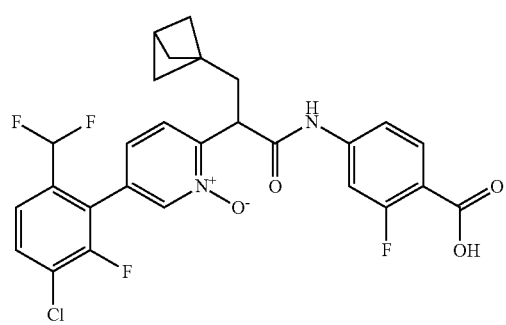 [SMILES: O=C(O)c1ccc(NC(=O)C(CC23CC(C2)C3)c2ccc(-c3c(C(F)F)ccc(Cl)c3F)c[n+]2[O-])cc1F] | 2-(3-(bicyclo[1.1.1]pentan-1-yl)-1-((4-carboxy-3-fluorophenyl)amino)-1-oxopropan-2-yl)-5-(3-chloro-6-(difluoromethyl)-2-fluorophenyl)pyridine 1-oxide | 549.3 | Second eluted isomer SFC AD column |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations (IC50), or the inhibitory constant, $K_i$.

Compounds were pre-incubated for 30 minutes at 25° C. with human (0.04 nM) Factor XIa in 50 mM HEPES buffer with 150 mM sodium chloride, 5 mM calcium chloride, 0.1% PEG 8000, pH 7.4. Factor XIa enzymatic activity was determined by addition of the substrate glycine-proline-arginine-7-amido-4-trifluoromethylcoumarin (GPR-AFC) and measurement of the fluorescence at 400/505 nm after a 60 minute incubation at 25° C. The % inhibition for each data point was calculated from the data and analyzed using the log (inhibitor) vs. response four parameters equation to determine the half-maximal inhibitory concentrations (IC50). The IC50 were converted to equilibrium inhibitory constants (Ki) using the Cheng-Prusoff equation.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations (IC50), or the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma # C6608) at a concentration of 100 mM.

Activity assays were performed by diluting a stock solution of substrate at least tenfold to a final concentration ≤0.2 Km into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Activated Partial Thromboplastin Time (aPTT) Assay

Activated partial thromboplastin time (aPTT) is a clotting test that measures the intrinsic coagulation cascade. The test is performed in sodium citrated plasma. Human plasma is made by collecting blood from healthy donors of both genders into Na citrate tubes (Sarstedt coagulation 9NC/10 ml). Blood is centrifuged at 1500×g and the plasma is collected. aPTT is checked on each individual donor and those within the normal range (28-40 seconds) are pooled, aliquoted, and stored at −80 C. Test samples are prepared by spiking inhibitors or vehicle into plasma. These spiked samples are then run on a coagulation analyzer (STA-R Evolution, Stago Diagnostica). In general, the analyzer performs the following steps: Factor XII is activated by addition of ellagic acid (Pacific Hemostasis), and then time to clot is measured after re-calcification of the sample. Inhibition of FXI will cause aPTT clot time to be prolonged. The data is expressed as percent increase over vehicle control clot time and the concentration that causes a 50% (1.5×) percent increase of clot time are reported.

In Vitro Permeability Assay

The in vitro permeation studies are similar to those described by He et al, (He, H.; Lyons, K.; Shen, X.; Yao, Z.; Bleasby, K.; Chan, G.; Hafey, M.; Li, X.; Xu, S.; Salituro, G.; Cohen, L. H., Tang, W. Utility of unbound plasma drug levels and p-glycoprotein transport data in prediction of central nervous system exposure. Xenobiotica 2009, 39, 687-693). LLC-PK1 cells were cultured in 96-well transwell culture plates. The area of membrane was 0.11 $cm^2$. Each test compound (final concentration 1 µM) was prepared in Hank's Balanced Salt Solution (HBSS) with 10 mM HEPES. Substrate solution (150 µL) was added to either the apical (A) or the basolateral (B) compartment of the culture plate, and buffer (150 µL; +10 mM HEPES) was added to the compartment opposite to that containing the compound. At t=3 h, 50 µL of sample was taken out from both sides and analyzed by LC-MS/MS. Verapamil (1 µM) was used as the positive control. The experiment was performed in triplicate. Apparent permeation ($P_{app}$) is reported as the average of the $P_{app}$ for transport from A to B and $P_{app}$ for transport from B to A at t=3 h and is expressed as $10^{-6}$ cm/s.

Rat Pharmacokinetic Screening IV/PO General Procedure

Plasma pharmacokinetic parameters for clearance (Cl), volume of distribution, mean residence time (MRT) and oral bioavailability (% F) were determined in rats from oral administration and IV administration studies. 4 male rats, typically weighing 225-260 gram, were fasted overnight prior to dosing. Compounds were prepared for oral and IV dosing by addition to a vehicle, depending on the dose used. For a typical preparation, 1 mg per mL (IV) or 1.5 mg per mL (oral) of test compound was added to vehicle comprised of 20% dimethyl sulfoxide (DMSO), 60% polyethylene glycol 400 (PEG400) and 20% water. IV formulation was administered to 2 rats via pre-cannulated jugular vein, and oral dosing was administered to 2 rats via oral gavage. Blood was collected by pre-cannulated artery, typically at predose, 2, 8, 15, 30 min, 1, 2, 4, 6, and 8 hr postdose for IV, and at predose, 15, 30 min, 1, 2, 4, 6, 8 hr for oral dosing. Samples were collected in K2EDTA tubes, stored on ice, and centrifuged. Plasma was transferred to a micro titer plate and stored at −70° C. until analysis. Plasma samples were extracted using protein precipitation and analyzed by liquid chromatography separation followed by mass spec detection (LC-MS/MS), using a standard curve for each compound. Plasma pharmacokinetic parameters were calculated for IV and oral dosing data by non-compartmental methods. Oral bioavailability was determined as the ratio of the dose-normalized plasma area under the curve (AUC) following oral dosing vs. IV dosing.

Factor XIa (FXIa), Plasma Kallikrein (P. KLK), and aPTT data for selected compounds are as follows (ND=not determined):

| Ex. | FXIa IC$_{50}$, nM (% Inh. @ 1000 nM) | P. KLK IC$_{50}$, nM | aPTT (1.5x), μM |
|---|---|---|---|
| 1 | >1000 (47%) | ND | ND |
| 2 | 2.1 | 79 | 1.16 |
| 3 | 39 | ND | >100 |
| 4 | 0.36 | 4.7 | 0.55 |
| 5 | 166 | ND | ND |
| 6 | >1000 (30%) | ND | >100 |
| 7 | 7.6 | 265 | 16.38 |
| 8 | 968 | ND | >100 |
| 9 | 9.0 | 857 | 13 |
| 10 | >1000 (13%) | ND | ND |
| 11 | 36 | ND | ND |
| 12 | >1000 (35%) | ND | ND |
| 13 | 6.9 | 984 | 11.1 |
| 14 | 47 | ND | ND |
| 15 | 0.56 | 20 | 0.75 |
| 16 | >1000 (33%) | ND | >100 |
| 17 | 24 | ND | >100 |
| 18 | 100 | ND | >100 |
| 19 | 0.45 | 20 | 1.3 |
| 20 | >1000 (13%) | ND | ND |
| 21 | 83 | ND | ND |
| 22 | 240 | ND | ND |
| 23 | 0.90 | 22 | 0.61 |
| 24 | >1000 (33%) | ND | ND |
| 25 | 16 | 756 | 10.28 |
| 26 | >1000 (39%) | ND | ND |
| 27 | 2.8 | 162 | 2.68 |
| 28 | 293 | ND | >100 |
| 29 | 4.3 | 84 | 2.07 |
| 30 | 7.6 | 155 | 5.27 |
| 31 | 3.0 | 31 | 0.88 |
| 32 | 471 | ND | ND |
| 33 | 3.5 | 81 | ND |
| 34 | 34 | ND | ND |
| 35 | 0.14 | 12 | 0.39 |
| 36 | 26 | ND | ND |
| 37 | 0.33 | 5.7 | 0.4 |
| 38 | 53 | ND | ND |
| 39 | 2.1 | 25 | 1.30 |
| 40 | 3.2 | 35 | ND |
| 41 | >1000 (49%) | ND | ND |
| 42 | 227 | ND | ND |
| 43 | 0.45 | 20 | 0.55 |
| 44 | 299 | ND | ND |
| 45 | 2.7 | 12 | 1.16 |
| 46 | 128 | ND | ND |
| 47 | 0.56 | 20 | 0.59 |
| 48 | 10 | ND | ND |
| 49 | >1000 (47%) | ND | ND |
| 50 | 3.8 | 47 | 1.33 |
| 51 | 228 | ND | ND |
| 52 | 0.93 | 14 | 1.17 |
| 53 | 155 | ND | ND |
| 54 | 370 | ND | ND |
| 55 | 0.38 | 21 | 0.53 |
| 56 | 0.38 | 16 | 1.34 |
| 57 | >1000 (48%) | ND | ND |
| 58 | 334 | ND | ND |
| 59 | 286 | ND | ND |
| 60 | 62 | ND | ND |
| 61 | 55 | ND | ND |
| 62 | 0.21 | 6.1 | 0.35 |
| 63 | 0.19 | 2.9 | 2.13 |
| 64 | 177 | ND | ND |
| 65 | 1.8 | 51 | 1.86 |
| 66 | >1000 (34%) | ND | ND |
| 67 | 11 | ND | ND |
| 68 | 200 | ND | ND |
| 69 | 2.1 | 42 | 1.92 |
| 70 | 0.31 | 3.3 | 0.82 |
| 71 | 0.47 | 11 | 1.24 |
| 72 | 196 | ND | ND |
| 73 | 3.3 | 88 | 2.15 |
| 74 | 1.3 | 19.2 | 2.77 |
| 75 | 3.3 | 77.8 | |
| 76 | 2.0 | 14.5 | 0.72 |
| 77 | 2.3 | 37.6 | |
| 78 | 132.0 | | |
| 79 | 65.1 | | |
| 80 | 484.4 | | |
| 81 | 1.2 | 8.4 | 0.58 |
| 82 | 80.0 | | |
| 83 | 0.6 | 9.4 | 0.62 |
| 84 | 133.00 | | |
| 85 | 2.6 | 38.0 | 1 |
| 86 | 93.6 | | |
| 87 | 0.4 | 2.7 | 0.92 |
| 88 | 0.8 | 3.6 | 1.43 |
| 89 | 0.6 | 7.1 | 0.68 |
| 90 | 1.1 | 5.3 | 0.57 |
| 91 | 27.9 | | 5.93 |
| 92 | 247.5 | | 100 |
| 93 | 3.3 | 28.0 | 0.8 |
| 94 | 0.4 | 6.0 | 0.4 |
| 95 | 0.4 | 9.6 | 0.43 |
| 96 | 502.9 | | |
| 97 | 150.5 | | |
| 98 | 0.3 | 11.3 | 0.72 |
| 99 | 2.1 | 92 | 2.78 |
| 100 | 144.5 | | |
| 101 | 1000 (44%) | | |
| 102 | 1.8 | 31.8 | 1 |
| 103 | 153.00 | | |
| 104 | 1000 (37%) | | |
| 105 | 0.61 | 15.7 | 1.13 |
| 106 | 3.79 | 59.9 | |
| 107 | 3.2 | 24.2 | 1.74 |
| 108 | 101.7 | | |
| 109 | 1.2 | 25.2 | 0.76 |
| 110 | 1000 (29%) | | |
| 111 | 157.00 | | |
| 112 | 0.4 | 21.3 | 2.21 |
| 113 | 1000 (6%) | | |
| 114 | 1000 (45%) | 201.2 | |
| 115 | 1000 (0%) | | |
| 116 | 881.8 | | |
| 117 | 58.4 | | |
| 118 | 0.6 | 14.6 | 0.66 |
| 119 | 80.3 | | |
| 120 | 0.1 | 2.1 | 0.75 |
| 121 | 620.3 | | |
| 122 | 9.9 | 69.8 | |
| 123 | 24.7 | | |
| 124 | 0.8 | 4.7 | 1.76 |

Rat pharmacokinetic (PK) data for selected compounds are as follows:

| Example | Cl (mL/min/kg) | MRT (h) | % F |
|---|---|---|---|
| 2 | 5.0 | 2.5 | 56 |
| 4 | 5.1 | 2.5 | 34 |
| 23 | 1.9 | 2.9 | 89 |
| 55 | 4.3 | 2.6 | 63 |
| 76 | 12.1 | 2.3 | 70 |

What is claimed is:

1. A compound of the formula:

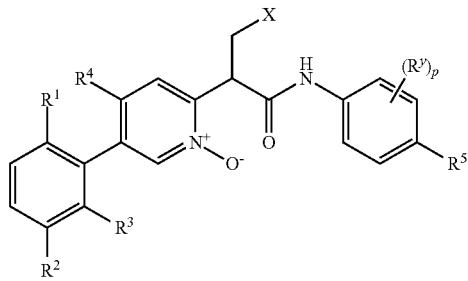

wherein X is

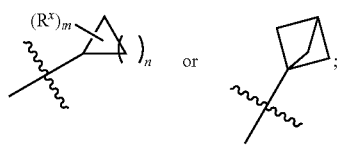

R¹ is CF₂H, CF₃, OCF₂H, O(C₁₋₃ alkyl) or OCH₂(cyclopropyl);
R² is chloro or fluoro;
R³ is hydrogen, chloro or fluoro;
R⁴ is hydrogen, C₁₋₃ alkyl or O(C₁₋₃ alkyl), wherein said alkyl groups are optionally substituted with one to three groups independently selected from the group consisting of halo and hydroxyl;
R⁵ is (C=O)OH or (C=O)O(C₁₋₆ alkyl), wherein said alkyl groups are optionally substituted with one to three groups independently selected from the group consisting of halo and hydroxyl;
each Rˣ is independently selected from halo, hydroxyl, cyano, oxo, methyl, ethyl, CH₂F, CHF₂, CF₃ or CH₂OH;
Rʸ is halo or methyl;
m is zero, one or two;
n is one, two, three or four;
p is zero or one;
or a pharmaceutically acceptable salt thereof.

2. The compound of claim 1 of the formula:

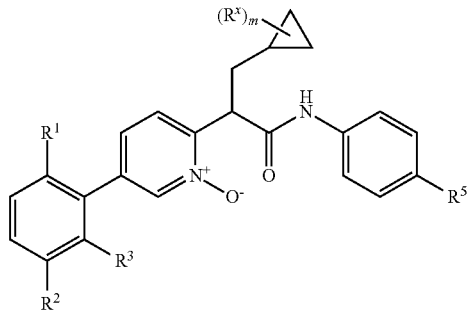

wherein R¹ is CF₂H, CF₃, or OCF₂H;
R² is chloro or fluoro;
R³ is hydrogen, chloro or fluoro;
R⁵ is (C=O)OH or (C=O)O(C₁₋₆ alkyl), wherein said alkyl groups are optionally substituted with one to three groups independently selected from the group consisting of halo and hydroxyl;

each Rˣ is independently selected from halo, hydroxyl, cyano, oxo or methyl;
m is zero, one or two;
or a pharmaceutically acceptable salt thereof.

3. The compound of claim 1 wherein R¹ is OCF₂H; or a pharmaceutically acceptable salt thereof.

4. The compound of claim 1 wherein R¹ is CF₂H; or a pharmaceutically acceptable salt thereof.

5. The compound of claim 1 wherein R² is chloro and R³ is fluoro; or a pharmaceutically acceptable salt thereof.

6. The compound of claim 1 wherein R⁵ is (C=O)OH; or a pharmaceutically acceptable salt thereof.

7. The compound of claim 1 wherein m is zero; or a pharmaceutically acceptable salt thereof.

8. The compound of claim 1 selected from:

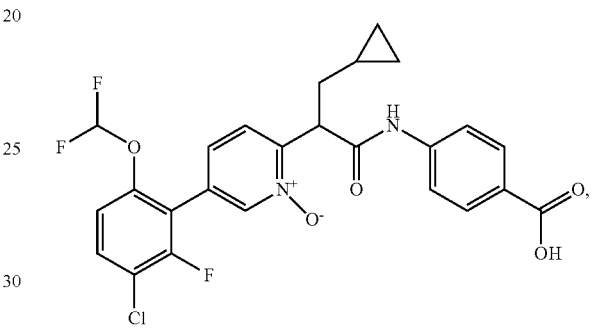

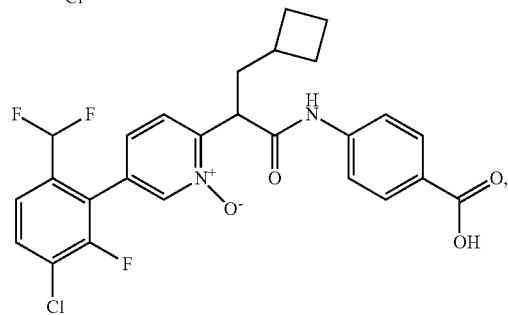

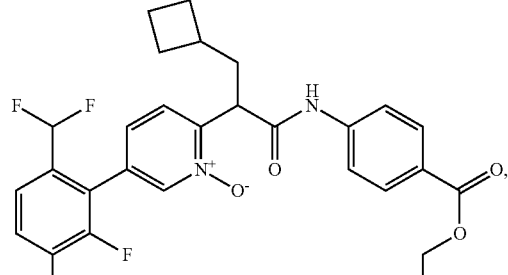

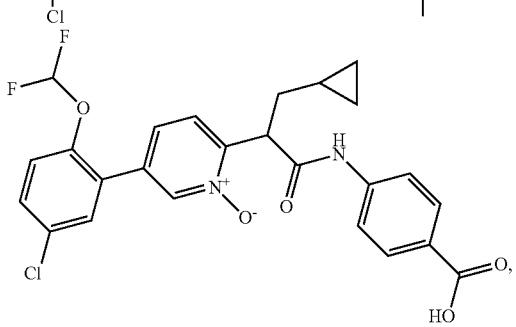

143
-continued
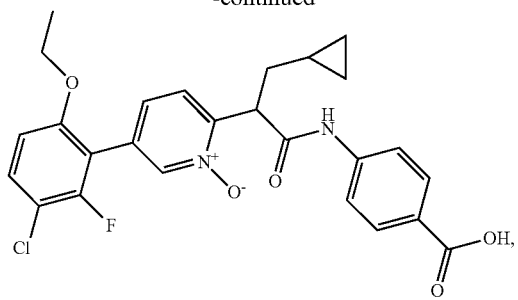
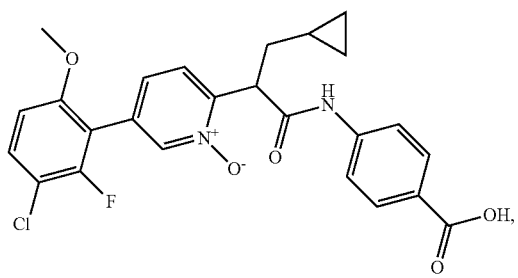
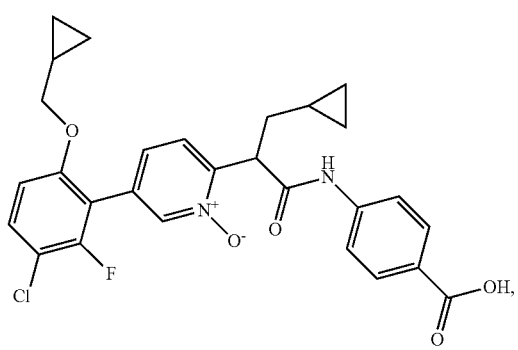
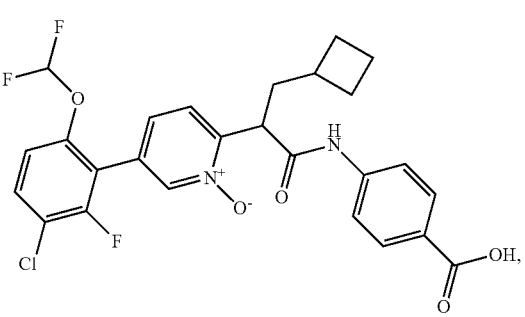
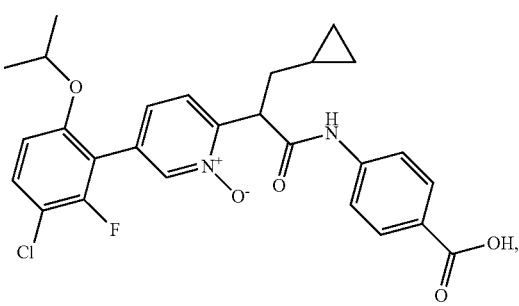
144
-continued
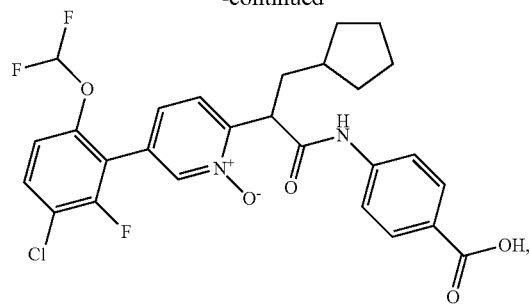
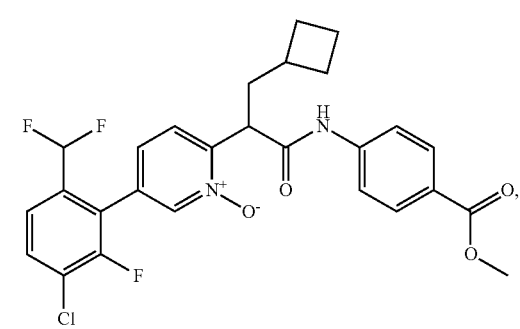
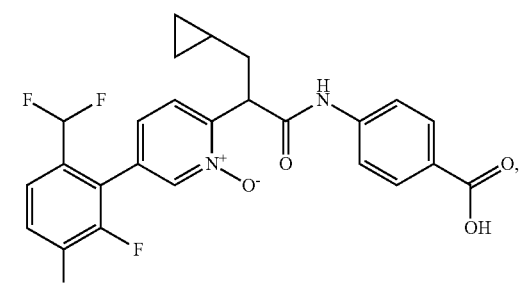
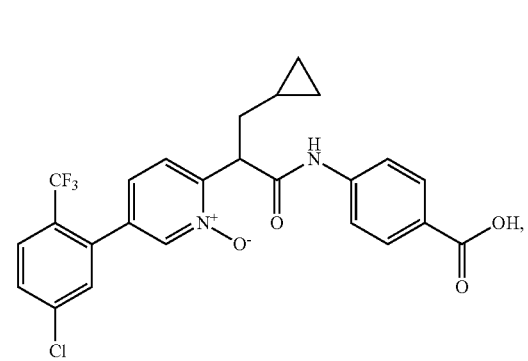
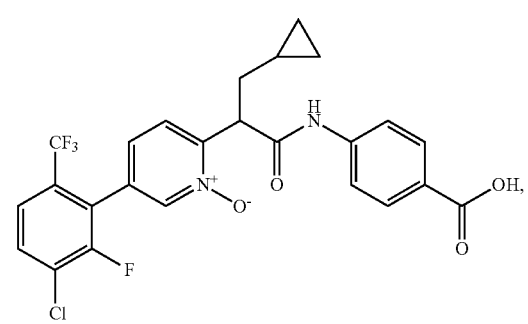

-continued
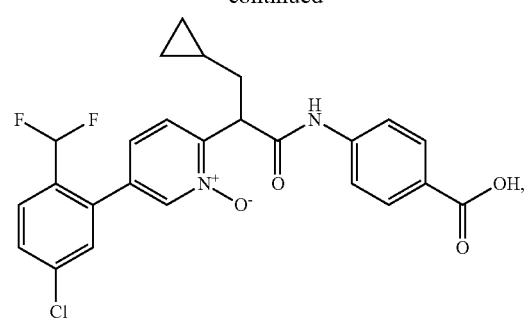
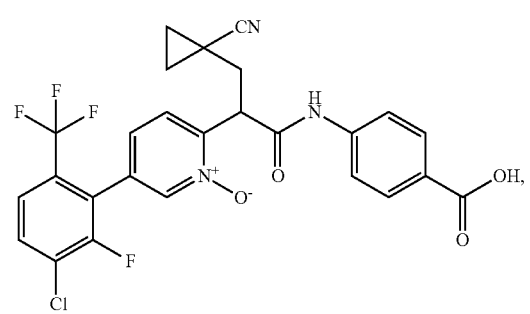
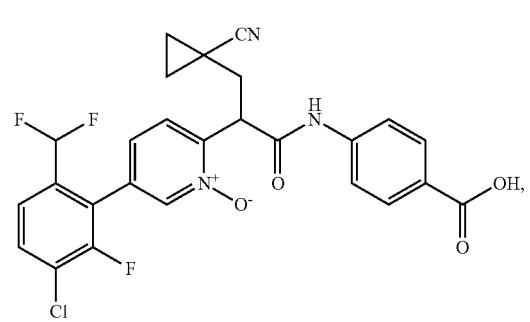
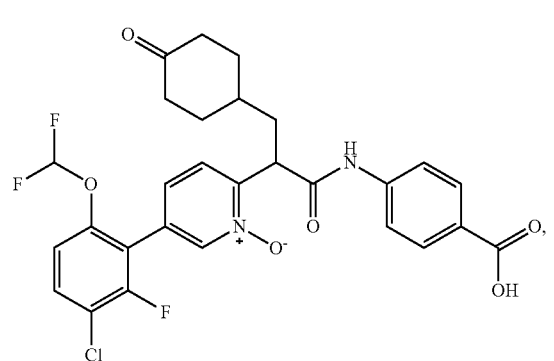
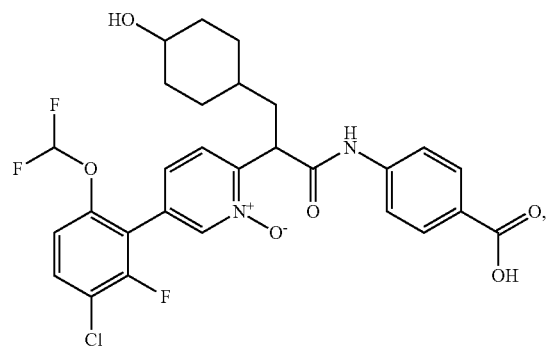
-continued
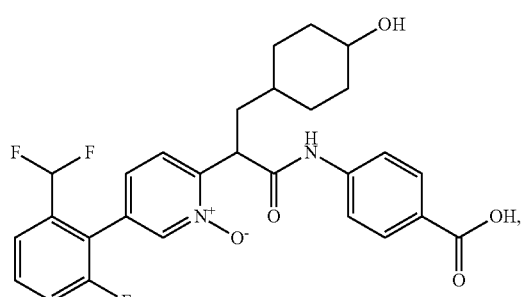
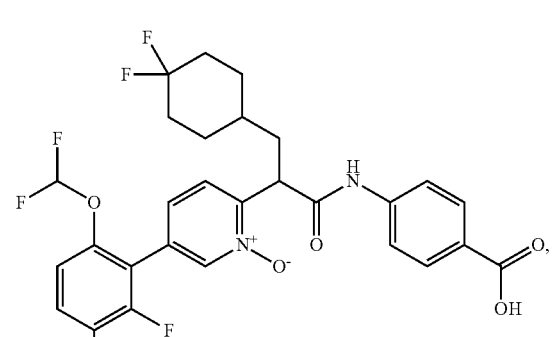
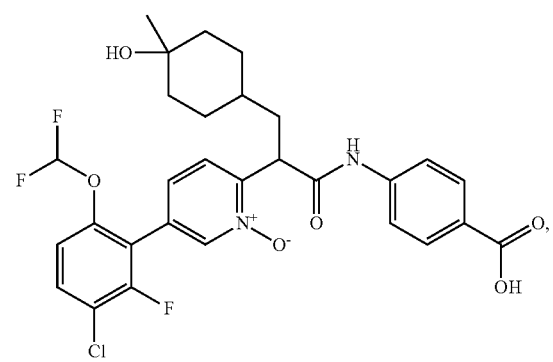
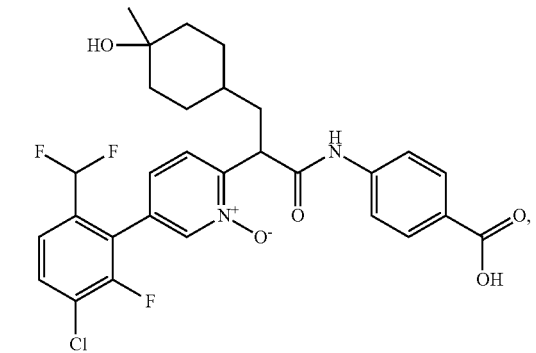

147
-continued
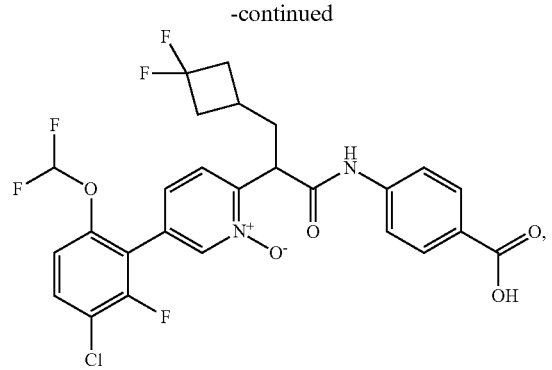
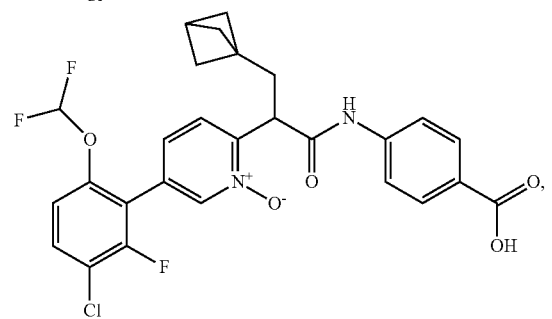
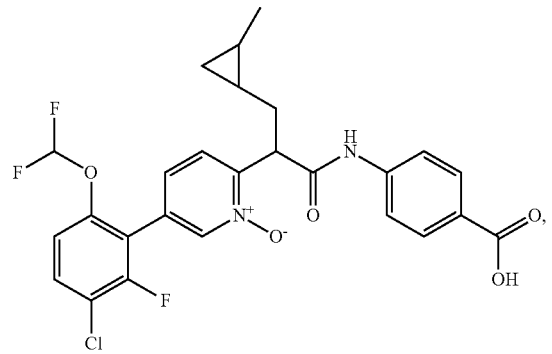
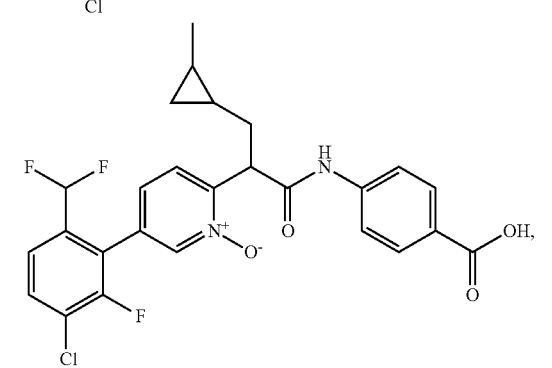
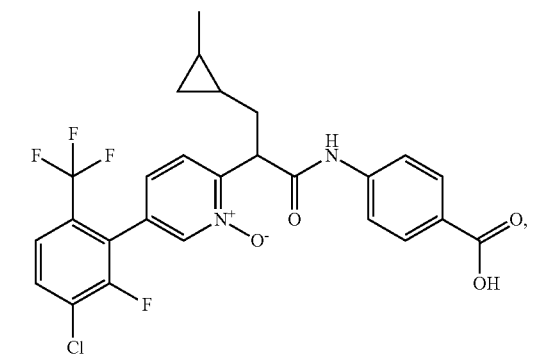
148
-continued
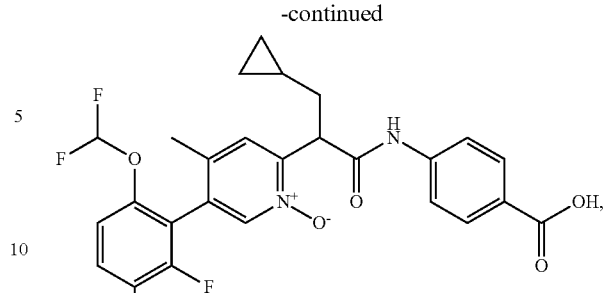
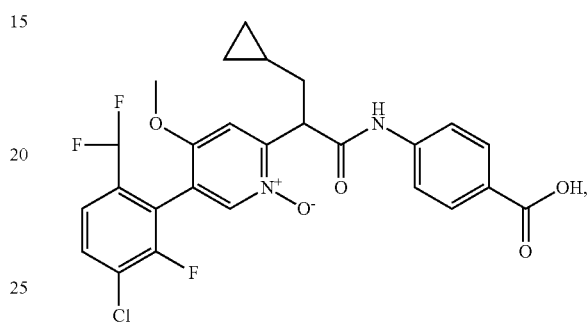
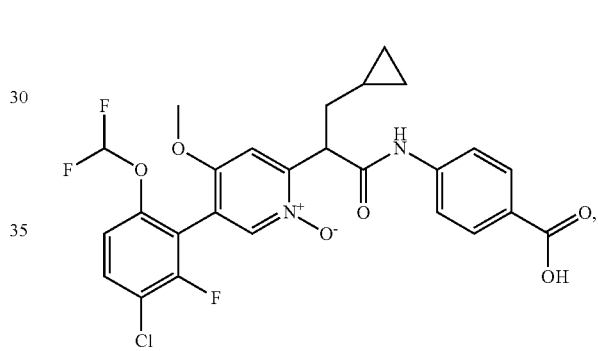
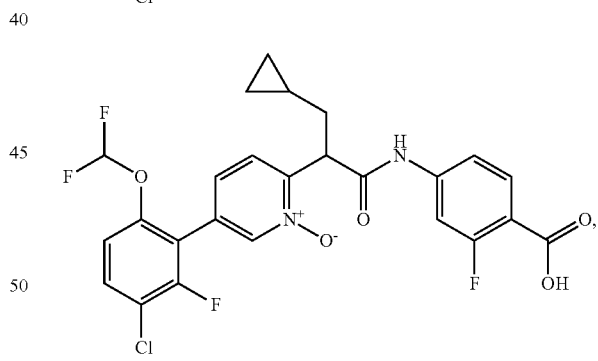
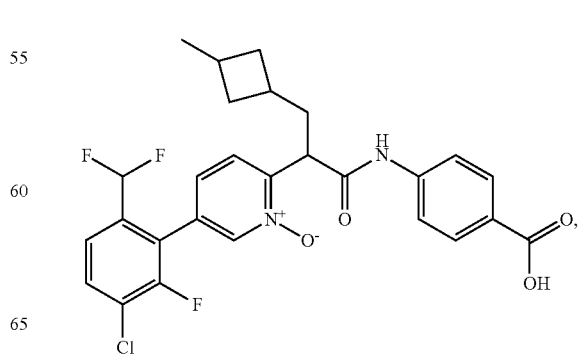

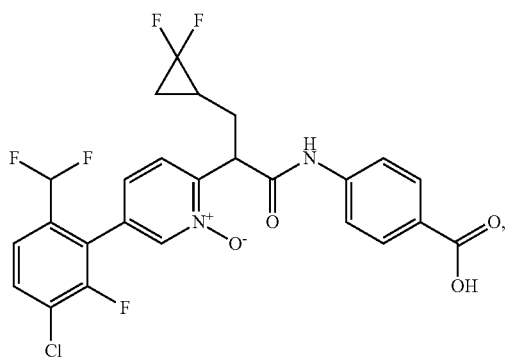
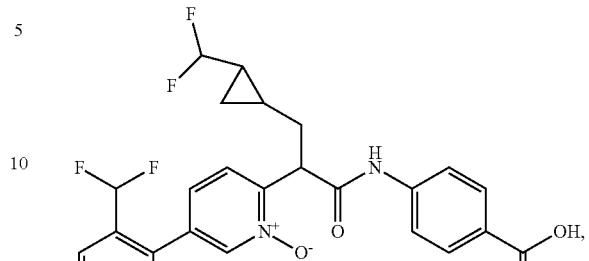
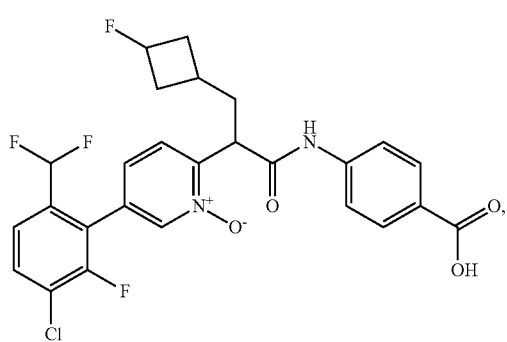
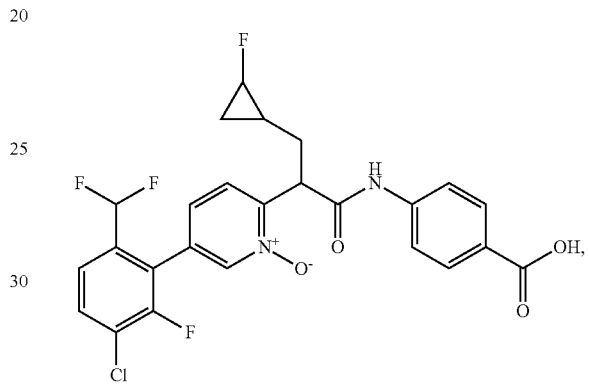
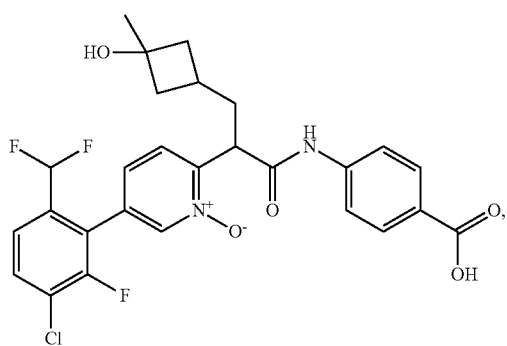
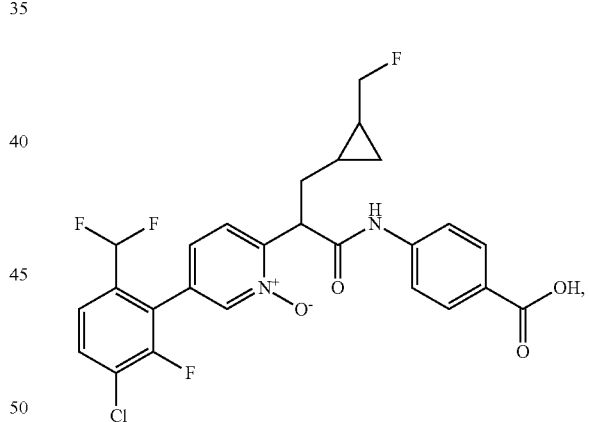
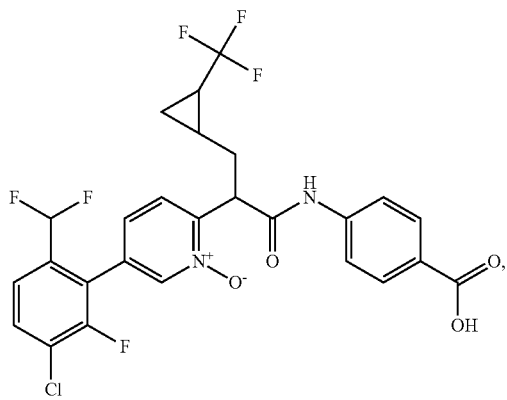
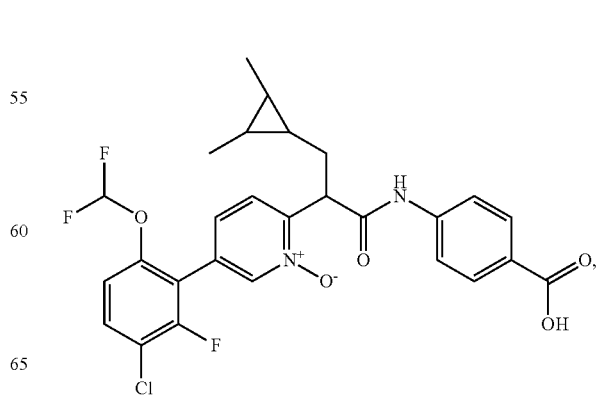

151
-continued
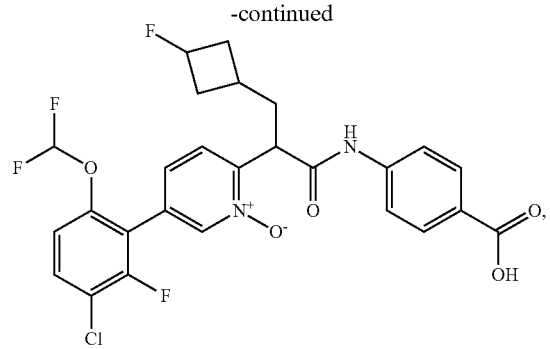
152
-continued
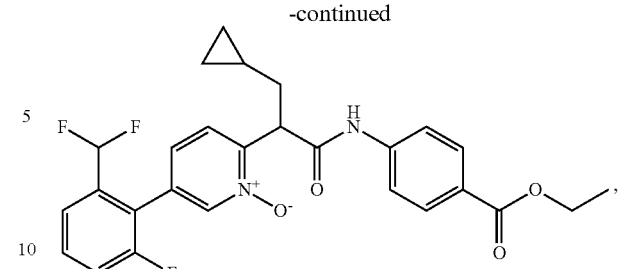
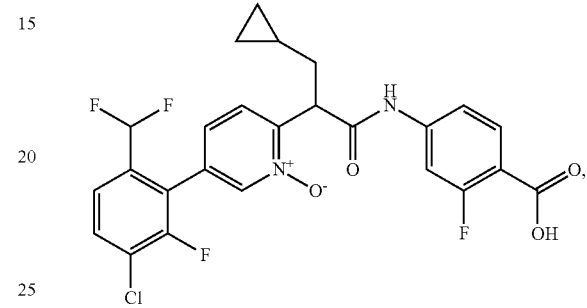
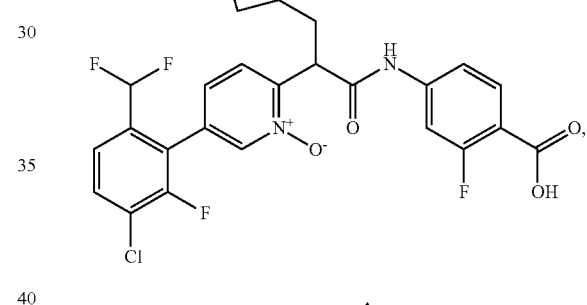
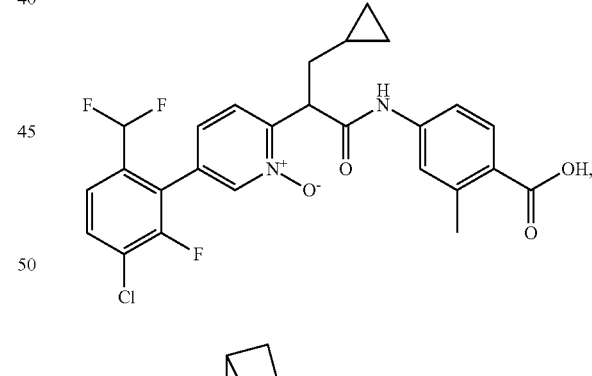
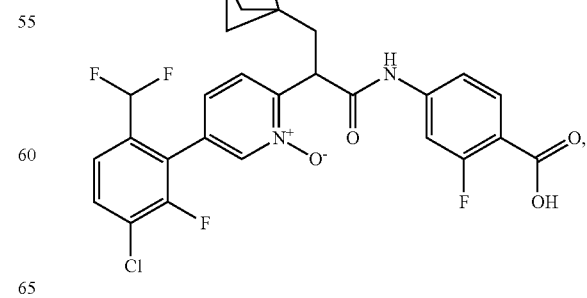
or a pharmaceutically acceptable salt thereof.

9. The compound of claim 8 selected from
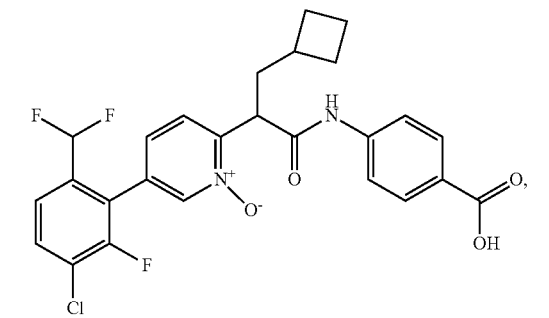
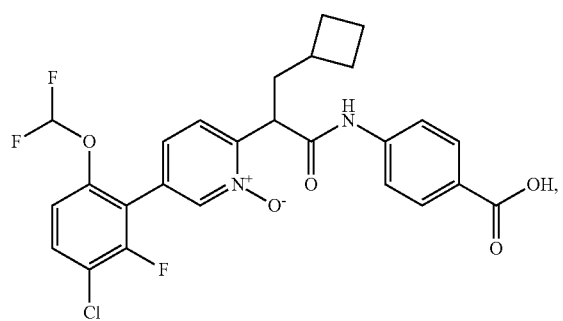
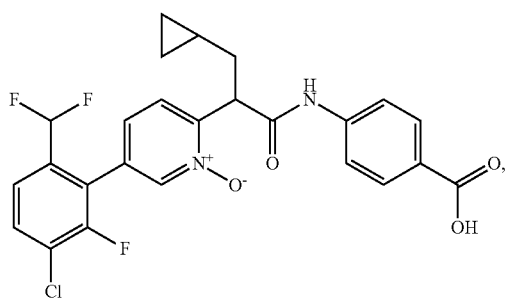
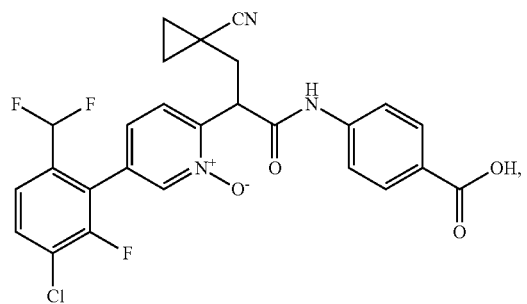
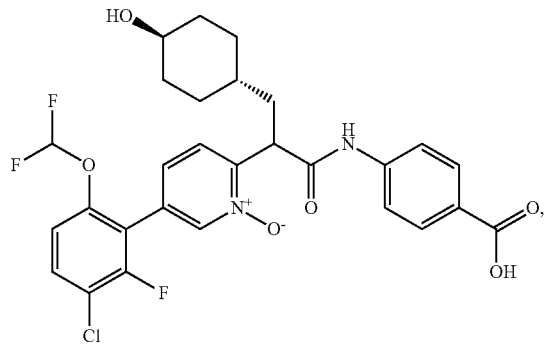
-continued
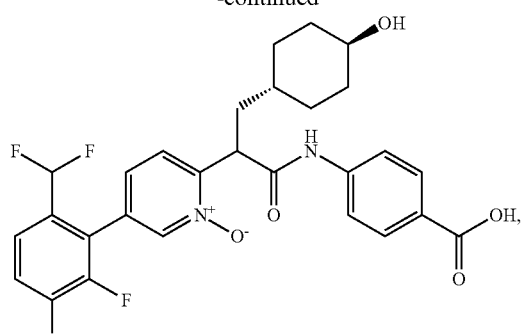
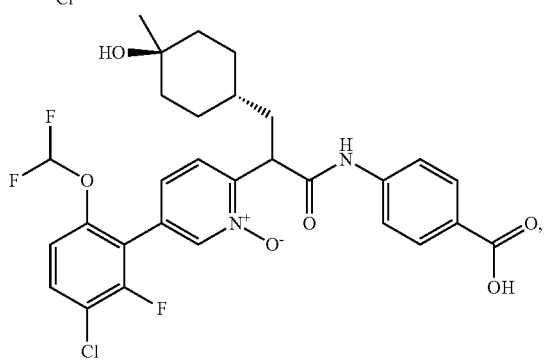
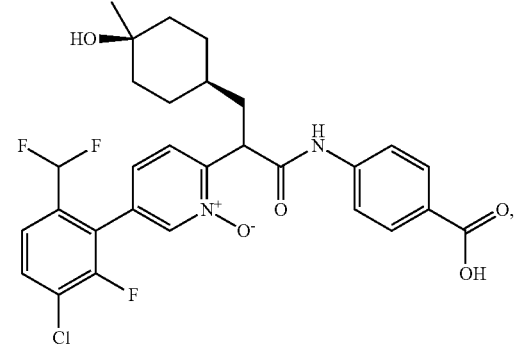
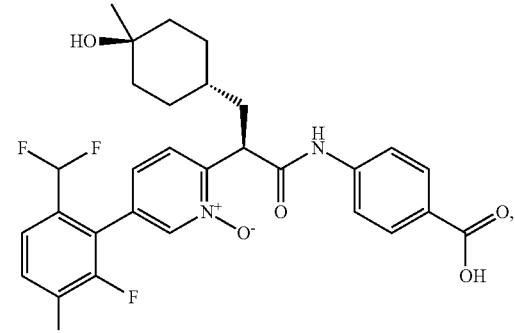
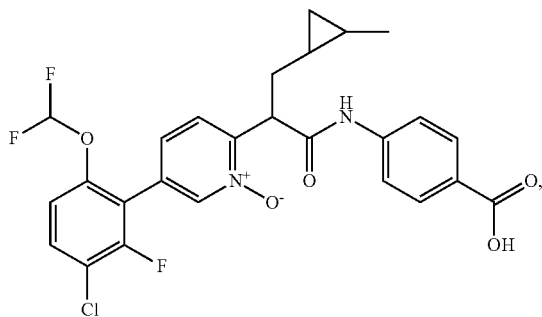

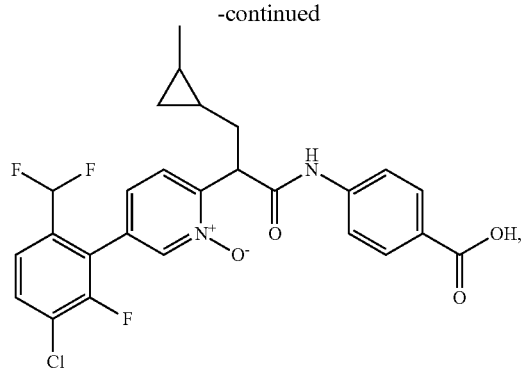
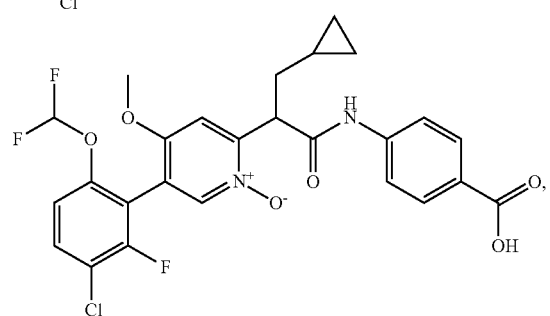
or a pharmaceutically acceptable salt thereof.
10. The compound of claim 9 selected from
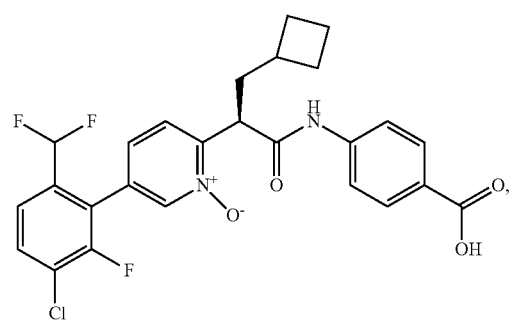
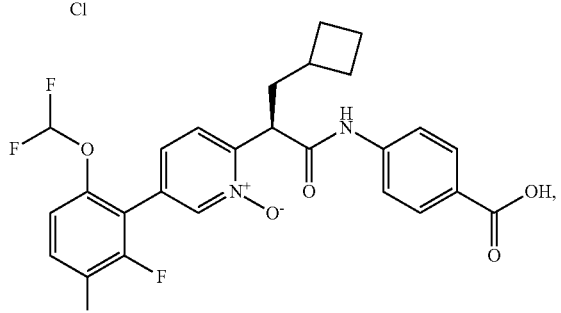
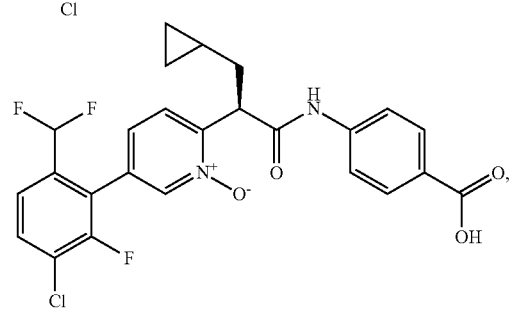
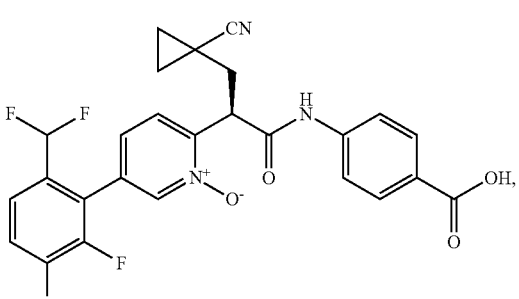
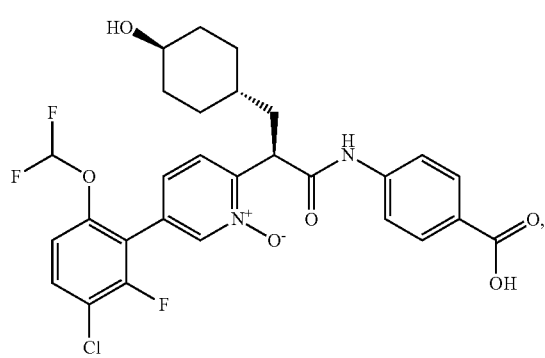
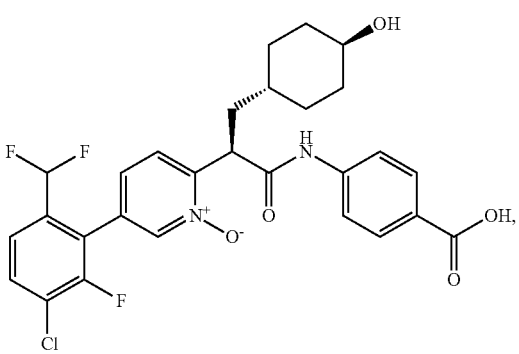
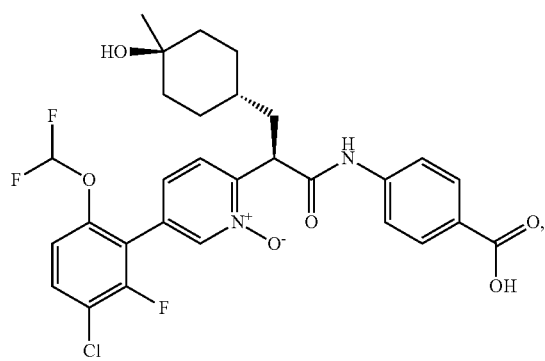

-continued

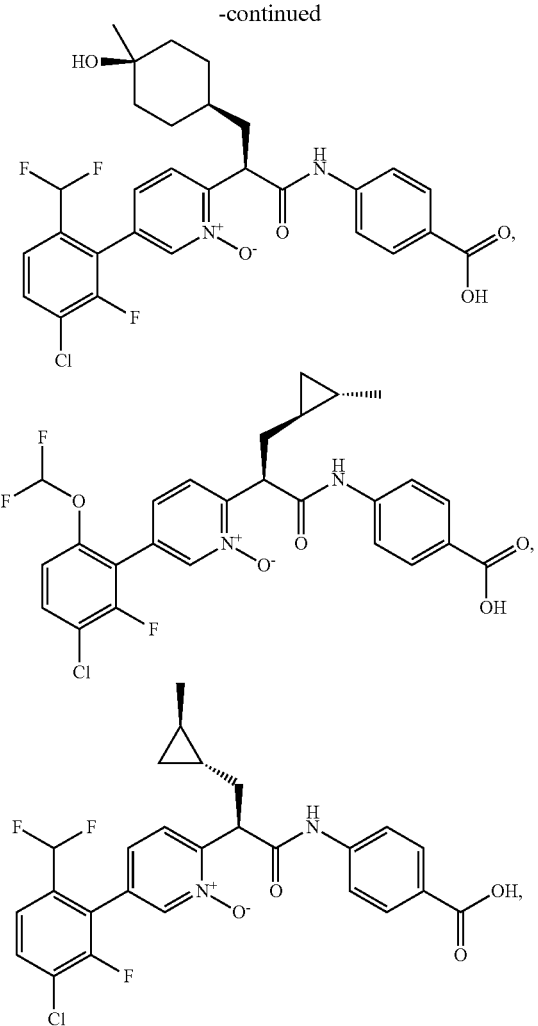

-continued

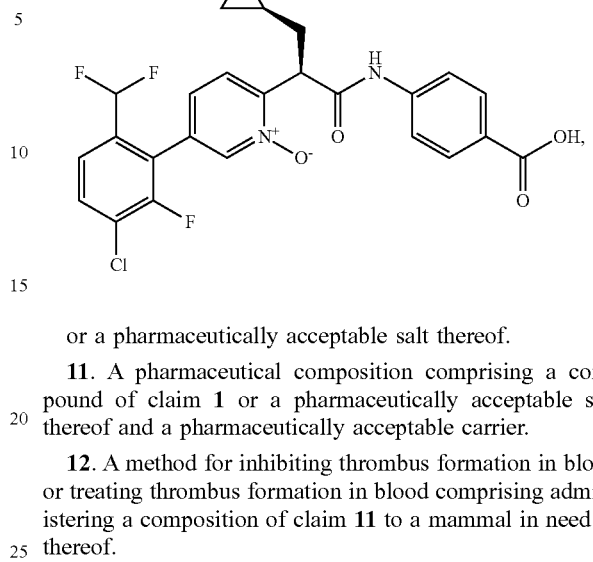

or a pharmaceutically acceptable salt thereof.

11. A pharmaceutical composition comprising a compound of claim 1 or a pharmaceutically acceptable salt thereof and a pharmaceutically acceptable carrier.

12. A method for inhibiting thrombus formation in blood or treating thrombus formation in blood comprising administering a composition of claim 11 to a mammal in need of thereof.

13. A method for preventing thrombus formation in blood comprising administering a composition of claim 11 to a mammal in need thereof.

14. A method of treating venous thromboembolism and pulmonary embolism in a mammal comprising administering a composition of claim 11 to a mammal in need thereof.

15. A method of treating deep vein thrombosis in a mammal comprising administering a composition of claim 11 to a mammal in need thereof.

16. A method of treating thromboembolic stroke in a mammal comprising administering a composition of claim 11 to a mammal in need thereof.

* * * * *